US008153391B2

(12) United States Patent
Dayton et al.

(10) Patent No.: US 8,153,391 B2
(45) Date of Patent: Apr. 10, 2012

(54) HYDROLASES, NUCLEIC ACIDS ENCODING THEM AND METHODS FOR MAKING AND USING THEM

(75) Inventors: Christopher L. G. Dayton, Bourbonnais, IL (US); Tim Hitchman, Encinitas, CA (US); Katie Kline, San Diego, CA (US); Jonathan Lyon, San Diego, CA (US); Mark A. Wall, San Diego, CA (US); Nelson R. Barton, San Diego, CA (US)

(73) Assignee: Bunge Oils, Inc., Saint Louis, MO (US)

( * ) Notice: Subject to any disclaimer, the term of this patent is extended or adjusted under 35 U.S.C. 154(b) by 644 days.

(21) Appl. No.: 12/202,204

(22) Filed: Aug. 29, 2008

(65) Prior Publication Data

US 2010/0055234 A1    Mar. 4, 2010

(51) Int. Cl.
| | |
|---|---|
| *C12Q 1/34* | (2006.01) |
| *C12Q 1/00* | (2006.01) |
| *C12N 9/14* | (2006.01) |
| *C12N 1/20* | (2006.01) |
| *C12N 15/00* | (2006.01) |
| *C12P 7/00* | (2006.01) |
| *C12P 21/04* | (2006.01) |
| *C12P 21/06* | (2006.01) |
| *C07H 21/04* | (2006.01) |

(52) U.S. Cl. ......... 435/18; 435/195; 435/440; 435/69.1; 435/71.1; 435/252.3; 435/320.1; 435/132; 435/4; 536/23.2

(58) Field of Classification Search .................. None
See application file for complete search history.

(56) References Cited

U.S. PATENT DOCUMENTS

| | | | |
|---|---|---|---|
| 3,949,105 A | 4/1976 | Wieske et al. |
| 4,261,868 A | 4/1981 | Hora et al. |
| 4,404,128 A | 9/1983 | Anderson |
| 4,458,066 A | 7/1984 | Caruthers et al. |
| 4,683,195 A | 7/1987 | Mullis et al. |
| 4,683,202 A | 7/1987 | Mullis |
| 4,707,364 A | 11/1987 | Barach et al. |
| 4,752,483 A | 6/1988 | Hagberg et al. |
| 4,767,628 A | 8/1988 | Hutchinson |
| 4,818,695 A | 4/1989 | Eigtved |
| 4,897,268 A | 1/1990 | Tice et al. |
| 4,925,673 A | 5/1990 | Steiner et al. |
| 4,944,944 A | 7/1990 | Tang et al. |
| 4,946,778 A | 8/1990 | Ladner et al. |
| 4,962,028 A | 10/1990 | Bedbrook et al. |
| 4,987,071 A | 1/1991 | Cech et al. |
| 5,000,975 A | 3/1991 | Tomarelli |
| 5,015,580 A | 5/1991 | Christou et al. |
| 5,069,810 A | 12/1991 | Holmes et al. |
| 5,087,571 A | 2/1992 | Leder et al. |
| 5,143,854 A | 9/1992 | Pirrung et al. |
| 5,204,015 A | 4/1993 | Caldwell et al. |
| 5,217,879 A | 6/1993 | Huang et al. |
| 5,264,367 A | 11/1993 | Aalrust et al. |
| 5,288,619 A | 2/1994 | Brown et al. |
| 5,387,742 A | 2/1995 | Cordell |
| 5,434,049 A | 7/1995 | Okano et al. |
| 5,454,971 A | 10/1995 | Sakai et al. |
| 5,552,317 A | 9/1996 | Houng et al. |
| 5,556,752 A | 9/1996 | Lockhart et al. |
| 5,569,594 A | 10/1996 | Ikuta et al. |
| 5,573,933 A | 11/1996 | Seamark et al. |
| 5,602,321 A | 2/1997 | John |
| 5,605,793 A | 2/1997 | Stemmer |
| 5,608,148 A | 3/1997 | John |
| 5,632,957 A | 5/1997 | Heller et al. |
| 5,633,440 A | 5/1997 | Dunsmuir et al. |
| 5,639,940 A | 6/1997 | Garner et al. |
| 5,681,730 A | 10/1997 | Ellis |
| 5,691,181 A | 11/1997 | Lowe |
| 5,700,637 A | 12/1997 | Southern |
| 5,712,135 A | 1/1998 | D'Halluin et al. |
| 5,744,305 A | 4/1998 | Fodor et al. |
| 5,750,870 A | 5/1998 | Mathews et al. |
| 5,770,456 A | 6/1998 | Holmes |
| 5,773,266 A | 6/1998 | Bosley et al. |
| 5,795,737 A | 8/1998 | Seed et al. |
| 5,800,992 A | 9/1998 | Fodor et al. |
| 5,807,522 A | 9/1998 | Brown et al. |
| 5,811,238 A | 9/1998 | Stemmer et al. |
| 5,824,514 A | 10/1998 | Kauffman et al. |
| 5,827,718 A | 10/1998 | Ishida et al. |

(Continued)

FOREIGN PATENT DOCUMENTS

EP    0 093 602    3/1995

(Continued)

OTHER PUBLICATIONS

Branden et al. Introduction to Protein Structure, Garland Publishing Inc., New York, p. 247, 1991.*
Svenden A. (2000), Biochima et Biophysica ACTA vol. 1543, No. 2: 223-238.
Shu Z. Y. et al. (2010), J. Mol Catalysis 62, No. 1: 1-8.
U.S. Appl. No. 09/407,800, filed Sep. 28, 1999, Patten et al.
U.S. Appl. No. 09/618,579, filed Jul. 18, 2000, Selifonov et al.
U.S. Appl. No. 09/656,549, filed Sep. 6, 2000, Affholter.
Adams (1983), J. Am. Chem. Soc. 105:661.
Ader (1997), Methods Enzymol. 286:351-386.
Altschul (1977), Nuc. Acids Res. 25:3389-3402.
Altschul et al. (1990), J. Mol. Biol. 215(3):403-410.
Altschul et al. (1993), Nature Genetics 3:266-272.
Angell (1997), EMBO J. 16:3675-3684.
Arkin (1992), Proc. Natl. Acad. Sci. USA 89:7811-7815.
Arnold (1993), Current Opinion in Biotechnology 4:450-455.
Baca (2000), Int. J. Parasitol. 30:113-118.
Baguisi (1999), Nat. Biotechnol. 17:456-461.

(Continued)

*Primary Examiner* — Yong Pak
(74) *Attorney, Agent, or Firm* — Jones Day

(57) ABSTRACT

Provided are hydrolases, including lipases, saturases, palmitases and/or stearatases, and polynucleotides encoding them, and methods of making and using these polynucleotides and polypeptides. Further provided are polypeptides, e.g., enzymes, having a hydrolase activity, e.g., lipases, saturases, palmitases and/or stearatases and methods for preparing low saturate or low trans fat oils, such as low saturate or low trans fat animal or vegetable oils, e.g., soy or canola oils.

16 Claims, 32 Drawing Sheets

U.S. PATENT DOCUMENTS

| | | | |
|---|---|---|---|
| 5,830,645 A | 11/1998 | Pinkel et al. |
| 5,830,696 A | 11/1998 | Short |
| 5,830,721 A | 11/1998 | Stemmer et al. |
| 5,834,252 A | 11/1998 | Stemmer et al. |
| 5,834,259 A | 11/1998 | Pantaleone et al. |
| 5,837,458 A | 11/1998 | Minshull et al. |
| 5,856,164 A | 1/1999 | Outtrup et al. |
| 5,856,174 A | 1/1999 | Lipshutz et al. |
| 5,858,755 A | 1/1999 | Lowe |
| 5,880,327 A | 3/1999 | Lubon et al. |
| 5,891,698 A | 4/1999 | Prieto et al. |
| 5,892,070 A | 4/1999 | Prieto et al. |
| 5,902,617 A | 5/1999 | Pabst |
| 5,922,854 A | 7/1999 | Kumar et al. |
| 5,939,250 A | 8/1999 | Short |
| 5,955,358 A | 9/1999 | Huse |
| 5,959,098 A | 9/1999 | Goldberg et al. |
| 5,959,171 A | 9/1999 | Hyttinen et al. |
| 5,965,408 A | 10/1999 | Short |
| 5,965,452 A | 10/1999 | Kovacs |
| 6,013,440 A | 1/2000 | Lipshutz et al. |
| 6,022,963 A | 2/2000 | Gall et al. |
| 6,025,171 A | 2/2000 | Fabian et al. |
| 6,045,996 A | 4/2000 | Cronin et al. |
| 6,048,695 A | 4/2000 | Bradley et al. |
| 6,054,270 A | 4/2000 | Southern |
| 6,107,541 A | 8/2000 | Arnold |
| 6,111,166 A | 8/2000 | Van de Winkel |
| 6,118,044 A | 9/2000 | Karasuyama et al. |
| 6,153,410 A | 11/2000 | Arnold et al. |
| 6,156,952 A | 12/2000 | Bryant et al. |
| 6,171,820 B1 | 1/2001 | Short |
| 6,177,263 B1 | 1/2001 | Arnold et al. |
| 6,187,992 B1 | 2/2001 | Zheng et al. |
| 6,197,070 B1 | 3/2001 | Horner et al. |
| 6,204,232 B1 | 3/2001 | Borchert et al. |
| 6,211,428 B1 | 4/2001 | Singh et al. |
| 6,238,884 B1 | 5/2001 | Short et al. |
| 6,258,606 B1 | 7/2001 | Kovacs |
| 6,261,776 B1 | 7/2001 | Pirrung et al. |
| 6,277,489 B1 | 8/2001 | Abbott et al. |
| 6,277,628 B1 | 8/2001 | Johann et al. |
| 6,280,926 B1 | 8/2001 | Short |
| 6,287,861 B1 | 9/2001 | Stemmer et al. |
| 6,287,862 B1 | 9/2001 | delCardayre et al. |
| 6,291,242 B1 | 9/2001 | Stemmer |
| 6,297,038 B1 | 10/2001 | Bisg.ang.rd-Frantzen et al. |
| 6,309,871 B1 | 10/2001 | Outrupp et al. |
| 6,309,872 B1 | 10/2001 | Rey et al. |
| 6,313,081 B1 | 11/2001 | Lenting et al. |
| 6,319,714 B1 | 11/2001 | Crameri et al. |
| 6,322,595 B1 | 11/2001 | Boyer |
| 6,326,341 B1 | 12/2001 | Chatterjee et al. |
| 6,329,333 B1 | 12/2001 | Merz et al. |
| 6,333,301 B1 | 12/2001 | Kamiya |
| 6,337,187 B1 | 1/2002 | Kapeller-Libermann |
| 6,361,974 B1 | 3/2002 | Short et al. |
| 6,365,561 B1 | 4/2002 | Vinson et al. |
| 6,368,861 B1 | 4/2002 | Crameri et al. |
| 6,376,246 B1 | 4/2002 | Crameri et al. |
| 6,379,964 B1 | 4/2002 | delCardayre et al. |
| 6,380,147 B1 | 4/2002 | Speckmann et al. |
| 6,399,121 B1 | 6/2002 | Nielsen |
| 6,399,561 B1 | 6/2002 | Schneider et al. |
| 6,413,928 B1 | 7/2002 | Painter et al. |
| 6,423,542 B1 | 7/2002 | Crameri et al. |
| 6,426,224 B1 | 7/2002 | Crameri et al. |
| 6,436,675 B1 | 8/2002 | Welch et al. |
| 6,489,127 B1 | 12/2002 | Duyk et al. |
| 6,506,559 B1 | 1/2003 | Fire et al. |
| 6,511,824 B1 | 1/2003 | Buchman et al. |
| 6,515,109 B1 | 2/2003 | Ollmann et al. |
| 6,537,776 B1 | 3/2003 | Short |
| 6,551,635 B2 | 4/2003 | Nielsen |
| 6,579,258 B1 | 6/2003 | Atkin et al. |
| 6,605,449 B1 | 8/2003 | Short |
| 6,635,449 B2 | 10/2003 | Short |
| 6,713,282 B2 | 3/2004 | Short et al. |
| 6,740,506 B2 | 5/2004 | Short et al. |
| 6,773,900 B2 | 8/2004 | Short et al. |
| 2001/0008765 A1 | 7/2001 | Shinoki et al. |
| 2001/0012537 A1 | 8/2001 | Anderson et al. |
| 2001/0014448 A1 | 8/2001 | Chappa et al. |
| 2001/0014449 A1 | 8/2001 | Nerenberg et al. |
| 2001/0016322 A1 | 8/2001 | Caren et al. |
| 2001/0018642 A1 | 8/2001 | Balaban et al. |
| 2001/0019827 A1 | 9/2001 | Dawson et al. |
| 2005/0130160 A1 | 6/2005 | Chew et al. |
| 2005/0186666 A1 | 8/2005 | Schneider et al. |
| 2008/0058262 A1 | 3/2008 | Rasochova et al. |
| 2008/0138867 A1 | 6/2008 | Dayton et al. |
| 2009/0297495 A1 | 12/2009 | Kerovuo et al. |

FOREIGN PATENT DOCUMENTS

| | | |
|---|---|---|
| EP | 0 513 709 | 3/1995 |
| EP | 0 932 670 | 10/1997 |
| EP | 752 008 | 4/2002 |
| WO | WO 91/16427 | 10/1991 |
| WO | WO 95/22625 | 8/1995 |
| WO | WO 96/17958 | 6/1996 |
| WO | WO 96/33207 | 10/1996 |
| WO | WO 96/39154 | 12/1996 |
| WO | WO 97/01629 | 1/1997 |
| WO | WO 97/03211 | 1/1997 |
| WO | WO 97/20078 | 6/1997 |
| WO | WO 97/35966 | 10/1997 |
| WO | WO 97/46313 | 12/1997 |
| WO | WO 98/27230 | 6/1998 |
| WO | WO 98/31837 | 7/1998 |
| WO | WO 98/41622 | 9/1998 |
| WO | WO 98/41653 | 9/1998 |
| WO | WO 98/42727 | 10/1998 |
| WO | WO 98/42832 | 10/1998 |
| WO | WO 99/09217 | 2/1999 |
| WO | WO 99/21979 | 5/1999 |
| WO | WO 99/23107 | 5/1999 |
| WO | WO 99/29902 | 6/1999 |
| WO | WO 99/41368 | 8/1999 |
| WO | WO 99/41369 | 8/1999 |
| WO | WO 99/41383 | 8/1999 |
| WO | WO 99/41402 | 8/1999 |
| WO | WO 99/51773 | 10/1999 |
| WO | WO 99/66805 | 12/1999 |
| WO | WO 00/00632 | 1/2000 |
| WO | WO 00/42561 | 1/2000 |
| WO | WO 00/09679 | 2/2000 |
| WO | WO 00/42559 | 7/2000 |
| WO | WO 00/42560 | 7/2000 |
| WO | WO 00/54601 | 9/2000 |
| WO | WO 03/070013 | 8/2003 |
| WO | WO 2005/032496 * | 4/2005 |

OTHER PUBLICATIONS

Barringer (1990),Gene 89:117.
Bass et al. (1988), Science 242:240-245.
Bateman, A. et al. (2002), Nucleic Acids Research, 30(1):276-280.
Beaucage (1981), Tetra. Lett. 22:1859.
Belousov (1997), Nucleic Acids Res. 25:3440-3444.
Berger (1987), Methods Enzymol. 152:307-316.
Blazquez (1998), Plant Cell 10:791-800.
Blommers (1994), Biochemistry 33:7886-7896.
Blume (1997), Plant J. 12:731 746.
Botstein & Shortle (1985), Science 229:1193-1201.
Bowtell (1999), Nature Genetics Supp. 21:25-32.
Brindisi (2001), J. of Food Sci. 66:1100-1107.
Brown (1979), Meth. Enzymol. 68:109.
Burg (1996), Mol. Cell. Probes 10:257-271.
Busk (1997), Plant J. 11:1285 1295.
Caldwell, R. C. & Joyce G.F. (1992), PCR Methods Applic., 2:28-33.
Cardon (1997), *Plant J* 12:367-77.
Carter (1986), Biochem. J. 237:1-7.
Carter (1987), Methods in Enzymol. 154: 382-403.
Carter et al. (1985), Nucl. Acids Res. 13: 4431-4443.
Caruthers (1980), Nucleic Acids Res. Symp. Ser. 215-223.
Casper (1996), Gene 173:69-73.

Cecchini (1997), Mol. Plant Microbe Interact. 10:1094-1101.
Chang (1999), Nature Biotechnology 17:793-797.
Chen (1996), Plant J. 10: 955-966.
Chong (1997), Transgenic Res. 6:289-296.
Christians (1999), Nature Biotechnology 17:259-264.
Christou (1997), Plant Mol. Biol. 35:197-203.
Cole (1985), Monoclonal Antibodies and Cancer Therapy, Alan R. Liss, Inc., pp. 77-96.
Covey (1990), Proc. Natl. Acad. Sci. USA 87:1633-1637.
Crameri (1995), Biotechniques 18:194-196.
Crameri (1997), Nature Biotechnology 15:436-438.
Crameri (1998), Nature 391:288-291.
Crameri et al. (1996), Nature Medicine 2:100-103.
Dale et al. (1996), Methods Mol. Biol. 57:369-374.
De Veylder (1997), Plant Cell Physiol. 38:568-577).
Delegrave (1993), Biotechnology Res. 11:1548-1552.
DeLisle (1990), Int. Rev. Cytol. 123:39-60).
Dobeli (1998), Protein Expr. Purif. 12:404-414.
Dolja (1997), Virology 234:243-252.
Eghtedarzadeh (1986), Nucl. Acids Res. 14: 5115.
Feng (2000), Biochemistry 39:15399-15409.
Ficker (1997), Plant Mol. Biol. 35:425 431.
Fraley (1983), *Proc. Natl. Acad. Sci. USA* 80:4803 (1983).
Frenkel (1995), Free Radic. Biol. Med. 19:373-380.
Fritz et al. (1988), Nucl. Acids Res. 16: 6987-6999).
Gates et al. (1996), Journal of Molecular Biology 255:373-386.
Gold (1995), J. of Biol. Chem. 270:13581-13584.
Gonnet et al. (1992), Science 256:1443-1445.
Grundstrom et al. (1985), Nucl. Acids Res. 13: 3305-3316.
Guatelli (1990), Proc. Natl. Acad. Sci. USA 87:1874.
Guerrero (1990), Mol. Gen. Genet. 224:161 168.
Guerrier-Takada (1983), Cell 35:849.
Geysen et al. (1984), Proc. Natl. Acad. Sci., USA, 81:3998.
Hale (1998), Protein Expr. Purif. 12:185-188.
Hampel (1989), Biochemistry 28:4929.
Hampel (1990), Nuc. Acids Res. 18:299.
Henikoff & Henikoff (1992), Proc. Natl. Acad. Sci. USA 89:10915.
Henikoff and Henikoff (1993), Proteins 17:49-61.
Hiei (1997), Plant Mol. Biol. 35:205-218.
Higgins et al. (1996), Methods Enzymol. 266:383-402.
Hillman (1989), Virology 169:42-50.
Ho (2000), Methods Enzymol. 314:168-183.
Hoogenboom (1997), Trends Biotechnol. 15:62-70.
Horn (1980), Nucleic Acids Res. Symp. Ser. 225-232.
Horsch (1984), *Science* (1984),233:496-498.
Huang (1996), *Plant Mol. Biol.* 33:125-139.
Humphreys (2000), Protein Expr. Purif. 20:252-264.
Jaeger (1994), FEMS Microbiol. Rev. 15:29-63.
John (1997), Proc. Natl. Acad. Sci. USA 89:5769-5773.
Johnston (1998), Curr. Biol. 8:R171-R174.
Karlin & Altschul (1993), Proc. Natl. Acad. Sci. USA 90:5873.
Katz (1997), Annu. Rev. Biophys. Biomol. Struct. 26:27-45.
Kern (1997), Biotechniques 23:120-124.
Kirch (1997), Plant Mol. Biol. 33:897 909.
Klee (1987), Ann. Rev. of Plant Phys. 38:467-486.
Klein (1987), Nature 327:70-73.
Kohler (1975), Nature 256:495.
Kramer & Fritz (1987), Methods in Enzymol., 154:350-367.
Kramer (1984), Cell 38:879-887.
Kramer et al. (1984), Nucl. Acids Res. 12: 9441-9456.
Kramer et al. (1988), Nucl. Acids Res. 16: 7207.
Kroll (1993), DNA Cell. Biol., 12:441-53.
Kumagai (1995), Proc. Natl. Acad. Sci. USA 92:1679-1683.
Kunkel (1985), Proc. Natl. Acad. Sci. USA 82:488-492.
Kunkel et al. (1987), Methods in Enzymol. 154, 367-382.
Kunze (1996), Curr. Top. Microbiol. Immunol. 204:161-194.
Kwoh (1989), Proc. Natl. Acad. Sci. USA 86:1173.
Landegren (1988), Science 241:1077.
Leung, D. W., et al. (1989), Technique, 1:11-15.
Ling et al. (1997), Anal Biochem. 254(2): 157-178.
Liu (1997), Plant Physiol. 115:397-407.
Mandecki (1986), Proc. Natl. Acad. Sci. USA, 83:7177-7181.
Mandel (1995), Plant Molecular Biology, vol. 29, pp. 995-1004.

Manjunath (1997), *Plant Mol. Biol*. 33:97-112.
Martinez (1989), *J. Mol. Biol* 208:551-565).
Masgrau (1997), Plant J. 11:465-473.
Mata (1997), Toxicol Appl Pharmacol 144:189-197.
Merrifield, R. B. (1963), J. Am. Chem. Soc., 85:2149-2154.
Merrifield (1997), Methods Enzymol. 289:3-13.
Miao (1995), Plant J 7:359-365.
Minshull (1999), Current Opinion in Chemical Biology 3:284-290.
Moise et al., (2005), J. Biol. Chem. 280(3):27815-27825.
Morinaga (1993), Microbiol Immunol. 37:471-476.
Nakamaye (1986), Nucl. Acids Res. 14: 9679-9698.
Nambiar et al. (1984), Science 223: 1299-1301.
Narang (1979), Meth. Enzymol. 68:90.
Narum (2001), Infect. Immun. 69:7250-7253.
Needleman & Wunsch (1970), J. Mol. Biol. 48:443.
Nielsen, et al. (1997), Protein Engineering, vol. 10, No. 1, p. 1-6.
Outchkourov (2002), Protein Expr. Purif. 24:18-24.
Palmgren (1997), Trends Genet. 13:348.
Park (1996), Plant Mol. Biol. 32:1135-1148.
Patten et al. (1997), Current Opinion in Biotechnology 8:724-733.
Pawlowski (1996), Mol. Biotechnol. 6:17-30.
Pearson and Lipman (1988), Proc. Natl. Acad. Sci. USA 85(8):2444-2448.
Perrotta (1992), Biochemistry 31:16.
Pollock (1999), J. Immunol. Methods 231:147-157.
Porta (1996), Mol. Biotechnol. 5:209-221.
Reidhaar-Olson (1988), Science 241:53-57.
Reiser (1995), Cell 83:735-742.
Renard (1987), Lipids 22: 539-541.
Rice (1992), Proc. Natl. Acad. Sci. USA 89:5467-5471.
Roberge (1995), Science 269:202.
Rosenfeld (1997), Nat. Genet. 15:333-335.
Rossi (1992), Aids Research and Human Retroviruses 8:183.
Rouwendal (1997), Plant Mol. Biol. 33:989-999.
Rubin (1997), Mol. Cell. Biol. 17:6294-6302.
Sakai (1996), Plant Cell Phsyiol. 37:906-913.
Sakamar and Khorana (1988), Nucl. Acids Res. 14: 6361-6372.
Samstag (1996), Antisense Nucleic Acid Drug Dev 6:153-156.
Sayers et al. (1988), Nucl. Acids Res. 16: 803-814.
Sayers et al. (1988), Nucl. Acids Res. 16:791-802.
Schlappi (1996), Plant Mol. Biol. 32:717-725.
Schummer (1997), Biotechniques 23:1087-1092.
Sheen (1996), Science 274:1900-1902).
Shuey (2002), Drug Discov. Today 7:1040-1046.
Smith & Waterman (1981), Adv. Appl. Math. 2:482.
Smith (1985), Ann. Rev. Genet. 19:423-462.
Smith (1997), J. Clin. Microbiol. 35:1477-1491.
Smith (2000), Eur. J. Pharm. Sci. 11:191-198.
Solinas-Toldo (1997), Genes, Chromosomes & Cancer 20:399-407.
Solocombe (1994), *Plant Physiol*. 104:1167-1176.
Sooknanan (1995), Biotechnology 13:563-564.
Stange (1997), Plant J. 11:1315-1324).
Stemmer (1994), Proc. Natl. Acad. Sci. USA 91:10747-10751.
Stemmer (1994), Nature 370:389-391.
Stemmer (1995), Bio/Technology 13:549-553.
Stemmer (1995), Science 270: 1510.
Stemmer (1996), The Encyclopedia of Molecular Biology. VCH Publishers, New York. pp. 447-457.
Stemmer et al. (1999), Nature Biotechnology 17:893-896.
Stemmer et al. (1995), Gene, 164:49-53.
Stewart et al. (1984), Solid Phase Peptide Synthesis, 2nd Ed., Pierce Chemical Co., Rockford, Ill., pp. 11-12.
Strauss-Soukup (1997), Biochemistry 36:8692-8698.
Streit (1997), Mol. Plant Microbe Interact. 10:933-937.
Strepp (1998), Proc Natl. Acad. Sci. USA 95:4368-4373.
Takumi (1997), Genes Genet. Syst. 72:63-69.
Taylor et al. (1985), Nucl. Acids Res. 13: 8749-8764.
Taylor et al. (1985), Nucl. Acids Res. 13: 8765-8787 (1985).
Thompson et al. (1994), Nucleic Acids Res. 22(2):4673-4680.
Thykjaer et al. (1997), Plant Molecular Biology 35:523-530.
Van de Ven (1993), Crit. Rev. Oncog. 4(2):115-136.
Verdaguer (1996), Plant Mol. Biol. 31:1129-1139.
Vorderwülbecke (1992), Enzyme Microb. Technol. 14:631-639.

Ward et al., (1989), Nature 341:544-546.
Weising (1988), Ann. Rev. Genet. 22:421-477.
Wells et al. (1985), Gene 34:315-323.
Wells et al. (1986), Phil. Trans. R. Soc. Lond. A 317: 415-423.
Williams (1995), Biochemistry 34:1787-1797.
Wilson (1994), J. Immunol. Methods 175:267-273.

Woon (1998), Genomics 50:306-316.
Wu (1989), Genomics 4:560.
Zoller et al. (1983), Methods in Enzymol. 100: 468-500.
Zoller et al. (1987), Methods in Enzymol. 154: 329-350.

* cited by examiner

Figure 7

```
MLKPPPYGRL LRELADIPAI VTAPFRGAAK MGKLADGEPV LVLPGFLADD
                   20L

NATSVLRKTF DVAGFACSGW ERGFNLGIRG DLVDRLVDRL RAVSEAAGGQ
           61A,E     72E,K           77P   83C  88H
                  62S
                  113G

KVIVVGWSLG GLYARELGHK APELIRMVVT LGSPFAGDLH ANHAWKIYEA
              116A,Q,R,T,V;G,T         133A        140K      146S 167S
151G,A   163R
INSHTVDNLP IPVDFQIKPP VRTIAVWSPL DGVVAPETSE GSPEQSDERL
          164R                              180E         194M 212Y
         211Q   218H,S  225M,Q
ELAVTHMGFA ASKTGAEAVV RLVAARL-                (SEQ ID NO:2)
          215C,V,W 223A
```

Figure 8-1

| Amino Acid - residue position number and amino acid in that position | | | | | | | | Secondary Screen | | | | | | | | | | | | |
|---|---|---|---|---|---|---|---|---|---|---|---|---|---|---|---|---|---|---|---|---|
| | | | | | | | Other amino | Percentage Released FAs | | | | | | Amount Released FAs (ug) | | | | | | |
| 61 | 72 | 116 | 133 | 151 | 163 | 164 | acid changes | Linolenic | Linoleic | Oleic | Palmitic | Stearic | Linolenic | Linoleic | Oleic | Palmitic | Stearic | Total FA |
| E | K | V | A | A | R | | | 0.0% | 1.1% | 0.0% | 98.9% | 0.0% | 0.00 | 0.04 | 0.00 | 4.03 | 0.00 | 4.07 |
| E | K | V | A | A | | | | 0.0% | 2.7% | 2.9% | 94.4% | 0.0% | 0.00 | 0.19 | 0.20 | 6.70 | 0.00 | 7.10 |
| E | K | V | A | | | R | | High | High | Low | High | High | No Peak | No Peak | 0.00 | No Peak | No Peak | High |
| E | K | V | | G | R | | | Low | Low | Low | Low | Low | 0.00 | 0.00 | 0.00 | 0.00 | 0.00 | 0.00 |
| E | K | V | | A | | | | Low | Low | Low | Low | Low | 0.00 | 0.00 | 0.00 | 0.00 | 0.00 | 0.00 |
| E | K | V | | | R | | | 0.3% | 5.0% | 3.5% | 91.2% | 0.0% | 0.03 | 0.55 | 0.38 | 10.00 | 0.00 | 10.96 |
| E | K | V | | | | | | 0.0% | 0.0% | 0.0% | 99.9% | 0.1% | 0.00 | 0.00 | 0.00 | 2.86 | 0.00 | 2.86 |
| E | K | V | | | | R | | 0.0% | 1.0% | 0.0% | 99.0% | 0.0% | 0.00 | 0.06 | 0.00 | 5.52 | 0.00 | 5.58 |
| E | K | V | | | | | | 0.0% | 3.1% | 0.0% | 96.9% | 0.0% | 0.00 | 0.21 | 0.00 | 6.50 | 0.00 | 6.71 |
| E | K | T | | A | R | | | 0.0% | 0.0% | 0.0% | 100.0% | 0.0% | 0.00 | 0.00 | 0.00 | 5.53 | 0.00 | 5.53 |
| E | K | T | | A | R | | | Low | Low | Low | Low | Low | Low | Low | Low | Low | Low | Low |
| E | K | T | | A | R | | | Low | Low | Low | Low | Low | Low | Low | Low | Low | Low | Low |
| E | K | Q | | A | R | | | 4.0% | 7.8% | 5.4% | 82.5% | 0.3% | 0.50 | 0.15 | 0.23 | 6.88 | 0.08 | 7.83 |
| E | K | Q | | A | R | | | 4.5% | 9.4% | 5.6% | 80.5% | 0.0% | 0.56 | 0.18 | 0.24 | 6.71 | 0.00 | 7.69 |
| E | K | Q | | A | R | | | 11.0% | 38.5% | 34.4% | High | 16.1% | 1.38 | 0.73 | 1.49 | High | 4.03 | High |
| E | K | Q | | A | R | | | 4.2% | 8.6% | 6.4% | 80.2% | 0.7% | 0.52 | 0.16 | 0.28 | 6.68 | 0.17 | 7.81 |
| E | K | A | A | A | R | | | 0.0% | 1.7% | 3.7% | 98.3% | 0.0% | 0.00 | 0.11 | 0.00 | 6.47 | 0.00 | 6.58 |
| E | K | A | A | A | R | | | 0.0% | 3.7% | 0.0% | 96.3% | 0.0% | 0.00 | 0.30 | 0.00 | 7.80 | 0.00 | 8.10 |
| E | K | A | A | A | R | | | 0.9% | 4.1% | 6.7% | 88.0% | 0.4% | 0.09 | 0.43 | 0.70 | 9.26 | 0.04 | 10.52 |
| E | K | A | A | G | | | | 0.0% | 0.0% | 0.0% | 100.0% | 0.0% | 0.00 | 0.00 | 0.00 | 0.94 | 0.00 | 0.94 |
| E | K | A | A | A | | | | 0.0% | 0.0% | 0.0% | 100.0% | 0.0% | 0.00 | 0.00 | 0.00 | 0.97 | 0.00 | 0.97 |
| E | K | A | A | | | R | | 0.0% | 2.6% | 4.3% | 93.1% | 0.5% | 0.00 | 0.15 | 0.26 | 5.56 | 0.00 | 5.97 |
| E | K | A | A | | | R | | 0.0% | 2.2% | 5.0% | 92.4% | 0.4% | 0.00 | 0.19 | 0.44 | 8.20 | 0.04 | 8.88 |
| E | K | A | A | | | R | | 0.0% | 3.0% | 4.7% | 91.9% | 0.4% | 0.00 | 0.19 | 0.30 | 5.79 | 0.03 | 6.30 |
| E | K | A | A | | | R | | 1.0% | 5.2% | 6.4% | 87.2% | 0.3% | 0.08 | 0.41 | 0.51 | 6.97 | 0.02 | 8.00 |
| E | K | A | A | | | | | 0.0% | 6.2% | 0.0% | 93.8% | 0.0% | 0.00 | 0.36 | 0.00 | 5.44 | 0.00 | 5.80 |
| E | K | A | | G | | R | S18G,K12M | Low | Low | Low | Low | Low | 0.00 | 0.00 | 0.00 | 0.00 | 0.00 | 0.00 |
| E | K | A | A | A | R | | L86M | 5.2% | 14.1% | 8.1% | 72.6% | 0.0% | 0.66 | 0.27 | 0.35 | 6.05 | 0.00 | 7.32 |

Figure 8-2

| Amino Acid - residue position number and amino acid in that position | | | | | | | | Secondary Screen | | | | | | | | | | |
|---|---|---|---|---|---|---|---|---|---|---|---|---|---|---|---|---|---|---|
| | | | | | | | | Percentage Released FAs | | | | | Amount Released FAs (ug) | | | | | |
| 61 | 72 | 116 | 133 | 151 | 163 | 164 | Other amino acid changes | Linolenic | Linoleic | Oleic | Palmitic | Stearic | Linolenic | Linoleic | Oleic | Palmitic | Stearic | Total FA |
| E | K | | A | A | R | | L86M | 0.0% | 10.3% | 5.6% | 84.1% | 0.0% | 0.00 | 0.19 | 0.24 | 7.01 | 0.00 | 7.45 |
| E | K | | A | A | | | | Low | Low | Low | Low | Low | 0.00 | 0.00 | 0.00 | 0.00 | 0.00 | 0.00 |
| E | K | | A | A | | | K12M | Low | Low | Low | Low | Low | Low | Low | Low | Low | Low | Low |
| E | K | | A | A | | | K12M | Low | Low | Low | Low | Low | Low | Low | Low | Low | Low | Low |
| E | K | | A | A | | | W17L | Low | Low | Low | Low | Low | Low | Low | Low | Low | Low | Low |
| E | K | | A | A | | R | | Low | Low | Low | Low | Low | Low | Low | Low | Low | Low | Low |
| E | K | | A | A | | R | | Low | Low | Low | Low | Low | Low | Low | Low | Low | Low | Low |
| E | K | | A | A | R | | | 0.6% | 3.7% | 3.7% | 91.9% | 0.0% | 0.09 | 0.55 | 0.55 | 13.50 | 0.00 | 14.68 |
| E | E | V | A | A | | | | 0.0% | 0.0% | 0.0% | 100.0% | 0.0% | 0.00 | 0.00 | 0.00 | 0.60 | 0.00 | 0.60 |
| E | E | V | A | A | | | | 0.0% | 0.0% | 0.0% | 100.0% | 0.0% | 0.00 | 0.00 | 0.00 | 1.30 | 0.00 | 1.30 |
| E | E | V | A | | R | | | 0.0% | 3.8% | 3.0% | 93.2% | 0.0% | 0.00 | 0.31 | 0.24 | 7.53 | 0.00 | 8.08 |
| E | E | V | A | | | | | 0.0% | 0.0% | 0.0% | 100.0% | 0.0% | 0.00 | 0.00 | 0.00 | 2.17 | 0.00 | 2.17 |
| E | E | V | A | | | | A52S | Low | Low | Low | Low | Low | 0.00 | 0.00 | 0.00 | 0.00 | 0.00 | 0.00 |
| E | E | V | A | | | R | A52S | 0.0% | 0.0% | 0.0% | 100.0% | 0.0% | 0.00 | 0.00 | 0.00 | 4.73 | 0.00 | 4.73 |
| E | E | V | A | | | | | 0.0% | 8.0% | 8.0% | 83.9% | 0.0% | 0.00 | 0.64 | 0.64 | 6.68 | 0.00 | 7.96 |
| E | E | V | A | | | R | | 0.0% | 1.9% | 4.0% | 94.1% | 0.0% | 0.00 | 0.08 | 0.18 | 4.17 | 0.00 | 4.43 |
| E | E | V | | | G | | | Low | Low | Low | Low | Low | 0.00 | 0.00 | 0.00 | 0.00 | 0.00 | 0.00 |
| E | E | V | A | | | | | 1.3% | 7.4% | 4.9% | 86.4% | 0.0% | 0.16 | 0.85 | 0.56 | 9.92 | 0.00 | 11.48 |
| E | E | V | | | R | | | 0.0% | 0.0% | 0.0% | 100.0% | 0.0% | 0.00 | 0.00 | 0.00 | 2.31 | 0.00 | 2.31 |
| E | E | V | A | | G | | | 0.0% | 0.0% | 0.0% | 100.0% | 0.0% | 0.00 | 0.00 | 0.00 | 2.23 | 0.00 | 2.23 |
| E | E | V | | | A | | | 6.0% | 0.0% | 0.0% | 94.0% | 0.0% | 0.17 | 0.00 | 0.00 | 2.61 | 0.00 | 2.78 |
| E | E | V | A | | A | | | 0.0% | 0.0% | 0.0% | 100.0% | 0.0% | 0.00 | 0.00 | 0.00 | 0.90 | 0.00 | 0.90 |
| E | E | V | A | | A | | | 0.0% | 0.0% | 0.0% | 100.0% | 0.0% | 0.00 | 0.00 | 0.00 | 2.43 | 0.00 | 2.43 |
| E | E | V | A | | R | | | 0.0% | 0.0% | 0.0% | 100.0% | 0.0% | 0.00 | 0.00 | 0.00 | 4.89 | 0.00 | 4.89 |
| E | E | V | A | | R | | | 1.7% | 3.3% | 0.0% | 98.3% | 0.0% | 0.05 | 0.17 | 0.00 | 2.59 | 0.00 | 2.64 |
| E | E | V | A | | | R | | 0.0% | 0.0% | 0.0% | 96.7% | 0.0% | 0.00 | 0.00 | 0.00 | 4.91 | 0.00 | 5.08 |
| E | T | | A | | R | | | 0.0% | 0.0% | 0.0% | 100.0% | 0.0% | 0.00 | 0.00 | 0.00 | 8.01 | 0.00 | 8.01 |
| E | Q | A | G | | | | | 5.9% | 11.7% | 11.6% | 67.2% | 3.6% | 0.73 | 0.22 | 0.50 | 5.60 | 0.91 | 7.97 |

Figure 8-3

| Amino Acid - residue position number and amino acid in that position | | | | | | | Percentage Released FAs | | | | | Secondary Screen Amount Released FAs (ug) | | | | | |
|---|---|---|---|---|---|---|---|---|---|---|---|---|---|---|---|---|---|
| 61 | 72 | 116 | 133 | 151 | 163 | 164 | Other amino acid changes | Linolenic | Linoleic | Oleic | Palmitic | Stearic | Linolenic | Linoleic | Oleic | Palmitic | Stearic | Total FA |
| E | E | Q | A | G | | | | 4.1% | 12.6% | 11.7% | 68.1% | 3.5% | 0.52 | 0.24 | 0.51 | 5.67 | 0.88 | 7.82 |
| E | E | A | A | G | | | | 0.0% | 13.5% | 23.3% | 63.2% | 0.0% | 0.00 | 0.11 | 0.20 | 0.53 | 0.00 | 0.84 |
| E | E | A | A | G | | | | 2.6% | 0.0% | 0.0% | 97.4% | 0.0% | 0.04 | 0.00 | 0.00 | 1.57 | 0.00 | 1.61 |
| E | E | A | A | A | R | | | 0.0% | 0.0% | 0.0% | 100.0% | 0.0% | 0.00 | 0.00 | 0.00 | 1.99 | 0.00 | 1.99 |
| E | E | A | A | A | R | | | 0.0% | 1.0% | 2.3% | 96.3% | 0.5% | 0.00 | 0.06 | 0.15 | 6.27 | 0.03 | 6.51 |
| E | E | A | A | A | | | | 0.0% | 4.9% | 2.8% | 92.2% | 0.0% | 0.00 | 0.14 | 0.08 | 2.53 | 0.00 | 2.74 |
| E | E | A | A | | R | | | 2.2% | 7.6% | 6.8% | 83.4% | 0.0% | 0.28 | 0.99 | 0.87 | 10.80 | 0.00 | 12.95 |
| E | E | A | A | | | | | 0.0% | 2.3% | 3.4% | 94.3% | 0.0% | 0.00 | 0.13 | 0.19 | 5.36 | 0.00 | 5.68 |
| E | E | A | A | | | | | 1.9% | 4.1% | 6.3% | 87.1% | 0.5% | 0.13 | 0.27 | 0.42 | 5.78 | 0.03 | 6.63 |
| E | E | A | | | | | | 0.0% | 2.9% | 0.0% | 97.1% | 0.0% | 0.00 | 0.12 | 0.00 | 4.07 | 0.00 | 4.19 |
| E | E | A | | A | | R | | 0.0% | 0.0% | 0.0% | 100.0% | 0.0% | 0.00 | 0.00 | 0.00 | 0.93 | 0.00 | 0.93 |
| E | E | A | | A | | R | | 1.6% | 5.8% | 5.4% | 86.3% | 0.9% | 0.20 | 0.73 | 0.69 | 10.90 | 0.12 | 12.63 |
| E | E | A | | A | | R | | 1.3% | 4.7% | 4.7% | 88.1% | 1.2% | 0.11 | 0.39 | 0.40 | 7.37 | 0.10 | 8.37 |
| E | E | | | | R | | | 1.7% | 5.1% | 6.4% | 85.8% | 1.0% | 0.18 | 0.56 | 0.70 | 9.32 | 0.11 | 10.86 |
| E | E | A | | | R | | | 0.0% | 2.9% | 0.0% | 97.1% | 0.0% | 0.00 | 0.17 | 0.00 | 5.79 | 0.00 | 5.96 |
| E | E | A | | A | R | | | 0.0% | 2.8% | 0.0% | 97.2% | 0.0% | 0.00 | 0.23 | 0.00 | 8.19 | 0.00 | 8.42 |
| E | E | | A | | | | | 0.0% | 0.0% | 0.0% | 100.0% | 0.0% | 0.00 | 0.00 | 0.00 | 0.18 | 0.00 | 0.18 |
| E | E | | A | G | | | | 6.6% | 7.6% | 8.5% | 77.1% | 0.2% | 0.35 | 0.40 | 0.45 | 4.06 | 0.01 | 5.27 |
| E | E | | A | G | R | | | 0.0% | 0.0% | 0.0% | 100.0% | 0.0% | 0.00 | 0.00 | 0.00 | 5.53 | 0.00 | 5.53 |
| E | E | | A | A | R | | P18S,A21V | 0.0% | 0.0% | 0.0% | 100.0% | 0.0% | 0.00 | 0.00 | 0.00 | 0.10 | 0.00 | 0.10 |
| E | E | | A | A | R | | | 2.5% | 9.4% | 7.2% | 78.0% | 3.0% | 0.31 | 0.18 | 0.31 | 6.50 | 0.75 | 8.04 |
| E | E | | A | A | R | | | 5.8% | 14.4% | 8.2% | 71.6% | 0.0% | 0.73 | 0.27 | 0.35 | 5.97 | 0.00 | 7.32 |
| E | E | | A | A | R | | | 4.5% | 11.9% | 8.6% | 73.5% | 1.6% | 0.56 | 0.22 | 0.37 | 6.12 | 0.39 | 7.67 |
| E | E | | A | A | R | | K12M | 4.4% | 10.4% | 5.8% | 79.4% | 0.0% | 0.55 | 0.20 | 0.25 | 6.62 | 0.00 | 7.62 |
| E | E | | A | | R | | K12M | 4.4% | 10.2% | 7.0% | 76.7% | 1.7% | 0.55 | 0.19 | 0.31 | 6.39 | 0.43 | 7.87 |
| E | E | | A | | R | | | 4.8% | 8.6% | 7.0% | 79.5% | 0.1% | 0.60 | 0.16 | 0.30 | 6.63 | 0.01 | 7.71 |
| E | E | | | | R | | | Low | Low | Low | Low | Low | 0.00 | 0.00 | 0.00 | 0.00 | 0.00 | 0.00 |
| E | E | | | G | | R | | 2.7% | 7.8% | 10.2% | 79.2% | 0.0% | 0.47 | 1.35 | 1.77 | 13.70 | 0.00 | 17.29 |
| E | E | | | A | R | | | 0.0% | 0.0% | 0.0% | 100.0% | 0.0% | 0.00 | 0.00 | 0.00 | 3.61 | 0.00 | 3.61 |

Figure 8-4

| Amino Acid - residue position number and amino acid in that position | | | | | | | | Other amino acid changes | Secondary Screen | | | | | | | | | | | | |
|---|---|---|---|---|---|---|---|---|---|---|---|---|---|---|---|---|---|---|---|---|---|
| | | | | | | | | | Percentage Released FAs | | | | | Amount Released FAs (ug) | | | | | | | |
| 61 | 72 | 116 | 133 | 151 | 163 | 164 | | | Linolenic | Linoleic | Oleic | Palmitic | Stearic | Linolenic | Linoleic | Oleic | Palmitic | Stearic | Total FA |
| E | E | | | G | R | | F65V | | Low | Low | Low | Low | Low | Low | Low | Low | Low | Low | Low |
| E | E | | | G | R | | F65V | | Low | Low | Low | Low | Low | Low | Low | Low | Low | Low |
| E | | | | G | R | | | | Low | Low | Low | Low | Low | 0.00 | 0.00 | 0.00 | 0.00 | 0.00 | 0.00 |
| E | | V | A | G | | | | | Low | Low | Low | Low | Low | 0.00 | 0.00 | 0.00 | 0.00 | 0.00 | 0.00 |
| E | | V | A | A | R | | | | 0.0% | 0.0% | 0.0% | 100.0% | 0.0% | 0.00 | 0.00 | 0.00 | 5.31 | 0.00 | 5.31 |
| E | | V | A | A | R | | | | 0.0% | 0.5% | 1.1% | 97.3% | 1.1% | 0.00 | 0.04 | 0.10 | 8.81 | 0.10 | 9.05 |
| E | | V | A | A | R | | | | 0.0% | 0.0% | 0.0% | 100.0% | 0.0% | 0.00 | 0.00 | 0.00 | 2.51 | 0.00 | 2.51 |
| E | | V | A | A | R | | | | 0.0% | 0.0% | 0.0% | 100.0% | 0.0% | 0.00 | 0.00 | 0.00 | 1.71 | 0.00 | 1.71 |
| E | | V | A | A | | | | | 0.0% | 0.0% | 0.0% | 100.0% | 0.0% | 0.00 | 0.00 | 0.00 | 1.68 | 0.00 | 1.68 |
| E | | V | A | | R | | | | 0.0% | 2.9% | 2.4% | 94.6% | 0.0% | 0.00 | 0.24 | 0.20 | 7.83 | 0.00 | 8.27 |
| E | | V | A | | R | | | | 0.0% | 0.0% | 0.8% | 99.2% | 0.0% | 0.00 | 0.00 | 0.06 | 7.62 | 0.00 | 7.68 |
| E | | V | A | | R | | | | 1.7% | 5.7% | 5.4% | 87.3% | 0.0% | 0.19 | 0.62 | 0.60 | 9.63 | 0.00 | 11.04 |
| E | | V | A | | | | | | 0.4% | 3.6% | 0.0% | 95.8% | 0.2% | 0.03 | 0.25 | 0.00 | 6.52 | 0.01 | 6.80 |
| E | | V | | A | R | | | | 0.4% | 3.4% | 3.2% | 92.5% | 0.5% | 0.05 | 0.42 | 0.40 | 11.40 | 0.06 | 12.33 |
| E | | V | | | R | | | | 1.7% | 5.8% | 6.3% | 86.2% | 0.0% | 0.20 | 0.66 | 0.72 | 9.82 | 0.00 | 11.40 |
| E | | V | | | | R | | | 0.0% | 0.4% | 2.7% | 96.9% | 0.0% | 0.00 | 0.03 | 0.17 | 6.01 | 0.00 | 6.20 |
| E | | Q | | | | | | | 2.7% | 7.7% | 10.9% | 77.5% | 1.2% | 0.75 | 2.16 | 3.08 | 21.80 | 0.34 | 28.13 |
| E | | Q | A | | | R | | | 5.4% | 12.0% | 15.2% | 66.1% | 1.3% | 1.07 | 2.37 | 2.99 | 13.00 | 0.25 | 19.68 |
| E | | Q | | A | R | | | | 1.9% | 4.1% | 4.6% | 88.9% | 0.5% | 0.31 | 0.68 | 0.75 | 14.60 | 0.08 | 16.42 |
| E | | A | A | G | R | | | | Low | Low | Low | Low | Low | 0.00 | 0.00 | 0.00 | 0.00 | 0.00 | 0.00 |
| E | | A | A | A | | | | | 0.4% | 0.0% | 0.0% | 99.6% | 0.0% | 0.00 | 0.00 | 0.00 | 0.73 | 0.00 | 0.73 |
| E | | A | A | A | R | | | | 2.6% | 6.4% | 8.5% | 81.5% | 1.0% | 0.19 | 0.45 | 0.59 | 5.71 | 0.07 | 7.01 |
| E | | A | | A | R | | | | Low | Low | Low | Low | Low | 0.00 | 0.00 | 0.00 | 0.00 | 0.00 | 0.00 |
| E | | A | | A | R | | | | 0.0% | 0.0% | 0.0% | 100.0% | 0.0% | 0.00 | 0.00 | 0.00 | 2.07 | 0.00 | 2.07 |
| E | | A | | A | | | | | 0.0% | 0.0% | 2.2% | 97.8% | 0.0% | 0.00 | 0.00 | 0.07 | 2.93 | 0.00 | 3.00 |
| E | | A | | A | | | | | 0.0% | 3.6% | 0.0% | 96.4% | 0.0% | 0.00 | 0.14 | 0.00 | 3.64 | 0.00 | 3.78 |
| E | | A | | | R | | G132V | | 0.1% | 0.0% | 0.0% | 99.9% | 0.0% | 0.00 | 0.00 | 0.00 | 1.99 | 0.00 | 1.99 |
| E | | A | | | | R | | | 3.3% | 2.5% | 6.3% | 87.9% | 0.0% | 0.15 | 0.11 | 0.28 | 3.89 | 0.00 | 4.43 |
| E | | | | G | R | | K12M | | Low | Low | Low | Low | Low | 0.00 | 0.00 | 0.00 | 0.00 | 0.00 | 0.00 |

Figure 8-5

| Amino Acid - residue position number and amino acid in that position | | | | | | | | Secondary Screen | | | | | | | | | | | |
|---|---|---|---|---|---|---|---|---|---|---|---|---|---|---|---|---|---|---|---|
| | | | | | | | | Percentage Released FAs | | | | | Amount Relased FAs (ug) | | | | | |
| 61 | 72 | 116 | 133 | 151 | 163 | 164 | Other amino acid changes | Linolenic | Linoleic | Oleic | Palmitic | Stearic | Linolenic | Linoleic | Oleic | Palmitic | Stearic | Total FA |
| E | | | | | | | K12M | 0.0% | 0.0% | 0.0% | 100.0% | 0.0% | 0.00 | 0.00 | 0.00 | 0.04 | 0.00 | 0.04 |
| E | | | | G | | R | A15S | 4.1% | 10.5% | 14.4% | 70.2% | 0.8% | 0.43 | 1.11 | 1.52 | 7.41 | 0.08 | 10.55 |
| E | | | A | A | R | | | 0.0% | 0.0% | 0.0% | 100.0% | 0.0% | 0.00 | 0.00 | 0.00 | 0.29 | 0.00 | 0.29 |
| E | | Q | | | R | | | 5.1% | 9.7% | 7.0% | 77.6% | 0.6% | 0.63 | 0.18 | 0.30 | 6.46 | 0.16 | 7.74 |
| E | | Q | | | | | | 5.4% | 8.4% | 7.6% | 78.6% | 0.0% | 0.68 | 0.16 | 0.33 | 6.55 | 0.00 | 7.71 |
| E | | Q | A | | | R | | 4.2% | 14.2% | 12.1% | 62.6% | 7.0% | 0.52 | 0.27 | 0.53 | 5.21 | 1.75 | 8.28 |
| E | | Q | A | G | | R | | 7.9% | 12.0% | 13.7% | 65.5% | 0.9% | 0.98 | 0.23 | 0.60 | 5.46 | 0.21 | 7.48 |
| E | | | | | R | | | Low | Low | Low | Low | Low | Low | Low | Low | Low | Low | Low |
| E | | | | | R | | | Low | Low | Low | Low | Low | Low | Low | Low | Low | Low | Low |
| E | | | A | | | R | | 4.9% | 11.3% | 8.3% | 73.9% | 1.7% | 0.62 | 0.21 | 0.36 | 6.16 | 0.41 | 7.76 |
| E | | | A | | R | | | 4.6% | 10.2% | 8.1% | 77.1% | 0.0% | 0.57 | 0.19 | 0.35 | 6.42 | 0.00 | 7.54 |
| E | | | A | | | | | 3.3% | 8.5% | 6.9% | 77.8% | 3.5% | 0.42 | 0.16 | 0.30 | 6.49 | 0.87 | 8.23 |
| E | | | A | | R | R | | 5.0% | 8.6% | 7.8% | 76.2% | 2.4% | 0.63 | 0.16 | 0.34 | 6.35 | 0.60 | 8.08 |
| A | V | | A | | R | | | 0.0% | 0.0% | 0.0% | 100.0% | 0.0% | 0.00 | 0.00 | 0.00 | 6.48 | 0.00 | 6.48 |
| A | K | V | A | A | | | | 1.1% | 3.0% | 2.4% | 93.5% | 0.0% | 0.12 | 0.33 | 0.25 | 10.00 | 0.00 | 10.70 |
| A | K | V | A | A | | | | 0.0% | 0.0% | 0.0% | 100.0% | 0.0% | 0.00 | 0.00 | 0.00 | 2.75 | 0.00 | 2.75 |
| A | K | V | A | A | | | | 0.0% | 0.0% | 0.0% | 100.0% | 0.0% | 0.00 | 0.00 | 0.00 | 3.20 | 0.00 | 3.20 |
| A | K | V | A | A | | | | 0.0% | 0.6% | 0.0% | 99.4% | 0.0% | 0.00 | 0.02 | 0.00 | 3.55 | 0.00 | 3.57 |
| A | K | V | A | | | | | 0.0% | 0.0% | 0.0% | 100.0% | 0.0% | 0.00 | 0.00 | 0.00 | 2.92 | 0.00 | 2.92 |
| A | K | V | A | A | | | | 0.9% | 3.6% | 0.0% | 95.5% | 0.0% | 0.05 | 0.19 | 0.00 | 4.88 | 0.00 | 5.11 |
| A | K | V | | A | R | | | 0.0% | 0.0% | 0.0% | 100.0% | 0.0% | 0.00 | 0.00 | 0.00 | 4.32 | 0.00 | 4.32 |
| A | K | V | | A | | | | 0.0% | 0.0% | 0.0% | 100.0% | 0.0% | 0.00 | 0.00 | 0.00 | 2.16 | 0.00 | 2.16 |
| A | K | V | | | | R | | 0.0% | 0.0% | 0.8% | 99.2% | 0.0% | 0.00 | 0.00 | 0.06 | 7.36 | 0.00 | 7.42 |
| A | K | V | | | | | | 0.0% | 0.0% | 0.0% | 100.0% | 0.0% | 0.00 | 0.00 | 0.00 | 2.85 | 0.00 | 2.85 |
| A | K | V | | | | R | | 0.0% | 0.0% | 0.0% | 100.0% | 0.1% | 0.00 | 0.00 | 0.00 | 4.81 | 0.01 | 4.81 |
| A | K | V | | | | | | 2.3% | 8.0% | 8.5% | 81.1% | 0.0% | 0.23 | 0.79 | 0.84 | 8.01 | 0.00 | 9.87 |
| A | K | T | A | | | | | 6.7% | 10.5% | 9.2% | 73.6% | 0.0% | 0.84 | 0.20 | 0.40 | 6.13 | 0.00 | 7.57 |
| A | K | T | A | A | | | | 7.1% | 9.6% | 7.9% | 75.4% | 0.0% | 0.89 | 0.18 | 0.34 | 6.28 | 0.00 | 7.70 |
| A | K | T | A | | R | | | 5.1% | 8.3% | 6.0% | 79.2% | 1.4% | 0.63 | 0.16 | 0.26 | 6.60 | 0.36 | 8.01 |

Figure 8-6

| Amino Acid - residue position number and amino acid in that position ||||||||| Secondary Screen ||||||||||||
|---|---|---|---|---|---|---|---|---|---|---|---|---|---|---|---|---|---|---|
| | | | | | | | | Other amino | Percentage Released FAs ||||| Amount Released FAs (ug) |||||| |
| 61 | 72 | 116 | 133 | 151 | 163 | 164 | acid changes | Linolenic | Linoleic | Oleic | Palmitic | Stearic | Linolenic | Linoleic | Oleic | Palmitic | Stearic | Total FA |
| A | K | T | A | | R | | | 4.8% | 6.2% | 5.3% | 83.7% | 0.0% | 0.60 | 0.12 | 0.23 | 6.97 | 0.00 | 7.92 |
| A | K | Q | A | G | | | A48S | Low | Low | Low | Low | Low | 0.00 | 0.00 | 0.00 | 0.00 | 0.00 | 0.00 |
| A | K | Q | A | G | R | | | 3.8% | 9.0% | 5.8% | 79.9% | 1.5% | 0.48 | 0.17 | 0.25 | 6.66 | 0.37 | 7.93 |
| A | K | Q | A | G | R | | | 0.0% | 7.5% | 5.8% | 86.7% | 0.0% | 0.00 | 0.14 | 0.25 | 7.23 | 0.00 | 7.62 |
| A | K | A | | | R | | | 1.4% | 5.9% | 5.2% | 87.4% | 0.0% | 0.27 | 1.12 | 1.00 | 16.60 | 0.00 | 18.98 |
| A | K | A | A | | R | | | 1.9% | 5.5% | 5.0% | 87.6% | 0.0% | 0.30 | 0.84 | 0.77 | 13.40 | 0.00 | 15.31 |
| A | K | A | | | R | | | 0.0% | 0.2% | 0.4% | 99.5% | 0.0% | 0.00 | 0.01 | 0.02 | 6.25 | 0.00 | 6.28 |
| A | K | A | | A | R | | | 0.0% | 3.2% | 0.0% | 96.8% | 0.0% | 0.00 | 0.17 | 0.00 | 4.95 | 0.00 | 5.12 |
| A | K | A | | A | | | | Low | Low | Low | Low | Low | 0.00 | 0.00 | 0.00 | 0.00 | 0.00 | 0.00 |
| A | K | A | | | R | | | 2.2% | 2.3% | 1.8% | 93.7% | 0.0% | 0.15 | 0.16 | 0.12 | 6.37 | 0.00 | 6.80 |
| A | K | | | | | | | 0.0% | 3.1% | 3.0% | 93.3% | 0.6% | 0.00 | 0.21 | 0.21 | 6.50 | 0.04 | 6.96 |
| A | K | | | G | R | | | 5.8% | 11.8% | 10.4% | 69.2% | 2.8% | 0.72 | 0.22 | 0.45 | 5.77 | 0.71 | 7.87 |
| A | K | | | G | R | | | 7.7% | 11.6% | 11.5% | 68.2% | 1.0% | 0.97 | 0.22 | 0.50 | 5.68 | 0.24 | 7.61 |
| A | K | | A | A | R | | | 5.4% | 13.0% | 8.0% | 73.7% | 0.0% | 0.67 | 0.25 | 0.35 | 6.14 | 0.00 | 7.40 |
| A | K | | A | A | R | | | 4.2% | 10.3% | 7.3% | 78.3% | 0.0% | 0.52 | 0.19 | 0.32 | 6.52 | 0.00 | 7.55 |
| A | K | | A | A | R | | A48S | 5.0% | 12.2% | 7.5% | 75.3% | 0.0% | 0.62 | 0.23 | 0.33 | 6.28 | 0.00 | 7.45 |
| A | K | | A | | R | | A48S | 0.0% | 13.8% | 0.0% | 86.2% | 0.0% | 0.00 | 0.26 | 0.00 | 7.19 | 0.00 | 7.45 |
| A | K | | A | | R | | | 4.4% | 7.9% | 6.4% | 80.3% | 1.0% | 0.55 | 0.15 | 0.28 | 6.69 | 0.25 | 7.92 |
| A | K | | A | | R | | | 5.3% | 10.9% | 7.6% | 76.2% | 0.0% | 0.67 | 0.21 | 0.33 | 6.35 | 0.00 | 7.55 |
| A | K | | | A | | | | Low | Low | Low | Low | Low | 0.00 | 0.00 | 0.00 | 0.00 | 0.00 | 0.00 |
| A | K | | | | R | | K12M | Low | Low | Low | Low | Low | 0.00 | 0.00 | 0.00 | 0.00 | 0.00 | 0.00 |
| A | K | | | | | | | 3.6% | 8.9% | 8.9% | 78.6% | 0.0% | 0.77 | 1.91 | 1.92 | 16.90 | 0.00 | 21.50 |
| A | K | | A | A | R | | | 6.0% | 9.8% | 7.5% | 76.0% | 0.7% | 0.75 | 0.19 | 0.33 | 6.33 | 0.18 | 7.77 |
| A | K | | A | A | R | | | 0.0% | 6.6% | 4.2% | 87.9% | 1.3% | 0.00 | 0.12 | 0.18 | 7.33 | 0.33 | 7.96 |
| A | K | | A | A | R | | | 4.1% | 11.2% | 7.1% | 76.2% | 1.4% | 0.52 | 0.21 | 0.31 | 6.35 | 0.36 | 7.74 |
| A | K | | A | A | R | | | 4.9% | 12.0% | 7.2% | 76.0% | 0.0% | 0.61 | 0.23 | 0.31 | 6.33 | 0.00 | 7.48 |
| A | E | V | A | G | | R | G99C | 0.0% | 0.0% | 0.0% | 100.0% | 0.0% | 0.00 | 0.00 | 0.00 | 4.59 | 0.00 | 4.59 |
| A | E | V | A | A | R | | | 0.0% | 0.0% | 0.0% | 100.0% | 0.0% | 0.00 | 0.00 | 0.00 | 0.78 | 0.00 | 0.78 |
| A | E | V | A | A | | | | 0.0% | 0.0% | 0.0% | 100.0% | 0.0% | 0.00 | 0.00 | 0.00 | 2.53 | 0.00 | 2.53 |

Figure 8-7

| Amino Acid - residue position number and amino acid in that position | | | | | | | | Secondary Screen | | | | | | | | | | |
|---|---|---|---|---|---|---|---|---|---|---|---|---|---|---|---|---|---|---|
| | | | | | | | | Percentage Released FAs | | | | | Amount Relased FAs (ug) | | | | | |
| 61 | 72 | 116 | 133 | 151 | 163 | 164 | Other amino acid changes | Linolenic | Linoleic | Oleic | Palmitic | Stearic | Linolenic | Linoleic | Oleic | Palmitic | Stearic | Total FA |
| A | E | V | A | | R | | | 0.0% | 4.0% | 3.6% | 92.4% | 0.0% | 0.00 | 0.33 | 0.30 | 7.60 | 0.00 | 8.23 |
| A | E | V | A | | R | | | 0.0% | 4.2% | 3.8% | 92.1% | 0.0% | 0.00 | 0.36 | 0.33 | 8.02 | 0.00 | 8.71 |
| A | E | V | A | | R | | | 0.0% | 0.0% | 0.0% | 100.0% | 0.0% | 0.00 | 0.00 | 0.00 | 1.02 | 0.00 | 1.02 |
| A | E | V | A | | | | | 2.7% | 4.3% | 4.2% | 88.8% | 0.0% | 0.13 | 0.20 | 0.20 | 4.17 | 0.00 | 4.70 |
| A | E | V | | G | | | | Low | Low | Low | Low | Low | 0.00 | 0.00 | 0.00 | 0.00 | 0.00 | 0.00 |
| A | E | V | | A | R | | | 0.0% | 0.0% | 0.0% | 100.0% | 0.0% | 0.00 | 0.00 | 0.00 | 0.31 | 0.00 | 0.31 |
| A | E | V | | A | R | | | 0.0% | 0.0% | 0.0% | 100.0% | 0.0% | 0.00 | 0.00 | 0.00 | 0.53 | 0.00 | 0.53 |
| A | E | V | | A | R | | | 0.0% | 0.0% | 0.0% | 100.0% | 0.0% | 0.00 | 0.00 | 0.00 | 0.71 | 0.00 | 0.71 |
| A | E | V | | A | R | | | 1.6% | 7.1% | 1.8% | 89.6% | 0.0% | 0.18 | 0.81 | 0.20 | 10.20 | 0.00 | 11.39 |
| A | E | V | | A | | R | | Low | Low | Low | Low | Low | 0.00 | 0.00 | 0.00 | 0.00 | 0.00 | 0.00 |
| A | E | V | | A | | R | | 0.0% | 0.0% | 0.0% | 100.0% | 0.0% | 0.00 | 0.00 | 0.00 | 1.09 | 0.00 | 1.09 |
| A | E | V | | | R | | | 0.8% | 5.3% | 4.2% | 89.7% | 0.0% | 0.07 | 0.50 | 0.39 | 8.39 | 0.00 | 9.35 |
| A | E | V | | | | | | 0.0% | 5.4% | 0.0% | 94.6% | 0.0% | 0.00 | 0.39 | 0.00 | 6.77 | 0.00 | 7.16 |
| A | E | Q | A | | R | | | 0.0% | 1.2% | 2.4% | 96.5% | 0.0% | 0.00 | 0.13 | 0.26 | 10.70 | 0.00 | 11.09 |
| A | E | Q | | G | | | | 5.2% | 12.4% | 11.4% | 69.3% | 1.7% | 0.65 | 0.23 | 0.50 | 5.77 | 0.41 | 7.57 |
| A | E | Q | | G | | R | | 6.1% | 15.9% | 10.6% | 67.4% | 0.0% | 0.76 | 0.30 | 0.46 | 5.62 | 0.00 | 7.14 |
| A | E | A | A | G | | | | 0.0% | 0.0% | 0.0% | 100.0% | 0.0% | 0.00 | 0.00 | 0.00 | 0.19 | 0.00 | 0.19 |
| A | E | A | A | | R | | | 0.0% | 4.2% | 6.2% | 89.7% | 0.0% | 0.00 | 0.32 | 0.48 | 6.93 | 0.00 | 7.73 |
| A | E | A | A | | | | | 0.0% | 0.0% | 0.0% | 100.0% | 0.0% | 0.00 | 0.00 | 0.00 | 7.06 | 0.00 | 7.06 |
| A | E | A | | | | | | 1.2% | 5.5% | 6.4% | 85.9% | 1.0% | 0.09 | 0.42 | 0.48 | 6.52 | 0.07 | 7.59 |
| A | E | A | | | R | | | 0.0% | 0.0% | 1.0% | 99.0% | 0.0% | 0.00 | 0.00 | 0.06 | 5.72 | 0.00 | 5.78 |
| A | E | A | | G | R | | | 0.8% | 0.0% | 0.0% | 99.2% | 0.0% | 0.01 | 0.00 | 0.00 | 1.31 | 0.00 | 1.32 |
| A | E | A | | A | | | | 0.0% | 3.7% | 0.0% | 96.3% | 0.0% | 0.00 | 0.23 | 0.00 | 6.12 | 0.00 | 6.35 |
| A | E | A | | A | R | | | 0.0% | 0.0% | 0.0% | 100.0% | 0.0% | 0.00 | 0.00 | 0.00 | 0.91 | 0.00 | 0.91 |
| A | E | A | | A | | | | 1.1% | 8.8% | 2.3% | 86.3% | 1.4% | 0.08 | 0.59 | 0.16 | 5.79 | 0.09 | 6.71 |
| A | E | A | | | | | | Low | Low | Low | Low | Low | 0.00 | 0.00 | 0.00 | 0.00 | 0.00 | 0.00 |
| A | E | | | | | | | Low | Low | Low | Low | Low | Low | Low | Low | Low | Low | Low |
| A | E | | | | R | | | Low | Low | Low | Low | Low | Low | Low | Low | Low | Low | Low |
| A | E | | | A | R | | | Low | Low | Low | Low | Low | Low | Low | Low | Low | Low | Low |
| A | E | | A | | R | | K12M | 2.9% | 10.9% | 7.7% | 75.3% | 3.3% | 0.37 | 0.21 | 0.33 | 6.27 | 0.81 | 7.99 |

Figure 8-8

| Amino Acid - residue position number and amino acid in that position | | | | | | | | Secondary Screen | | | | | | | | | | |
|---|---|---|---|---|---|---|---|---|---|---|---|---|---|---|---|---|---|---|
| | | | | | | | | Percentage Released FAs | | | | | Amount Released FAs (ug) | | | | | |
| 61 | 72 | 116 | 133 | 151 | 163 | 164 | Other amino acid changes | Linolenic | Linoleic | Oleic | Palmitic | Stearic | Linolenic | Linoleic | Oleic | Palmitic | Stearic | Total FA |
| A | E | | | A | R | | K12M | 5.5% | 13.8% | 7.7% | 71.7% | 1.3% | 0.69 | 0.26 | 0.34 | 5.97 | 0.33 | 7.59 |
| A | V | A | A | A | R | | | 0.0% | 0.0% | 0.0% | 100.0% | 0.0% | 0.00 | 0.00 | 0.00 | 0.39 | 0.00 | 0.39 |
| A | V | A | A | A | | | | 0.0% | 0.0% | 0.0% | 100.0% | 0.0% | 0.00 | 0.00 | 0.00 | 0.87 | 0.00 | 0.87 |
| A | V | A | A | A | | | | 0.0% | 3.6% | 0.0% | 96.4% | 0.0% | 0.00 | 0.12 | 0.00 | 3.05 | 0.00 | 3.17 |
| A | V | A | | | R | | | 0.0% | 0.0% | 0.0% | 100.0% | 0.0% | 0.00 | 0.00 | 0.00 | 3.16 | 0.00 | 3.16 |
| A | V | A | | | R | | | 0.0% | 4.8% | 5.9% | 89.3% | 0.0% | 0.00 | 0.44 | 0.54 | 8.18 | 0.00 | 9.16 |
| A | V | A | | | R | | | 0.0% | 1.4% | 0.0% | 98.6% | 0.0% | 0.00 | 0.11 | 0.00 | 7.57 | 0.00 | 7.68 |
| A | V | A | | | | R | | 4.7% | 11.0% | 10.4% | 74.0% | 0.0% | 0.50 | 1.18 | 1.12 | 7.96 | 0.00 | 10.76 |
| A | V | A | | | | R | | 0.4% | 3.3% | 4.0% | 90.9% | 1.4% | 0.02 | 0.18 | 0.22 | 4.92 | 0.08 | 5.41 |
| A | V | A | | | | R | | 1.9% | 5.5% | 1.7% | 90.9% | 0.0% | 0.18 | 0.50 | 0.16 | 8.33 | 0.00 | 9.17 |
| A | V | A | | | | R | | 0.0% | 3.7% | 0.0% | 96.3% | 0.0% | 0.00 | 0.16 | 0.00 | 4.10 | 0.00 | 4.26 |
| A | V | A | | | | R | | 0.0% | 0.0% | 0.0% | 100.0% | 0.0% | 0.00 | 0.00 | 0.00 | 1.79 | 0.00 | 1.79 |
| A | V | | A | | | | | 0.1% | 4.6% | 0.0% | 95.3% | 0.0% | 0.01 | 0.34 | 0.00 | 7.05 | 0.00 | 7.40 |
| A | V | | | G | R | | | Low | Low | Low | Low | Low | 0.00 | 0.00 | 0.00 | 0.00 | 0.00 | 0.00 |
| A | V | | | A | | R | | 0.0% | 0.0% | 0.0% | 100.0% | 0.0% | 0.00 | 0.00 | 0.00 | 1.04 | 0.00 | 1.04 |
| A | V | | | | | R | | 4.3% | 9.0% | 9.7% | 76.9% | 0.0% | 0.59 | 1.23 | 1.33 | 10.50 | 0.00 | 13.65 |
| A | V | | | | | R | | 0.7% | 3.4% | 3.5% | 92.1% | 0.3% | 0.05 | 0.25 | 0.26 | 6.80 | 0.02 | 7.39 |
| A | V | | | | | | | 0.3% | 7.6% | 0.0% | 92.1% | 0.0% | 0.02 | 0.41 | 0.00 | 4.98 | 0.00 | 5.41 |
| A | V | | | | R | | | 2.6% | 8.3% | 4.2% | 84.7% | 0.2% | 0.29 | 0.91 | 0.45 | 9.23 | 0.03 | 10.90 |
| A | V | | | | | | V22D | 0.1% | 3.9% | 0.5% | 95.5% | 0.0% | 0.01 | 0.26 | 0.03 | 6.43 | 0.00 | 6.73 |
| A | V | | | | | R | D138E,K213E | 0.0% | 0.0% | 0.0% | 100.0% | 0.0% | 0.00 | 0.00 | 0.00 | 0.35 | 0.00 | 0.35 |
| A | T | | | | | | | Low | Low | Low | Low | Low | 0.00 | 0.00 | 0.00 | 0.00 | 0.00 | 0.00 |
| A | Q | A | | | | | | 0.0% | 0.0% | 0.0% | 100.0% | 0.0% | 0.00 | 0.00 | 0.00 | 3.54 | 0.00 | 3.54 |
| A | A | A | G | | | | | 0.0% | 0.0% | 0.0% | 100.0% | 0.0% | 0.00 | 0.00 | 0.00 | 0.39 | 0.00 | 0.39 |
| A | A | A | A | | R | | K146N | 1.7% | 6.4% | 6.6% | 85.3% | 0.0% | 0.25 | 0.90 | 0.93 | 12.10 | 0.00 | 14.18 |
| A | A | A | A | | | | | 1.7% | 4.5% | 8.2% | 83.8% | 1.7% | 0.18 | 0.46 | 0.85 | 8.64 | 0.18 | 10.31 |
| A | A | | A | | | | | 0.0% | 0.0% | 0.0% | 100.0% | 0.0% | 0.00 | 0.00 | 0.00 | 1.45 | 0.00 | 1.45 |
| A | A | | A | | R | | | 0.0% | 0.0% | 0.0% | 100.0% | 0.0% | 0.00 | 0.00 | 0.00 | 1.65 | 0.00 | 1.65 |
| A | A | | | | | R | | 1.2% | 4.1% | 5.6% | 88.8% | 0.3% | 0.13 | 0.45 | 0.63 | 9.85 | 0.03 | 11.09 |

Figure 8-9

| Amino Acid - residue position number and amino acid in that position | | | | | | | | Percentage Released FAs (Secondary Screen) | | | | | Amount Released FAs (ug) (Secondary Screen) | | | | | |
|---|---|---|---|---|---|---|---|---|---|---|---|---|---|---|---|---|---|---|
| 61 | 72 | 116 | 133 | 151 | 163 | 164 | Other amino acid changes | Linolenic | Linoleic | Oleic | Palmitic | Stearic | Linolenic | Linoleic | Oleic | Palmitic | Stearic | Total FA |
| A | | | | | | | | Low | Low | Low | Low | Low | 0.00 | 0.00 | 0.00 | 0.00 | 0.00 | 0.00 |
| A | | | A | | R | | S54L | 5.3% | 11.0% | 8.2% | 74.6% | 0.9% | 0.66 | 0.21 | 0.36 | 6.22 | 0.24 | 7.67 |
| A | | | A | | R | | S54L | 5.2% | 9.3% | 9.1% | 76.5% | 0.0% | 0.65 | 0.18 | 0.39 | 6.37 | 0.00 | 7.59 |
| A | | | A | | R | | K12M | 4.4% | 10.2% | 7.0% | 76.8% | 1.6% | 0.55 | 0.19 | 0.31 | 6.40 | 0.40 | 7.84 |
| A | | | A | | R | | K12M | 5.3% | 10.1% | 8.4% | 75.4% | 0.9% | 0.66 | 0.19 | 0.36 | 6.28 | 0.22 | 7.72 |
| | K | V | A | G | | | | 3.8% | 8.3% | 7.9% | 80.0% | 0.0% | 0.62 | 1.37 | 1.31 | 13.20 | 0.00 | 16.50 |
| | K | V | A | G | | | | Low | Low | Low | Low | Low | 0.00 | 0.00 | 0.00 | 0.00 | 0.00 | 0.00 |
| | K | V | A | A | R | | | 0.0% | 0.0% | 0.0% | 100.0% | 0.0% | 0.00 | 0.00 | 0.00 | 2.25 | 0.00 | 2.25 |
| | K | V | A | A | R | | | 0.5% | 0.0% | 0.0% | 99.5% | 0.0% | 0.02 | 0.00 | 0.00 | 3.73 | 0.00 | 3.75 |
| | K | V | A | A | R | | | 0.7% | 0.0% | 0.0% | 99.3% | 0.0% | 0.03 | 0.00 | 0.00 | 3.76 | 0.00 | 3.79 |
| | K | V | A | | R | | | 0.7% | 0.0% | 0.0% | 99.3% | 0.0% | 0.02 | 0.00 | 0.00 | 3.10 | 0.00 | 3.12 |
| | K | V | A | | R | | A141T | 0.0% | 0.0% | 0.0% | 100.0% | 0.0% | 0.00 | 0.00 | 0.00 | 4.54 | 0.00 | 4.54 |
| | K | V | A | | R | | | 0.0% | 0.0% | 0.0% | 100.0% | 0.0% | 0.00 | 0.00 | 0.00 | 3.16 | 0.00 | 3.16 |
| | K | V | A | | R | | | 0.0% | 0.0% | 0.0% | 100.0% | 0.0% | 0.00 | 0.00 | 0.00 | 3.68 | 0.00 | 3.68 |
| | K | V | A | | R | | V62F | 0.0% | 0.0% | 0.0% | 100.0% | 0.0% | 0.00 | 0.00 | 0.00 | 7.51 | 0.00 | 7.51 |
| | K | V | A | | | | P162S | 2.2% | 8.5% | 7.5% | 81.8% | 0.0% | 0.39 | 1.51 | 1.32 | 14.50 | 0.00 | 17.72 |
| | K | V | A | G | | R | | 1.2% | 0.0% | 0.0% | 98.8% | 0.0% | 0.00 | 0.00 | 0.00 | 0.33 | 0.00 | 0.33 |
| | K | V | A | A | R | | | 0.0% | 0.0% | 0.0% | 100.0% | 0.0% | 0.00 | 0.00 | 0.00 | 0.43 | 0.00 | 0.43 |
| | K | V | A | A | R | | | 0.0% | 0.0% | 0.0% | 100.0% | 0.0% | 0.00 | 0.00 | 0.00 | 0.58 | 0.00 | 0.58 |
| | K | V | A | A | | R | | Low | Low | Low | Low | Low | 0.00 | 0.00 | 0.00 | 0.00 | 0.00 | 0.00 |
| | K | V | A | A | | | | 0.0% | 0.0% | 0.0% | 100.0% | 0.0% | 0.00 | 0.00 | 0.00 | 0.14 | 0.00 | 0.14 |
| | K | V | A | | | | | 0.0% | 0.0% | 0.0% | 100.0% | 0.0% | 0.00 | 0.00 | 0.00 | 1.38 | 0.00 | 1.38 |
| | K | V | A | | R | | A35V | 0.0% | 0.0% | 0.0% | 100.0% | 0.0% | 0.00 | 0.00 | 0.00 | 6.35 | 0.00 | 6.35 |
| | K | V | | | R | | | 0.0% | 0.0% | 0.0% | 100.0% | 0.0% | 0.00 | 0.00 | 0.00 | 4.56 | 0.00 | 4.56 |
| | K | V | | | R | | | 2.7% | 1.8% | 0.0% | 95.5% | 0.0% | 0.19 | 0.12 | 0.00 | 6.64 | 0.00 | 6.95 |
| | K | V | | | | | | 2.2% | 9.4% | 9.5% | 78.9% | 0.0% | 0.27 | 1.15 | 1.16 | 9.63 | 0.00 | 12.21 |
| | K | V | | | | | | 0.0% | 0.8% | 1.1% | 98.1% | 0.0% | 0.00 | 0.04 | 0.06 | 5.11 | 0.00 | 5.21 |
| | K | T | A | G | | | | 6.8% | 0.0% | 0.0% | 93.2% | 0.0% | 0.11 | 0.00 | 0.00 | 1.51 | 0.00 | 1.62 |
| | K | Q | A | | R | | | 0.3% | 2.4% | 1.9% | 95.4% | 0.0% | 0.04 | 0.36 | 0.28 | 14.00 | 0.00 | 14.68 |

Figure 8-10

| Amino Acid - residue position number and amino acid in that position | | | | | | | | Secondary Screen | | | | | | | | | | |
|---|---|---|---|---|---|---|---|---|---|---|---|---|---|---|---|---|---|---|
| | | | | | | | | Percentage Released FAs | | | | | Amount Released FAs (ug) | | | | | |
| 61 | 72 | 116 | 133 | 151 | 163 | 164 | Other amino acid changes | Linolenic | Linoleic | Oleic | Palmitic | Stearic | Linolenic | Linoleic | Oleic | Palmitic | Stearic | Total FA |
| | K | Q | A | | R | | | 0.5% | 2.5% | 1.8% | 95.1% | 0.1% | 0.07 | 0.38 | 0.28 | 14.20 | 0.01 | 14.93 |
| | K | A | A | A | R | | | 0.0% | 1.8% | 0.0% | 98.2% | 0.0% | 0.00 | 0.13 | 0.00 | 7.33 | 0.00 | 7.46 |
| | K | A | A | A | | | | 0.0% | 0.0% | 0.0% | 100.0% | 0.0% | 0.00 | 0.00 | 0.00 | 0.84 | 0.00 | 0.84 |
| | K | A | A | | R | | | 1.7% | 6.0% | 5.6% | 86.6% | 0.0% | 0.42 | 1.47 | 1.37 | 21.10 | 0.00 | 24.36 |
| | K | A | A | | | | | 1.0% | 5.3% | 2.4% | 91.3% | 0.0% | 0.09 | 0.45 | 0.20 | 7.76 | 0.00 | 8.50 |
| | K | A | | G | | | | 6.7% | 0.0% | 0.0% | 93.3% | 0.0% | 0.05 | 0.00 | 0.00 | 0.69 | 0.00 | 0.74 |
| | K | A | | | R | | | 0.1% | 1.4% | 0.9% | 97.6% | 0.0% | 0.01 | 0.09 | 0.06 | 6.73 | 0.00 | 6.90 |
| | K | A | | | R | | | 0.0% | 0.0% | 0.0% | 100.0% | 0.0% | 0.00 | 0.00 | 0.00 | 4.17 | 0.00 | 4.17 |
| | K | A | | | R | | | 3.6% | 0.4% | 0.1% | 95.9% | 0.0% | 0.20 | 0.02 | 0.01 | 5.34 | 0.00 | 5.57 |
| | K | A | | | | | | 0.8% | 4.7% | 6.0% | 88.5% | 0.0% | 0.05 | 0.32 | 0.40 | 5.92 | 0.00 | 6.69 |
| | K | A | | | | R | | 0.5% | 5.1% | 0.0% | 94.5% | 0.0% | 0.03 | 0.26 | 0.00 | 4.93 | 0.00 | 5.22 |
| | E | V | A | G | R | | | 2.8% | 2.4% | 0.0% | 94.8% | 0.0% | 0.05 | 0.04 | 0.00 | 1.59 | 0.00 | 1.68 |
| | E | V | A | A | R | | | 0.0% | 0.0% | 0.0% | 100.0% | 0.0% | 0.00 | 0.00 | 0.00 | 1.47 | 0.00 | 1.47 |
| | E | V | A | A | | | | 0.0% | 0.0% | 0.0% | 100.0% | 0.0% | 0.00 | 0.00 | 0.00 | 1.53 | 0.00 | 1.53 |
| | E | V | A | | R | | | 0.0% | 0.0% | 0.0% | 100.0% | 0.0% | 0.00 | 0.00 | 0.00 | 4.27 | 0.00 | 4.27 |
| | E | V | A | | | R | | 0.7% | 5.3% | 5.7% | 87.6% | 0.7% | 0.06 | 0.45 | 0.49 | 7.50 | 0.06 | 8.56 |
| | E | V | | G | | | | 0.0% | 0.0% | 0.0% | 100.0% | 0.0% | 0.00 | 0.00 | 0.00 | 0.55 | 0.00 | 0.55 |
| | E | V | | G | | | | 0.0% | 0.0% | 0.0% | 100.0% | 0.0% | 0.00 | 0.00 | 0.00 | 0.06 | 0.00 | 0.06 |
| | E | V | | A | R | | | 0.0% | 0.0% | 0.0% | 100.0% | 0.0% | 0.00 | 0.00 | 0.00 | 2.25 | 0.00 | 2.25 |
| | E | V | | | R | | | 0.0% | 4.9% | 3.6% | 91.5% | 0.0% | 0.00 | 0.38 | 0.28 | 7.10 | 0.00 | 7.76 |
| | E | V | | | R | | | 0.0% | 0.0% | 0.0% | 100.0% | 0.0% | 0.00 | 0.00 | 0.00 | 2.01 | 0.00 | 2.01 |
| | E | V | | | R | | | 0.0% | 0.0% | 0.0% | 100.0% | 0.0% | 0.00 | 0.00 | 0.00 | 4.03 | 0.00 | 4.03 |
| | E | V | | | | | | 0.0% | 0.0% | 0.0% | 100.0% | 0.0% | 0.00 | 0.00 | 0.00 | 3.80 | 0.00 | 3.80 |
| | E | V | | | | | | 0.0% | 0.0% | 0.0% | 100.0% | 0.0% | 0.00 | 0.00 | 0.00 | 0.72 | 0.00 | 0.72 |
| | E | V | | | | R | | 0.0% | 0.3% | 0.0% | 99.7% | 0.0% | 0.00 | 0.01 | 0.00 | 3.03 | 0.00 | 3.03 |
| | E | T | A | G | R | | | 2.8% | 1.1% | 1.6% | 94.6% | 0.0% | 0.15 | 0.06 | 0.08 | 4.93 | 0.00 | 4.94 |
| | E | Q | A | A | R | | N55M | 1.9% | 1.7% | 3.1% | 93.4% | 0.0% | 0.20 | 0.18 | 0.33 | 5.03 | 0.00 | 5.32 |
| | E | Q | | G | | R | | 4.4% | 4.6% | 6.5% | 84.5% | 0.0% | 0.28 | 0.29 | 0.41 | 5.34 | 0.00 | 6.32 |

Figure 8-11

| Amino Acid - residue position number and amino acid in that position | | | | | | | | Other amino acid changes | Percentage Released FAs | | | | | | Amount Released FAs (ug) | | | | | |
|---|---|---|---|---|---|---|---|---|---|---|---|---|---|---|---|---|---|---|---|---|
| 61 | 72 | 116 | 133 | 151 | 163 | 164 | | Linolenic | Linoleic | Oleic | Palmitic | Stearic | Linolenic | Linoleic | Oleic | Palmitic | Stearic | Total FA |
| E | | A | A | G | R | | | 0.0% | 2.8% | 0.0% | 97.2% | 0.0% | 0.00 | 0.11 | 0.00 | 3.75 | 0.00 | 3.86 |
| E | | A | A | G | R | | | 0.0% | 0.0% | 0.0% | 100.0% | 0.0% | 0.00 | 0.00 | 0.00 | 1.36 | 0.00 | 1.36 |
| E | | A | A | G | | | | 0.0% | 0.0% | 0.0% | 100.0% | 0.0% | 0.00 | 0.00 | 0.00 | 0.01 | 0.00 | 0.01 |
| E | | A | A | A | R | | | 0.2% | 2.9% | 5.0% | 91.1% | 0.8% | 0.02 | 0.27 | 0.47 | 8.50 | 0.08 | 9.33 |
| E | | A | A | A | | | | 1.3% | 5.3% | 6.6% | 86.3% | 0.5% | 0.08 | 0.34 | 0.42 | 5.55 | 0.03 | 6.43 |
| E | | A | A | | | R | | 0.0% | 5.6% | 1.7% | 92.6% | 0.0% | 0.00 | 0.40 | 0.12 | 6.59 | 0.00 | 7.12 |
| E | | A | | | | | | Low | Low | Low | Low | Low | 0.00 | 0.00 | 0.00 | 0.00 | 0.00 | 0.00 |
| E | | A | | G | R | | | 0.0% | 0.0% | 0.9% | 99.1% | 0.0% | 0.00 | 0.00 | 0.03 | 3.25 | 0.00 | 3.28 |
| E | | A | | G | R | | | 0.0% | 3.8% | 3.1% | 93.1% | 0.0% | 0.00 | 0.16 | 0.13 | 3.86 | 0.00 | 4.15 |
| E | | A | | G | | R | | 4.1% | 14.7% | 9.4% | 68.8% | 3.0% | 0.34 | 1.21 | 0.78 | 5.67 | 0.25 | 8.24 |
| E | | A | | | | | | 1.3% | 6.4% | 1.0% | 90.9% | 0.5% | 0.08 | 0.40 | 0.06 | 5.69 | 0.03 | 6.26 |
| E | | A | | A | | R | A35V | 2.9% | 6.3% | 7.6% | 83.2% | 0.0% | 0.51 | 1.13 | 1.36 | 14.90 | 0.00 | 17.90 |
| E | | | | A | | R | K12M | 5.4% | 14.5% | 16.2% | 60.6% | 3.3% | 1.06 | 2.86 | 3.21 | 12.00 | 0.66 | 19.79 |
| E | | | A | | R | | | 0.0% | 0.0% | 0.0% | 100.0% | 0.0% | 0.00 | 0.00 | 0.00 | 5.27 | 0.00 | 5.27 |
| E | | | | | R | | V128A | 0.4% | 3.1% | 3.5% | 93.0% | 0.0% | 0.04 | 0.38 | 0.43 | 11.30 | 0.00 | 12.15 |
| | V | A | A | | R | | | 0.0% | 0.0% | 0.0% | 100.0% | 0.0% | 0.00 | 0.00 | 0.00 | 3.79 | 0.00 | 3.79 |
| | V | A | A | A | R | | | 0.0% | 0.0% | 0.0% | 100.0% | 0.0% | 0.00 | 0.00 | 0.00 | 0.54 | 0.00 | 0.54 |
| | V | A | A | A | R | | | 2.9% | 7.7% | 9.0% | 78.5% | 1.8% | 0.43 | 1.13 | 1.32 | 11.50 | 0.27 | 14.65 |
| | V | A | A | A | R | | | 1.8% | 0.0% | 0.0% | 98.2% | 0.0% | 0.07 | 0.00 | 0.00 | 3.72 | 0.00 | 3.79 |
| | V | A | A | | | | | 0.0% | 0.0% | 0.0% | 100.0% | 0.0% | 0.00 | 0.00 | 0.00 | 3.85 | 0.00 | 3.85 |
| | V | | A | | | | | 2.8% | 8.2% | 9.4% | 79.6% | 0.0% | 0.28 | 0.84 | 0.97 | 8.15 | 0.00 | 10.24 |
| | V | | | G | | | | 1.9% | 0.0% | 0.0% | 98.1% | 0.0% | 0.04 | 0.00 | 0.00 | 1.90 | 0.00 | 1.94 |
| | V | | | | | | | 0.0% | 0.0% | 0.0% | 100.0% | 0.0% | 0.00 | 0.00 | 0.00 | 1.16 | 0.00 | 1.16 |
| | V | | | | | R | | Low | Low | Low | Low | Low | 0.00 | 0.00 | 0.00 | 0.00 | 0.00 | 0.00 |
| | | A | A | | | | | 0.0% | 0.0% | 0.0% | 100.0% | 0.0% | 0.00 | 0.00 | 0.00 | 1.67 | 0.00 | 1.67 |
| | | A | A | A | R | | | 0.3% | 1.7% | 2.1% | 95.9% | 0.0% | 0.02 | 0.15 | 0.00 | 5.08 | 0.00 | 5.08 |
| | | A | A | | R | | | 2.2% | 6.7% | 7.1% | 84.0% | 0.0% | 0.02 | 0.15 | 0.19 | 8.42 | 0.00 | 8.78 |
| | | A | A | | R | | | 2.2% | 6.7% | 7.1% | 84.0% | 0.0% | 0.38 | 1.16 | 1.23 | 14.60 | 0.00 | 17.37 |
| | | A | A | | R | | | 7.3% | 8.6% | 5.2% | 71.8% | 7.1% | 0.79 | 0.92 | 0.56 | 7.72 | 0.77 | 10.76 |

| 61 | 72 | 116 | 133 | 151 | 163 | 164 | Other amino acid changes | Linolenic | Linoleic | Oleic | Palmitic | Stearic | Linolenic | Linoleic | Oleic | Palmitic | Stearic | Total FA |
|---|---|---|---|---|---|---|---|---|---|---|---|---|---|---|---|---|---|---|
|  |  | A | A |  |  |  | P179Q | 0.3% | 2.6% | 6.3% | 90.7% | 0.0% | 0.02 | 0.17 | 0.41 | 5.83 | 0.00 | 6.42 |
|  |  | A | A |  |  | R |  | 0.0% | 5.7% | 8.7% | 85.2% | 0.5% | 0.00 | 0.32 | 0.50 | 4.87 | 0.03 | 5.72 |
|  |  | A |  | A |  |  |  | Low | Low | Low | Low | Low | 0.00 | 0.00 | 0.00 | 0.00 | 0.00 | 0.00 |
|  |  | A |  | A |  | R |  | 0.0% | 0.0% | 0.0% | 100.0% | 0.0% | 0.00 | 0.00 | 0.00 | 0.73 | 0.00 | 0.73 |
|  |  | A |  |  | R |  |  | 3.0% | 8.2% | 7.2% | 81.4% | 0.2% | 0.92 | 2.55 | 2.24 | 25.30 | 0.06 | 31.07 |
|  |  | A |  |  | R |  |  | Low | Low | Low | Low | Low | 0.00 | 0.00 | 0.00 | 0.00 | 0.00 | 0.00 |
|  |  | A |  |  |  | R |  | 0.9% | 6.1% | 4.8% | 87.1% | 1.1% | 0.06 | 0.43 | 0.34 | 6.15 | 0.08 | 7.06 |
|  |  | A |  |  |  | R |  | 2.9% | 4.5% | 10.1% | 80.9% | 1.6% | 0.22 | 0.34 | 0.77 | 6.15 | 0.12 | 7.61 |
|  |  |  |  |  |  |  | wt | 5.1% | 14.5% | 17.4% | 61.2% | 1.7% | 0.75 | 2.12 | 2.55 | 8.96 | 0.26 | 14.63 |
|  |  |  |  |  |  |  | mixed | 0.0% | 1.4% | 0.8% | 97.8% | 0.0% | 0.00 | 0.24 | 0.14 | 17.00 | 0.00 | 17.38 |
|  | K |  |  | A |  | R |  | 5.5% | 10.4% | 6.4% | 76.1% | 1.5% | 0.69 | 0.20 | 0.28 | 6.34 | 0.37 | 7.88 |
|  | K | T |  | A |  | R |  | 5.5% | 8.7% | 5.6% | 80.1% | 0.0% | 0.69 | 0.16 | 0.24 | 6.68 | 0.00 | 7.78 |
|  | K | Q | A | A |  |  |  | 4.4% | 8.7% | 9.9% | 74.8% | 2.2% | 0.54 | 0.16 | 0.43 | 6.24 | 0.54 | 7.92 |
|  | K | Q | A | A |  |  |  | 7.6% | 11.1% | 9.4% | 71.9% | 0.0% | 0.95 | 0.21 | 0.41 | 5.99 | 0.00 | 7.56 |
|  | K | Q | A | G |  | R |  | 3.6% | 7.6% | 7.7% | 80.1% | 1.0% | 0.46 | 0.14 | 0.33 | 6.67 | 0.25 | 7.86 |
|  | K | Q | A | G |  | R |  | 3.7% | 8.1% | 5.8% | 82.4% | 0.0% | 0.46 | 0.15 | 0.25 | 6.86 | 0.00 | 7.73 |
|  | K |  | A |  | R |  |  | 4.3% | 10.0% | 6.7% | 78.1% | 0.9% | 0.54 | 0.19 | 0.29 | 6.51 | 0.23 | 7.76 |
|  | K |  | A |  | R |  |  | 4.0% | 9.9% | 6.3% | 79.6% | 0.2% | 0.50 | 0.19 | 0.28 | 6.64 | 0.04 | 7.64 |
|  | E |  | A | A |  |  |  | 3.5% | 10.9% | 7.9% | 74.9% | 2.8% | 0.44 | 0.21 | 0.34 | 6.24 | 0.70 | 7.93 |
|  | E |  | A | A |  |  |  | 5.6% | 13.2% | 7.2% | 74.0% | 0.0% | 0.70 | 0.25 | 0.31 | 6.17 | 0.00 | 7.43 |
|  | E |  | A | G |  | R |  | 5.7% | 12.8% | 11.1% | 67.5% | 2.9% | 0.72 | 0.24 | 0.48 | 5.62 | 0.72 | 7.79 |
|  | E |  | A | G |  | R |  | 7.1% | 13.9% | 12.4% | 64.9% | 1.8% | 0.88 | 0.26 | 0.54 | 5.41 | 0.45 | 7.54 |
|  | E |  | A | A |  | R |  | 5.7% | 11.9% | 11.1% | 69.5% | 1.9% | 0.71 | 0.22 | 0.48 | 5.79 | 0.47 | 7.67 |
|  | E |  | A | A |  | R |  | 6.6% | 13.2% | 10.9% | 68.2% | 1.1% | 0.82 | 0.25 | 0.48 | 5.68 | 0.26 | 7.50 |
|  |  | Q |  | A |  | R | A97V | 3.8% | 7.6% | 6.2% | 80.9% | 1.5% | 0.47 | 0.14 | 0.27 | 6.74 | 0.38 | 8.00 |
|  |  | Q |  | A | R |  | A97V | 4.1% | 7.7% | 5.9% | 82.3% | 0.0% | 0.51 | 0.15 | 0.26 | 6.86 | 0.00 | 7.77 |
|  |  |  | A | A | R |  |  | 0.6% | 4.3% | 3.6% | 91.4% | 0.0% | 0.06 | 0.42 | 0.35 | 8.87 | 0.00 | 9.70 |

| Amino Acid - residue position number and amino acid in that position | | | | | | | | Primary Screen | | | | | | | | | | |
|---|---|---|---|---|---|---|---|---|---|---|---|---|---|---|---|---|---|---|
| | | | | | | | | Percentage Released Fas | | | | | Amount Released Fas (ug) | | | | | |
| 61 | 72 | 116 | 133 | 151 | 163 | 164 | Other amino acid changes | Linolenic | Linoleic | Oleic | Palmitic | Stearic | Linolenic | Linoleic | Oleic | Palmitic | Stearic | Total FA |
| E | K | V | A | A | R | | | 0.0% | 0.0% | 0.0% | 100.0% | 0.0% | 0.00 | 0.00 | 0.00 | 14.20 | 0.00 | 14.20 |
| E | K | V | A | A | | | | 0.0% | 5.4% | 0.0% | 94.6% | 0.0% | 0.00 | 0.52 | 0.00 | 9.01 | 0.00 | 9.53 |
| E | K | V | A | | | R | | 2.5% | 4.9% | 3.4% | 89.2% | 0.0% | 1.23 | 2.44 | 1.69 | 44.10 | 0.00 | 49.46 |
| E | K | V | | G | | | | 0.0% | 5.2% | 0.0% | 94.8% | 0.0% | 0.00 | 0.18 | 0.00 | 3.27 | 0.00 | 3.45 |
| E | K | V | | A | | | | 0.0% | 0.0% | 0.0% | 100.0% | 0.0% | 0.00 | 0.00 | 0.00 | 4.69 | 0.00 | 4.69 |
| E | K | V | | | R | | | 1.5% | 3.7% | 2.6% | 92.2% | 0.0% | 0.67 | 1.69 | 1.19 | 42.20 | 0.00 | 45.75 |
| E | K | V | | | R | | | 0.3% | 5.3% | 6.1% | 88.2% | 0.0% | 0.03 | 0.50 | 0.57 | 8.23 | 0.00 | 9.33 |
| E | K | V | | | | R | | 0.0% | 0.0% | 0.0% | 100.0% | 0.0% | 0.00 | 0.00 | 0.00 | 19.70 | 0.00 | 19.70 |
| E | K | V | | | | | | 0.0% | 0.0% | 0.0% | 100.0% | 0.0% | 0.00 | 0.00 | 0.00 | 12.70 | 0.00 | 12.70 |
| E | K | T | | A | R | | | 3.5% | 8.3% | 11.9% | 76.3% | 0.0% | 1.31 | 3.16 | 4.52 | 28.90 | 0.00 | 37.89 |
| E | K | T | | A | R | | | 3.5% | 8.3% | 11.9% | 76.3% | 0.0% | 1.31 | 3.16 | 4.52 | 28.90 | 0.00 | 37.89 |
| E | K | T | | A | R | | | 3.5% | 8.3% | 11.9% | 76.3% | 0.0% | 1.31 | 3.16 | 4.52 | 28.90 | 0.00 | 37.89 |
| E | K | Q | | A | R | | | 5.9% | 12.1% | 11.4% | 67.4% | 3.2% | 5.51 | 11.30 | 10.60 | 62.80 | 2.97 | 93.18 |
| E | K | Q | | A | R | | | 5.9% | 12.1% | 11.4% | 67.4% | 3.2% | 5.51 | 11.30 | 10.60 | 62.80 | 2.97 | 93.18 |
| E | K | Q | | A | R | | | 5.3% | 11.8% | 13.4% | 66.9% | 2.5% | 4.65 | 10.40 | 11.80 | 58.70 | 2.23 | 87.78 |
| E | K | Q | | A | R | | | 5.3% | 11.8% | 13.4% | 66.9% | 2.5% | 4.65 | 10.40 | 11.80 | 58.70 | 2.23 | 87.78 |
| E | K | Q | | A | R | | | 0.0% | 0.0% | 0.0% | 100.0% | 0.0% | 0.00 | 0.00 | 0.00 | 19.50 | 0.00 | 19.50 |
| E | K | A | | A | R | | | 0.0% | 0.0% | 0.0% | 100.0% | 0.0% | 0.00 | 0.00 | 0.00 | 19.00 | 0.00 | 19.00 |
| E | K | A | | | | | | 0.0% | 2.5% | 0.0% | 97.5% | 0.0% | 0.00 | 0.21 | 0.00 | 8.16 | 0.00 | 8.37 |
| E | K | A | | G | | | | 2.6% | 6.4% | 6.1% | 84.9% | 0.0% | 0.67 | 1.64 | 1.57 | 21.90 | 0.00 | 25.78 |
| E | K | A | | A | | | | 0.0% | 6.0% | 3.2% | 90.7% | 0.0% | 0.00 | 0.77 | 0.41 | 11.50 | 0.00 | 12.67 |
| E | K | A | | | | R | | 0.0% | 6.5% | 4.6% | 88.9% | 0.0% | 0.00 | 1.19 | 0.85 | 16.30 | 0.00 | 18.34 |
| E | K | A | | | | R | | 0.0% | 7.8% | 2.8% | 89.4% | 0.0% | 0.00 | 1.04 | 0.37 | 11.90 | 0.00 | 13.31 |
| E | K | A | | | | R | | 0.0% | 2.0% | 2.0% | 96.0% | 0.0% | 0.00 | 0.43 | 0.45 | 21.10 | 0.00 | 21.98 |
| E | K | A | | | | R | | 0.0% | 0.0% | 0.0% | 100.0% | 0.0% | 0.00 | 0.00 | 0.00 | 17.10 | 0.00 | 17.10 |
| E | K | A | | | | R | S18G,K12M | Low | Low | Low | High | Low | 0.00 | 0.00 | 0.00 | High | 0.00 | 0.00 |
| E | K | | A | A | R | | L86M | 0.0% | 11.8% | 7.3% | 76.8% | 4.0% | 0.01 | 4.44 | 2.77 | 29.00 | 1.52 | 37.74 |
| E | K | | A | A | R | | L86M | 0.0% | 11.8% | 7.3% | 76.8% | 4.0% | 0.01 | 4.44 | 2.77 | 29.00 | 1.52 | 37.74 |

Figure 8-14

| Amino Acid - residue position number and amino acid in that position | | | | | | | | Primary Screen | | | | | | | | | | |
|---|---|---|---|---|---|---|---|---|---|---|---|---|---|---|---|---|---|---|
| 61 | 72 | 116 | 133 | 151 | 163 | 164 | Other amino acid changes | Percentage Released Fas | | | | | Amount Released Fas (ug) | | | | | |
| | | | | | | | | Linolenic | Linoleic | Oleic | Palmitic | Stearic | Linolenic | Linoleic | Oleic | Palmitic | Stearic | Total FA |
| E | K | | A | A | | | | 8.0% | 12.6% | 16.2% | 63.2% | 0.0% | 5.42 | 8.48 | 10.90 | 42.60 | 0.00 | 67.40 |
| E | K | | A | A | | | K12M | 4.4% | 7.9% | 15.9% | 71.7% | 0.0% | 2.56 | 4.55 | 9.20 | 41.40 | 0.02 | 57.73 |
| E | K | | A | A | | | K12M | 4.4% | 7.9% | 15.9% | 71.7% | 0.0% | 2.56 | 4.55 | 9.20 | 41.40 | 0.02 | 57.73 |
| E | K | | A | | | | W17L | 11.2% | 7.5% | 19.3% | 55.6% | 6.4% | 3.04 | 2.03 | 5.25 | 15.10 | 1.74 | 27.16 |
| E | K | | A | | | R | | 3.0% | 11.9% | 11.7% | 73.3% | 0.0% | 1.17 | 4.60 | 4.52 | 28.30 | 0.00 | 38.59 |
| E | K | | A | | | R | | 3.0% | 11.9% | 11.7% | 73.3% | 0.0% | 1.17 | 4.60 | 4.52 | 28.30 | 0.00 | 38.59 |
| E | K | | A | | R | | | 3.9% | 7.7% | 6.3% | 76.5% | 5.5% | 2.19 | 4.34 | 3.54 | 43.00 | 3.11 | 56.18 |
| E | E | V | A | A | | | | 2.4% | 3.9% | 3.2% | 90.5% | 0.0% | 0.46 | 0.77 | 0.63 | 17.70 | 0.00 | 19.56 |
| E | E | V | A | A | | | | 1.1% | 2.7% | 2.6% | 93.6% | 0.0% | 0.16 | 0.38 | 0.37 | 13.30 | 0.00 | 14.21 |
| E | E | V | A | | R | | | 1.2% | 2.6% | 2.6% | 93.6% | 0.0% | 0.14 | 0.29 | 0.30 | 10.70 | 0.00 | 11.43 |
| E | E | V | A | | | | A52S | 1.1% | 6.3% | 4.6% | 88.0% | 0.0% | 0.09 | 0.53 | 0.39 | 7.40 | 0.00 | 8.41 |
| E | E | V | A | | | | A52S | 7.1% | 11.2% | 24.7% | 56.6% | 0.5% | 3.04 | 4.83 | 10.60 | 24.30 | 0.19 | 42.96 |
| E | E | V | A | | | | | 2.3% | 8.2% | 3.9% | 83.8% | 1.8% | 0.24 | 0.88 | 0.42 | 8.95 | 0.19 | 10.67 |
| E | E | V | A | | | R | | 2.2% | 2.1% | 3.0% | 91.7% | 1.1% | 0.36 | 0.35 | 0.50 | 15.30 | 0.18 | 16.68 |
| E | E | V | A | | | | | 0.0% | 2.9% | 0.0% | 97.1% | 0.0% | 0.00 | 0.32 | 0.00 | 10.80 | 0.00 | 11.12 |
| E | E | V | | G | | R | | 0.2% | 12.9% | 5.0% | 82.0% | 0.0% | 0.01 | 0.53 | 0.21 | 3.39 | 0.00 | 4.14 |
| E | E | V | A | | R | | | 1.4% | 4.4% | 2.8% | 91.0% | 0.4% | 0.19 | 0.60 | 0.38 | 12.50 | 0.06 | 13.73 |
| E | E | V | A | | | | | 1.2% | 7.9% | 3.8% | 87.2% | 0.0% | 0.07 | 0.45 | 0.22 | 5.00 | 0.00 | 5.74 |
| E | E | V | A | A | | | | 0.0% | 0.0% | 0.0% | 100.0% | 0.0% | 0.00 | 0.00 | 0.00 | 0.73 | 0.00 | 0.73 |
| E | E | V | | G | | | | 0.0% | 0.0% | 0.0% | 100.0% | 0.0% | 0.00 | 0.00 | 0.00 | 2.00 | 0.00 | 2.00 |
| E | E | V | A | | R | | | 0.0% | 0.0% | 0.0% | 100.0% | 0.0% | 0.00 | 0.00 | 0.00 | 5.98 | 0.00 | 5.98 |
| E | E | V | A | A | R | | | 0.0% | 0.0% | 0.0% | 100.0% | 0.0% | 0.00 | 0.00 | 0.00 | 5.83 | 0.00 | 5.83 |
| E | E | V | A | A | R | | | 0.0% | 0.0% | 0.0% | 100.0% | 0.0% | 0.00 | 0.00 | 0.00 | 12.50 | 0.00 | 12.50 |
| E | E | V | A | | R | R | | 0.0% | 6.9% | 0.9% | 92.2% | 0.0% | 0.00 | 0.23 | 0.03 | 3.04 | 0.00 | 3.30 |
| E | E | V | | | | | | 0.0% | 0.0% | 0.0% | 100.0% | 0.0% | 0.00 | 0.00 | 0.00 | 15.00 | 0.00 | 15.00 |
| E | T | | | | R | | | 3.6% | 6.8% | 4.2% | 85.4% | 0.0% | 0.82 | 1.54 | 0.95 | 19.30 | 0.00 | 22.60 |
| E | Q | A | G | | | | | 0.0% | 17.5% | 8.2% | 74.3% | 0.0% | 0.00 | 1.17 | 0.55 | 4.98 | 0.00 | 6.70 |
| E | Q | A | G | | | | | 0.0% | 17.5% | 8.2% | 74.3% | 0.0% | 0.00 | 1.17 | 0.55 | 4.98 | 0.00 | 6.70 |
| E | A | A | G | | | | | 0.0% | 0.0% | 0.0% | 100.0% | 0.0% | 0.00 | 0.00 | 0.00 | 0.01 | 0.00 | 0.01 |

| Amino Acid - residue position number and amino acid in that position | | | | | | | | Percentage Released Fas | | | | | Amount Released Fas (ug) | | | | | |
|---|---|---|---|---|---|---|---|---|---|---|---|---|---|---|---|---|---|---|
| 61 | 72 | 116 | 133 | 151 | 163 | 164 | Other amino acid changes | Linolenic | Linoleic | Oleic | Palmitic | Stearic | Linolenic | Linoleic | Oleic | Palmitic | Stearic | Total FA |
| E | E | A | A | G | | | | 0.0% | 8.5% | 0.0% | 91.5% | 0.0% | 0.00 | 0.38 | 0.00 | 4.09 | 0.00 | 4.47 |
| E | E | A | A | A | R | | | 1.3% | 3.5% | 3.5% | 91.8% | 0.0% | 0.34 | 0.93 | 0.93 | 24.60 | 0.00 | 26.80 |
| E | E | A | A | A | R | | | 0.0% | 3.0% | 0.0% | 97.0% | 0.0% | 0.00 | 0.41 | 0.00 | 13.20 | 0.00 | 13.61 |
| E | E | A | A | A | | | | 1.4% | 4.9% | 4.0% | 87.4% | 2.3% | 0.31 | 1.11 | 0.91 | 19.90 | 0.53 | 22.76 |
| E | E | A | A | | R | | | 3.2% | 4.1% | 3.7% | 88.9% | 0.0% | 1.22 | 1.56 | 1.41 | 33.70 | 0.00 | 37.89 |
| E | E | A | A | | | | | 0.1% | 5.5% | 5.9% | 88.4% | 0.0% | 0.02 | 0.76 | 0.82 | 12.30 | 0.00 | 13.91 |
| E | E | A | A | | | | | 0.0% | 0.0% | 1.5% | 98.5% | 0.0% | 0.00 | 0.00 | 0.29 | 18.50 | 0.00 | 18.79 |
| E | E | A | | | | R | | 0.0% | 0.3% | 0.0% | 99.7% | 0.0% | 0.00 | 0.02 | 0.00 | 6.23 | 0.00 | 6.25 |
| E | E | A | | A | | R | | 11.1% | 54.2% | 26.3% | High | 8.4% | 0.99 | 4.81 | 2.33 | High | 0.74 | 8.87 |
| E | E | A | | A | | | | 0.0% | 6.3% | 4.6% | 89.1% | 0.0% | 0.00 | 0.78 | 0.57 | 11.00 | 0.00 | 12.35 |
| E | E | A | | A | | R | | 0.0% | 5.7% | 4.5% | 89.9% | 0.0% | 0.00 | 0.85 | 0.67 | 13.40 | 0.00 | 14.91 |
| E | E | A | | | R | | | 0.0% | 1.4% | 0.0% | 98.6% | 0.0% | 0.00 | 0.16 | 0.00 | 11.40 | 0.00 | 11.56 |
| E | E | A | | | R | | | 0.0% | 0.0% | 0.0% | 100.0% | 0.0% | 0.00 | 0.00 | 0.00 | 8.61 | 0.00 | 8.61 |
| E | E | A | | | R | | | 0.0% | 0.0% | 0.0% | 100.0% | 0.0% | 0.00 | 0.00 | 0.00 | 28.30 | 0.00 | 28.30 |
| E | E | | A | G | | | | 5.6% | 18.7% | 11.5% | 61.3% | 2.8% | 2.86 | 9.52 | 5.86 | 31.20 | 1.44 | 50.88 |
| E | E | | A | G | | | | 0.0% | 0.0% | 0.0% | 100.0% | 0.0% | 0.00 | 0.00 | 0.00 | 0.94 | 0.00 | 0.94 |
| E | E | | A | A | R | | | 0.3% | 10.6% | 12.8% | 76.2% | 0.0% | 0.06 | 1.90 | 2.29 | 13.60 | 0.00 | 17.85 |
| E | E | | A | A | R | | P18S,A21V | 2.2% | 7.7% | 3.3% | 83.7% | 3.2% | 0.24 | 0.87 | 0.37 | 9.43 | 0.36 | 11.26 |
| E | E | | A | A | R | | | 0.3% | 10.6% | 12.8% | 76.2% | 0.0% | 0.06 | 1.90 | 2.29 | 13.60 | 0.00 | 17.85 |
| E | E | | A | A | R | | | 0.3% | 10.6% | 12.8% | 76.2% | 0.0% | 0.06 | 1.90 | 2.29 | 13.60 | 0.00 | 17.85 |
| E | E | | A | A | R | | | 0.1% | 12.0% | 4.3% | 83.6% | 0.0% | 0.02 | 2.74 | 0.99 | 19.10 | 0.00 | 22.85 |
| E | E | | A | A | R | | | 0.1% | 12.0% | 4.3% | 83.6% | 0.0% | 0.02 | 2.74 | 0.99 | 19.10 | 0.00 | 22.85 |
| E | E | | A | A | R | | K12M | 3.0% | 10.0% | 12.4% | 71.8% | 2.7% | 0.82 | 2.69 | 3.36 | 19.40 | 0.73 | 27.00 |
| E | E | | A | A | R | | K12M | 3.0% | 10.0% | 12.4% | 71.8% | 2.7% | 0.82 | 2.69 | 3.36 | 19.40 | 0.73 | 27.00 |
| E | E | | | G | R | | | 0.0% | 18.2% | 5.5% | 76.4% | 0.0% | 0.00 | 1.47 | 0.44 | 6.18 | 0.00 | 8.09 |
| E | E | | | G | | R | | 12.8% | 9.1% | 15.4% | 60.3% | 2.4% | 4.47 | 3.19 | 5.40 | 21.10 | 0.84 | 35.00 |
| E | E | A | | G | R | | | 0.2% | 10.5% | 10.0% | 79.4% | 0.0% | 0.05 | 3.53 | 3.35 | 26.70 | 0.00 | 33.63 |
| E | E | | | G | R | | F65V | 0.0% | 0.0% | 2.1% | 84.0% | 13.9% | 0.00 | 0.00 | 0.51 | 20.40 | 3.37 | 24.28 |
| E | E | | | G | R | | F65V | 0.0% | 0.0% | 2.1% | 84.0% | 13.9% | 0.00 | 0.00 | 0.51 | 20.40 | 3.37 | 24.28 |

Figure 8-15

| Amino Acid - residue position number and amino acid in that position | | | | | | | | Other amino acid changes | Primary Screen | | | | | | | | | | |
|---|---|---|---|---|---|---|---|---|---|---|---|---|---|---|---|---|---|---|---|
| | | | | | | | | | Percentage Released Fas | | | | | | Amount Released Fas (ug) | | | | |
| 61 | 72 | 116 | 133 | 151 | 163 | 164 | | | Linolenic | Linoleic | Oleic | Palmitic | Stearic | Linolenic | Linoleic | Oleic | Palmitic | Stearic | Total FA |
| E | | V | A | G | R | | | | 1.8% | 9.3% | 4.3% | 83.8% | 0.9% | 0.11 | 0.57 | 0.26 | 5.13 | 0.05 | 6.12 |
| E | | V | A | G | | | | | 1.4% | 12.3% | 5.4% | 80.9% | 0.0% | 0.07 | 0.64 | 0.28 | 4.18 | 0.00 | 5.17 |
| E | | V | A | A | R | | | | 2.6% | 5.9% | 5.8% | 85.7% | 0.0% | 0.56 | 1.25 | 1.24 | 18.30 | 0.00 | 21.35 |
| E | | V | A | A | R | | | | 0.0% | 1.6% | 0.0% | 98.4% | 0.0% | 0.00 | 0.09 | 0.00 | 5.58 | 0.00 | 5.67 |
| E | | V | A | A | R | | | | 2.9% | 6.4% | 3.8% | 85.8% | 1.1% | 0.80 | 1.76 | 1.04 | 23.70 | 0.31 | 27.62 |
| E | | V | A | A | R | | | | 0.0% | 0.0% | 0.0% | 100.0% | 0.0% | 0.00 | 0.00 | 0.00 | 9.14 | 0.00 | 9.14 |
| E | | V | A | A | | | | | 0.0% | 0.0% | 0.0% | 100.0% | 0.0% | 0.00 | 0.00 | 0.00 | 9.13 | 0.00 | 9.13 |
| E | | V | A | | R | | | | 2.3% | 4.8% | 3.5% | 88.3% | 1.0% | 0.36 | 0.73 | 0.55 | 13.60 | 0.16 | 15.40 |
| E | | V | A | | R | | | | 1.9% | 4.0% | 3.1% | 90.9% | 0.0% | 0.84 | 1.77 | 1.37 | 39.90 | 0.00 | 43.88 |
| E | | V | A | | | | | | 0.0% | 0.0% | 0.0% | 100.0% | 0.0% | 0.00 | 0.00 | 0.00 | 8.55 | 0.00 | 8.55 |
| E | | V | | A | R | | | | 0.0% | 2.5% | 0.0% | 97.5% | 0.0% | 0.00 | 0.33 | 0.00 | 12.60 | 0.00 | 12.93 |
| E | | V | | | R | | | | 18.2% | 39.1% | 29.5% | High | 13.2% | 0.47 | 1.01 | 0.76 | High | 0.34 | 2.58 |
| E | | V | | | | | | | 0.0% | 2.9% | 0.0% | 97.1% | 0.0% | 0.00 | 0.24 | 0.00 | 7.89 | 0.00 | 8.13 |
| E | | Q | | | | | | | 6.4% | 8.1% | 14.7% | 70.6% | 0.2% | 2.57 | 3.28 | 5.92 | 28.40 | 0.08 | 40.25 |
| E | | Q | A | | | R | | | 8.9% | 5.3% | 25.6% | 57.2% | 2.9% | 1.92 | 1.15 | 5.51 | 12.30 | 0.63 | 21.51 |
| E | | Q | | | R | | | | 1.4% | 7.1% | 5.8% | 85.7% | 0.0% | 0.32 | 1.63 | 1.33 | 19.60 | 0.00 | 22.88 |
| E | | A | A | G | R | | | | 0.0% | 0.9% | 0.0% | 99.1% | 0.0% | 0.00 | 0.08 | 0.00 | 8.13 | 0.00 | 8.21 |
| E | | A | A | | | | | | 0.0% | 11.4% | 1.3% | 87.3% | 0.0% | 0.00 | 0.31 | 0.04 | 2.36 | 0.00 | 2.70 |
| E | | A | | | | | | | 0.0% | 3.2% | 5.2% | 91.5% | 0.0% | 0.00 | 0.75 | 1.21 | 21.10 | 0.00 | 23.06 |
| E | | A | | | R | | | | 0.0% | 13.2% | 0.0% | 86.8% | 0.0% | 0.00 | 0.22 | 0.00 | 1.45 | 0.00 | 1.67 |
| E | | A | | A | R | | | | 2.7% | 6.1% | 4.5% | 86.0% | 0.6% | 1.90 | 4.28 | 3.17 | 60.20 | 0.42 | 69.97 |
| E | | A | | A | | | | | 0.0% | 7.5% | 4.3% | 88.3% | 0.0% | 0.00 | 0.75 | 0.43 | 8.86 | 0.00 | 10.04 |
| E | | A | | A | | | | | 0.0% | 0.0% | 0.0% | 100.0% | 0.0% | 0.00 | 0.00 | 0.00 | 11.80 | 0.00 | 11.80 |
| E | | A | | | | | G132V | | 2.5% | 5.1% | 3.9% | 88.4% | 0.0% | 0.06 | 0.12 | 0.09 | 2.00 | 0.00 | 2.26 |
| E | | A | | | R | | | | 0.0% | 9.1% | 5.5% | 84.8% | 0.6% | 0.00 | 1.44 | 0.87 | 13.40 | 0.09 | 15.80 |
| E | | | G | | | R | K12M | | 9.4% | 24.0% | 20.5% | 40.6% | 5.5% | 6.69 | 17.00 | 14.50 | 28.80 | 3.89 | 70.88 |
| E | | | G | | | R | K12M | | 9.4% | 24.0% | 20.5% | 40.6% | 5.5% | 6.69 | 17.00 | 14.50 | 28.80 | 3.89 | 70.88 |
| E | | | A | | | | A15S | | 8.5% | 15.4% | 18.9% | 53.7% | 3.5% | 9.98 | 18.00 | 22.10 | 62.70 | 4.03 | 116.81 |

| Amino Acid - residue position number and amino acid in that position | | | | | | | | Primary Screen | | | | | | | | | | |
|---|---|---|---|---|---|---|---|---|---|---|---|---|---|---|---|---|---|---|
| | | | | | | | | Percentage Released Fas | | | | | Amount Released Fas (ug) | | | | | |
| 61 | 72 | 116 | 133 | 151 | 163 | 164 | Other amino acid changes | Linolenic | Linoleic | Oleic | Palmitic | Stearic | Linolenic | Linoleic | Oleic | Palmitic | Stearic | Total FA |
| E | | | | A | | | | | | | | | | | | | | |
| E | | Q | | A | R | | | 2.3% | 6.6% | 6.7% | 82.3% | 2.1% | 2.29 | 6.75 | 6.81 | 83.60 | 2.09 | 101.54 |
| E | | Q | | | R | | | 2.3% | 6.6% | 6.7% | 82.3% | 2.1% | 2.29 | 6.75 | 6.81 | 83.60 | 2.09 | 101.54 |
| E | | Q | A | G | | R | | Low | Low | Low | High | Low | 0.00 | 0.00 | 0.00 | High | 0.00 | 0.00 |
| E | | Q | A | G | | R | | Low | Low | Low | High | Low | 0.00 | 0.00 | 0.00 | High | 0.00 | 0.00 |
| E | | | | | R | | | 3.7% | 8.4% | 8.2% | 79.7% | 0.0% | 3.20 | 7.17 | 6.97 | 68.00 | 0.00 | 85.34 |
| E | | | | | R | | | 3.7% | 8.4% | 8.2% | 79.7% | 0.0% | 3.20 | 7.17 | 6.97 | 68.00 | 0.00 | 85.34 |
| E | | | A | | | R | | 4.9% | 8.6% | 9.9% | 76.5% | 0.0% | 2.92 | 5.12 | 5.91 | 45.50 | 0.00 | 59.45 |
| E | | | A | | | R | | 4.9% | 8.6% | 9.9% | 76.5% | 0.0% | 2.92 | 5.12 | 5.91 | 45.50 | 0.00 | 59.45 |
| E | | | A | | R | | | 4.5% | 9.7% | 10.7% | 72.9% | 2.2% | 6.00 | 12.90 | 14.30 | 97.00 | 2.89 | 133.09 |
| E | | | A | | R | | | 4.5% | 9.7% | 10.7% | 72.9% | 2.2% | 6.00 | 12.90 | 14.30 | 97.00 | 2.89 | 133.09 |
| A | K | V | A | A | R | | | 0.3% | 6.6% | 3.1% | 90.0% | 0.0% | 0.02 | 0.39 | 0.18 | 5.33 | 0.00 | 5.92 |
| A | K | V | A | A | R | | | 0.0% | 1.5% | 0.0% | 98.5% | 0.0% | 0.00 | 0.12 | 0.00 | 7.53 | 0.00 | 7.65 |
| A | K | V | A | A | | | | 0.0% | 0.0% | 0.0% | 100.0% | 0.0% | 0.00 | 0.00 | 0.00 | 8.48 | 0.00 | 8.48 |
| A | K | V | A | A | | | | 0.0% | 0.0% | 0.0% | 100.0% | 0.0% | 0.00 | 0.00 | 0.00 | 5.67 | 0.00 | 5.67 |
| A | K | V | A | | | | | 0.0% | 0.0% | 0.0% | 100.0% | 0.0% | 0.00 | 0.00 | 0.00 | 8.05 | 0.00 | 8.05 |
| A | K | V | | | | R | | 0.0% | 0.0% | 0.0% | 100.0% | 0.0% | 0.00 | 0.00 | 0.00 | 12.70 | 0.00 | 12.70 |
| A | K | V | | A | R | | | 1.7% | 4.7% | 4.4% | 87.5% | 1.7% | 0.44 | 1.19 | 1.12 | 22.30 | 0.43 | 25.48 |
| A | K | V | | A | R | | | 0.0% | 0.7% | 0.0% | 99.3% | 0.0% | 0.00 | 0.07 | 0.00 | 9.38 | 0.00 | 9.45 |
| A | K | V | | | R | | | 1.6% | 7.2% | 3.5% | 87.7% | 0.0% | 0.15 | 0.68 | 0.33 | 8.21 | 0.00 | 9.37 |
| A | K | V | | | | R | | 2.4% | 7.7% | 4.1% | 84.8% | 0.9% | 0.35 | 1.16 | 0.62 | 12.70 | 0.14 | 14.97 |
| A | K | V | | | | | | 3.9% | 9.5% | 5.3% | 80.5% | 0.8% | 0.60 | 1.44 | 0.80 | 12.20 | 0.12 | 15.16 |
| A | K | T | | | | | | 0.0% | 2.2% | 0.0% | 97.8% | 0.0% | 0.00 | 0.17 | 0.00 | 7.70 | 0.00 | 7.87 |
| A | K | T | A | A | | | | 4.8% | 8.0% | 12.9% | 74.4% | 0.0% | 1.02 | 1.69 | 2.74 | 15.80 | 0.00 | 21.25 |
| A | K | T | A | A | | | | 4.8% | 8.0% | 12.9% | 74.4% | 0.0% | 1.02 | 1.69 | 2.74 | 15.80 | 0.00 | 21.25 |
| A | K | T | | | R | | | 1.6% | 11.9% | 6.6% | 79.9% | 0.0% | 0.47 | 3.49 | 1.92 | 23.40 | 0.00 | 29.28 |
| A | K | T | | | R | | | 1.6% | 11.9% | 6.6% | 79.9% | 0.0% | 0.47 | 3.49 | 1.92 | 23.40 | 0.00 | 29.28 |
| A | K | Q | A | G | | | A48S | | | | | | | | | | | |

Figure 8-18

| Amino Acid - residue position number and amino acid in that position ||||||||| Primary Screen |||||||||
|---|---|---|---|---|---|---|---|---|---|---|---|---|---|---|---|---|
| | | | | | | | | Other amino | Percentage Released Fas |||||| Amount Released Fas (ug) ||||
| 61 | 72 | 116 | 133 | 151 | 163 | 164 | acid changes | Linolenic | Linoleic | Oleic | Palmitic | Stearic | Linolenic | Linoleic | Oleic | Palmitic | Stearic | Total FA |
| A | K | Q | | G | R | | | 1.3% | 4.5% | 4.2% | 89.9% | 0.0% | 0.69 | 2.43 | 2.27 | 48.20 | 0.00 | 53.59 |
| A | K | Q | | G | R | | | 1.3% | 4.5% | 4.2% | 89.9% | 0.0% | 0.69 | 2.43 | 2.27 | 48.20 | 0.00 | 53.59 |
| A | K | | A | | R | | | 2.4% | 6.6% | 3.2% | 87.8% | 0.0% | 1.22 | 3.27 | 1.61 | 43.80 | 0.00 | 49.90 |
| A | K | | A | | R | | | 1.6% | 3.7% | 2.3% | 92.3% | 0.0% | 0.94 | 2.20 | 1.38 | 54.40 | 0.00 | 58.92 |
| A | K | | A | | R | | | 1.6% | 7.6% | 5.1% | 85.7% | 0.0% | 0.14 | 0.68 | 0.46 | 7.62 | 0.00 | 8.90 |
| A | K | | A | | R | | | 0.0% | 0.0% | 0.0% | 100.0% | 0.0% | 0.00 | 0.00 | 0.00 | 14.90 | 0.00 | 14.90 |
| A | K | | A | A | | | | 3.3% | 8.2% | 7.1% | 80.5% | 0.9% | 0.38 | 0.95 | 0.83 | 9.36 | 0.11 | 11.62 |
| A | K | | A | A | | | | 2.0% | 7.9% | 5.6% | 84.6% | 0.0% | 0.21 | 0.81 | 0.57 | 8.70 | 0.00 | 10.29 |
| A | K | | A | | | R | | 0.0% | 6.7% | 3.7% | 89.6% | 0.0% | 0.00 | 1.09 | 0.59 | 14.50 | 0.00 | 16.18 |
| A | K | | A | G | | R | | 5.0% | 4.7% | 17.5% | 72.8% | 0.0% | 1.44 | 1.35 | 5.05 | 21.00 | 0.00 | 28.84 |
| A | K | | A | G | | R | | 5.0% | 4.7% | 17.5% | 72.8% | 0.0% | 1.44 | 1.35 | 5.05 | 21.00 | 0.00 | 28.84 |
| A | K | | A | A | R | | A48S | 0.3% | 12.7% | 9.3% | 77.6% | 0.0% | 0.09 | 3.63 | 2.66 | 22.10 | 0.00 | 28.48 |
| A | K | | A | A | R | | A48S | 0.3% | 12.7% | 9.3% | 77.6% | 0.0% | 0.09 | 3.63 | 2.66 | 22.10 | 0.00 | 28.48 |
| A | K | | A | A | R | | | 0.3% | 12.7% | 9.3% | 77.6% | 0.0% | 0.09 | 3.63 | 2.66 | 22.10 | 0.00 | 28.48 |
| A | K | | A | | R | | | 3.4% | 8.7% | 11.8% | 76.1% | 0.0% | 1.28 | 3.29 | 4.49 | 28.90 | 0.00 | 37.96 |
| A | K | | A | | R | | | 3.4% | 8.7% | 11.8% | 76.1% | 0.0% | 1.28 | 3.29 | 4.49 | 28.90 | 0.00 | 37.96 |
| A | K | | | A | R | | | 1.8% | 10.0% | 3.7% | 83.8% | 0.6% | 0.19 | 1.04 | 0.39 | 8.70 | 0.06 | 10.38 |
| A | K | | | | R | | K12M | 13.4% | 5.3% | 21.4% | 51.1% | 8.8% | 3.70 | 1.46 | 5.90 | 14.10 | 2.42 | 27.58 |
| A | K | | | | R | | | 9.0% | 16.7% | 17.4% | 51.6% | 5.3% | 3.74 | 6.92 | 7.21 | 21.40 | 2.21 | 41.48 |
| A | K | | | A | R | | | 0.0% | 10.0% | 7.6% | 82.4% | 0.0% | 0.00 | 1.82 | 1.38 | 15.00 | 0.00 | 18.20 |
| A | K | | | A | R | | | 0.0% | 10.0% | 7.6% | 82.4% | 0.0% | 0.00 | 1.82 | 1.38 | 15.00 | 0.00 | 18.20 |
| A | K | | | A | R | | | 1.6% | 3.9% | 18.7% | 75.8% | 0.0% | 0.59 | 1.42 | 6.76 | 27.40 | 0.00 | 36.17 |
| A | K | | | A | R | | | 1.6% | 3.9% | 18.7% | 75.8% | 0.0% | 0.59 | 1.42 | 6.76 | 27.40 | 0.00 | 36.17 |
| A | E | V | A | G | | R | G99C | 2.5% | 5.6% | 4.6% | 87.0% | 0.4% | 0.57 | 1.29 | 1.06 | 20.20 | 0.09 | 23.21 |
| A | E | V | A | A | R | | | 0.6% | 2.3% | 3.1% | 94.0% | 0.0% | 0.12 | 0.43 | 0.59 | 17.80 | 0.00 | 18.94 |
| A | E | V | A | A | | | | 0.0% | 0.0% | 0.0% | 100.0% | 0.0% | 0.00 | 0.00 | 0.00 | 7.03 | 0.00 | 7.03 |
| A | E | V | A | | R | | | 1.7% | 4.4% | 2.8% | 90.9% | 0.3% | 0.20 | 0.52 | 0.34 | 10.90 | 0.03 | 12.00 |
| A | E | V | A | | R | | | 0.1% | 1.0% | 1.0% | 98.0% | 0.0% | 0.01 | 0.15 | 0.14 | 14.10 | 0.00 | 14.39 |

Figure 8-19

| Amino Acid - residue position number and amino acid in that position | | | | | | | | Primary Screen | | | | | | | | | | |
|---|---|---|---|---|---|---|---|---|---|---|---|---|---|---|---|---|---|---|
| | | | | | | | | Percentage Released Fas | | | | | Amount Released Fas (ug) | | | | | |
| 61 | 72 | 116 | 133 | 151 | 163 | 164 | Other amino acid changes | Linolenic | Linoleic | Oleic | Palmitic | Stearic | Linolenic | Linoleic | Oleic | Palmitic | Stearic | Total FA |
| A | E | V | A | | R | | | 0.0% | 0.0% | 0.0% | 100.0% | 0.0% | 0.00 | 0.00 | 0.00 | 0.62 | 0.00 | 0.62 |
| A | E | V | A | | | | | 0.0% | 0.0% | 0.0% | 100.0% | 0.0% | 0.00 | 0.00 | 0.00 | 3.97 | 0.00 | 3.97 |
| A | E | V | | G | | | | 0.0% | 11.2% | 2.6% | 86.1% | 0.0% | 0.00 | 0.46 | 0.11 | 3.56 | 0.00 | 4.13 |
| A | E | V | | A | R | | | 0.5% | 0.0% | 0.0% | 99.5% | 0.0% | 0.04 | 0.00 | 0.00 | 9.40 | 0.00 | 9.44 |
| A | E | V | | A | R | | | 0.1% | 0.0% | 1.2% | 98.7% | 0.0% | 0.02 | 0.00 | 0.12 | 10.10 | 0.00 | 10.23 |
| A | E | V | | A | R | | | 1.2% | 2.2% | 1.1% | 95.5% | 0.0% | 0.20 | 0.35 | 0.17 | 15.20 | 0.00 | 15.92 |
| A | E | V | | A | R | | | 0.0% | 0.0% | 0.0% | 100.0% | 0.0% | 0.00 | 0.00 | 0.00 | 9.77 | 0.00 | 9.77 |
| A | E | V | | A | | R | | 2.9% | 9.7% | 5.3% | 82.1% | 0.0% | 0.31 | 1.04 | 0.57 | 8.80 | 0.00 | 10.72 |
| A | E | V | | A | | R | | 0.0% | 1.3% | 0.0% | 98.7% | 0.0% | 0.00 | 0.09 | 0.00 | 6.64 | 0.00 | 6.73 |
| A | E | V | | | R | | | 1.5% | 4.6% | 3.3% | 89.2% | 1.4% | 0.59 | 1.87 | 1.32 | 36.10 | 0.58 | 40.46 |
| A | E | V | | | | | | 0.0% | 0.0% | 0.0% | 100.0% | 0.0% | 0.00 | 0.00 | 0.00 | 10.90 | 0.00 | 10.90 |
| A | E | Q | A | | R | | | 1.4% | 8.5% | 3.0% | 87.2% | 0.0% | 0.21 | 1.28 | 0.45 | 13.20 | 0.00 | 15.14 |
| A | E | Q | | G | | | | | | | | | | | | | | |
| A | E | Q | | G | | | | | | | | | | | | | | |
| A | E | Q | | G | | R | | 4.2% | 1.2% | 94.6% | 0.0% | 94.6% | 0.10 | 0.03 | 2.27 | 0.00 | 2.40 | 37.86 |
| A | E | A | A | | | | | 1.1% | 1.9% | 2.5% | 92.2% | 2.3% | 0.44 | 0.70 | 0.96 | 34.90 | 0.86 | 37.86 |
| A | E | A | A | | | | | 1.4% | 8.1% | 5.4% | 85.0% | 0.0% | 0.11 | 0.62 | 0.42 | 6.53 | 0.00 | 7.68 |
| A | E | A | A | | R | | | 0.0% | 1.6% | 1.3% | 97.1% | 0.0% | 0.00 | 0.35 | 0.29 | 21.20 | 0.00 | 21.84 |
| A | E | A | A | | R | | | 0.0% | 7.1% | 4.6% | 88.3% | 0.0% | 0.00 | 1.02 | 0.66 | 12.70 | 0.00 | 14.38 |
| A | E | A | | | | R | | 0.0% | 3.4% | 0.0% | 96.6% | 0.0% | 0.00 | 0.03 | 0.00 | 0.73 | 0.00 | 0.76 |
| A | E | A | | G | | | | 0.0% | 0.0% | 0.0% | 100.0% | 0.0% | 0.00 | 0.00 | 0.00 | 11.40 | 0.00 | 11.40 |
| A | E | A | | A | R | | | 0.0% | 0.0% | 0.0% | 100.0% | 0.0% | 0.00 | 0.00 | 0.00 | 8.22 | 0.00 | 8.22 |
| A | E | A | | A | | | | 0.0% | 0.0% | 0.0% | 100.0% | 0.0% | 0.00 | 0.00 | 0.00 | 12.00 | 0.00 | 12.00 |
| A | E | | | | | | | 10.3% | 7.0% | 23.5% | 58.2% | 0.9% | 2.56 | 1.73 | 5.82 | 14.40 | 0.23 | 24.74 |
| A | E | | | | R | | | 3.9% | 10.4% | 7.6% | 77.1% | 1.0% | 1.09 | 2.92 | 2.12 | 21.60 | 0.28 | 28.01 |
| A | E | | | | R | | K12M | 3.9% | 10.4% | 7.6% | 77.1% | 1.0% | 1.09 | 2.92 | 2.12 | 21.60 | 0.28 | 28.01 |
| A | E | | | A | R | | K12M | 4.4% | 5.5% | 9.5% | 80.6% | 0.0% | 1.83 | 2.31 | 4.00 | 33.90 | 0.00 | 42.04 |
| A | E | | | A | R | | | 4.4% | 5.5% | 9.5% | 80.6% | 0.0% | 1.83 | 2.31 | 4.00 | 33.90 | 0.00 | 42.04 |
| A | V | | | A | R | | | 1.4% | 0.9% | 2.4% | 95.3% | 0.0% | 0.27 | 0.19 | 0.48 | 18.90 | 0.00 | 19.83 |

| Amino Acid - residue position number and amino acid in that position | | | | | | | | Primary Screen | | | | | | | | | | |
|---|---|---|---|---|---|---|---|---|---|---|---|---|---|---|---|---|---|---|
| | | | | | | | | Percentage Released Fas | | | | | Amount Released Fas (ug) | | | | | |
| 61 | 72 | 116 | 133 | 151 | 163 | 164 | Other amino acid changes | Linolenic | Linoleic | Oleic | Palmitic | Stearic | Linolenic | Linoleic | Oleic | Palmitic | Stearic | Total FA |
| A | | | A | A | | | | 0.0% | 0.0% | 0.0% | 100.0% | 0.0% | 0.00 | 0.00 | 0.00 | 9.82 | 0.00 | 9.82 |
| A | V | | A | A | | | | 0.0% | 0.0% | 0.0% | 100.0% | 0.0% | 0.00 | 0.00 | 0.00 | 11.30 | 0.00 | 11.30 |
| A | V | | A | | R | | | 3.1% | 5.4% | 2.9% | 87.4% | 1.2% | 0.38 | 0.65 | 0.35 | 10.60 | 0.15 | 12.13 |
| A | V | | A | | R | | | 3.1% | 5.1% | 4.0% | 87.8% | 0.0% | 1.41 | 2.34 | 1.85 | 40.40 | 0.00 | 46.00 |
| A | V | | A | | R | | | 0.0% | 0.0% | 0.0% | 100.0% | 0.0% | 0.00 | 0.00 | 0.00 | 8.05 | 0.00 | 8.05 |
| A | V | | A | | | R | | 3.3% | 6.7% | 5.0% | 85.0% | 0.0% | 0.98 | 1.98 | 1.50 | 25.30 | 0.00 | 29.76 |
| A | V | | A | | | R | | 0.0% | 5.3% | 2.0% | 92.7% | 0.0% | 0.00 | 0.74 | 0.28 | 12.80 | 0.00 | 13.81 |
| A | V | | A | | | R | | 0.0% | 0.0% | 0.0% | 100.0% | 0.0% | 0.00 | 0.00 | 0.00 | 13.90 | 0.00 | 13.90 |
| A | V | | A | | | R | | 0.0% | 0.0% | 0.0% | 100.0% | 0.0% | 0.00 | 0.00 | 0.00 | 22.80 | 0.00 | 22.80 |
| A | V | | A | | | R | | 0.0% | 0.0% | 0.0% | 100.0% | 0.0% | 0.00 | 0.00 | 0.00 | 5.39 | 0.00 | 5.39 |
| A | V | | A | | | R | | 0.0% | 0.0% | 0.0% | 100.0% | 0.0% | 0.00 | 0.00 | 0.00 | 5.39 | 0.00 | 5.39 |
| A | V | | | G | R | | | 0.0% | 0.0% | 0.0% | 100.0% | 0.0% | 0.00 | 0.00 | 0.00 | 1.21 | 0.00 | 1.21 |
| A | V | | | A | | R | | 2.8% | 9.6% | 6.2% | 81.4% | 0.0% | 0.29 | 0.98 | 0.64 | 8.31 | 0.00 | 10.21 |
| A | V | | | | | R | | 2.5% | 5.4% | 5.2% | 86.5% | 0.4% | 1.16 | 2.48 | 2.39 | 39.80 | 0.21 | 46.04 |
| A | V | | | | | R | | 0.0% | 6.2% | 0.7% | 93.2% | 0.0% | 0.00 | 0.82 | 0.09 | 12.40 | 0.00 | 13.31 |
| A | V | | | | | | | 0.0% | 0.0% | 0.0% | 100.0% | 0.0% | 0.00 | 0.00 | 0.00 | 8.62 | 0.00 | 8.62 |
| A | V | | | | | R | | 0.0% | 0.8% | 0.0% | 99.2% | 0.0% | 0.00 | 0.06 | 0.00 | 15.40 | 0.00 | 15.40 |
| A | V | | | | | | V22D | 0.0% | 0.0% | 0.0% | 100.0% | 0.0% | 0.00 | 0.00 | 0.00 | 7.27 | 0.00 | 7.33 |
| A | V | | | | | R | | 0.0% | 0.0% | 0.0% | 100.0% | 0.0% | 0.00 | 0.00 | 0.00 | 0.85 | 0.00 | 0.85 |
| A | T | | | | | | D138E,K213E | 18.1% | 44.5% | 28.1% | High | 9.3% | 0.42 | 1.04 | 0.66 | High | 0.22 | 2.34 |
| A | Q | | A | A | R | | | 3.9% | 8.9% | 6.2% | 77.1% | 4.0% | 3.33 | 7.59 | 5.26 | 65.70 | 3.38 | 85.26 |
| A | A | | A | G | | R | | 0.0% | 0.0% | 0.0% | 100.0% | 0.0% | 0.00 | 0.00 | 0.00 | 3.72 | 0.00 | 3.72 |
| A | A | | | | R | | K146N | 16.4% | 41.1% | 28.3% | High | 14.2% | 0.56 | 1.39 | 0.96 | High | 0.48 | 3.38 |
| A | A | | A | | | | | 0.0% | 0.0% | 3.1% | 96.9% | 0.0% | 0.00 | 0.00 | 0.57 | 17.70 | 0.00 | 18.27 |
| A | A | | A | A | | | | 13.9% | 39.1% | 35.5% | High | 11.4% | 0.62 | 1.75 | 1.59 | High | 0.51 | 4.47 |
| A | A | | | A | | | | 0.0% | 7.7% | 5.6% | 86.6% | 0.0% | 0.00 | 0.98 | 0.71 | 10.90 | 0.00 | 12.58 |
| A | A | | | A | R | | | 0.0% | 2.5% | 0.8% | 96.7% | 0.0% | 0.00 | 0.43 | 0.14 | 16.50 | 0.00 | 17.07 |
| A | A | | A | | R | | | 10.3% | 8.7% | 14.8% | 58.5% | 7.7% | 2.66 | 2.25 | 3.83 | 15.10 | 1.99 | 25.83 |
| A | | | A | | R | | S54L | 4.1% | 11.2% | 11.3% | 70.6% | 2.8% | 1.96 | 5.43 | 5.45 | 34.10 | 1.35 | 48.29 |

| Amino Acid - residue position number and amino acid in that position | | | | | | | | Other amino acid changes | Percentage Released Fas | | | | | Amount Released Fas (ug) | | | | | |
|---|---|---|---|---|---|---|---|---|---|---|---|---|---|---|---|---|---|---|---|
| 61 | 72 | 116 | 133 | 151 | 163 | 164 | | Linolenic | Linoleic | Oleic | Palmitic | Stearic | Linolenic | Linoleic | Oleic | Palmitic | Stearic | Total FA |
| A | | | A | A | R | | S54L | 4.1% | 11.2% | 11.3% | 70.6% | 2.8% | 1.96 | 5.43 | 5.45 | 34.10 | 1.35 | 48.29 |
| A | | | A | A | R | | K12M | 2.2% | 13.6% | 12.0% | 72.1% | 0.0% | 0.42 | 2.57 | 2.27 | 13.60 | 0.00 | 18.86 |
| A | | | A | A | R | | K12M | 2.2% | 13.6% | 12.0% | 72.1% | 0.0% | 0.42 | 2.57 | 2.27 | 13.60 | 0.00 | 18.86 |
| | K | V | A | G | | | | 2.9% | 5.8% | 4.1% | 87.2% | 0.0% | 1.23 | 2.44 | 1.70 | 36.50 | 0.00 | 41.87 |
| | K | V | A | G | | | | Low | Low | Low | Low | Low | 0.00 | 0.00 | 0.00 | 0.00 | 0.00 | 0.00 |
| | K | V | A | A | R | | | 0.0% | 0.0% | 0.0% | 100.0% | 0.0% | 0.00 | 0.00 | 0.00 | 4.18 | 0.00 | 4.18 |
| | K | V | A | A | R | | | 0.0% | 0.0% | 0.0% | 100.0% | 0.0% | 0.00 | 0.00 | 0.00 | 4.07 | 0.00 | 4.07 |
| | K | V | A | A | | | | 0.0% | 0.0% | 0.0% | 100.0% | 0.0% | 0.00 | 0.00 | 0.00 | 4.64 | 0.00 | 4.64 |
| | K | V | A | | R | A141T | | 1.2% | 6.0% | 3.8% | 89.0% | 0.0% | 0.11 | 0.53 | 0.33 | 7.76 | 0.00 | 8.72 |
| | K | V | A | | R | | | 0.0% | 0.0% | 0.0% | 100.0% | 0.0% | 0.00 | 0.00 | 0.00 | 7.10 | 0.00 | 7.10 |
| | K | V | A | | R | | | 0.0% | 0.0% | 0.0% | 100.0% | 0.0% | 0.00 | 0.00 | 0.00 | 23.50 | 0.00 | 23.50 |
| | K | V | A | | | V62F | | 0.0% | 0.0% | 0.0% | 100.0% | 0.0% | 0.00 | 0.00 | 0.00 | 6.40 | 0.00 | 6.40 |
| | K | V | A | | | P162S | | 2.2% | 6.7% | 3.8% | 87.3% | 0.0% | 1.00 | 3.03 | 1.71 | 39.30 | 0.00 | 45.04 |
| | K | V | | G | | R | | 0.0% | 0.0% | 0.0% | 100.0% | 0.0% | 0.00 | 0.00 | 0.00 | 0.52 | 0.00 | 0.52 |
| | K | V | A | A | R | | | 1.3% | 4.9% | 3.0% | 89.5% | 1.4% | 0.16 | 0.63 | 0.38 | 11.40 | 0.17 | 12.74 |
| | K | V | A | A | R | | | 1.2% | 5.5% | 2.0% | 91.3% | 0.0% | 0.29 | 1.31 | 0.47 | 21.60 | 0.00 | 23.67 |
| | K | V | A | A | | | | 1.7% | 4.4% | 3.5% | 90.4% | 0.0% | 0.36 | 0.92 | 0.72 | 18.80 | 0.00 | 20.80 |
| | K | V | A | A | | R | | 0.0% | 0.0% | 0.0% | 100.0% | 0.0% | 0.00 | 0.00 | 0.00 | 5.77 | 0.00 | 5.77 |
| | K | V | A | A | | | | 0.0% | 0.0% | 0.0% | 100.0% | 0.0% | 0.00 | 0.00 | 0.00 | 9.05 | 0.00 | 9.05 |
| | K | V | A | | R | | | 0.6% | 7.2% | 3.1% | 89.2% | 0.0% | 0.06 | 0.79 | 0.34 | 9.83 | 0.00 | 11.02 |
| | K | V | A | | R | A35V | | 0.0% | 0.0% | 0.0% | 100.0% | 0.0% | 0.00 | 0.00 | 0.00 | 21.10 | 0.00 | 21.10 |
| | K | V | A | | R | | | 0.2% | 6.1% | 1.6% | 92.2% | 0.0% | 0.01 | 0.31 | 0.08 | 4.72 | 0.00 | 5.12 |
| | K | V | A | | | | | 3.4% | 6.2% | 4.6% | 85.8% | 0.0% | 1.33 | 2.44 | 1.80 | 33.60 | 0.00 | 39.17 |
| | K | V | A | | | | | 0.0% | 7.4% | 0.1% | 92.6% | 0.0% | 0.00 | 0.99 | 0.01 | 12.40 | 0.00 | 13.40 |
| | K | V | A | | | | | 0.0% | 0.0% | 0.0% | 100.0% | 0.0% | 0.00 | 0.00 | 0.00 | 0.75 | 0.00 | 0.75 |
| | K | T | A | G | | | | 2.3% | 8.6% | 4.1% | 84.9% | 0.0% | 1.25 | 4.56 | 2.20 | 45.20 | 0.00 | 53.21 |
| | K | Q | A | | R | | | 0.6% | 5.1% | 3.6% | 90.4% | 0.3% | 0.16 | 1.30 | 0.90 | 22.90 | 0.07 | 25.33 |
| | K | Q | A | A | R | | | 0.0% | 0.0% | 0.0% | 100.0% | 0.0% | 0.00 | 0.00 | 0.00 | 29.70 | 0.00 | 29.70 |
| | K | A | A | A | R | | | | | | | | | | | | | |

| Amino Acid - residue position number and amino acid in that position | | | | | | | Other amino | Percentage Released Fas | | | | | Amount Released Fas (ug) | | | | | |
|---|---|---|---|---|---|---|---|---|---|---|---|---|---|---|---|---|---|---|
| 61 | 72 | 116 | 133 | 151 | 163 | 164 | acid changes | Linolenic | Linoleic | Oleic | Palmitic | Stearic | Linolenic | Linoleic | Oleic | Palmitic | Stearic | Total FA |
| K | A | A | A | A |   |   |   | 2.8% | 5.4% | 5.9% | 84.0% | 1.9% | 0.66 | 1.27 | 1.40 | 19.80 | 0.46 | 23.58 |
| K | A | A | A |   | R |   |   | 1.8% | 5.3% | 3.0% | 89.5% | 0.4% | 1.71 | 4.92 | 2.78 | 83.70 | 0.39 | 93.50 |
| K | A | A | A |   |   |   |   | 0.0% | 0.0% | 0.0% | 100.0% | 0.0% | 0.00 | 0.00 | 0.00 | 15.30 | 0.00 | 15.30 |
| K | A | A |   | G |   |   |   | 0.0% | 0.0% | 0.0% | 100.0% | 0.0% | 0.00 | 0.00 | 0.00 | 0.65 | 0.00 | 0.65 |
| K | A | A |   |   | R |   |   | 0.0% | 1.6% | 0.0% | 98.4% | 0.0% | 0.00 | 0.21 | 0.00 | 12.90 | 0.00 | 13.11 |
| K | A | A |   |   | R |   |   | 1.7% | 8.6% | 4.0% | 85.8% | 0.0% | 0.14 | 0.70 | 0.33 | 6.98 | 0.00 | 8.14 |
| K | A | A |   |   | R |   |   | 0.9% | 8.9% | 5.8% | 84.4% | 0.0% | 0.06 | 0.61 | 0.40 | 5.80 | 0.00 | 6.88 |
| K | A | A |   |   |   | R |   | 0.0% | 5.4% | 0.7% | 93.9% | 0.0% | 0.00 | 0.57 | 0.08 | 9.83 | 0.00 | 10.47 |
| K | A | A |   |   |   |   |   | 0.0% | 0.0% | 0.0% | 100.0% | 0.0% | 0.00 | 0.00 | 0.00 | 20.50 | 0.00 | 20.50 |
| E | V | A |   | G | R |   |   | 0.0% | 2.4% | 0.0% | 97.6% | 0.0% | 0.00 | 0.07 | 0.00 | 2.98 | 0.00 | 3.05 |
| E | V | A | A |   | R |   |   | 0.5% | 5.9% | 1.3% | 92.2% | 0.0% | 0.04 | 0.43 | 0.10 | 6.67 | 0.00 | 7.23 |
| E | V | A | A |   |   |   |   | 1.5% | 0.0% | 0.8% | 97.8% | 0.0% | 0.09 | 0.00 | 0.05 | 5.83 | 0.00 | 5.96 |
| E | V | A |   |   |   |   |   | 0.0% | 0.0% | 0.0% | 100.0% | 0.0% | 0.00 | 0.00 | 0.00 | 5.40 | 0.00 | 5.40 |
| E | V | A |   |   | R |   |   | 0.0% | 2.2% | 0.0% | 97.8% | 0.0% | 0.00 | 0.19 | 0.00 | 8.28 | 0.00 | 8.47 |
| E | V |   |   | G |   |   |   | 0.0% | 12.8% | 3.1% | 84.1% | 0.0% | 0.00 | 0.98 | 0.24 | 6.40 | 0.00 | 7.61 |
| E | V |   |   | G |   |   |   | Low | Low | Low | Low | Low | 0.00 | 0.00 | 0.00 | 0.00 | 0.00 | 0.00 |
| E | V | A |   |   | R |   |   | 0.6% | 10.7% | 2.7% | 86.1% | 0.0% | 0.03 | 0.54 | 0.14 | 4.38 | 0.00 | 5.09 |
| E | V |   |   |   | R |   |   | 2.2% | 0.0% | 1.9% | 95.9% | 0.0% | 0.35 | 0.00 | 0.30 | 15.40 | 0.00 | 16.06 |
| E | V |   |   |   | R |   |   | 0.0% | 2.7% | 0.0% | 97.3% | 0.0% | 0.00 | 0.20 | 0.00 | 7.30 | 0.00 | 7.50 |
| E | V |   |   |   |   |   |   | 0.0% | 0.0% | 0.0% | 100.0% | 0.0% | 0.00 | 0.00 | 0.00 | 12.00 | 0.00 | 12.00 |
| E | V |   |   |   |   |   |   | 0.0% | 0.0% | 0.0% | 100.0% | 0.0% | 0.00 | 0.00 | 0.00 | 7.92 | 0.00 | 7.92 |
| E | V |   |   |   |   | R |   | 2.6% | 6.8% | 3.7% | 84.4% | 2.5% | 0.24 | 0.64 | 0.35 | 7.84 | 0.23 | 9.29 |
| E | V |   |   |   |   | R |   | 0.0% | 6.0% | 0.0% | 94.0% | 0.0% | 0.00 | 0.58 | 0.00 | 9.15 | 0.00 | 9.73 |
| E | V |   |   |   | R |   |   | 0.0% | 0.0% | 0.0% | 100.0% | 0.0% | 0.00 | 0.00 | 0.00 | 12.20 | 0.00 | 12.20 |
| E | T | A |   | G | R |   | N55M | 0.0% | 0.0% | 0.0% | 100.0% | 0.0% | 0.00 | 0.00 | 0.00 | 0.42 | 0.00 | 0.42 |
| E | Q | A | A |   | R |   |   | 0.0% | 0.0% | 0.0% | 100.0% | 0.0% | 0.00 | 0.00 | 0.00 | 1.98 | 0.00 | 1.98 |
| E | Q |   |   | G |   | R |   | 0.0% | 9.6% | 3.8% | 86.7% | 0.0% | 0.00 | 0.44 | 0.17 | 4.02 | 0.00 | 4.64 |
| E | A | A |   | G | R | R |   | 0.0% | 5.9% | 2.8% | 91.3% | 0.0% | 0.00 | 0.63 | 0.30 | 9.74 | 0.00 | 10.67 |

Primary Screen

| Amino Acid - residue position number and amino acid in that position | | | | | | | Other amino acid changes | Primary Screen | | | | | | | | | | |
|---|---|---|---|---|---|---|---|---|---|---|---|---|---|---|---|---|---|---|
| | | | | | | | | Percentage Released Fas | | | | | Amount Released Fas (ug) | | | | | |
| 61 | 72 | 116 | 133 | 151 | 163 | 164 | | Linolenic | Linoleic | Oleic | Palmitic | Stearic | Linolenic | Linoleic | Oleic | Palmitic | Stearic | Total FA |
| E | A | A | A | G | | | | Low | Low | Low | Low | Low | 0.00 | 0.00 | 0.00 | 0.00 | 0.00 | 0.00 |
| E | A | A | A | A | R | | | 0.0% | 5.2% | 3.2% | 91.5% | 0.0% | 0.00 | 1.36 | 0.86 | 24.10 | 0.01 | 26.33 |
| E | A | A | A | A | | | | 0.0% | 6.6% | 1.1% | 92.2% | 0.0% | 0.00 | 0.66 | 0.11 | 9.16 | 0.00 | 9.93 |
| E | A | A | A | | | R | | 0.0% | 0.0% | 0.0% | 100.0% | 0.0% | 0.00 | 0.00 | 0.00 | 12.30 | 0.00 | 12.30 |
| E | A | A | A | G | R | | | Low | Low | Low | Low | Low | 0.00 | 0.00 | 0.00 | 0.00 | 0.00 | 0.00 |
| E | A | A | A | G | R | | | 18.1% | 44.5% | 28.1% | High | 9.3% | 0.42 | 1.04 | 0.66 | High | 0.22 | 2.34 |
| E | A | A | | G | R | | | 0.0% | 10.5% | 0.0% | 89.5% | 0.0% | 0.00 | 0.82 | 0.00 | 7.01 | 0.00 | 7.83 |
| E | A | A | | | | R | | 0.0% | 0.0% | 0.0% | 100.0% | 0.0% | 0.00 | 0.00 | 0.00 | 10.20 | 0.00 | 10.20 |
| E | A | A | | | | | | 0.0% | 0.0% | 1.0% | 99.0% | 0.0% | 0.00 | 0.00 | 0.19 | 18.40 | 0.00 | 18.59 |
| E | | | A | A | | | A35V | 3.6% | 6.7% | 14.9% | 70.4% | 4.4% | 2.83 | 5.18 | 11.60 | 54.60 | 3.39 | 77.60 |
| E | | | | | | | K12M | 11.4% | 15.9% | 11.9% | 57.2% | 3.6% | 3.76 | 5.22 | 3.91 | 18.80 | 1.19 | 32.88 |
| E | | A | | | R | | | 3.7% | 10.1% | 6.1% | 79.9% | 0.2% | 1.20 | 3.24 | 1.94 | 25.60 | 0.06 | 32.04 |
| E | | | | | R | | V128A | 3.8% | 7.3% | 5.6% | 79.5% | 3.7% | 3.99 | 7.64 | 5.80 | 82.70 | 3.83 | 103.96 |
| E | | | | | R | | | 3.7% | 8.4% | 8.2% | 79.7% | 0.0% | 3.20 | 7.17 | 6.97 | 68.00 | 0.00 | 85.34 |
| | V | A | A | | R | | | 2.7% | 1.8% | 2.8% | 92.7% | 0.0% | 0.56 | 0.37 | 0.59 | 19.30 | 0.00 | 20.82 |
| | V | A | A | | R | | | 0.0% | 1.9% | 0.0% | 98.1% | 0.0% | 0.00 | 0.18 | 0.00 | 8.93 | 0.00 | 9.11 |
| | V | A | A | | R | | | 0.0% | 6.1% | 0.0% | 93.9% | 0.0% | 0.00 | 0.15 | 0.00 | 2.30 | 0.00 | 2.45 |
| | V | A | A | | R | | | 3.2% | 6.7% | 3.9% | 85.1% | 1.1% | 0.67 | 1.39 | 0.80 | 17.60 | 0.23 | 20.69 |
| | V | A | | | | | | 2.9% | 3.0% | 5.4% | 87.4% | 1.3% | 0.59 | 0.61 | 1.10 | 17.70 | 0.26 | 20.26 |
| | V | | | | | | | 0.0% | 0.0% | 0.0% | 100.0% | 0.0% | 0.00 | 0.00 | 0.00 | 1.75 | 0.00 | 1.75 |
| | V | | | G | | R | | 3.3% | 8.2% | 6.4% | 80.9% | 1.2% | 0.49 | 1.21 | 0.96 | 12.00 | 0.18 | 14.83 |
| | V | | | | | | | 0.0% | 0.0% | 100.0% | High | 0.0% | 0.00 | 0.00 | 0.09 | High | 0.00 | 0.09 |
| | V | | | | | | | 1.4% | 5.6% | 4.1% | 88.4% | 0.6% | 0.11 | 0.43 | 0.32 | 6.85 | 0.05 | 7.75 |
| | A | A | A | | | | | 0.0% | 0.0% | 0.0% | 100.0% | 0.0% | 0.00 | 0.00 | 0.00 | 18.30 | 0.00 | 18.30 |
| | A | A | | | R | | | 1.9% | 5.6% | 3.8% | 87.8% | 0.9% | 0.29 | 0.87 | 0.59 | 13.60 | 0.13 | 15.49 |
| | A | A | | | R | | | 2.4% | 5.2% | 4.2% | 88.2% | 0.0% | 0.92 | 2.00 | 1.64 | 34.20 | 0.00 | 38.76 |
| | A | A | | | R | | | 0.0% | 0.0% | 0.0% | 100.0% | 0.0% | 0.00 | 0.00 | 0.00 | 20.70 | 0.00 | 20.70 |
| | A | A | | | | | P179Q | 0.0% | 0.3% | 2.9% | 96.8% | 0.0% | 0.00 | 0.06 | 0.56 | 18.90 | 0.00 | 19.52 |
| | A | | | | | R | | 0.0% | 5.2% | 0.0% | 94.8% | 0.0% | 0.00 | 0.38 | 0.00 | 6.88 | 0.00 | 7.26 |

| Amino Acid - residue position number and amino acid in that position | | | | | | | | Primary Screen | | | | | | | | | | | |
|---|---|---|---|---|---|---|---|---|---|---|---|---|---|---|---|---|---|---|---|
| | | | | | | | | Percentage Released Fas | | | | | Amount Released Fas (ug) | | | | | | |
| 61 | 72 | 116 | 133 | 151 | 163 | 164 | Other amino acid changes | Linolenic | Linoleic | Oleic | Palmitic | Stearic | Linolenic | Linoleic | Oleic | Palmitic | Stearic | Total FA |
| | | A | | A | R | | | 2.2% | 5.7% | 4.4% | 86.7% | 1.0% | 0.47 | 1.20 | 0.94 | 18.40 | 0.22 | 21.22 |
| | | A | | A | R | | | 1.8% | 4.4% | 4.6% | 89.2% | 0.0% | 0.45 | 1.09 | 1.14 | 22.10 | 0.00 | 24.78 |
| | | A | | | R | | | 18.4% | 42.4% | 32.4% | High | 6.8% | 0.69 | 1.60 | 1.22 | High | 0.26 | 3.77 |
| | | A | | | R | | | 13.9% | 38.8% | 40.0% | High | 7.2% | 1.63 | 4.56 | 4.70 | High | 0.85 | 11.74 |
| | | A | | | | R | | 0.0% | 0.0% | 0.0% | 100.0% | 0.0% | 0.00 | 0.00 | 0.00 | 13.30 | 0.00 | 13.30 |
| | | A | | | | R | | 0.0% | 0.0% | 0.0% | 100.0% | 0.0% | 0.00 | 0.00 | 0.00 | 4.28 | 0.00 | 4.28 |
| | | | | | | | wt | 3.2% | 7.2% | 5.9% | 78.5% | 5.2% | 1.82 | 4.04 | 3.30 | 44.00 | 2.89 | 56.05 |
| | | | | | | | mixed | 1.8% | 7.3% | 6.6% | 84.3% | 0.0% | 0.52 | 2.16 | 1.94 | 24.90 | 0.00 | 29.52 |
| | K | T | | A | R | | | 1.8% | 7.3% | 6.6% | 84.3% | 0.0% | 0.52 | 2.16 | 1.94 | 24.90 | 0.00 | 29.52 |
| | K | T | | A | R | | | 4.7% | 6.2% | 9.4% | 79.7% | 0.0% | 2.94 | 3.83 | 5.83 | 49.60 | 0.00 | 62.20 |
| | K | Q | A | A | | | | 4.7% | 6.2% | 9.4% | 79.7% | 0.0% | 2.94 | 3.83 | 5.83 | 49.60 | 0.00 | 62.20 |
| | K | Q | A | A | | | | 0.0% | 8.0% | 10.6% | 81.4% | 0.0% | 0.00 | 1.30 | 1.72 | 13.20 | 0.00 | 16.22 |
| | K | Q | A | G | R | | | 0.0% | 8.0% | 10.6% | 81.4% | 0.0% | 0.00 | 1.30 | 1.72 | 13.20 | 0.00 | 16.22 |
| | K | Q | A | G | R | | | 0.2% | 8.8% | 8.4% | 82.6% | 0.0% | 0.05 | 1.79 | 1.71 | 16.90 | 0.00 | 20.45 |
| | K | | A | A | R | | | 0.2% | 8.8% | 8.4% | 82.6% | 0.0% | 0.05 | 1.79 | 1.71 | 16.90 | 0.00 | 20.45 |
| | K | | A | A | R | | | 5.5% | 11.2% | 8.5% | 74.8% | 0.0% | 6.91 | 14.20 | 10.80 | 94.70 | 0.00 | 126.61 |
| | E | | A | A | R | | | 5.5% | 11.2% | 8.5% | 74.8% | 0.0% | 6.91 | 14.20 | 10.80 | 94.70 | 0.00 | 126.61 |
| | E | | A | A | R | | | 4.0% | 7.2% | 11.8% | 77.0% | 0.0% | 1.95 | 3.48 | 5.70 | 37.20 | 0.00 | 48.33 |
| | E | | A | G | R | | | 4.0% | 7.2% | 11.8% | 77.0% | 0.0% | 1.95 | 3.48 | 5.70 | 37.20 | 0.00 | 48.33 |
| | E | | A | G | R | | | 4.5% | 9.7% | 10.7% | 72.9% | 2.2% | 6.00 | 12.90 | 14.30 | 97.00 | 2.89 | 133.09 |
| | E | | A | A | R | | | 4.5% | 9.7% | 10.7% | 72.9% | 2.2% | 6.00 | 12.90 | 14.30 | 97.00 | 2.89 | 133.09 |
| | | Q | | A | R | | A97V | 1.4% | 4.2% | 8.4% | 86.0% | 0.0% | 0.52 | 1.59 | 3.16 | 32.30 | 0.00 | 37.57 |
| | | Q | | A | R | | A97V | 1.4% | 4.2% | 8.4% | 86.0% | 0.0% | 0.52 | 1.59 | 3.16 | 32.30 | 0.00 | 37.57 |
| | | | A | | R | | | 5.3% | 9.1% | 7.4% | 76.9% | 1.4% | 4.69 | 8.02 | 6.56 | 68.10 | 1.21 | 88.58 |

Figure 8-24

SEQUENCE LISTING

```
<160> NUMBER OF SEQ ID NOS: 21

<210> SEQ ID NO 1
<211> LENGTH: 684
<212> TYPE: DNA
<213> ORGANISM: Unknown
<220> FEATURE:
<223> OTHER INFORMATION: DNA obtained from environmental sample

<400> SEQUENCE: 1
atgctgaaac cgcctcccta cggacgcctg ctgcgcgaac tggccgatat cccggccatc      60
gtgacggcac cgttccgggg cgctgcgaaa atgggcaaac tggcggatgg cgagccggta     120
ctggtgctgc ccggcttcct ggccgacgac aacgccacct cggtgctgcg caagaccttc     180
```

-continued

```
gatgtcgcgg gctttgcctg ttcgggctgg gaacgcggct tcaacctcgg cattcgtggc      240
gacctcgtgg accggctggt cgaccggctg cgggcggtgt cggaggcggc cggtggtcag      300
aaggtgatcg tggtcggctg gagcctcggc ggcctctatg cgcgcgagct gggccacaag      360
gcgcccgaac tgatccggat ggtcgtcacg ctcggcagtc cgttcgcggg cgacctccac      420
gccaaccatg cgtggaagat ctacgaggcg atcaacagcc acacggtcga caacctgccg      480
atcccggtcg atttccagat taagccgccg gtgcgcacca tcgcggtgtg gtcgccgctc      540
gacggggtgg tggcgccgga gacctcggaa ggctcgcccg agcagtcgga cgagcggcta      600
gagctggcgg tgacccacat gggctttgcc gcatcgaaga ccggggccga ggctgtggtc      660
cggctggtcg cggcgcggct ctag                                             684
```

<210> SEQ ID NO 2
<211> LENGTH: 227
<212> TYPE: PRT
<213> ORGANISM: Unknown
<220> FEATURE:
<223> OTHER INFORMATION: Protein obtained from environmental sample
<220> FEATURE:
<221> NAME/KEY: SITE
<222> LOCATION: (51)...(54)
<223> OTHER INFORMATION: N-glycosylation site. Prosite id = PS00001
<220> FEATURE:
<221> NAME/KEY: SITE
<222> LOCATION: (103)...(112)
<223> OTHER INFORMATION: Lipases, serine active site. Prosite id = PS00120

<400> SEQUENCE: 2

```
Met Leu Lys Pro Pro Tyr Gly Arg Leu Leu Arg Glu Leu Ala Asp
1               5                   10                  15

Ile Pro Ala Ile Val Thr Ala Pro Phe Arg Gly Ala Ala Lys Met Gly
            20                  25                  30

Lys Leu Ala Asp Gly Glu Pro Val Leu Val Leu Pro Gly Phe Leu Ala
        35                  40                  45

Asp Asp Asn Ala Thr Ser Val Leu Arg Lys Thr Phe Asp Val Ala Gly
    50                  55                  60

Phe Ala Cys Ser Gly Trp Glu Arg Gly Phe Asn Leu Gly Ile Arg Gly
65                  70                  75                  80

Asp Leu Val Asp Arg Leu Val Asp Arg Leu Arg Ala Val Ser Glu Ala
                85                  90                  95

Ala Gly Gly Gln Lys Val Ile Val Val Gly Trp Ser Leu Gly Gly Leu
            100                 105                 110

Tyr Ala Arg Glu Leu Gly His Lys Ala Pro Glu Leu Ile Arg Met Val
        115                 120                 125

Val Thr Leu Gly Ser Pro Phe Ala Gly Asp Leu His Ala Asn His Ala
    130                 135                 140

Trp Lys Ile Tyr Glu Ala Ile Asn Ser His Thr Val Asp Asn Leu Pro
145                 150                 155                 160

Ile Pro Val Asp Phe Gln Ile Lys Pro Pro Val Arg Thr Ile Ala Val
                165                 170                 175

Trp Ser Pro Leu Asp Gly Val Val Ala Pro Glu Thr Ser Glu Gly Ser
            180                 185                 190

Pro Glu Gln Ser Asp Glu Arg Leu Glu Leu Ala Val Thr His Met Gly
        195                 200                 205

Phe Ala Ala Ser Lys Thr Gly Ala Glu Ala Val Val Arg Leu Val Ala
    210                 215                 220
```

Ala Arg Leu
225

<210> SEQ ID NO 3
<211> LENGTH: 633
<212> TYPE: DNA
<213> ORGANISM: Unknown
<220> FEATURE:
<223> OTHER INFORMATION: DNA obtained from environmental sample

<400> SEQUENCE: 3

```
atggccggcc accagggcgc gcggggcccc aaagacggtc cgccggcgat ggtgatcccg    60
ggcttcctcg cccacgacag gcacacgaca cgattgcgcc gggaactcgc cgaggcgggg   120
ttcagggttc acccctggcg gcagggctgg aacatgggag cgcgtgccga cacgctcgag   180
aaattgaagc gggcagtgga ccagtgcggt catgacgagc cgatcctgct ggtcggctgg   240
agtctgggcg gctctacgc gagggaggtc gcgcgcgccg agccggatca ggtgcgggcg   300
gtggtcactc ttggttcccc ggtgtcgggc gaccggcgcc gctacaccaa cgtgtggaag   360
ctgtacgaat gggtggcggg tcacccggtg gacgacccgc cgatccccga caaggaggaa   420
aagccgccgg tgccgaccct ggctttgtgg tcggcggatg acgggatcgt cggcgccccg   480
tcggcgcgcg ggactcagtt atctcacgac aaggcggtcg agatgcgaac gagccacatg   540
ggctttgcca tgtcggcgaa gagcgcacgc tttgttgtcg ccgagatcgt gaagttcctg   600
aagaaaaccg aaggttccga gtcgcacgat tga                                 633
```

<210> SEQ ID NO 4
<211> LENGTH: 210
<212> TYPE: PRT
<213> ORGANISM: Unknown
<220> FEATURE:
<223> OTHER INFORMATION: Protein obtained from environmental sample
<220> FEATURE:
<221> NAME/KEY: SITE
<222> LOCATION: (76)...(85)
<223> OTHER INFORMATION: Lipases, serine active site. Prosite id = PS00120

<400> SEQUENCE: 4

Met Ala Gly His Gln Gly Ala Arg Gly Pro Lys Asp Gly Pro Pro Ala
1               5                   10                  15

Met Val Ile Pro Gly Phe Leu Ala His Asp Arg His Thr Thr Arg Leu
            20                  25                  30

Arg Arg Glu Leu Ala Glu Ala Gly Phe Arg Val His Pro Trp Arg Gln
        35                  40                  45

Gly Trp Asn Met Gly Ala Arg Ala Asp Thr Leu Glu Lys Leu Lys Arg
    50                  55                  60

Ala Val Asp Gln Cys Gly His Asp Glu Pro Ile Leu Leu Val Gly Trp
65                  70                  75                  80

Ser Leu Gly Gly Leu Tyr Ala Arg Glu Val Ala Arg Ala Glu Pro Asp
                85                  90                  95

Gln Val Arg Ala Val Val Thr Leu Gly Ser Pro Val Ser Gly Asp Arg
            100                 105                 110

Arg Arg Tyr Thr Asn Val Trp Lys Leu Tyr Glu Trp Val Ala Gly His
        115                 120                 125

Pro Val Asp Asp Pro Pro Ile Pro Asp Lys Glu Glu Lys Pro Pro Val
    130                 135                 140

Pro Thr Leu Ala Leu Trp Ser Ala Asp Asp Gly Ile Val Gly Ala Pro
145                 150                 155                 160

```
Ser Ala Arg Gly Thr Gln Leu Ser His Asp Lys Ala Val Glu Met Arg
            165                 170                 175

Thr Ser His Met Gly Phe Ala Met Ser Ala Lys Ser Ala Arg Phe Val
        180                 185                 190

Val Ala Glu Ile Val Lys Phe Leu Lys Lys Thr Glu Gly Ser Glu Ser
    195                 200                 205

His Asp
    210

<210> SEQ ID NO 5
<211> LENGTH: 711
<212> TYPE: DNA
<213> ORGANISM: Unknown
<220> FEATURE:
<223> OTHER INFORMATION: DNA obtained from environmental sample

<400> SEQUENCE: 5
gtgagcgaga aaggcgcacc caagggaagg cagcggctga aggagatcgg cgcgcttctg    60
ttccacgcgc tcgcagctt gggccatctg ggcgcgcgcg ccccaagga cggtcctccg    120 gtgatggtca tcccgggatt cctcgcgcac gacttgcata cgacgcagtt gcgccgggcg   180
ctcgcgaagg caggcttccg agtgcatccg tggcggcagg gatgaaccct ggagcgcgc    240 gccgatacgc tcgaaattct gaagcgcgcg gtggattcct gcggctcgag cgagccgatg   300
ctgctcgtcg gctggagcct gggcggtctc tatgcccggg agatcgcgcg tgcggagccg   360
gaccgggtgc gggcggtggt gacgatggga tcgccggtgt ggggcgaccg caggcgctac   420
accaacgtgt ggaagctgta cgaacggatt gccggccatc cggtcgacaa gccgccgatc   480
ccggacaaga gccagaagcc gccggtgccg actctggctt tgtggtcgca gcatgatggc   540
atcgtcggcg cgccctcggc gagagggacg aagaagaccc gcgacaaggc ggtcgccatc   600
gacacgactc acatgggggtt tgccatgtcg cccaagacga cgcgcgcggc agtgcgtgag   660
atcgtgggct ttttgaatga agtcgaaggc ggttcgtcac cccgggcgtg a             711

<210> SEQ ID NO 6
<211> LENGTH: 236
<212> TYPE: PRT
<213> ORGANISM: Unknown
<220> FEATURE:
<223> OTHER INFORMATION: Protein obtained from environmental sample

<400> SEQUENCE: 6

Met Ser Glu Lys Gly Ala Pro Lys Gly Arg Gln Arg Leu Lys Glu Ile
1               5                   10                  15

Gly Ala Leu Leu Phe His Ala Pro Arg Ser Leu Gly His Leu Gly Ala
            20                  25                  30

Arg Gly Pro Lys Asp Gly Pro Val Met Val Ile Pro Gly Phe Leu
        35                  40                  45

Ala His Asp Leu His Thr Thr Gln Leu Arg Arg Ala Leu Ala Lys Ala
    50                  55                  60

Gly Phe Arg Val His Pro Trp Arg Gln Gly Met Asn Leu Gly Ala Arg
65                  70                  75                  80

Ala Asp Thr Leu Glu Ile Leu Lys Arg Ala Val Asp Ser Cys Gly Ser
            85                  90                  95

Ser Glu Pro Met Leu Leu Val Gly Trp Ser Leu Gly Gly Leu Tyr Ala
        100                 105                 110

Arg Glu Ile Ala Arg Ala Glu Pro Asp Arg Val Arg Ala Val Val Thr
    115                 120                 125
```

```
Met Gly Ser Pro Val Trp Gly Asp Arg Arg Tyr Thr Asn Val Trp
            130                 135                 140

Lys Leu Tyr Glu Arg Ile Ala Gly His Pro Val Asp Lys Pro Pro Ile
145                 150                 155                 160

Pro Asp Lys Ser Gln Lys Pro Pro Val Pro Thr Leu Ala Leu Trp Ser
                165                 170                 175

Gln His Asp Gly Ile Val Gly Ala Pro Ser Ala Arg Gly Thr Lys Lys
            180                 185                 190

Thr Arg Asp Lys Ala Val Ala Ile Asp Thr Thr His Met Gly Phe Ala
        195                 200                 205

Met Ser Pro Lys Thr Thr Arg Ala Ala Val Arg Glu Ile Val Gly Phe
    210                 215                 220

Leu Asn Glu Val Glu Gly Gly Ser Ser Pro Arg Ala
225                 230                 235

<210> SEQ ID NO 7
<211> LENGTH: 669
<212> TYPE: DNA
<213> ORGANISM: Unknown
<220> FEATURE:
<223> OTHER INFORMATION: DNA obtained from environmental sample

<400> SEQUENCE: 7
atgaggctgc gcgagggggg cgcgctcgta tcgcgggcct atcgcgcctt cgggcgcctc      60
ggcgagcgcg ggccggcgga cgggccgccg ctgatggtga tcccgggctt cctcgccacc     120
gatcgcacca ctttggggct gcagcgggcg ctggccaagg gcggctacaa ggtgaccgga     180
tggggcatgg gcctcaacag cggcgtcacc gaagacatag tcgaccgcat cgccgctcgg     240
gtcgaaaggt ttggagccgg ccgcaaagtg atcctcgtcg gctggagcct cggcggactc     300
tacgcgcgcg tggtcgcgca ggagcggccg gatctcgtcg acaaggtggt cacgctcggc     360 tcgcccttt cgggcgacag cgccgcaac aacaatgtct ggcggctcta cgagttcgtc      420
gccggccatc cggtcaacag cccgccgatc gacaaggacc ccgaggtgaa gccgccggtg     480
ccgacgctcg ctatctggtc gcggcgcgac ggcatcgtct ctccggcggg cgcgcgcggg     540
cgggagggag agcgcgacgc cgagctcgag ctcgactgca gccacatggg ctttgcggtc     600
agcgccaggg cttatcccaa gatcgtggag gcggtgcggg cgtttccgga aaacatccgt     660
tcgcgctga                                                             669

<210> SEQ ID NO 8
<211> LENGTH: 222
<212> TYPE: PRT
<213> ORGANISM: Unknown
<220> FEATURE:
<223> OTHER INFORMATION: Protein obtained from environmental sample
<220> FEATURE:
<221> NAME/KEY: SITE
<222> LOCATION: (91)...(100)
<223> OTHER INFORMATION: Lipases, serine active site. Prosite id =
      PS00120

<400> SEQUENCE: 8

Met Arg Leu Arg Glu Gly Gly Ala Leu Val Ser Arg Ala Tyr Arg Ala
1               5                  10                  15

Phe Gly Arg Leu Gly Glu Arg Gly Pro Ala Asp Gly Pro Pro Leu Met
                20                  25                  30

Val Ile Pro Gly Phe Leu Ala Thr Asp Arg Thr Thr Leu Gly Leu Gln
            35                  40                  45

Arg Ala Leu Ala Lys Gly Gly Tyr Lys Val Thr Gly Trp Gly Met Gly
```

```
                50                  55                  60
Leu Asn Ser Gly Val Thr Glu Asp Ile Val Asp Arg Ile Ala Ala Arg
 65                  70                  75                  80

Val Glu Arg Phe Gly Ala Gly Arg Lys Val Ile Leu Val Gly Trp Ser
                 85                  90                  95

Leu Gly Gly Leu Tyr Ala Arg Val Val Ala Gln Arg Pro Asp Leu
            100                 105                 110

Val Asp Lys Val Val Thr Leu Gly Ser Pro Phe Ser Gly Asp Arg Arg
            115                 120                 125

Arg Asn Asn Asn Val Trp Arg Leu Tyr Glu Phe Val Ala Gly His Pro
    130                 135                 140

Val Asn Ser Pro Pro Ile Asp Lys Asp Pro Glu Val Lys Pro Pro Val
145                 150                 155                 160

Pro Thr Leu Ala Ile Trp Ser Arg Arg Asp Gly Ile Val Ser Pro Ala
                165                 170                 175

Gly Ala Arg Gly Arg Glu Gly Glu Arg Asp Ala Glu Leu Glu Leu Asp
            180                 185                 190

Cys Ser His Met Gly Phe Ala Val Ser Ala Arg Ala Tyr Pro Lys Ile
            195                 200                 205

Val Glu Ala Val Arg Ala Phe Pro Glu Asn Ile Arg Ser Arg
            210                 215                 220

<210> SEQ ID NO 9
<211> LENGTH: 669
<212> TYPE: DNA
<213> ORGANISM: Unknown
<220> FEATURE:
<223> OTHER INFORMATION: DNA obtained from environmental sample

<400> SEQUENCE: 9
atgaagccgc cgcccggatg gatgaagatc cgggaggcgg gctcgctcct cgcgcgcttc     60
taccgcgcgt tcggcaagct cgagccgcgc gggccggcgg acgggccgaa gctgatggtg    120
atcccgggtt tcctcgcggg cgacaggacg acgctcgggc tgcagcgagc gctggccggc    180
ggcggctacc gggtcgccgg ctgggggctg ggggtgaacc gcggcgtttc ggaggacgtg    240
gtcgaccgga tcggccagca agtcgcgcgg ttcgggcgg gcgagaaggt gatcctggtc    300
ggctggagcc ttggcgggct ttatgcgcgc gtggtggcgc aggagcggcc cgacctcgtc    360
gagaaggtgg tgaccttggg ctcgccgttt cgggcgacc ggcggcgcaa caacaatgtg    420
tggcggctct atgagtgggt ggctgggcat ccggtgaacg atccgccgat cgacaaggac    480
ccggcgaaga agcccccggt gccgacgctc gcgatctggt cgcggcgtga tgggatcgtg    540
gcggtcgaag gcgcgcgggg gcggccgag gagcgggatg ccgagctgga gatcgattgc    600
agccacatgg ggtttggggt cagcggcaag gcgtttcccc gaatcgtaga ggcggtgaag    660
gggttctaa                                                            669

<210> SEQ ID NO 10
<211> LENGTH: 222
<212> TYPE: PRT
<213> ORGANISM: Unknown
<220> FEATURE:
<223> OTHER INFORMATION: Protein obtained from environmental sample
<220> FEATURE:
<221> NAME/KEY: SITE
<222> LOCATION: (98)...(107)
<223> OTHER INFORMATION: Lipases, serine active site. Prosite id =
      PS00120

<400> SEQUENCE: 10
```

```
Met Lys Pro Pro Gly Trp Met Lys Ile Arg Glu Ala Ser Leu
1               5                   10                  15

Leu Ala Arg Phe Tyr Arg Ala Phe Gly Lys Leu Glu Pro Arg Gly Pro
            20                  25                  30

Ala Asp Gly Pro Lys Leu Met Val Ile Pro Gly Phe Leu Ala Gly Asp
            35                  40                  45

Arg Thr Thr Leu Gly Leu Gln Arg Ala Leu Ala Gly Gly Tyr Arg
    50                  55                  60

Val Ala Gly Trp Gly Leu Gly Val Asn Arg Gly Val Ser Glu Asp Val
65                  70                  75                  80

Val Asp Arg Ile Gly Gln Gln Val Ala Arg Phe Gly Ala Gly Glu Lys
                85                  90                  95

Val Ile Leu Val Gly Trp Ser Leu Gly Gly Leu Tyr Ala Arg Val Val
                100                 105                 110

Ala Gln Glu Arg Pro Asp Leu Val Glu Lys Val Val Thr Leu Gly Ser
            115                 120                 125

Pro Phe Ser Gly Asp Arg Arg Arg Asn Asn Asn Val Trp Arg Leu Tyr
    130                 135                 140

Glu Trp Val Ala Gly His Pro Val Asn Asp Pro Ile Asp Lys Asp
145                 150                 155                 160

Pro Ala Lys Lys Pro Pro Val Pro Thr Leu Ala Ile Trp Ser Arg Arg
                165                 170                 175

Asp Gly Ile Val Ala Val Glu Gly Ala Arg Gly Arg Pro Glu Glu Arg
            180                 185                 190

Asp Ala Glu Leu Glu Ile Asp Cys Ser His Met Gly Phe Gly Val Ser
            195                 200                 205

Gly Lys Ala Phe Pro Arg Ile Val Glu Ala Val Lys Gly Phe
210                 215                 220

<210> SEQ ID NO 11
<211> LENGTH: 570
<212> TYPE: DNA
<213> ORGANISM: Unknown
<220> FEATURE:
<223> OTHER INFORMATION: DNA obtained from environmental sample

<400> SEQUENCE: 11
gtgttggtgc tgccggcgtt cctcgccaac gaccttccca cttcgcttct ccgcaggacg      60
ctgaaggcga acgggtttcg cccgttcggc tgggcgaacg gtttcaactt aggtgcacgg     120
ccggacacgc tccagcgcct gagcgcacgg ctcgatgcgg tggttcagga agcgggcagg     180
ccggttgcat tgatcggctg gagccttggc gggctttatg cccgagagct ggcgaaacgc     240
aggtcggctg aggtgtcggc agtgatcacg ctcggcacgc ccttctcggt tgacctcaga     300
cgcaacaacg cctggaagct gtacgagctc atcaacgatc atcctgtcga tgcccctccc     360
ttggatgttc aggtcgacgc gaagccaccc gtccgaacct tcgctttgtg gtcgcgtcgc     420
gacgggatcg tagcgcccgc gagcgcgcac ggcatggagg gcgagttcga ccaggcgatc     480
gagctgcagt gcacgcacaa cgagatggtc agtgatccgg aggccctctc cacgatcgtt     540
accttgctgc gggaaaatgt tggctcctga                                     570

<210> SEQ ID NO 12
<211> LENGTH: 189
<212> TYPE: PRT
<213> ORGANISM: Unknown
<220> FEATURE:
<223> OTHER INFORMATION: Protein obtained from environmental sample
```

<400> SEQUENCE: 12

```
Met Leu Val Leu Pro Ala Phe Leu Ala Asn Asp Leu Pro Thr Ser Leu
1               5                   10                  15

Leu Arg Arg Thr Leu Lys Ala Asn Gly Phe Arg Pro Phe Gly Trp Ala
            20                  25                  30

Asn Gly Phe Asn Leu Gly Ala Arg Pro Asp Thr Leu Gln Arg Leu Ser
        35                  40                  45

Ala Arg Leu Asp Ala Val Val Gln Glu Ala Gly Arg Pro Val Ala Leu
    50                  55                  60

Ile Gly Trp Ser Leu Gly Gly Leu Tyr Ala Arg Glu Leu Ala Lys Arg
65                  70                  75                  80

Arg Ser Ala Glu Val Ser Ala Val Ile Thr Leu Gly Thr Pro Phe Ser
                85                  90                  95

Val Asp Leu Arg Arg Asn Asn Ala Trp Lys Leu Tyr Glu Leu Ile Asn
            100                 105                 110

Asp His Pro Val Asp Ala Pro Pro Leu Asp Val Gln Val Asp Ala Lys
        115                 120                 125

Pro Pro Val Arg Thr Phe Ala Leu Trp Ser Arg Asp Gly Ile Val
    130                 135                 140

Ala Pro Ala Ser Ala His Gly Met Glu Gly Glu Phe Asp Gln Ala Ile
145                 150                 155                 160

Glu Leu Gln Cys Thr His Asn Glu Met Val Ser Asp Pro Glu Ala Leu
                165                 170                 175

Ser Thr Ile Val Thr Leu Leu Arg Glu Asn Val Gly Ser
            180                 185
```

<210> SEQ ID NO 13
<211> LENGTH: 807
<212> TYPE: DNA
<213> ORGANISM: Unknown
<220> FEATURE:
<223> OTHER INFORMATION: DNA obtained from environmental sample

<400> SEQUENCE: 13

| | | | | | |
|---|---|---|---|---|---|
| gtgaatacag | ccgacctatt | gaagccacca | cccgcaagca | tgacagttct | cgaggcgaga | 60 |
| gcgctgctgg | acatatgcaa | gatgagcgcc | ccattggcgc | gcttgctatt | caaaaagaac | 120 |
| tcgccctggc | gcaaacaacg | ggttctcgta | ataccggct | ttggcgctga | tgatcgctac | 180 |
| acctggccgt | tgcgcaattt | cgtccaggca | cagggctatg | ccacgactgg | ctggggcctg | 240 |
| ggcaccaaca | aggcaggtct | caatatgccg | catcaactat | ccgacgtcca | ccccagatgg | 300 |
| aagctaaaac | ccaagacgcc | gtaccgtggt | gaggcgggcg | taccttacgt | gattgaccgc | 360 |
| ttgatcgaac | ggtttgacga | attggcatcg | acggatccgc | aacccatcgc | acttataggt | 420 |
| tggagtctgg | gtggtttcat | ggcccgtgaa | gttgcccgag | agcgcccaaa | ccaggtgagt | 480 |
| caggttatta | ccctcggttc | tcctgtcatc | ggaggcccaa | aatacaccct | cgctgcatcg | 540 |
| gctttcatcc | ggcgcaaata | cgatttggac | tgggtggagc | aagtgatcgc | ggagcgggaa | 600 |
| gatcgcccca | ttactgttcc | tattacagca | atagtcagcc | agtctgatgg | catcgtcgga | 660 |
| tattcagcgg | caatcgatca | ccacagtccc | gctgtgcagc | atttacatat | ggatgttgcc | 720 |
| catttgggct | tccttacaa | cacgaggggtt | tggtcagaaa | tcgccaatgc | gctcaactct | 780 |
| ttagaggtgg | agaaggagcg | tgtttag | | | | 807 |

<210> SEQ ID NO 14
<211> LENGTH: 268

```
<212> TYPE: PRT
<213> ORGANISM: Unknown
<220> FEATURE:
<223> OTHER INFORMATION: Protein obtained from environmental sample
<220> FEATURE:
<221> NAME/KEY: SITE
<222> LOCATION: (138)...(147)
<223> OTHER INFORMATION: Lipases, serine active site. Prosite id =
      PS00120

<400> SEQUENCE: 14

Met Asn Thr Ala Asp Leu Leu Lys Pro Pro Ala Ser Met Thr Val
1               5                   10                  15

Leu Glu Ala Arg Ala Leu Leu Asp Ile Cys Lys Met Ser Ala Pro Leu
            20                  25                  30

Ala Arg Leu Leu Phe Lys Lys Asn Ser Pro Trp Arg Lys Gln Arg Val
        35                  40                  45

Leu Val Ile Pro Gly Phe Gly Ala Asp Asp Arg Tyr Thr Trp Pro Leu
    50                  55                  60

Arg Asn Phe Val Gln Ala Gln Gly Tyr Ala Thr Gly Trp Gly Leu
65                  70                  75                  80

Gly Thr Asn Lys Ala Gly Leu Asn Met Pro His Gln Leu Ser Asp Val
                85                  90                  95

His Pro Arg Trp Lys Leu Lys Pro Lys Thr Pro Tyr Arg Gly Glu Ala
            100                 105                 110

Gly Val Pro Tyr Val Ile Asp Arg Leu Ile Glu Arg Phe Asp Glu Leu
        115                 120                 125

Ala Ser Thr Asp Pro Gln Pro Ile Ala Leu Ile Gly Trp Ser Leu Gly
    130                 135                 140

Gly Phe Met Ala Arg Glu Val Ala Arg Glu Arg Pro Asn Gln Val Ser
145                 150                 155                 160

Gln Val Ile Thr Leu Gly Ser Pro Val Ile Gly Gly Pro Lys Tyr Thr
                165                 170                 175

Leu Ala Ala Ser Ala Phe Ile Arg Arg Lys Tyr Asp Leu Asp Trp Val
            180                 185                 190

Glu Gln Val Ile Ala Glu Arg Glu Asp Arg Pro Ile Thr Val Pro Ile
        195                 200                 205

Thr Ala Ile Val Ser Gln Ser Asp Gly Ile Val Gly Tyr Ser Ala Ala
    210                 215                 220

Ile Asp His His Ser Pro Ala Val Gln His Leu His Met Asp Val Ala
225                 230                 235                 240

His Leu Gly Phe Pro Tyr Asn Thr Arg Val Trp Ser Glu Ile Ala Asn
                245                 250                 255

Ala Leu Asn Ser Leu Glu Val Glu Lys Glu Arg Val
            260                 265

<210> SEQ ID NO 15
<211> LENGTH: 804
<212> TYPE: DNA
<213> ORGANISM: Unknown
<220> FEATURE:
<221> NAME/KEY: misc_feature
<223> OTHER INFORMATION: Bacterial DNA

<400> SEQUENCE: 15
atggagctcg ccaaggtcac cgccctgatg aaggccaccg ccctcgagat cgcgatcctc      60
accggccacc tcgtcctcta cccctccggg atcgtggccg agcgcctcgc ggccgccccc     120
tcttcaccgt cctccccgtc cgcggggccg acgggccgac gtccggtcgt cctgctgcac     180
```

```
ggtttcgtgg acaaccgctc ggtcttcgtc ctgctgcgcc gtgccctcac ccggagcggc      240
cgtgactgcg tcgagtcgct caactactcg ccgctcacct gcgacctgcg ggccgccgcc      300
gaactgctgg ggcgccgggt ggacgagatc cgcgcccgga ccggacacgc cgaggtcgac      360
atcgtcggcc acagcctggg cgggctcatc gcccgttatt acgtacagcg tctcggcggt      420
gacagccggg tgcgcaccct ggtcatgctc ggcaccccgc actccggcac caccgtggcc      480
cggctcgccg acgcgcatcc gctggtgcgg cagatgcggc cgggttcgga ggtgctgcgg      540
gagctcgccg cgccctcgcc cggctgccgt acccggttcg tgagcttctg gagcgacctc      600
gaccaggtga tggtgccggt ggacacggcc tgcctggacc accccgacct gctggtgcac      660
aacgtccggg tcagcgggat cggtcatctc gcgctgccgg tccatcccac ggtggcggcc      720
ggggtccggg aggccctcga cgcgagcggc gcggggtcc cggggtgcg ggaggagggg       780 cccggcgccg cgccgtggc gtga                                             804
```

```
<210> SEQ ID NO 16
<211> LENGTH: 267
<212> TYPE: PRT
<213> ORGANISM: Unknown
<220> FEATURE:
<221> NAME/KEY: misc_feature
<223> OTHER INFORMATION: Bacterial protein
<220> FEATURE:
<221> NAME/KEY: SITE
<222> LOCATION: (120)...(129)
<223> OTHER INFORMATION: Lipases, serine active site. Prosite id =
      PS00120

<400> SEQUENCE: 16

Met Glu Leu Ala Lys Val Thr Ala Leu Met Lys Ala Thr Ala Leu Glu
1               5                   10                  15

Ile Ala Ile Leu Thr Gly His Leu Val Leu Tyr Pro Ser Gly Ile Val
                20                  25                  30

Ala Glu Arg Leu Ala Ala Ala Pro Ser Ser Pro Ser Ser Pro Ser Ala
            35                  40                  45

Gly Pro Thr Gly Arg Arg Pro Val Val Leu Leu His Gly Phe Val Asp
        50                  55                  60

Asn Arg Ser Val Phe Val Leu Leu Arg Arg Ala Leu Thr Arg Ser Gly
65                  70                  75                  80

Arg Asp Cys Val Glu Ser Leu Asn Tyr Ser Pro Leu Thr Cys Asp Leu
                85                  90                  95

Arg Ala Ala Ala Glu Leu Leu Gly Arg Arg Val Asp Glu Ile Arg Ala
            100                 105                 110

Arg Thr Gly His Ala Glu Val Asp Ile Val Gly His Ser Leu Gly Gly
        115                 120                 125

Leu Ile Ala Arg Tyr Tyr Val Gln Arg Leu Gly Gly Asp Ser Arg Val
    130                 135                 140

Arg Thr Leu Val Met Leu Gly Thr Pro His Ser Gly Thr Thr Val Ala
145                 150                 155                 160

Arg Leu Ala Asp Ala His Pro Leu Val Arg Gln Met Arg Pro Gly Ser
                165                 170                 175

Glu Val Leu Arg Glu Leu Ala Ala Pro Ser Pro Gly Cys Arg Thr Arg
            180                 185                 190

Phe Val Ser Phe Trp Ser Asp Leu Asp Gln Val Met Val Pro Val Asp
        195                 200                 205

Thr Ala Cys Leu Asp His Pro Asp Leu Leu Val His Asn Val Arg Val
    210                 215                 220
```

```
Ser Gly Ile Gly His Leu Ala Leu Pro Val His Pro Thr Val Ala Ala
225                 230                 235                 240

Gly Val Arg Glu Ala Leu Asp Ala Ser Gly Ala Gly Val Pro Gly Val
            245                 250                 255

Arg Glu Glu Gly Pro Gly Ala Gly Ala Val Ala
        260                 265
```

```
<210> SEQ ID NO 17
<211> LENGTH: 798
<212> TYPE: DNA
<213> ORGANISM: Unknown
<220> FEATURE:
<223> OTHER INFORMATION: DNA obtained from environmental sample

<400> SEQUENCE: 17
gtggccgccg cggacagcgg gacggcggaa gggcaaaggc ttcggccgcc gagcctgttc      60
ctgatgctgg ccgaggcgag gggcttgctc gaactgaact cgagcctgtt gttgtcgccg    120
ctgttgttgc gggcgccgaa gggcgacgga catccggtgc tggcgctgcc gggctttctc    180
gccagcgatc tgtcgatggc gccgatgcgg cgctatctga agaaactcgg ctacgatgcc    240
catgcgtgga acatgggccg caatctcggc ggcgtcgcgt ccaagcgcga agccttgcgc    300
gacctgttgc ggcgcattta cagccagacg ggccgcaagg tcagcctggt cggctggagt    360
ctcggcggcg tctatgcgcg cgatctcgct ttgcaggcgc ccgacatggt gcgttccgtg    420
atcacgctcg gcagtccgtt tgccagcgac atcagggcga ccaacgccac gcggctctac    480
gaggcgctgt cgggagaaag ggtcgacgac aatccggagt aacagcggc gatcgccggc     540 gacctgccgg tgccggcgac ctcgatctat tcccgtaccg acggtatcgt gaactggcac    600
accagcctgc tgcgtccttc cgcaacggct gaaaacatcg aggtttactt cgccagccat    660
atcgggctcg gcgtcaaccc ggcagcgctg tgggcggtgg ccgaccgcct ggcgcagccc    720
gagggggaat ttaagcattt tgaccggtcg ggtcccttg ccattgccta tggccccct     780 gaaaatgcac aatcctga                                                    798
```

```
<210> SEQ ID NO 18
<211> LENGTH: 265
<212> TYPE: PRT
<213> ORGANISM: Unknown
<220> FEATURE:
<223> OTHER INFORMATION: Protein obtained from environmental sample
<220> FEATURE:
<221> NAME/KEY: SITE
<222> LOCATION: (33)...(36)
<223> OTHER INFORMATION: N-glycosylation site. Prosite id = PS00001
<220> FEATURE:
<221> NAME/KEY: SITE
<222> LOCATION: (115)...(124)
<223> OTHER INFORMATION: Lipases, serine active site. Prosite id =
      PS00120
<220> FEATURE:
<221> NAME/KEY: SITE
<222> LOCATION: (157)...(160)
<223> OTHER INFORMATION: N-glycosylation site. Prosite id = PS00001

<400> SEQUENCE: 18

Met Ala Ala Ala Asp Ser Gly Thr Ala Glu Gly Gln Arg Leu Arg Pro
1               5                   10                  15

Pro Ser Leu Phe Leu Met Leu Ala Glu Ala Arg Gly Leu Leu Glu Leu
            20                  25                  30

Asn Ser Ser Leu Leu Leu Ser Pro Leu Leu Leu Arg Ala Pro Lys Gly
        35                  40                  45

Asp Gly His Pro Val Leu Ala Leu Pro Gly Phe Leu Ala Ser Asp Leu
```

```
                50                   55                    60
Ser Met Ala Pro Met Arg Arg Tyr Leu Lys Glu Leu Gly Tyr Asp Ala
 65                  70                   75                   80

His Ala Trp Asn Met Gly Arg Asn Leu Gly Gly Val Ala Ser Lys Arg
                 85                   90                   95

Glu Ala Leu Arg Asp Leu Leu Arg Arg Ile Tyr Ser Gln Thr Gly Arg
            100                 105                 110

Lys Val Ser Leu Val Gly Trp Ser Leu Gly Gly Val Tyr Ala Arg Asp
            115                 120                 125

Leu Ala Leu Gln Ala Pro Asp Met Val Arg Ser Val Ile Thr Leu Gly
130                 135                 140

Ser Pro Phe Ala Ser Asp Ile Arg Ala Thr Asn Ala Thr Arg Leu Tyr
145                 150                 155                 160

Glu Ala Leu Ser Gly Glu Arg Val Asp Asp Asn Pro Glu Leu Thr Ala
                165                 170                 175

Ala Ile Ala Gly Asp Leu Pro Val Pro Ala Thr Ser Ile Tyr Ser Arg
            180                 185                 190

Thr Asp Gly Ile Val Asn Trp His Thr Ser Leu Leu Arg Pro Ser Ala
            195                 200                 205

Thr Ala Glu Asn Ile Glu Val Tyr Phe Ala Ser His Ile Gly Leu Gly
210                 215                 220

Val Asn Pro Ala Ala Leu Trp Ala Val Ala Asp Arg Leu Ala Gln Pro
225                 230                 235                 240

Glu Gly Glu Phe Lys His Phe Asp Arg Ser Gly Pro Phe Ala Ile Ala
                245                 250                 255

Tyr Gly Pro Pro Glu Asn Ala Gln Ser
            260                 265

<210> SEQ ID NO 19
<211> LENGTH: 798
<212> TYPE: DNA
<213> ORGANISM: Unknown
<220> FEATURE:
<223> OTHER INFORMATION: DNA obtained from environmental sample

<400> SEQUENCE: 19
atgccggagc gaaacgaagc gcaggccccg ccgcgtcttc gtccgccggg gctcgggctg     60
ttcctcgccg aagcgcgggg cattttcgag ctcaacgcga gcctgttgct gtcgccgctt    120
ctgttgcgcg cgccgcgcgg cgacggccat ccggtgctgg cgttgccggg ctttcttgcc    180
agtgatctat cgatggcgcc gttgcgccgc tacctcaccg agctcggcta cgacacccac    240
gcctggcgca tgggccgcaa tgtcggcggc atcgcgaaga tgcggatcgc gctgctcgag    300
cggctcacgc agatccatgc cgagtgcggc cgcaaggtct cgattgtcgg ctggagtctc    360
ggcggcgtct atgcgcgcga cctcgcgttg caggcgcccg agatggtgcg ctacgtcgtc    420
accctcggca gccccttcgc cagcgacgtc cgcgccacca tgcgacgcg gctctatgag    480 gcgatgtcgg gcgaaacggt cggcgacaat gtcgacctcg tgcaggcgat tgccggcgac    540
ctgccggttc ccgtgacctc gatctattcg aagagcgacg gcatcgtgaa ctggcggacc    600
tgcctgctgc gcccgtccgc gaccgccgag aatatcgagg tctatttcgc gagccatgtc    660
ggcatcggcg tcaatccggc cgcgctgtgg gcgatcgcgg accggctggc ccagcgggaa    720
ggcgaattcc gccccttcga ccggtccggt ccttttgcca ttgcctacgc gcccccggaa    780
caggcacaat cgatctga                                                  798
```

-continued

```
<210> SEQ ID NO 20
<211> LENGTH: 265
<212> TYPE: PRT
<213> ORGANISM: Unknown
<220> FEATURE:
<223> OTHER INFORMATION: Protein obtained from environmental sample
<220> FEATURE:
<221> NAME/KEY: SITE
<222> LOCATION: (32)...(35)
<223> OTHER INFORMATION: N-glycosylation site. Prosite id = PS00001
<220> FEATURE:
<221> NAME/KEY: SITE
<222> LOCATION: (114)...(123)
<223> OTHER INFORMATION: Lipases, serine active site. Prosite id =
      PS00120
<220> FEATURE:
<221> NAME/KEY: SITE
<222> LOCATION: (156)...(159)
<223> OTHER INFORMATION: N-glycosylation site. Prosite id = PS00001

<400> SEQUENCE: 20

Met Pro Glu Arg Asn Glu Ala Gln Ala Pro Pro Arg Leu Arg Pro Pro
1               5                   10                  15

Gly Leu Gly Leu Phe Leu Ala Glu Ala Arg Gly Ile Phe Glu Leu Asn
            20                  25                  30

Ala Ser Leu Leu Leu Ser Pro Leu Leu Arg Ala Pro Arg Gly Asp
        35                  40                  45

Gly His Pro Val Leu Ala Leu Pro Gly Phe Leu Ala Ser Asp Leu Ser
    50                  55                  60

Met Ala Pro Leu Arg Arg Tyr Leu Thr Glu Leu Gly Tyr Asp Thr His
65                  70                  75                  80

Ala Trp Arg Met Gly Arg Asn Val Gly Gly Ile Ala Lys Met Arg Ile
                85                  90                  95

Ala Leu Leu Glu Arg Leu Thr Gln Ile His Ala Glu Cys Gly Arg Lys
            100                 105                 110

Val Ser Ile Val Gly Trp Ser Leu Gly Gly Val Tyr Ala Arg Asp Leu
        115                 120                 125

Ala Leu Gln Ala Pro Glu Met Val Arg Tyr Val Val Thr Leu Gly Ser
    130                 135                 140

Pro Phe Ala Ser Asp Val Arg Ala Thr Asn Ala Thr Arg Leu Tyr Glu
145                 150                 155                 160

Ala Met Ser Gly Glu Thr Val Gly Asp Asn Val Asp Leu Val Gln Ala
                165                 170                 175

Ile Ala Gly Asp Leu Pro Val Pro Val Thr Ser Ile Tyr Ser Lys Ser
            180                 185                 190

Asp Gly Ile Val Asn Trp Arg Thr Cys Leu Leu Arg Pro Ser Ala Thr
        195                 200                 205

Ala Glu Asn Ile Glu Val Tyr Phe Ala Ser His Val Gly Ile Gly Val
    210                 215                 220

Asn Pro Ala Ala Leu Trp Ala Ile Ala Asp Arg Leu Ala Gln Arg Glu
225                 230                 235                 240

Gly Glu Phe Arg Pro Phe Asp Arg Ser Gly Pro Phe Ala Ile Ala Tyr
                245                 250                 255

Ala Pro Pro Glu Gln Ala Gln Ser Ile
            260                 265

<210> SEQ ID NO 21
<211> LENGTH: 65
<212> TYPE: DNA
<213> ORGANISM: Artificial sequence
<220> FEATURE:
<223> OTHER INFORMATION: Synthetic construct
```

```
<220> FEATURE:
<221> NAME/KEY: misc_feature
<222> LOCATION: (1)...(65)
<223> OTHER INFORMATION: Cloning linker with cloning sites

<400> SEQUENCE: 21
tctagataac gagggcaaaa ccatgggagg atccagatct catcaccatc accatcacta    60
agctt                                                                65
```

HYDROLASES, NUCLEIC ACIDS ENCODING THEM AND METHODS FOR MAKING AND USING THEM

SEQUENCE LISTING

The present application is being filed with a computer readable form (CRF) copy of the Sequence Listing. The CRF entitled 011631-0045-999_SeqListing.txt, which was created on Aug. 29, 2008 and is 33 MB in size, is the same as the paper copy of the Sequence Listing also filed herewith, both of which are incorporated herein by reference in their entirety.

TECHNICAL FIELD

Provided herein are polypeptides having hydrolase activity, including lipase, saturase, palmitase and/or stearatase activity, polynucleotides encoding them, and methods of making and using these polynucleotides and polypeptides. Also provided herein are peptides and polypeptides, e.g., enzymes, having a hydrolase activity, e.g., lipases, saturases, palmitases and/or stearatases, and methods for treatment of fats and oils with such peptides and polypeptides to prepare hydrolyzed oil products such as low saturate animal or vegetable oils, e.g., soy or canola oils, the oil products so treated, and products comprising such treated oils.

BACKGROUND

The major industrial applications for hydrolases, e.g., lipases, saturases, palmitases and/or stearatases, include the food and beverage industry, as antistaling agents for bakery products, and in the production of margarine and other spreads with natural butter flavors; in waste systems; and in the pharmaceutical industry where they are used as digestive aids.

Processed oils and fats are a major component of foods, food additives and food processing aids, and are also important renewable raw materials for the chemical industry. They are available in large quantities from the processing of oilseeds from plants like rice bran, corn, rapeseed, canola, sunflower, olive, palm or soy. Other sources of valuable oils and fats include fish, restaurant waste, and rendered animal fats. These fats and oils are a mixture of triacylglycerides or lipids, i.e. fatty acids (FA) esterified on a glycerol scaffold. Each oil or fat contains a wide variety of different lipid structures, defined by the FA content and their regiochemical distribution on the glycerol backbone. These properties of the individual lipids determine the physical properties of the pure triacylglyceride. Hence, the triacylglyceride content of a fat or oil to a large extent determines the physical, chemical and biological properties of the oil. The value of lipids increases greatly as a function of their purity. High purity can be achieved by fractional chromatography or distillation, separating the desired triacylglyceride from the mixed background of the fat or oil source. However, this is costly and yields are often limited by the low levels at which the triacylglyceride occurs naturally. In addition, the ease of purifying the product is often compromised by the presence of many structurally and physically or chemically similar triacylglycerides in the oil.

An alternative to purifying triacylglycerides or other lipids from a natural source is to synthesize the lipids. The products of such processes are called structured lipids because they contain a defined set of fatty acids distributed in a defined manner on the glycerol backbone. The value of lipids also increases greatly by controlling the fatty acid content and distribution within the lipid. Elimination from triglycerides, fats or oils of undesirable FA, or replacement of FA with undesirable properties by fatty acids with better or more desirable chemical, physical or biological properties, increases the value of the lipids. In particular, a need exists for lipases that can hydrolyze, e.g. selectively hydrolyze, a saturated fatty acid (a "saturase"), or those that in particular, can hydrolyze, e.g. selectively hydrolyze, a palmitic acid (a "palmitase") or a stearic acid (a "stearatase") from a glycerol backbone. Lipases, such as saturases, e.g. palmitases and/or stearatases can be used to effect such control where the FA being removed, added or replaced are saturated fatty acids, e.g. palmitatic acid or stearic acid.

SUMMARY

Provided herein are polypeptides having hydrolase activity, including lipase activity. In one aspect, provided herein are novel classes of lipases termed "saturases", "palmitases" and "stearatases". Also provided are polynucleotides encoding polypeptides having saturase, e.g. palmitase and/or stearatase activity, and methods of making and using these polynucleotides and polypeptides. In one aspect, provided herein are polypeptides, e.g., enzymes, having a hydrolase activity, e.g., lipase, saturase, palmitase and/or stearatase activity having thermostable and/or thermotolerant enzyme (catalytic) activity. The enzymatic activities of the polypeptides and peptides as provided herein include (comprise or consist of) a saturase activity or a lipase activity, including hydrolysis of lipids, acidolysis reactions (e.g., to replace an esterified fatty acid with a free fatty acid), transesterification reactions (e.g., exchange of fatty acids between triacylglycerides), ester synthesis, ester interchange reactions and lipid acyl hydrolase (LAH) activity. In another aspect, the polypeptides as provided herein are used to synthesize enantiomerically pure chiral products.

The polypeptides as provided herein can be used in a variety of pharmaceutical, agricultural and industrial contexts, including the manufacture of cosmetics and nutraceuticals. Additionally, the polypeptides as provided herein can be used in food processing, brewing, bath additives, alcohol production, peptide synthesis, enantioselectivity, hide preparation in the leather industry, waste management and animal waste degradation, silver recovery in the photographic industry, medical treatment, silk degumming, biofilm degradation, biomass conversion to ethanol, biodefense, antimicrobial agents and disinfectants, personal care and cosmetics, biotech reagents, in increasing starch yield from corn wet milling, and as pharmaceuticals such as digestive aids and anti-inflammatory (anti-phlogistic) agents.

In certain embodiments, provided herein are compositions (e.g., lipases, saturases, palmitases and/or stearatases) and methods for producing low saturate oils, e.g., oils with a lower saturated fatty acid content, including oils low in palmitate, stearate, myristate, laurate or butyrate fatty acids and/or caprylic acid (octanoic acid). Any vegetable oil, e.g. canola oil, soybean oil, or animal oil or fat, e.g., tallow, can be treated with a composition, or by a method, as provided herein. Any foods, edible items, or baking, frying or cooking products (e.g., sauces, marinades, condiments, spray oils, margarines, baking oils, mayonnaise, cooking oils, salad oils, spoonable and pourable dressings, and the like, and products made therewith) can comprise a vegetable oil or animal fat that has been treated with a composition or by a method as provided herein. Vegetable oils modified to be lower saturate oils can be used in any foods, edible items or baking or cooking products, e.g., sauces, marinades, condiments, spray oils, margarines, baking oils, mayonnaise, cooking oils, salad oils, spoonable and pourable dressings and the like. In one embodiment, provided herein are oils, such as vegetable oils, e.g., canola oil or soybean oil, and foods or baking or cooking products, including sauces, marinades, condiments, spray oils, margarines, mayonnaise, baking oils, cooking oils, frying oils, salad oils, spoonable and pourable dressings, and the like, wherein the oil or food, baking or cooking product has been modified using an enzyme as provided herein. In one aspect, these vegetable oils, e.g. canola oil, castor oil, coconut oil, coriander oil, corn oil, cottonseed oil, hazelnut oil, hempseed oil, linseed oil, meadowfoam oil, olive oil, palm oil, palm kernel oil, peanut oil, rapeseed oil, rice bran oil, safflower oil, sasanqua oil, soybean oil, sunflower seed oil, tall oil, tsubaki oil, varieties of "natural" oils having altered fatty acid compositions via Genetically Modified Organisms (GMO) or traditional "breeding" such as high oleic, low linolenic, or low saturate oils (high oleic canola oil, low linolenic soybean oil or high stearic sunflower oils), animal fats (tallow, lard, butter fat, and chicken fat), fish oils (candlefish oil, cod-liver oil, orange roughy oil, sardine oil, herring oil, and menhaden oil), or blends of any of the above, and foods or baking, frying or cooking products, comprise oils with a lower saturated fatty acid content, including oils low in palmitic acid, myristic acid, lauric acid, stearic acid, caprylic acid (octanoic acid) etc., processed by using a composition or method as provided herein.

In one aspect, provided herein are polypeptides, for example, enzymes and catalytic antibodies, having a hydrolase activity, e.g., lipase, saturase, palmitase and/or stearatase activity, including thermostable and thermotolerant enzymatic activities, and fatty acid specific or fatty acid selective activities, and low or high pH tolerant enzymatic activities, and polynucleotides encoding these polypeptides, including vectors, host cells, transgenic plants and non-human animals, and methods for making and using these polynucleotides and polypeptides.

In another aspect, provided herein are isolated, synthetic or recombinant nucleic acids comprising
(a) a nucleic acid (polynucleotide) encoding at least one polypeptide, wherein the nucleic acid comprises a sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to:
  (i) SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19 or
  (ii) the nucleic acid of SEQ ID NO:1 having one or more nucleotide changes (or the equivalent thereof) encoding one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four or more or all the amino acid changes (or the equivalent thereof) as set forth in Table 3 or Table 4,
  wherein the nucleic acid of (i) or (ii) encodes at least one polypeptide having a hydrolase activity, e.g. a lipase, a saturase, a palmitase and/or a stearatase activity, or encodes a polypeptide or peptide capable of generating a hydrolase (e.g. a lipase, a saturase, a palmitase and/or a stearatase) specific antibody (polypeptide or peptide that acts as an epitope or immunogen),
(b) the nucleic acid (polynucleotide) of (a), wherein the sequence identities are determined: (A) by analysis with a sequence comparison algorithm or by visual inspection, or (B) over a region of at least about 10, 15, 20, 25, 30, 35, 40, 45, 50, 55, 60, 65, 70, 75, 100, 125, 150, 175, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550 or more residues, or the full length of a cDNA, transcript (mRNA) or gene,
(c) the nucleic acid (polypeptide) of (a) or (b), wherein, the sequence comparison algorithm is a BLAST version 2.2.2 algorithm where a filtering setting is set to blastall-p blastp-d "nr pataa"-F F, and all other options are set to default,
(d) a nucleic acid (polynucleotide) encoding at least one polypeptide or peptide having a hydrolase activity, e.g. a lipase, a saturase, a palmitase and/or a stearatase activity, wherein the nucleic acid comprises a sequence that hybridizes under stringent conditions to the complement of the nucleic acid of (a), (b) or (c), wherein the stringent conditions comprise a wash step comprising a wash in 0.2×SSC at a temperature of about 65° C. for about 15 minutes,
(e) a nucleic acid (polynucleotide) encoding at least one polypeptide having a hydrolase activity, e.g. a lipase, a saturase, a palmitase and/or a stearatase activity, wherein the polypeptide comprises the sequence of SEQ ID NO:2, or enzymatically active fragments thereof, having at least one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, or more or all the amino acid changes (or the equivalent thereof) as set forth in Table 3 or Table 4,
(f) a nucleic acid (polynucleotide) encoding at least one polypeptide having a hydrolase activity, e.g. a lipase, a saturase, a palmitase and/or a stearatase activity, wherein the polypeptide comprises the sequence of SEQ ID NO:2, SEQ ID NO:4, SEQ ID NO:6, SEQ ID NO:8, SEQ ID NO:10, SEQ ID NO:12, SEQ ID NO:14, SEQ ID NO: 16, SEQ ID NO: 18, or SEQ ID NO:20 or enzymatically active fragments thereof,
(g) (A) the nucleic acid (polynucleotide) of any of (a) to (f) and encoding a polypeptide having at least one conservative amino acid substitution and retaining its hydrolase activity, e.g. lipase, saturase, palmitase and/or stearatase activity, or, (B) the nucleic acid of (g)(A), wherein the at least one conservative amino acid substitution comprises substituting an amino acid with another amino acid of like characteristics; or, a conservative substitution comprises: replacement of an aliphatic amino acid with another aliphatic amino acid; replacement of a serine with a threonine or vice versa; replacement of an acidic residue with another acidic residue; replacement of a residue bearing an amide group with another residue bearing an amide group; exchange of a basic residue with another basic residue; or replacement of an aromatic residue with another aromatic residue,
(h) the nucleic acid (polynucleotide) of any of (a) to (g) encoding a polypeptide having a hydrolase activity, e.g. a lipase, a saturase, a palmitase and/or a stearatase activity but lacking a signal sequence, (i) the nucleic acid (polynucleotide) of any of (a) to (h) encoding a polypeptide having a hydrolase activity, e.g. a lipase, a saturase, a palmitase and/or a stearatase activity further comprising a heterologous sequence, (j) the nucleic acid (polynucleotide) of (i), wherein the heterologous sequence comprises, or consists of a sequence encoding: (A) a heterologous signal sequence, (B) the sequence of (A), wherein the heterologous signal sequence is derived from a heterologous enzyme, or, (C) a tag, an epitope, a targeting peptide, a cleavable sequence, a detectable moiety or an enzyme, or (k) a nucleic acid sequence (polynucleotide) fully (completely) complementary to the sequence of any of (a) to (j).

In one aspect, the isolated, synthetic or recombinant nucleic acid encodes a polypeptide or peptide having a hydrolase activity, e.g., lipase, saturase, palmitase and/or stearatase activity, which is thermostable. The polypeptides and peptides encoded by nucleic acids as provided herein, or any polypeptide or peptide as provided herein, can retain enzymatic or binding activity (e.g., substrate binding) under conditions comprising a temperature range of between about −100° C. to about −80° C., about −80° C. to about −40° C., about −40° C. to about −20° C., about −20° C. to about 0° C., about 0° C. to about 5° C., about 5° C. to about 15° C., about 15° C. to about 25° C., about 25° C. to about 37° C., about 37° C. to about 45° C., about 45° C. to about 55° C., about 55° C. to about 70° C., about 70° C. to about 75° C., about 75° C. to about 85° C., about 85° C. to about 90° C., about 90° C. to about 95° C., about 95° C. to about 100° C., about 100° C. to about 105° C., 5 about 105° C. to about 110° C., about 110° C. to about 120° C., or 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C. or more. Provided herein are the thermostable polypeptides that retain a hydrolase activity, e.g., lipase, saturase, palmitase and/or stearatase activity, at a temperature in the ranges described above, at about pH 3.0, about pH 3.5, about pH 4.0, about pH 4.5, about pH 5.0, about pH 5.5, about pH 6.0, about pH 6.5, about pH 7.0, about pH 7.5, about pH 8.0, about pH 8.5, about pH 9.0, about pH 9.5, about pH 10.0, about pH 10.5, about pH 11.0, about pH 11.5, about pH 12.0 or more.

In one aspect, polypeptides as provided herein can be thermotolerant and can retain a hydrolase activity, e.g. lipase, saturase, palmitase and/or stearatase activity after exposure to a temperature in the range from about −100° C. to about −80° C., about −80° C. to about −40° C., about −40° C. to about −20° C., about −20° C. to about 0° C., about 0° C. to about 5° C., about 5° C. to about 15° C., about 15° C. to about 25° C., about 25° C. to about 37° C., about 37° C. to about 45° C., about 45° C. to about 55° C., about 55° C. to about 70° C., about 70° C. to about 75° C., about 75° C. to about 85° C., about 85° C. to about 90° C., about 90° C. to about 95° C., about 95° C. to about 100° C., about 100° C. to about 105° C., about 105° C. to about 110° C., about 110° C. to about 120° C., or 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C., or more.

In some embodiments, the thermotolerant polypeptides retain a hydrolase activity, e.g. lipase, saturase, palmitase and/or stearatase activity, after exposure to a temperature in the ranges described above, at about pH 3.0, about pH 3.5, about pH 4.0, about pH 4.5, about pH 5.0, about pH 5.5, about pH 6.0, about pH 6.5, about pH 7.0, about pH 7.5, about pH 8.0, about pH 8.5, about pH 9.0, about pH 9.5, about pH 10.0, about pH 10.5, about pH 11.0, about pH 11.5, about pH 12.0 or more.

In one embodiment, isolated, synthetic or recombinant nucleic acids comprise a sequence that hybridizes under stringent conditions to a nucleic acid as provided herein, e.g., an exemplary nucleic acid as provided herein comprising a sequence as set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19 or a sequence as set forth in SEQ ID NO:1 having one, two, three, four, five, six, seven, eight, nine, ten, eleven or twelve or more or all the residue changes (sequence modifications to SEQ ID NO:1) set forth in Table 3 or Table 4, or fragments or subsequences thereof, and the sequences (fully) complementary thereto. In one aspect, the nucleic acid encodes a polypeptide having a hydrolase activity, e.g., lipase, saturase, palmitase and/or stearatase activity. The nucleic acid can be at least about 10, 15, 20, 25, 30, 35, 40, 45, 50, 55, 60, 65, 70, 75, 100, 125, 150, 175, 200, 250, 300, 350, 400, 450, 500, 550, 600, 650, 700 or more residues in length or the full length of a gene or transcript comprising SEQ ID NO:1, and having a sequence as set forth in SEQ ID NO:1 having one, two, three, four, five, six, seven, eight, nine, ten, eleven or twelve or more or all the residue changes (amino acid sequence modifications) to SEQ ID NO:1 set forth in Table 3 or Table 4; and the sequences (fully) complementary thereto. In one aspect, the stringent conditions include a wash step comprising a wash in 0.2×SSC at a temperature of about 65° C. for about 15 minutes.

In one embodiment, a nucleic acid probe, e.g., a probe for identifying a nucleic acid encoding a polypeptide having a hydrolase activity, e.g., lipase, saturase, palmitase and/or stearatase activity, comprises a probe comprising or consisting of at least about 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000 or more, consecutive bases of a sequence as provided herein, or fragments or subsequences thereof, wherein the probe identifies the nucleic acid by binding or hybridization. The probe can comprise an oligonucleotide comprising at least about 10 to 50, about 20 to 60, about 30 to 70, about 40 to 80, or about 60 to 100 consecutive bases of a sequence comprising a sequence as provided herein, or fragments or subsequences thereof. The probe can comprise an oligonucleotide comprising at least about 10 to 50, about 20 to 60, about 30 to 70, about 40 to 80, or about 60 to 100 consecutive bases of a nucleic acid sequence as provided herein, or a subsequence thereof.

In one embodiment, an amplification primer sequence pair for amplifying a nucleic acid encoding a polypeptide having a hydrolase activity, e.g., lipase, saturase, palmitase and/or stearatase activity, comprises a primer pair comprising or consisting of a primer pair capable of amplifying a nucleic acid comprising a sequence as provided herein, or fragments or subsequences thereof. One or each member of the amplification primer sequence pair can comprise an oligonucleotide comprising at least about 10 to 50 consecutive bases of the sequence.

In one embodiment, methods of amplifying a nucleic acid encoding a polypeptide having a hydrolase activity, e.g., lipase, saturase, palmitase and/or stearatase activity, comprise amplification of a template nucleic acid with an amplification primer sequence pair capable of amplifying a nucleic acid sequence as provided herein, or fragments or subsequences thereof.

In one embodiment, expression cassettes comprise a nucleic acid as provided herein or a subsequence thereof. In one aspect, the expression cassette can comprise the nucleic acid that is operably linked to a promoter. The promoter can be a viral, bacterial, mammalian or plant promoter. In one aspect, the plant promoter can be a potato, rice, corn, wheat, tobacco or barley promoter. The promoter can be a constitutive promoter. The constitutive promoter can comprise CaMV35S. In another aspect, the promoter can be an inducible promoter. In one aspect, the promoter can be a tissue-specific promoter or an environmentally regulated or a developmentally regulated promoter. Thus, the promoter can be, e.g., a seed-specific, a leaf-specific, a root-specific, a stem-specific or an abscission-induced promoter. In one aspect, the expression cassette can further comprise a plant or plant virus expression vector.

In one embodiment, cloning vehicles comprise an expression cassette (e.g., a vector) as provided herein or a nucleic acid as provided herein. The cloning vehicle can be a viral vector, a plasmid, a phage, a phagemid, a cosmid, a fosmid, a bacteriophage or an artificial chromosome. The viral vector can comprise an adenovirus vector, a retroviral vector or an adeno-associated viral vector. The cloning vehicle can comprise a bacterial artificial chromosome (BAC), a plasmid, a bacteriophage P1-derived vector (PAC), a yeast artificial chromosome (YAC), or a mammalian artificial chromosome (MAC).

In one embodiment, transformed cells comprise a nucleic acid as provided herein or an expression cassette (e.g., a vector) as provided herein, or a cloning vehicle as provided herein. In one aspect, the transformed cell can be a bacterial cell, a mammalian cell, a fungal cell, a yeast cell, an insect cell or a plant cell. In one aspect, the plant cell can be a potato, wheat, rice, corn, tobacco or barley cell. The transformed cell may be any of the host cells familiar to those skilled in the art, including prokaryotic cells, eukaryotic cells, such as bacterial cells, fungal cells, yeast cells, mammalian cells, insect cells, or plant cells. Exemplary bacterial cells include any species within the genera *Escherichia*, *Bacillus*, *Streptomyces*, *Salmonella*, *Pseudomonas* and *Staphylococcus*, including, e.g., *Escherichia coli*, *Lactococcus lactis*, *Bacillus subtilis*, *Bacillus cereus*, *Salmonella typhimurium*, *Pseudomonas fluorescens*. Exemplary fungal cells include any species of *Aspergillus*. Exemplary yeast cells include any species of *Pichia*, *Saccharomyces*, *Schizosaccharomyces*, or *Schwanniomyces*, including *Pichia pastoris*, *Saccharomyces cerevisiae*, or *Schizosaccharomyces pombe*. Exemplary insect cells include any species of *Spodoptera* or *Drosophila*, including *Drosophila* S2 and *Spodoptera* Sf9. Exemplary animal cells include CHO, COS or Bowes melanoma or any mouse or human cell line.

In one embodiment, transgenic plants comprise a nucleic acid as provided herein or an expression cassette (e.g., a vector) as provided herein. The transgenic plant can be a corn plant, a potato plant, a tomato plant, a wheat plant, an oilseed plant, a rapeseed plant, a soybean plant, a rice plant, a barley plant or a tobacco plant.

In one embodiment, transgenic seeds comprise a nucleic acid as provided herein or an expression cassette (e.g., a vector) as provided herein. The transgenic seed can be rice, a corn seed, a wheat kernel, an oilseed, a rapeseed, a soybean seed, a palm kernel, a sunflower seed, a sesame seed, a peanut or a tobacco plant seed.

In one embodiment, isolated, synthetic or recombinant polypeptides have a hydrolase activity, e.g. a lipase, a saturase, a palmitase and/or a stearatase activity, or polypeptides capable of generating an immune response specific for a hydrolase, e.g. a lipase, a saturase, a palmitase and/or a stearatase (e.g., an epitope); and in alternative aspects peptides and polypeptides as provided herein comprise a sequence:

(a) having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or has 100% (complete) sequence identity to:
  (i) the amino acid sequence of SEQ ID NO:2, or enzymatically active fragments thereof, and having at least one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four or more or all of the amino acid residue changes (or the equivalent thereof) as set forth in Table 3 or Table 4, or
  (ii) the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO: 18, or SEQ ID NO:20
    wherein the polypeptide or peptide of (i) or (ii) has a hydrolase activity, e.g. a lipase, a saturase, a palmitase and/or a stearatase activity, or the polypeptide or peptide is capable of generating a hydrolase (e.g. a lipase, a saturase, a palmitase and/or a stearatase) specific antibody (a polypeptide or peptide that acts as an epitope or immunogen), (b) the polypeptide or peptide of (a), wherein the sequence identities are determined: (A) by analysis with a sequence comparison algorithm or by a visual inspection, or (B) over a region of at least about 20, 25, 30, 35, 40, 45, 50, 55, 60, 75, 100, 150, 200, 250, 300 or more amino acid residues, or over the full length of the polypeptide or peptide or enzyme, and/or enzymatically active subsequences (fragments) thereof, (c) the polypeptide or peptide of (b), wherein the sequence comparison algorithm is a BLAST version 2.2.2 algorithm where a filtering setting is set to blastall-p blastp-d "nr pataa"-F F, and all other options are set to default;

(d) an amino acid sequence encoded by the nucleic acid provided herein, wherein the polypeptide has (i) a hydrolase activity, e.g. a lipase, a saturase, a palmitase and/or a stearatase activity, or, (ii) has immunogenic activity in that it is capable of generating an antibody that specifically binds to a polypeptide having a sequence of (a), and/or enzymatically active subsequences (fragments) thereof;

(e) the amino acid sequence of any of (a) to (d), and comprising at least one conservative amino acid residue substitution, and the polypeptide or peptide retains a hydrolase activity, e.g. a lipase, a saturase, a palmitase and/or a stearatase activity;

(f) the amino acid sequence of (e), wherein the conservative substitution comprises replacement of an aliphatic amino acid with another aliphatic amino acid; replacement of a serine with a threonine or vice versa; replacement of an acidic residue with another acidic residue; replacement of a residue bearing an amide group with another residue bearing an amide group; exchange of a basic residue with another basic residue; or, replacement of an aromatic residue with another aromatic residue, or a combination thereof, (g) the amino acid sequence of (f), wherein the aliphatic residue comprises alanine, valine, leucine, isoleucine or a synthetic equivalent thereof; the acidic residue comprises aspartic acid, glutamic acid or a synthetic equivalent thereof; the residue comprising an amide group comprises asparagine, glutamine or a synthetic equivalent thereof; the basic residue comprises lysine, arginine, histidine or a synthetic equivalent thereof; or, the aromatic residue comprises phenylalanine, tyrosine, tryptophan or a synthetic equivalent thereof;

(h) the polypeptide of any of (a) to (f) having a hydrolase activity, e.g. a lipase, a saturase, a palmitase and/or a stearatase activity but lacking a signal sequence, (i) the polypeptide of any of (a) to (h) having a hydrolase activity, e.g. a lipase, a saturase, a palmitase and/or a stearatase activity further comprising a heterologous sequence;

(j) the polypeptide of (i), wherein the heterologous sequence comprises, or consists of: (A) a heterologous signal sequence, (B) the sequence of (A), wherein the heterologous signal sequence is derived from a heterologous enzyme, and/or, (C) a tag, an epitope, a targeting peptide, a cleavable sequence, a detectable moiety or an enzyme; or (m) comprising an amino acid sequence encoded by any nucleic acid sequence as provided herein are.

Exemplary polypeptide or peptide sequences as provided herein include SEQ ID NO:2, and subsequences thereof and variants thereof, e.g., at least about 30, 35, 40, 45, 50, 75, 100, 150, 200, 250, 300, 350, 400, 450, 500 or more residues in length, or over the full length of an enzyme, all having one, two, three, four, five, six, seven, eight, nine, ten, eleven or twelve or more or all the amino acid residue changes (amino acid sequence modifications to SEQ ID NO:2) set forth in Table 3 or Table 4. Exemplary polypeptide or peptide sequences as provided herein include sequence encoded by a nucleic acid as provided herein. Exemplary polypeptide or peptide sequences as provided herein include polypeptides or peptides specifically bound by an antibody as provided herein. In one aspect, a polypeptide as provided herein has at least one hydrolase activity, e.g., lipase, saturase, palmitase and/or stearatase activity. In one aspect, the activity is a regioselective and/or chemoselective activity.

In one aspect, the isolated, synthetic or recombinant polypeptide can comprise the polypeptide as provided herein that lacks a signal (peptide) sequence, e.g., lacks its homologous signal sequence, and in one aspect, comprises a heterologous signal (peptide) sequence. In one aspect, the isolated, synthetic or recombinant polypeptide can comprise the polypeptide as provided herein comprising a heterologous signal sequence, such as a heterologous hydrolase or non-hydrolase (e.g., non-lipase, non-saturase or non-palmitase) signal sequence. In one aspect, chimeric proteins comprise a first domain comprising a signal sequence as provided herein and at least a second domain. The protein can be a fusion protein. The second domain can comprise an enzyme. The enzyme can be a hydrolase (e.g., a lipase, saturase, palmitase and/or stearatase) as provided herein, or, another hydrolase.

In one aspect, the hydrolase (e.g., lipase, saturase, palmitase and/or stearatase) activity comprises a specific activity at about 37° C. in the range from about 100 to about 1000 units per milligram of protein. In another aspect, the hydrolase (e.g., lipase, saturase, palmitase and/or stearatase) activity comprises a specific activity from about 500 to about 750 units per milligram of protein. Alternatively, the hydrolase activity comprises a specific activity at 37° C. in the range from about 500 to about 1200 units per milligram of protein. In one aspect, the hydrolase activity comprises a specific activity at 37° C. in the range from about 750 to about 1000 units per milligram of protein. In another aspect, the thermotolerance comprises retention of at least half of the specific activity of the hydrolase at 37° C. after being heated to an elevated temperature. Alternatively, the thermotolerance can comprise retention of specific activity at 37° C. in the range from about 500 to about 1200 units per milligram of protein after being heated to an elevated temperature.

In one embodiment, the isolated, synthetic or recombinant polypeptides as provided herein comprise at least one glycosylation site. In one aspect, glycosylation can be an N-linked glycosylation. In one aspect, the polypeptide can be glycosylated after being expressed in a P. pastoris or a S. pombe or in plants, such as oil producing plants e.g. soy bean, canola, rice, sunflower, or genetically-modified (GMO) variants of these plants.

In one aspect, the polypeptide can retain a hydrolase (e.g., lipase, saturase, palmitase and/or stearatase) activity under conditions comprising about pH 6.5, pH 6, pH 5.5, pH 5, pH 4.5 or pH 4.0 or lower. In another aspect, the polypeptide can retain a hydrolase (e.g., lipase, saturase, palmitase and/or stearatase) activity under conditions comprising about pH 7, pH 7.5, pH 8.0, pH 8.5, pH 9, pH 9.5, pH 10, pH 10.5, pH 11, pH 11.5, pH 12.0 or more.

In one embodiment, protein preparations comprise a polypeptide as provided herein, wherein the protein preparation comprises a liquid, a solid or a gel.

In one aspect, heterodimers as provided herein comprise a polypeptide and a second domain. In one aspect, the second domain can be a polypeptide and the heterodimer can be a fusion protein. In one aspect, the second domain can be an epitope or a tag. In one aspect, homodimers as provided herein comprise a polypeptide as provided herein.

In one embodiment, immobilized polypeptides as provided herein have a hydrolase (e.g., lipase, saturase, palmitase and/or stearatase) activity, wherein the polypeptide comprises a polypeptide as provided herein, a polypeptide encoded by a nucleic acid as provided herein, or a polypeptide comprising a polypeptide as provided herein and a second domain. In one aspect, a polypeptide as provided herein can be immobilized on a cell, a vesicle, a liposome, a film, a membrane, a metal, a resin, a polymer, a ceramic, a glass, a microelectrode, a graphitic particle, a bead, a gel, a plate, a crystal, a tablet, a pill, a capsule, a powder, an agglomerate, a surface, a porous structure, an array or a capillary tube, or materials such as grains, husks, bark, skin, hair, enamel, bone, shell and materials deriving from them. Polynucleotides, polypeptides and enzymes as provided herein can be formulated in a solid form such as a powder, a lyophilized preparation, granules, a tablet, a bar, a crystal, a capsule, a pill, a pellet, or in a liquid form such as an aqueous solution, an aerosol, a gel, a paste, a slurry, an aqueous/oil emulsion, a cream, a capsule, or a vesicular or micellar suspension.

In one embodiment, food supplements for an animal comprise a polypeptide as provided herein, e.g., a polypeptide encoded by the nucleic acid as provided herein. In one aspect, the polypeptide in the food supplement can be glycosylated. In one embodiment, edible enzyme delivery matrices comprise a polypeptide as provided herein, e.g., a polypeptide encoded by the nucleic acid as provided herein. In one aspect, the delivery matrix comprises a pellet. In one aspect, the polypeptide can be glycosylated. In one aspect, the hydrolase activity is thermotolerant. In another aspect, the hydrolase activity is thermostable.

In one embodiment, methods of isolating or identifying a polypeptide have a hydrolase (e.g., lipase, saturase, palmitase and/or stearatase) activity comprising the steps of: (a) providing an antibody as provided herein; (b) providing a sample comprising polypeptides; and (c) contacting the sample of step (b) with the antibody of step (a) under conditions wherein the antibody can specifically bind to the polypeptide, thereby isolating or identifying a polypeptide having a hydrolase (e.g., lipase, saturase, palmitase and/or stearatase) activity.

In one embodiment, methods of making an anti-hydrolase antibody comprise administering to a non-human animal a nucleic acid as provided herein or a polypeptide as provided herein or subsequences thereof in an amount sufficient to generate a humoral immune response, thereby making an anti-hydrolase antibody. Provided herein are methods of making an anti-hydrolase antibody comprising administering to a non-human animal a nucleic acid as provided herein or a polypeptide as provided herein or subsequences thereof in an amount sufficient to generate an immune response.

In one embodiment, methods of producing a recombinant polypeptide comprise the steps of: (a) providing a nucleic acid as provided herein operably linked to a promoter; and (b) expressing the nucleic acid of step (a) under conditions that allow expression of the polypeptide, thereby producing a recombinant polypeptide. In one aspect, the method can further comprise transforming a host cell with the nucleic acid of step (a) followed by expressing the nucleic acid of step (a), thereby producing a recombinant polypeptide in a transformed cell.

In one embodiment, methods for identifying a polypeptide having a hydrolase (e.g., lipase, saturase, palmitase and/or stearatase) activity comprise the following steps: (a) providing a polypeptide as provided herein; or a polypeptide encoded by a nucleic acid as provided herein; (b) providing a hydrolase substrate; and (c) contacting the polypeptide or a fragment or variant thereof of step (a) with the substrate of step (b) and detecting a decrease in the amount of substrate or an increase in the amount of a reaction product, wherein a decrease in the amount of the substrate or an increase in the amount of the reaction product detects a polypeptide having a hydrolase (e.g., lipase, saturase, palmitase and/or stearatase) activity.

In one embodiment, methods for identifying a hydrolase substrate comprise the following steps: (a) providing a polypeptide as provided herein; or a polypeptide encoded by a nucleic acid as provided herein; (b) providing a test substrate; and (c) contacting the polypeptide of step (a) with the test substrate of step (b) and detecting a decrease in the amount of substrate or an increase in the amount of reaction product, wherein a decrease in the amount of the substrate or an increase in the amount of a reaction product identifies the test substrate as a hydrolase (e.g., lipase, saturase, palmitase and/or stearatase) substrate.

In one embodiment, methods of determining whether a test compound specifically binds to a polypeptide comprise the following steps: (a) expressing a nucleic acid or a vector comprising the nucleic acid under conditions permissive for translation of the nucleic acid to a polypeptide, wherein the nucleic acid comprises a nucleic acid as provided herein, or, providing a polypeptide as provided herein; (b) providing a test compound; (c) contacting the polypeptide with the test compound; and (d) determining whether the test compound of step (b) specifically binds to the polypeptide.

In one embodiment, methods for identifying a modulator of a hydrolase (e.g., lipase, saturase, palmitase and/or stearatase) activity comprise the following steps: (a) providing a polypeptide as provided herein or a polypeptide encoded by a nucleic acid as provided herein; (b) providing a test compound; (c) contacting the polypeptide of step (a) with the test compound of step (b) and measuring an activity of the hydrolase, wherein a change in the hydrolase activity measured in the presence of the test compound compared to the activity in the absence of the test compound provides a determination that the test compound modulates the hydrolase activity. In one aspect, the hydrolase (e.g., lipase, saturase, palmitase and/or stearatase) activity can be measured by providing a hydrolase substrate and detecting a decrease in the amount of the substrate or an increase in the amount of a reaction product, or, an increase in the amount of the substrate or a decrease in the amount of a reaction product. A decrease in the amount of the substrate or an increase in the amount of the reaction product with the test compound as compared to the amount of substrate or reaction product without the test compound identifies the test compound as an activator of hydrolase activity. An increase in the amount of the substrate or a decrease in the amount of the reaction product with the test compound as compared to the amount of substrate or reaction product without the test compound identifies the test compound as an inhibitor of hydrolase activity.

In one embodiment, computer systems comprise a processor and a data storage device wherein said data storage device has stored thereon a polypeptide sequence or a nucleic acid sequence as provided herein (e.g., a polypeptide encoded by a nucleic acid as provided herein). In one aspect, the computer system can further comprise a sequence comparison algorithm and a data storage device having at least one reference sequence stored thereon. In another aspect, the sequence comparison algorithm comprises a computer program that indicates polymorphisms. In one aspect, the computer system can further comprise an identifier that identifies one or more features in said sequence. In one embodiment, computer readable media have stored thereon a polypeptide sequence or a nucleic acid sequence as provided herein.

In one embodiment, methods for identifying a feature in a sequence comprise the steps of: (a) reading the sequence using a computer program which identifies one or more features in a sequence, wherein the sequence comprises a polypeptide sequence or a nucleic acid sequence as provided herein; and (b) identifying one or more features in the sequence with the computer program.

In another embodiment, provided herein are methods for comparing a first sequence to a second sequence comprising the steps of: (a) reading the first sequence and the second sequence through use of a computer program which compares sequences, wherein the first sequence comprises a polypeptide sequence or a nucleic acid sequence as provided herein; and (b) determining differences between the first sequence and the second sequence with the computer program. The step of determining differences between the first sequence and the second sequence can further comprise the step of identifying polymorphisms. In one aspect, the method can further comprise an identifier that identifies one or more features in a sequence. In another aspect, the method can comprise reading the first sequence using a computer program and identifying one or more features in the sequence.

In one embodiment, methods for isolating or recovering a nucleic acid encoding a polypeptide have a hydrolase (e.g., lipase, saturase, palmitase and/or stearatase) activity from a sample comprising the steps of: (a) providing an amplification primer sequence pair for amplifying a nucleic acid encoding a polypeptide having a hydrolase activity, wherein the primer pair is capable of amplifying a nucleic acid as provided herein; (b) isolating a nucleic acid from the sample or treating the sample such that nucleic acid in the sample is accessible for hybridization to the amplification primer pair; and, (c) combining the nucleic acid of step (b) with the amplification primer pair of step (a) and amplifying nucleic acid from the sample, thereby isolating or recovering a nucleic acid encoding a polypeptide having a hydrolase activity from a sample. In one embodiment, the sample is an environmental sample, e.g., a water sample, a liquid sample, a soil sample, an air sample or a biological sample, e.g. a bacterial cell, a protozoan cell, an insect cell, a yeast cell, a plant cell, a fungal cell or a mammalian cell. One or each member of the amplification primer sequence pair can comprise an oligonucleotide comprising at least about 10 to 50 or more consecutive bases of a sequence as provided herein.

In one embodiment, methods of increasing thermotolerance or thermostability of a hydrolase polypeptide comprise glycosylating a hydrolase polypeptide, wherein the polypeptide comprises at least thirty contiguous amino acids of a polypeptide as provided herein; or a polypeptide encoded by a nucleic acid sequence as provided herein, thereby increasing the thermotolerance or thermostability of the hydrolase polypeptide. In one aspect, the hydrolase specific activity can be thermostable or thermotolerant at a temperature in the range from greater than about 37° C. to about 95° C.

In one embodiment, methods for overexpressing a recombinant hydrolase (e.g., lipase, saturase, palmitase and/or stearatase) polypeptide in a cell comprise expressing a vector comprising a nucleic acid as provided herein or a nucleic acid sequence as provided herein, wherein the sequence identities are determined by analysis with a sequence comparison algorithm or by visual inspection, wherein overexpression is effected by use of a high activity promoter, a dicistronic vector or by gene amplification of the vector.

In one embodiment, detergent compositions comprising a polypeptide as provided herein or a polypeptide encoded by a nucleic acid as provided herein comprise a hydrolase activity, e.g., lipase, saturase, palmitase and/or stearatase activity. In one aspect, the hydrolase can be a nonsurface-active hydrolase. In another aspect, the hydrolase can be a surface-active hydrolase.

In one embodiment, methods for washing an object comprise the following steps: (a) providing a composition comprising a polypeptide having a hydrolase activity, e.g., lipase, saturase, palmitase and/or stearatase activity, wherein the polypeptide comprises: a polypeptide as provided herein or a polypeptide encoded by a nucleic acid as provided herein; (b) providing an object; and (c) contacting the polypeptide of step (a) and the object of step (b) under conditions wherein the composition can wash the object.

In one embodiment, methods of making a transgenic plant comprise the following steps: (a) introducing a heterologous nucleic acid sequence into a plant cell, wherein the heterologous nucleic sequence comprises a nucleic acid sequence as provided herein, thereby producing a transformed plant cell; and (b) producing a transgenic plant from the transformed cell. In one aspect, the step (a) can further comprise introducing the heterologous nucleic acid sequence by electroporation or microinjection of plant cell protoplasts. In another aspect, the step (a) can further comprise introducing the heterologous nucleic acid sequence directly to plant tissue by DNA particle bombardment. Alternatively, the step (a) can further comprise introducing the heterologous nucleic acid sequence into the plant cell DNA using an Agrobacterium tumefaciens host. In one aspect, the plant cell can be a potato, corn, rice, wheat, tobacco, or barley cell.

In one embodiment, methods of expressing a heterologous nucleic acid sequence in a plant cell comprise the following steps: (a) transforming the plant cell with a heterologous nucleic acid sequence operably linked to a promoter, wherein the heterologous nucleic sequence comprises a nucleic acid as provided herein; (b) growing the plant under conditions wherein the heterologous nucleic acid sequence is expressed in the plant cell.

In one embodiment, a first method for biocatalytic synthesis of a structured lipid comprises the following steps: (a) providing a polypeptide (e.g., a lipase, saturase, palmitase and/or stearatase) as provided herein; (b) providing a composition comprising a triacylglyceride (TAG); (c) contacting the polypeptide of step (a) with the composition of step (b) under conditions wherein the polypeptide hydrolyzes an acyl residue at the Sn2 position of the triacylglyceride (TAG), thereby producing a 1,3-diacylglyceride (DAG); (d) providing an R1 ester; (e) providing an R1-specific hydrolase, and (f) contacting the 1,3-DAG of step (c) with the R1 ester of step (d) and the R1-specific hydrolase of step (e) under conditions wherein the R1-specific hydrolase catalyzes esterification of the Sn2 position, thereby producing the structured lipid. The hydrolase as provided herein can be an Sn2-specific lipase. The structured lipid can comprise a cocoa butter alternative (CBA), a synthetic cocoa butter, a natural cocoa butter, 1,3-dipalmitoyl-2-oleoylglycerol (POP), 1,3-distearoyl-2-oleoylglycerol (SOS), 1-palmitoyl-2-oleoyl-3-stearoylglycerol (POS) or 1-oleoyl-2,3-dimyristoylglycerol (OMM).

In one embodiment, a second method for biocatalytic synthesis of a structured lipid comprises the following steps: (a) providing a hydrolase (e.g., a lipase, saturase, palmitase and/or stearatase) as provided herein; (b) providing a composition comprising a triacylglyceride (TAG); (c) contacting the polypeptide of step (a) with the composition of step (b) under conditions wherein the polypeptide hydrolyzes an acyl residue at the Sn1 or Sn3 position of the triacylglyceride (TAG), thereby producing a 1,2-DAG or 2,3-DAG; and (d) promoting acyl migration in the 1,2-DAG or 2,3-DAG of the step (c) under kinetically controlled conditions, thereby producing a composition comprising a 1,3-DAG.

This second method can further comprise providing an R1 ester and an R1-specific lipase, and contacting the 1,3-DAG of step (d) with the R1 ester and the R1-specific lipase under conditions wherein the R1-specific lipase catalyzes esterification of the Sn2 position, thereby producing a structured lipid. The hydrolase e.g., a lipase, saturase, palmitase and/or stearatase as provided herein can be a Sn1 or a Sn3-specific enzyme. The structured lipid can comprise any vegetable oil, e.g., a soy oil, a canola oil, cocoa butter alternative (CBA), a synthetic cocoa butter, a natural cocoa butter, 1,3-dipalmitoyl-2-oleoylglycerol (POP), 1,3-distearoyl-2-oleoylglycerol (SOS), 1-palmitoyl-2-oleoyl-3-stearoylglycerol (POS) or 1-oleoyl-2,3-dimyristoylglycerol (OMM).

The R1 ester can comprise a moiety of lower saturation than the hydrolyzed acyl residue, in which case the structured lipid so produced is a lower-saturated fat or oil than the original TAG. The R1 ester can comprise one or more of an omega-3 fatty acid, an omega-6 fatty acid, a mono-unsaturated fatty acid, a poly-unsaturated fatty acid, a phosphogroup, a phytosterol ester, and oryzanol. More specifically the R1 ester can comprise a moiety selected from the group consisting of alpha-linolenic acid, eicosapentaenoic acid, docosahexaenoic acid, gamma-linolenic acid, dihomo-gamma-linolenic acid, arachidonic acid, oleic acid, palmoleic acid, choline, serine, beta-sitosterol, coumestrol, diethylstilbestrol, and oryzanol.

In one aspect of this second method, step (d) further comprises using ion exchange resins. The kinetically controlled conditions can comprise non-equilibrium conditions resulting in production of an end product having greater than a 2:1 ratio of 1,3-DAG to 2,3-DAG. The composition of step (b) can comprise a fluorogenic fatty acid (FA). The composition of step (b) can comprise an umbelliferyl FA ester. The end product can be enantiomerically pure.

In one embodiment, a method for making a lower saturate fat or oil comprises the following steps: (a) providing a polypeptide (a hydrolase, e.g., a lipase, saturase, palmitase and/or stearatase) as provided herein; (b) providing an oil or fat, and (c) contacting the polypeptide of step (a) with the oil or fat of step (b) under conditions wherein the hydrolase can modify the oil or fat, e.g., remove at least one saturated fatty acid, e.g., palmitic, stearic, lauric, caprylic acid (octanoic acid) and the like. The modification can comprise a hydrolase-catalyzed hydrolysis of the fat or oil. The hydrolysis can be a complete or a partial hydrolysis of the fat or oil. The hydrolyzed oil can comprise a glycerol ester of a polyunsaturated fatty acid which can replace the removed saturated fatty acid, or a fish, animal, or vegetable oil. The vegetable oil can comprise an olive, canola, sunflower, palm, soy or lauric oil or rice bran oil or a combination thereof.

In one embodiment, a method for making a lower saturate fat or oil, which may include essential fatty acids, comprises the following steps: (a) providing a polypeptide (e.g., a lipase, saturase, palmitase and/or stearatase) as provided herein; (b) providing a composition comprising a triacylglyceride (TAG); (c) contacting the polypeptide of step (a) with the composition of step (b) under conditions wherein the polypeptide hydrolyzes an acyl residue at the Sn1 or Sn3 position of the triacylglyceride (TAG), thereby producing a 1,2-DAG or 2,3-DAG; and (d) promoting acyl migration in the 1,2-DAG or 2,3-DAG of the step (c) under kinetically controlled conditions, thereby producing a 1,3-DAG.

The method can further comprise providing an R1 ester and an R1-specific lipase, and contacting the 1,3-DAG of step (d) with the R1 ester and the R1-specific lipase under conditions wherein the R1-specific lipase catalyzes esterification of the Sn2 position, thereby producing a structured lipid. The R1 ester can comprise a moiety of lower saturation than the hydrolyzed acyl residue, in which case the structured lipid so produced is a lower-saturated fat or oil than the original TAG. The R1 ester can comprise an omega-3 fatty acid (alpha-linolenic, eicosapentaenoic (EPA), docosahexaenoic (DHA)), an omega-6 fatty acid (gamma-linolenic, dihomo-gama-linolenic (DGLA), or arachidonic), a mono-unsaturated fatty acid (oleic, palmoleic, and the like), phospho-groups (choline and serine), phytosterol esters (beta-sitosterol, coumestrol, and diethylstilbestrol), and oryzanol. The hydrolase, e.g., a lipase, saturase, palmitase and/or stearatase as provided herein can be an Sn1 or an Sn3-specific enzyme. The lower saturated fat or oil can be made by the above-described hydrolysis of any algal oil, vegetable oil, or an animal fat or oil, e.g., *Neochloris oleoabundans* oil, *Scenedesmus dimorphus* oil, *Euglena gracilis* oil, *Phaeodactylum tricornmutum* oil, *Pleurochrysis carterae* oil, *Prymnesium parvum* oil, *Tetraselmis chui* oil, *Tetraselmis suecica* oil, *Isochrysis galbana* oil, *Nannochloropsis salina* oil, *Botryococcus braunii* oil, *Dunaliella tertiolecta* oil, *Nannochloris* species oil, *Spirulina* species oil, *Chlorophycease* (green algae) oil, and *Bacilliarophy* oil canola oil castor oil, coconut oil, coriander oil, corn oil, cottonseed oil, hazelnut oil, hempseed oil, linseed oil, meadowfoam oil, olive oil, palm oil, palm kernel oil, peanut oil, rapeseed oil, rice bran oil, safflower oil, sasanqua oil, soybean oil, sunflower seed oil, tall oil tsubaki oil, varieties of "natural" oils having altered fatty acid compositions via Genetically Modified Organisms (GMO) or traditional "breeding" such as high oleic, low linolenic, or low saturate oils (high oleic canola oil, low linolenic soybean oil or high stearic sunflower oils); animal fats (tallow, lard, butter fat, and chicken fat), fish oils (candlefish oil, cod-liver oil, orange roughy oil, sardine oil, herring oil, and menhaden oil), or blends of any of the above. The lower saturated fat or oil so made can be used in foods or in baking, frying or cooking products comprising oils or fats with a lower fatty acid content, including oils low in palmitic acid, oleic acid, lauric acid, stearic acid, caprylic acid (octanoic acid) etc., processed using a composition or method as provided herein.

In one embodiment, a method for refining a lubricant comprises the following steps: (a) providing a composition comprising a hydrolase (e.g., a lipase, saturase, palmitase and/or stearatase) as provided herein; (b) providing a lubricant; and (c) treating the lubricant with the hydrolase under conditions wherein the hydrolase (e.g., a lipase, saturase, palmitase and/or stearatase) as provided herein can selective hydrolyze oils in the lubricant, thereby refining it. The lubricant can be a hydraulic oil.

In one embodiment, a method of treating a fabric comprises the following steps: (a) providing a composition comprising a hydrolase (e.g., a lipase, saturase, palmitase and/or stearatase) as provided herein, wherein the hydrolase can selectively hydrolyze carboxylic esters; (b) providing a fabric; and (c) treating the fabric with the hydrolase under condition wherein the hydrolase can selectively hydrolyze carboxylic esters thereby treating the fabric. The treatment of the fabric can comprise improvement of the hand and drape of the final fabric, dyeing, obtaining flame retardancy, obtaining water repellency, obtaining optical brightness, or obtaining resin finishing. The fabric can comprise cotton, viscose, rayon, lyocell, flax, linen, ramie, all blends thereof, or blends thereof with polyesters, wool, polyamides acrylics or polyacrylics. In one embodiment, a fabric, yarn or fiber comprising a hydrolase as provided herein can be adsorbed, absorbed or immobilized on the surface of the fabric, yarn or fiber.

In one embodiment, a method for removing or decreasing the amount of a food or oil stain comprises contacting a hydrolase (e.g., a lipase, saturase, palmitase and/or stearatase) as provided herein with the food or oil stain under conditions wherein the hydrolase can hydrolyze oil or fat in the stain. The hydrolase (e.g., a lipase, saturase, palmitase and/or stearatase) as provided herein can have an enhanced stability to denaturation by surfactants and to heat deactivation. The hydrolase (e.g., a lipase, saturase, palmitase and/or stearatase) as provided herein can have a detergent or a laundry solution.

In one embodiment, a dietary composition comprises a hydrolase (e.g., a lipase, saturase, palmitase and/or stearatase) as provided herein. The dietary composition can further comprise a nutritional base comprising a fat. The hydrolase can be activated by a bile salt. The dietary composition can further comprise a cow's milk-based infant formula. The hydrolase can hydrolyze long chain fatty acids.

In one embodiment, a method of reducing fat content in milk or vegetable-based dietary compositions comprises the following steps: (a) providing a composition comprising a hydrolase (e.g., a lipase, saturase, palmitase and/or stearatase) as provided herein; (b) providing a composition comprising a milk or a vegetable oil, and (c) treating the composition of step (b) with the hydrolase under conditions wherein the hydrolase can hydrolyze the oil or fat in the composition. In one embodiment, a dietary composition for a human or for non-ruminant animals, comprises a nutritional base, wherein the base comprises a fat and no or little hydrolase, and an effective amount of a hydrolase (e.g., a lipase, saturase, palmitase and/or stearatase) as provided herein to increase fat absorption and growth of human or non-ruminant animal.

In one embodiment, a method of catalyzing an interesterification reaction to produce new triacylglycerides comprises the following steps: (a) providing a composition comprising a polypeptide (e.g., a lipase, saturase, palmitase and/or stearatase) as provided herein, wherein the polypeptide can catalyze an interesterification reaction; (b) providing a mixture of triacylglycerides and free fatty acids; (c) treating the mixture of step (b) with the polypeptide under conditions wherein the polypeptide can catalyze exchange of free fatty acids with the acyl groups of triacylglycerides, thereby producing new triacylglycerides enriched in the added fatty acids. The polypeptide can be an Sn1,3-specific lipase.

In one embodiment, an interesterification method for preparing an oil having a low trans-acid and a low intermediate chain fatty acid content, comprises the following steps: (a) providing an interesterification reaction mixture comprising a stearic acid source material selected from the group consisting of stearic acid, stearic acid monoesters of low molecular weight monohydric alcohols and mixtures thereof, (b) providing a liquid vegetable oil; (c) providing a polypeptide (e.g., a lipase, saturase, palmitase and/or stearatase) as provided herein, wherein the polypeptide comprises a 1,3-specific lipase activity; (d) interesterifying the stearic acid source material and the vegetable oil triacylglyceride, (e) separating interesterified free fatty acid components from glyceride components of the interesterification mixture to provide an interesterified margarine oil product and a fatty acid mixture comprising fatty acids, fatty acid monoesters or mixtures thereof released from the vegetable oil, and (f) hydrogenating the fatty acid mixture. In one embodiment of the interesterification method, the interesterification reaction continues until there is substantial equilibration of the ester groups in the 1-, 3-positions of the glyceride component with non-glyceride fatty acid components of the reaction mixture.

In one embodiment, a method for making a composition comprises 1-palmitoyl-3-stearoyl-2-monoleine (POSt) and 1,3-distearoyl-2-monoleine (StOSt) comprising providing a polypeptide (e.g., a lipase, saturase, palmitase and/or stearatase) as provided herein, wherein the polypeptide is capable of 1,3-specific lipase-catalyzed interesterification of 1,3-dipalmitoyl-2-monoleine (POP) with stearic acid or tristearin, and contacting said polypeptide with a composition comprising said POP in the presence of a stearin source such as stearic acid or tristearin to make a product enriched in the 1-palmitoyl-3-stearoyl-2-monoleine (POSt) or 1,3-distearoyl-2-monoleine (StOSt).

In one embodiment, a method for ameliorating or preventing lipopolysaccharide (LPS)-mediated toxicity comprises administering to a patient a pharmaceutical composition comprising a hydrolase (e.g., a lipase, saturase, palmitase and/or stearatase) as provided herein. In one embodiment, a method for detoxifying an endotoxin comprises contacting the endotoxin with a hydrolase (e.g., a lipase, saturase, palmitase and/or stearatase) as provided herein. In one embodiment, a method for deacylating a 2' or a 3' fatty acid chain from a lipid A comprises contacting the lipid A with a polypeptide as provided herein.

In one embodiment, methods for altering the substrate specificity or substrate preference of a parental lipase (fatty acid hydrolase) enzyme having an amino acid sequence corresponding to the amino acid sequence in SEQ ID NO:2 comprise the step of generating (inserting) at least 1, 2, 3, 4, 5, 6, 7, 8, 9, 10, 11 or 12 or more amino acid residue mutations in SEQ ID NO:2 as shown in Table 3 or Table 4, thereby generating a new hydrolase enzyme having a modified amino acid sequence and an altered substrate specificity or substrate preference as compared to the parental lipase (fatty acid hydrolase) enzyme SEQ ID NO:2. In one aspect, the substrate specificity or substrate preference of the new lipase (fatty acid hydrolase) enzyme comprises preferential or increased hydrolysis of palmitic acid from an oil, or, the substrate specificity or substrate preference of the new lipase (fatty acid hydrolase) enzyme comprises preferential or increased hydrolysis of stearic acid from an oil.

In one aspect, the modified amino acid sequence (as compared to the "parental" SEQ ID NO:2) comprises D61A; D61E; R72E; R72K; E116A; E116Q; E116R; E116T; E116V; S133A; I151G; I151A; V163R; D164R, or a combination thereof, and the substrate specificity or substrate preference of the new lipase (fatty acid hydrolase) enzyme comprises preferential or increased hydrolysis of palmitic acid from an oil. In one aspect, the modified amino acid sequence (as compared to the "parental" SEQ ID NO:2) comprises I20L; V62S; G77P; V83C; D88H; Y113G; E116T; E116G; H140K; K146S; I167S; L180E; E194M; A211Q; S212Y; G215C; G215V; G215W; A218H; A218S; V223A; A225M; A225Q, or a combination thereof, and the substrate specificity or substrate preference of the new lipase (fatty acid hydrolase) enzyme comprises preferential or increased hydrolysis of stearic acid from an oil.

In one embodiment, methods for making an enzyme having a substrate specificity or substrate preference comprise preferential or increased hydrolysis of palmitic acid from an oil, comprising the steps of: (a) providing a parental hydrolase (e.g., a lipase, saturase, palmitase and/or stearatase) enzyme having a substrate specificity or substrate preference comprising preferential hydrolysis of palmitic acid from an oil, wherein the parental hydrolase (e.g., a lipase, saturase, palmitase and/or stearatase) enzyme has a sequence as provided herein; and (b) making at least 1, 2, 3, 4, 5, 6, 7, 8, 9, 10, 11 or 12 or more amino acid residue modifications to the parental hydrolase (e.g., a lipase, saturase, palmitase and/or stearatase) enzyme, wherein the amino acid residue modifications correspond to the amino acid sequence mutations to SEQ ID NO:2 as shown in Table 3 or Table 4, thereby generating an enzyme having a substrate specificity or substrate preference comprising preferential or increased hydrolysis of palmitic acid from an oil.

In one embodiment, methods for making an enzyme having a substrate specificity or substrate preference comprise preferential or increased hydrolysis of stearic acid from an oil, comprising the steps of: (a) providing a parental hydrolase (e.g., a lipase, saturase, palmitase and/or stearatase) enzyme having a substrate specificity or substrate preference comprising preferential hydrolysis of stearic acid from an oil, wherein the parental hydrolase (e.g., a lipase, saturase, palmitase and/or stearatase) enzyme has a sequence as provided herein; and (b) making at least 1, 2, 3, 4, 5, 6, 7, 8, 9, 10, 11 or 12 or more amino acid residue modifications to the parental hydrolase (e.g., a lipase, saturase, palmitase and/or stearatase) enzyme, wherein the amino acid residue modifications correspond to the amino acid sequence mutations to SEQ ID NO:2 as shown in Table 3 or Table 4, thereby generating an enzyme having a substrate specificity or substrate preference comprising preferential or increased hydrolysis of stearic acid from an oil.

In one embodiment, methods for making a fatty acid hydrolase (e.g., a lipase, saturase, palmitase and/or stearatase) enzyme having a substrate specificity or substrate preference comprise preferential hydrolysis of a particular fatty acid, comprising the steps of (a) providing a fatty acid hydrolase (e.g., a lipase, saturase, palmitase and/or stearatase) enzyme sequence as provided herein; (b) generating (inserting) at least 1, 2, 3, 4, 5, 6, 7, 8, 9, 10, 11 or 12 or more base residue mutations in the nucleic acid, wherein the mutations correspond to those sequence changes as set forth Table 3 or Table 4; and, (c) testing the activity of the newly generated enzyme for a substrate specificity or substrate preference comprising preferential hydrolysis of a particular fatty acid, thereby making the new fatty acid hydrolase (e.g., a lipase, saturase, palmitase and/or stearatase) enzyme having a substrate specificity or substrate preference comprising preferential hydrolysis of a particular fatty acid. In one aspect, the fatty acid hydrolase (e.g., a lipase, saturase, palmitase and/or stearatase) enzyme comprises a sequence as set forth in SEQ ID NO:2. In one aspect, the fatty acid is linolenic acid, linoleic acid, oleic acid, palmitic acid or stearic acid.

In one embodiment, methods for making a fatty acid hydrolase (e.g., a lipase, saturase, palmitase and/or stearatase) enzyme having a substrate specificity or substrate preference comprise preferential hydrolysis of a particular fatty acid, and comprise the steps of (a) providing a fatty acid hydrolase (e.g., a lipase, saturase, palmitase and/or stearatase) enzyme-encoding nucleic acid sequence as provided herein; (b) generating (inserting) at least 1, 2, 3, 4, 5, 6, 7, 8, 9, 10, 11 or 12 or more base residue mutations in the nucleic acid, wherein the mutations correspond to those sequence changes as set forth Table 3 or Table 4; and, (c) expressing the generated nucleic acid to make the new fatty acid hydrolase (e.g., lipase, saturase, palmitase and/or stearatase) enzyme, thereby making a fatty acid hydrolase (e.g., lipase, saturase, palmitase and/or stearatase) enzyme having a substrate specificity or substrate preference comprising preferential hydrolysis of a particular fatty acid.

In one aspect, the fatty acid hydrolase (e.g., lipase, saturase, palmitase and/or stearatase) enzyme-encoding sequence comprises a sequence as set forth in SEQ ID NO:1. In one aspect, the fatty acid is linolenic acid, linoleic acid, oleic acid, palmitic acid or stearic acid. In one aspect, the substrate specificity or substrate preference of the new fatty acid hydrolase (e.g., lipase, saturase, palmitase and/or stearatase) enzyme is palmitic acid as compared to a substrate specificity or substrate preference of stearic acid for the parental fatty acid hydrolase (e.g., lipase, saturase, palmitase and/or stearatase) enzyme, or the substrate specificity or substrate preference of the new fatty acid hydrolase (e.g., lipase, saturase, palmitase and/or stearatase) enzyme is stearic acid as compared to a substrate specificity or substrate preference of palmitic acid for the parental fatty acid hydrolase (e.g., lipase, saturase, palmitase and/or stearatase) enzyme.

In one embodiment, lipases comprise an amino acid sequence as set forth in SEQ ID NO:2 but also comprising at least amino acid residue modification D61A; D61E; R72E; R72K; E116A; E116Q; E116R; E116T; E116V; S133A; 150G; I151A; V163R; D164R, or a combination thereof. In one embodiment, lipases comprise an amino acid sequence as set forth in SEQ ID NO:2 but also comprising at least amino acid residue modification I20L; V62S; G77P; V83C; D88H; Y113G; E116T; E116G; H140K; K146S; I167S; L180E; E194M; A211Q; S212Y; G215C; G215V; G215W; A218H; A218S; V223A; A225M; A225Q, or a combination thereof.

In one aspect, the substrate specificity or substrate preference of the new lipase comprises preferential or increased hydrolysis of a fatty acid from an oil as compared to the "parental" SEQ ID NO:2. In one aspect, the fatty acid is linolenic acid, linoleic acid, oleic acid, palmitic acid or stearic acid.

The details of one or more embodiments as provided herein are set forth in the accompanying drawings and the description below. Other features, objects, and advantages as provided herein will be apparent from the description and drawings, and from the claims.

All publications, patents, patent applications, GenBank sequences and ATCC deposits, cited herein are hereby expressly incorporated by reference for all purposes.

DESCRIPTION OF DRAWINGS

The following drawings are illustrative of embodiments as provided herein and are not meant to limit the scope of the claims.

The patent or application file contains at least one drawing executed in color. Copies of this patent or patent application publication with color drawing(s) will be provided by the Office upon request and payment of the necessary fee.

FIG. 7 shows SEQ ID NO:2, with the particular palmitate and stearate mutation positions listed in bold type of a larger font. Mutations underlined (e.g. 61A, E) are alternative amino acid residue positions (alternative sequences for alternative embodiments) for improving palmitate hydrolysis. Mutations in italics (e.g., 20L) are alternative amino acid residue positions (alternative sequences for alternative embodiments) for improving stearate hydrolysis. Position 116 is an alternative amino acid residue mutation position (an alternative sequence for an alternative embodiment) for improving hydrolysis of both palmitate and stearate.

FIG. 8 shows confirmatory soy oil assay data for selected clones from the palmitase library.

Like reference symbols in the various drawings indicate like elements.

DETAILED DESCRIPTION

Figure 1:
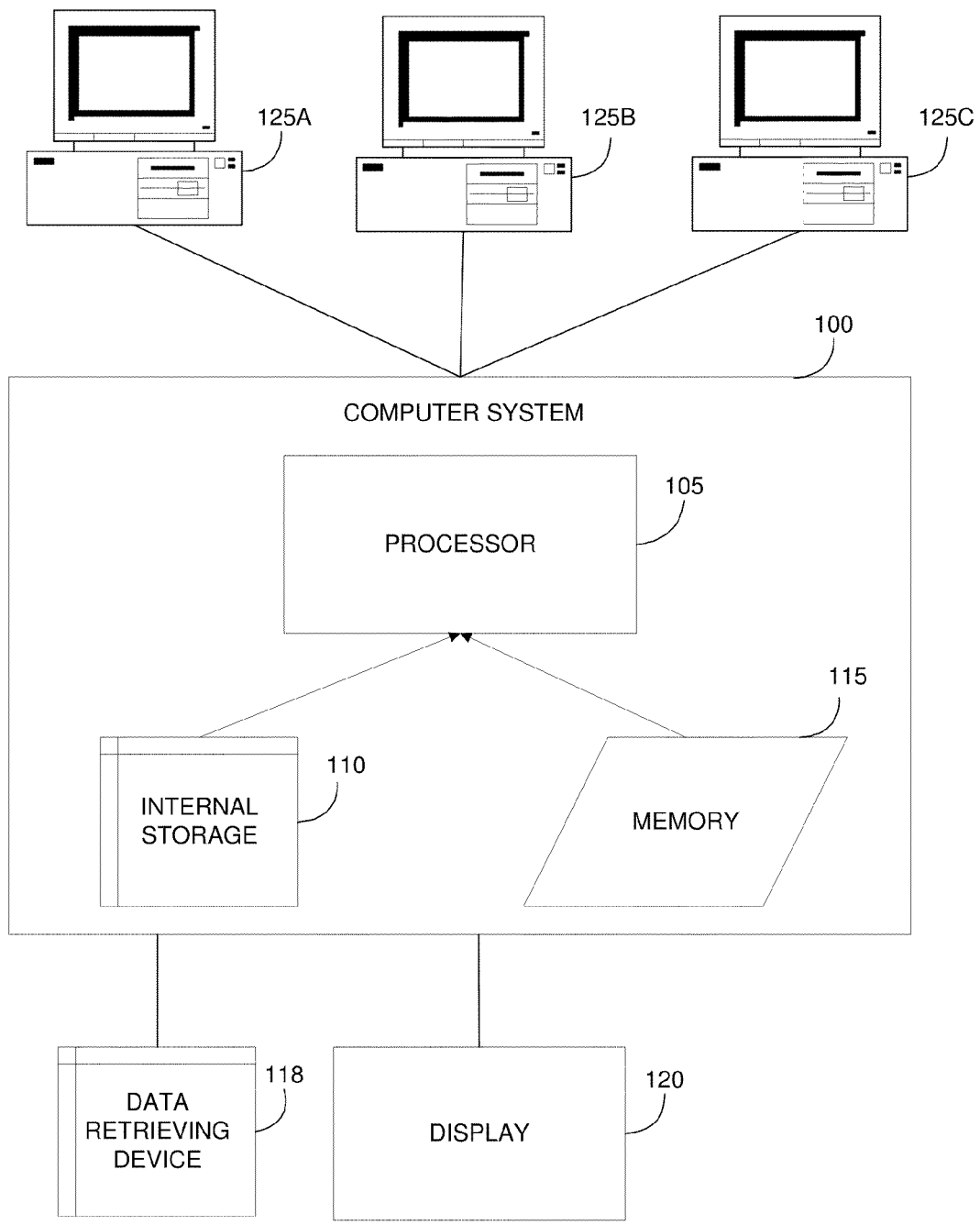
FIG. 1 is a block diagram of a computer system.

Alternative embodiments comprise polypeptides, including lipases, saturases, palmitases and/or stearatases, polynucleotides encoding them, and methods of making and using these polynucleotides and polypeptides. Alternative embodiments comprise polypeptides, e.g., enzymes, having a hydrolase activity, e.g., lipase, saturase, palmitase and/or stearatase activity, including thermostable and thermotolerant hydrolase activity, and polynucleotides encoding these enzymes, and making and using these polynucleotides and polypeptides. The hydrolase activities of the polypeptides and peptides as provided herein include lipase activity (hydrolysis of lipids), interesterification reactions, ester synthesis, ester interchange reactions, lipid acyl hydrolase (LAH) activity) and related enzymatic activity. For the purposes of this patent application, interesterification reactions can include acidolysis reactions (involving the reaction of a fatty acid and a triacylglyceride), alcoholysis (involving the reaction of an alcohol and a triacylglyceride), glycerolysis (involving the reaction of a glycerol and a triacylglyceride) and transesterification reactions (involving the reaction of an ester and a triacyglyceride). The polypeptides as provided herein can be used in a variety of pharmaceutical, agricultural and industrial contexts, including the manufacture of cosmetics and nutraceuticals. In another aspect, the polypeptides as provided herein are used to synthesize enantiomerically pure chiral products.

In certain embodiments, enzymes as provided herein can be highly selective catalysts. They can have the ability to catalyze reactions with stereo-, regio-, and chemo-selectivities not possible in conventional synthetic chemistry. In one embodiment, enzymes as provided herein can be versatile. In various aspects, they can function in organic solvents, operate at extreme pHs (for example, high pHs and low pHs), extreme temperatures (for example, high temperatures and low temperatures), extreme salinity levels (for example, high salinity and low salinity), and catalyze reactions with compounds that are structurally unrelated to their natural, physiological substrates.

In one aspect, the polypeptides as provided herein comprise hydrolases having lipase, saturase, palmitase and/or stearatase activity and can be used, e.g., in the biocatalytic synthesis of structured lipids (lipids that contain a defined set of fatty acids distributed in a defined manner on the glycerol backbone), including any vegetable oil, e.g., canola, soy, soy oil alternatives, cocoa butter alternatives, 1,3-diacyl glycerides (DAGs), 2-monoacylglycerides (MAGs) and triacylglycerides (TAGs), such as 1,3-dipalmitoyl-2-oleoylglycerol (POP), 1,3-distearoyl-2-oleoylglycerol (StOSt), 1-palmitoyl-2-oleoyl-3-stearoylglycerol (POSt) or 1-oleoyl-2,3-dimyristoylglycerol (OMM), poly-unsaturated fatty acids (PUFAs), long chain polyunsaturated fatty acids such as arachidonic acid, docosahexaenoic acid (DHA) and eicosapentaenoic acid (EPA).

In certain embodiment, the enzymes and methods as provided herein can be used to remove, add or exchange any fatty acid from a composition, e.g., make an oil with a lower saturated fatty acid content (e.g., a "low saturate" oil) or a different fatty acid content (e.g., converting an oil comprising "saturated" fatty acids to an oil comprising alternative "unsaturated" fatty acids).

Examples of saturated fatty acids that can be removed, added or "rearranged" on a lipid, e.g., an oil, using an enzyme or by practicing a method as provided herein include:
Acetic: $CH_3COOH$
Butyric: $CH_3(CH_2)_2COOH$
Caroic: $CH_3(CH_2)_4COOH$
Caprylic: $CH_3(CH_2)_6COOH$
Capric: $CH_3(CH_2)_8COOH$
Undacanoic: $CH_3(CH_2)_9COOH$
Lauric: (dodecanoic acid): $CH_3(CH_2)_{10}COOH$
Myristic: (tetradecanoic acid): $CH_3(CH_2)_{12}COOH$
Pentadecanoic: $CH_3(CH_2)_{13}COOH$
Palmitic: (hexadecanoic acid): $CH_3(CH_2)_{14}COOH$
Margaric: $CH_3(CH_2)_{15}COOH$
Stearic (octadecanoic acid): $CH_3(CH_2)_{16}COOH$
Arachidic (eicosanoic acid): $CH_3(CH_2)_{18}COOH$
Behenic: $CH_3(CH_2)_{20}COOH$ Examples of omega-3 unsaturated fatty acids that can be removed, added or "rearranged" on a lipid, e.g., an oil, using an enzyme or by practicing a method as provided herein include:
α-linolenic (ALA): $CH_3CH_2CH=CHCH_2CH=CHCH_2CH=CH(CH_2)_7COOH$
stearaiadonic (octadecatetraenoic): $CH_3CH_2CH=CHCH_2CH=CHCH_2CH=CHCH_2CH=CH(CH_2)_4COOH$
eicosapentaenoic (EPA): $CH_3CH_2CH=CHCH_2CH=CHCH_2CH=CHCH_2CH=CH(CH_2)_3COOH$
docosahexaenoic (DHA) $CH_3CH_2CH=CHCH_2CH=CHCH_2CH=CHCH_2CH=CHCH_2CH=CH(CH_2)_2COOH$ Examples of omega-6 unsaturated fatty acids that can be removed, added or "rearranged" on a lipid, e.g., an oil, using an enzyme or by practicing a method as provided herein include:
Linoleic (9,12-octadecadienoic acid): $CH_3(CH_2)_4CH=CHCH_2CH=CH(CH_2)_7COOH$
Gamma-linolenic (6,9,12-octadecatrienoic acid): $CH_3(CH_2)_4 CH=CHCH_2CH=CHCH_2CH=CH(CH_2)_4COOH$
Eicosadienoic (11,14-eicosadienoic acid): $CH_3(CH_2)_4CH=CHCH_2CH=CH(CH_2)_9COOH$
Dihomo-gamma-linolenic (8,11,14-eicosatrienoic acid): $CH_3(CH_2)_4CH=CHCH_2CH=CHCH_2CH=CH(CH_2)_6COOH$
Arachidonic (5,8,11,14-eicosatetraenoic acid): $CH_3(CH_2)_4CH=CHCH_2CH=CHCH_2CH=CHCH_2CH=CH(CH_2)_3COOH$
Docosadienoic (13,16-docosadienoic acid): $CH_3(CH_2)_4CH=CHCH_2CH=CH(CH_2)_{11}COOH$
Adrenic (7,10,13,16-docosatetraenoic acid): $CH_3(CH_2)_4CH=CHCH_2CH=CHCH_2CH=CHCH_2CH=CH(CH_2)_5COOH$
Docosapentaenoic (4,7,10,13,16-docosapentaenoic acid): $CH_3(CH_2)_4CH=CHCH_2CH=CHCH_2CH=CHCH_2CH=CHCH_2CH=CH(CH_2)_2COOH$ Examples of omega-9 fatty acids that also can be removed, added or "rearranged" on a lipid, e.g., an oil, using an enzyme or by practicing a method as provided herein, include:
Oleic (9-octadecenoic acid): $CH_3(CH_2)_7CH=CH(CH_2)_7COOH$
Eicosenoic (11-eicosenoic acid) $CH_3(CH_2)_7CH=CH(CH_2)_9COOH$
Mead (5,8,11-eicosatrienoic acid): $CH_3(CH_2)_7CH=CHCH_2CH=CHCH_2CH=CH(CH_2)_3COOH$
Euric (13-docosenoic acid): $CH_3(CH_2)_7CH=CH(CH_2)_{11}COOH$
Nervonic (15-tetracosenoic acid): $CH_3(CH_2)_7CH=CH(CH_2)_{13}COOH$.
Palmitoleic: $CH_3(CH_2)_7CH=CH(CH_2)_5COOH$ In one aspect, provided herein are novel classes of lipases termed "saturases", e.g. "palmitases" and "stearatases". The term "saturase" as previously used in the literature described an enzyme that carries out the saturation of specific bonds in a metabolic pathway, e.g. hydrogenation of a double bond (Moise, et. al., *J Biol Chem*, 2005, 280(30):27815-27825). However, provided herein are novel and previously undescribed "saturases", wherein the saturases described herein hydrolyze saturated fatty acid esters, wherein the hydrolyzed esters may be esters of saturated fatty acids and glycerol, umbelliferol or other alcohols.

Also provided herein are previously undescribed "palmitases" and "stearatases", wherein the palmitases and stearatases hydrolyze palmitic acid and stearic acid, respectively, for example, from the glycerol backbone. The "saturases" described herein may also be termed "saturate hydrolases". Similarly, the "palmitases" described herein may also be termed "palmitate hydrolases" and the "stearatases" described herein may also be termed "stearate hydrolases".

In another aspect, the saturases described herein selectively hydrolyze at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% of the saturated fatty acids. In another aspect, the palmitases described herein selectively hydrolyze fatty acids such that at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% of the fatty acids hydrolyzed are palmitic acid. In another aspect, the stearatases described herein selectively hydrolyze fatty acids such that at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% of the fatty acids hydrolyzed are stearic acid.

Figure 5:
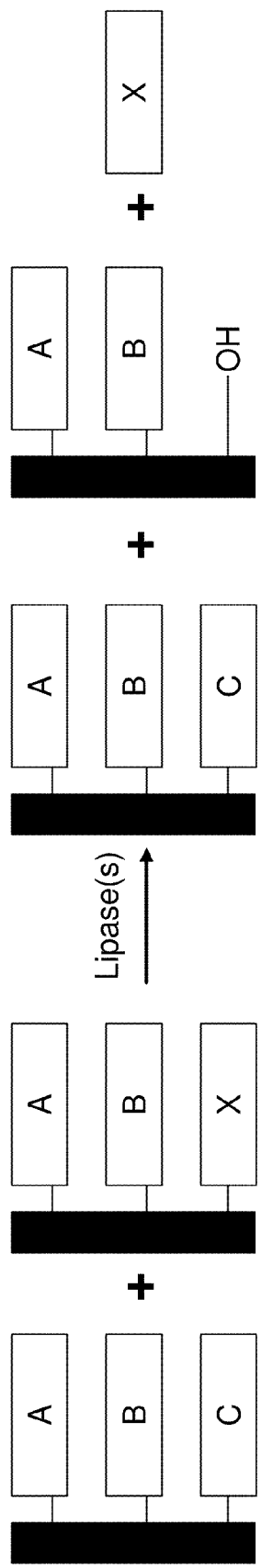
FIG. 5 illustrates an exemplary method as provided herein comprising use of lipases as provided herein to process a lipid, e.g., a lipid from a soy oil, to selectively hydrolyze a palmitic acid to produce a "reduced palmitic soy oil".

In one aspect, as illustrated in FIG. 5, methods of using an enzyme as provided herein can process a lipid, e.g., a lipid from a soy or other vegetable oil, to selectively hydrolyze a saturated fatty acid, e.g., a palmitic or stearic acid, (e.g., from an oil containing these saturated fatty acids) to produce a "low (or lower) saturate oil", e.g., a "reduced palmitic oil", such as a "reduced palmitic vegetable oil", e.g., a "reduced palmitic soy oil". Enzymes as provided herein can also be used to selectively hydrolyze any fatty acid, particularly saturated fatty acids, from a glycerol backbone to produce a "low (or lower) saturate oil", including selectively hydrolyzing a saturated fatty acid, e.g., a palmitic acid or a stearic acid, from an Sn1 or an Sn2 position of a glycerol backbone, in addition to hydrolysis from an Sn3 position (e.g., hydrolysis of palmitic acid from the illustrated Sn3 position in FIG. 5).

In one aspect, an exemplary synthesis of low saturate triglycerides, oils or fats is provided. This exemplary synthesis can use either free fatty acids or fatty acid esters, depending on the enzyme used. In one aspect, the hydrolases, e.g. lipases, saturases, palmitases and/or stearatases, as provided herein are used to remove or hydrolyze saturated fatty acids, such as acetic acid, butyric acid, caproic acid, caprylic acid, capric acid, undecanoic acid, lauric acid, myrsitic acid, pentadecanoic acid, palmitic acid, margaric acid, stearic acid, achidic acid, or behenic acid from a triglyceride, oil or fat. In one aspect, the removed or hydrolyzed fatty acids are replaced by fatty acids with improved health benefits (such as reduced correlation with cardiovascular disease), or improved chemical properties (such as oxidative stability or reactivity) or improved physical properties (such as melting point, or mouth feel). In one aspect the fatty acids added are omega-3 unsaturated fatty acids, such as α-linolenic acid, stearidonic acideicosapentaenoic acid (EPA), or docosahexaenoic acid (DHA), or PUFAs or fish oil fatty acids. In one aspect the fatty acids added are omega-6 unsaturated fatty acids, such as linoleic acid, gamma-linoleic acid, eicosadienoic acid, dihomo-gamma-linoleic acid, arachidonic acid, docoasdienoic acid, adrenic acid, or docosapentaenoic acid. In one aspect the added fatty acids are omega-9 unsaturated fatty acids, such as oleic acid, eicosaenoic acid, mead acid, erucic acid, nervonic acid, or palmitoleic acid. In one aspect the added fatty acids (e.g. omega-3, omega-6, or omega-9) are added by reaction of fatty acids with the triglycerides, oil or fat after the removal or hydrolysis of saturated fatty acids by the hydrolases, e.g. lipases, saturases, palmitases and/or stearatases, as provided herein. In one aspect the added fatty acids (e.g. omega-3, omega-6, or omega-9) are added by reaction of fatty acid esters, including glycerol esters, or ethyl or methyl esters, with the triglycerides, oil or fat after the removal or hydrolysis of saturated fatty acids by the hydrolases, e.g. lipases, saturases, palmitases and/or stearatases, as provided herein. In one aspect the reaction to add fatty acids (e.g. omega-3, omega-6, or omega-9) is catalyzed by a hydrolase or lipase, such as a non-specific lipase (including non-regiospecific and non-fatty acid specific), or a Sn1,3-specific lipase, or a Sn1-specific lipase, or a Sn3 specific lipase, or a Sn2 specific lipase, or a fatty acid-specific lipase.

The methods and compositions (hydrolases, e.g. lipases, saturases, palmitases and/or stearatases) as provided herein can be used in the production of nutraceuticals (e.g., polyunsaturated fatty acids and oils), various foods and food additives (e.g., emulsifiers, fat replacers, margarines and spreads), cosmetics (e.g., emulsifiers, creams), pharmaceuticals and drug delivery agents (e.g., liposomes, tablets, formulations), and animal feed additives (e.g., polyunsaturated fatty acids, such as linoleic acids).

In one aspect, lipases as provided herein can act on fluorogenic fatty acid (FA) esters, e.g., umbelliferyl FA esters. In one aspect, profiles of FA specificities of lipases made or modified by the methods as provided herein can be obtained by measuring their relative activities on a series of umbelliferyl FA esters, such as palmitate, stearate, oleate, laurate, PUFA, or butyrate esters.

In one aspect, a polypeptide (e.g., antibody or enzyme—e.g., a lipase, saturase, palmitase and/or stearatase) as provided herein for these reactions is immobilized, e.g., as described below. In alternative aspects, the methods as provided herein do not require an organic solvent, can proceed with relatively fast reaction rates. See, e.g., U.S. Pat. Nos. 5,552,317; 5,834,259.

In certain embodiments, the methods and compositions (lipases, saturases, palmitases and/or stearatases) as provided herein can be used to hydrolyze (including selectively hydrolyze) oils, such as fish, animal and vegetable oils, and lipids, such as poly-unsaturated fatty acids. In one aspect, the polypeptides as provided herein are used to make low saturate oils, e.g., by removing (hydrolyzing) at least one fatty acid from an oil; and the hydrolysis can be a selective hydrolysis, e.g., only removing a particular fatty acid, such as a palmitic, stearic, or other saturated fatty acid, or just removing a fatty acid from one position, e.g., Sn1, Sn2 or Sn3. In one aspect, the polypeptides as provided herein are used to process fatty acids (such as poly-unsaturated fatty acids), e.g., fish oil fatty acids, e.g., for use in or as a food or feed additive, or a cooking, frying, baking or edible oil. In another embodiment, the methods and compositions (lipases, saturases, palmitases and/or stearatases) as provided herein can be used to selectively hydrolyze saturated esters over unsaturated esters into acids or alcohols. In another embodiment, the methods and compositions (lipases, saturases, palmitases and/or stearatases) as provided herein can be used to treat latexes for a variety of purposes, e.g., to treat latexes used in hair fixative compositions to remove unpleasant odors. In another embodiment, the methods and compositions (lipases, saturases, palmitases and/or stearatases) as provided herein can be used in the treatment of a lipase deficiency in an animal, e.g., a mammal, such as a human. In another embodiment, the methods and compositions (lipases, saturases, palmitases and/or stearatases) as provided herein can be used to prepare lubricants, such as hydraulic oils. In another embodiment, the methods and compositions (lipases, saturases, palmitases and/or stearatases) as provided herein can be used in making and using detergents. In another embodiment, the methods and compositions (lipases, saturases, palmitases and/or stearatases) as provided herein can be used in processes for the chemical finishing of fabrics, fibers or yarns. In one aspect, the methods and compositions (lipases, saturases, palmitases and/or stearatases) as provided herein can be used for obtaining flame retardancy in a fabric using, e.g., a halogen-substituted carboxylic acid or an ester thereof, i.e. a fluorinated, chlorinated or bromated carboxylic acid or an ester thereof. In one aspect, the methods of generating lipases from environmental libraries are provided.

In one embodiment, the "hydrolases" as provided herein encompass polypeptides (e.g., antibodies, enzymes) and peptides (e.g., "active sites") having any hydrolase activity, i.e., the polypeptides as provided herein can have any hydrolase activity, including e.g., a lipase, saturase, palmitase and/or stearatase activity. In another embodiment, the "hydrolases" as provided herein include all polypeptides having any lipase, saturase, palmitase and/or stearatase activity, including lipid synthesis or lipid hydrolysis activity, i.e., the polypeptides as provided herein can have any lipase, saturase, palmitase and/or stearatase activity. In another embodiment, lipases, saturases, palmitases and/or stearatases as provided herein include enzymes active in the bioconversion of lipids through catalysis of hydrolysis, alcoholysis, acidolysis, esterification and aminolysis reactions. In one aspect, hydrolases (e.g. lipases, saturases, palmitases and/or stearatases) as provided herein can hydrolyze lipid emulsions. In one aspect, enzymes as provided herein can act preferentially on Sn-1, Sn-2 and/or Sn-3 bonds of triacylglycerides to release one or more fatty acids from the glycerol backbone. For example, hydrolase, lipase, saturase, palmitase and/or stearatase activity of the polypeptides as provided herein include synthesis of cocoa butter, poly-unsaturated fatty acids (PUFAs), 1,3-diacyl glycerides (DAGs), 2-monoacylglycerides (MAGs) and triacylglycerides (TAGs). In another embodiment, lipase, saturase, palmitase and/or stearatase activity of the polypeptides as provided herein also comprises production of low saturate oils, e.g., soy or canola oil, by removing a fatty acid, e.g., a palmitic, oleic, lauric or stearic acid. In alternative aspects, enzymes as provided herein also can hydrolyze and/or isomerize bonds at high temperatures, low temperatures, alkaline pHs and at acidic pHs. In one aspect the hydrolase e.g. lipase as provided herein is a saturase that catalyzes hydrolysis, alcoholysis, acidolysis, esterification and aminolysis reactions where the carboxylic or fatty acid in the molecule formed or reacted is a saturated fatty acid such as acetic acid, butyric acid, lauric acid, myristic acid, palmitic acid, stearic acid or arachidic acid. In one aspect the hydrolase e.g. lipase or saturase as provided herein is a palmitase that catalyzes hydrolysis, alcoholysis, acidolysis, esterification and aminolysis reactions where the carboxylic or fatty acid in the molecule formed or reacted is a palmitic acid. In one aspect the hydrolase e.g. lipase or saturase as provided herein is a stearatase that catalyzes hydrolysis, alcoholysis, acidolysis, esterification and aminolysis reactions where the carboxylic or fatty acid in the molecule formed or reacted is a stearic acid.

In certain embodiments, provided herein are enzymes comprising hydrolase variants (e.g., "lipase variant", "saturase variant", "palmitase variant" or "stearatase variant") of the enzymes as provided herein; these enzymes can have an amino acid sequence which is derived from the amino acid sequence of a "precursor". The precursor can include naturally-occurring hydrolase and/or a recombinant hydrolase. The amino acid sequence of the hydrolase variant is "derived" from the precursor hydrolase amino acid sequence by the substitution, deletion or insertion of one or more amino acids of the precursor amino acid sequence. Such modification is of the "precursor DNA sequence" which encodes the amino acid sequence of the precursor lipase rather than manipulation of the precursor hydrolase enzyme per se. Suitable methods for such manipulation of the precursor DNA sequence include methods disclosed herein, as well as methods known to those skilled in the art.

Generating and Manipulating Nucleic Acids

In one aspect, nucleic acids, including expression cassettes such as expression vectors, encoding the polypeptides (e.g., hydrolases, such as lipases saturases, palmitases and/or stearatases, and antibodies) are provided herein. In another aspect, provided herein are nucleic acids having a sequence as set forth in SEQ ID NO:1 and having at least one, two, three, four, five, six, seven, eight, nine, ten, eleven or twelve or more or all the base residue changes described in Table 3 or Table 4 (or the equivalent thereof). In one embodiment, provided herein are nucleic acids encoding polypeptides having a sequence as set forth in SEQ ID NO:2 and having at least one, two, three, four, five, six, seven, eight, nine, ten, eleven or twelve or more or all the amino acid residue changes described in Table 3 or Table 4 (or the equivalent thereof).

```
SEQ ID NO: 1
ATGCTGAAACCGCCTCCCTACGGACGCCTGCTGCGCGAACTGGCCGATAT

CCCGGCCATCGTGACGGCACCGTTCCGGGGCGCTGCGAAAATGGGCAAAC

TGGCGGATGGCGAGCCGGTACTGGTGCTGCCCGGCTTCCTGGCCGACGAC

AACGCCACCTCGGTGCTGCGCAAGACCTTCGATGTCGCGGGCTTTGCCTG

TTCGGGCTGGGAACGCGGCTTCAACCTCGGCATTCGTGGCGACCTCGTGG

ACCGGCTGGTCGACCGGCTGCGGGCGGTGTCGGAGGCGGCCGGTGGTCAG

AAGGTGATCGTGGTCGGCTGGAGCCTCGGCGGCCTCTATGCGCGCGAGCT

GGGCCACAAGGCGCCCGAACTGATCCGGATGGTCGTCACGCTCGGCAGTC

CGTTCGCGGGCGACCTCCACGCCAACCATGCGTGGAAGATCTACGAGGCG

ATCAACAGCCACACGGTCGACAACCTGCCGATCCCGGTCGATTTCCAGAT

TAAGCCGCCGGTGCGCACCATCGCGGTGTGGTCGCCGCTCGACGGGGTGG

TGGCGCCGGAGACCTCGGAAGGCTCGCCCGAGCAGTCGGACGAGCGGCTA

GAGCTGGCGGTGACCCACATGGGCTTTGCCGCATCGAAGACCGGGGCCGA

GGCTGTGGTCCGGCTGGTCGCGGCGCGGCTCTAG

SEQ ID NO: 2 (encoded by SEQ ID NO: 1):
1-letter code:
MLKPPPYGRLLRELADIPAIVTAPFRGAAKMGKLADGEPVLVLPGFLADD

NATSVLRKTFDVAGFACSGWERGFNLGIRGDLVDRLVDRLRAVSEAAGGQ

KVIVVGWSLGGLYARELGHKAPELIRMVVTLGSPFAGDLHANHAWKIYEA

INSHTVDNLPIPVDFQIKPPVRTIAVWSPLDGVVAPETSEGSPEQSDERL

ELAVTHMGFAASKTGAEAVVRLVAARL- 3-letter code:
Met Leu Lys Pro Pro Pro Tyr Gly Arg Leu Leu Arg Glu Leu Ala Asp Ile Pro Ala Ile Val Thr Ala Pro Phe Arg Gly Ala Ala Lys Met Gly Lys Leu Ala Asp Gly Glu Pro Val Leu Val Leu Pro Gly Phe Leu Ala Asp Asp Asn Ala Thr Ser Val Leu Arg Lys Thr Phe Asp Val Ala Gly Phe Ala Cys Ser Gly Trp Glu Arg Gly Phe Asn Leu Gly Ile Arg Gly Asp Leu Val Asp Arg Leu Val Asp Arg Leu Arg Ala Val Ser Glu Ala
```

-continued

Ala Gly Gly Gln Lys Val Ile Val Val Gly Trp Ser
Leu Gly Gly Leu Tyr Ala Arg Glu Leu Gly His Lys
Ala Pro Glu Leu Ile Arg Met Val Val Thr Leu Gly
Ser Pro Phe Ala Gly Asp Leu His Ala Asn His Ala
Trp Lys Ile Tyr Glu Ala Ile Asn Ser His Thr Val
Asp Asn Leu Pro Ile Pro Val Asp Phe Gln Ile Lys
Pro Pro Val Arg Thr Ile Ala Val Trp Ser Pro Leu
Asp Gly Val Val Ala Pro Glu Thr Ser Glu Gly Ser
Pro Glu Gln Ser Asp Glu Arg Leu Glu Leu Ala Val
Thr His Met Gly Phe Ala Ala Ser Lys Thr Gly Ala
Glu Ala Val Val Arg Leu Val Ala Ala Arg Leu

SEQ ID NO: 3:
ATGGCCGGCCACCAGGGCGCGCGGGGCCCCAAAGACGGTCCGCCGGCGAT
GGTGATCCCGGGCTTCCTCGCCCACGACAGGCACACGACACGATTGCGCC
GGGAACTCGCCGAGGCGGGGTTCAGGGTTCACCCCTGGCGGCAGGGCTGG
AACATGGGAGCGCGTGCCGACACGCTCGAGAAATTGAAGCGGGCAGTGGA
CCAGTGCGGTCATGACGAGCCGATCCTGCTGGTCGGCTGGAGTCTGGGCG
GGCTCTACGCGAGGGAGGTCGCGCGCGCCGAGCCGGATCAGGTGCGGGCG
GTGGTCACTCTTGGTTCCCCGGTGTCGGGCGACCGGCGCCGCTACACCAA
CGTGTGGAAGCTGTACGAATGGGTGGCGGGTCACCCGGTGGACGACCCGC
CGATCCCCGACAAGGAGGAAAAGCCGCCGGTGCCGACCCTGGCTTTGTGG
TCGGCGGATGACGGGATCGTCGGCGCCCCGTCGGCGCGCGGGACTCAGTT
ATCTCACGACAAGGCGGTCGAGATGCGAACGAGCCACATGGGCTTTGCCA
TGTCGGCGAAGAGCGCACGCTTTGTTGTCGCCGAGATCGTGAAGTTCCTG
AAGAAAACCGAAGGTTCCGAGTCGCACGATTGA

SEQ ID NO: 4 (encoded by SEQ ID NO: 3):
MAGHQGARGPKDGPPAMVIPGFLAHDRHTTRLRRELAEAGFRVHPWRQGW
NMGARADTLEKLKRAVDQCGHDEPILLVGWSLGGLYAREVARAEPDQVRA
VVTLGSPVSGDRRRYTNVWKLYEWVAGHPVDDPPIPDKEEKPPVPTLALW
SADDGIVGAPSARGTQLSHDKAVEMRTSHMGFAMSAKSARFVVAEIVKFL
KKTEGSESHD SEQ ID NO: 5:
GTGAGCGAGAAAGGCGCACCCAAGGGAAGGCAGCGGCTGAAGGAGATCGG
CGCGCTTCTGTTCCACGCGCCTCGCAGCTTGGGCCATCTGGGCGCGCGCG
GCCCCAAGGACGGTCCTCCGGTGATGGTCATCCCGGGATTCCTCGCGCAC
GACTTGCATACGACGCAGTTGCGCCGGGCGCTCGCGAAGGCAGGCTTCCG
AGTGCATCCGTGGCGGCAGGGGATGAACCTTGGAGCGCGCGCCGATACGC
TCGAAATTCTGAAGCGCGCGGTGGATTCCTGCGGCTCGAGCGAGCCGATG
CTGCTCGTCGGCTGGAGCCTGGCGGTCTCTATGCCCGGGAGATCGCGCG
TGCGGAGCCGGACCGGGTGCGGGCGGTGGTGACGATGGGATCGCCGGTGT
GGGGCGACCGCAGGCGCTACACCAACGTGTGGAAGCTGTACGAACGGATT
GCCGGCCATCCGGTCGACAAGCCGCCGATCCCCGACAAGAGCCAGAAGCC
GCCGGTGCCGACTCTGGCTTTGTGGTCGCAGCATGATGGCATCGTCGGCG
CGCCCTCGGCGAGAGGGACGAAGAAGACCCGCGACAAGGCGGTCGCCATC
GACACGACTCACATGGGGTTTGCCATGTCGCCCAAGACGACGCGCGCGGC
AGTGCGTGAGATCGTGGGCTTTTTGAATGAAGTCGAAGGCGGTTCGTCAC
CCCGGGCGTGA SEQ ID NO: 6 (encoded by SEQ ID NO: 5):
MSEKGAPKGRQRLKEIGALLFHAPRSLGHLGARGPKDGPPVMVIPGFLAH
DLHTTQLRRALAKAGFRVHPWRQGMNLGARADTLEILKRAVDSCGSSEPM
LLVGWSLGGLYAREIARAEPDRVRAVVTMGSPVWGDRRRYTNVWKLYERI
AGHPVDKPPIPDKSQKPPVPTLALWSQHDGIVGAPSARGTKKTRDKAVAI
DTTHMGFAMSPKTTRAAVREIVGFLNEVEGGSSPRA SEQ ID NO: 7:
ATGAGGCTGCGCGAGGGGGCGCGCTCGTATCGCGGGCCTATCGCGCCTT
CGGGCGCCTCGGCGAGCGCGGCCCGGCGGACGGGCCGCCGCTGATGGTGA
TCCCGGGCTTCCTCGCCACCGATCGCACCACTTTGGGGCTGCAGCGGGCG
CTGGCCAAGGGCGGCTACAAGGTGACCGGATGGGGCATGGGCCTCAACAG
CGGCGTCACCGAAGACATAGTCGACCGCATCGCCGCTCGGGTCGAAAGGT
TTGGAGCCGGCCGCAAAGTGATCCTCGTCGGCTGGAGCCTCGGCGGACTC
TACGCGCGCGTGGTCGCGCAGGAGCGGCCGGATCTCGTCGACAAGGTGGT
CACGCTCGGCTCGCCCTTTTCGGGCGACAGGCGCCGAACAACAATGTCT
GGCGGCTCTACGAGTTCGTCGCCGGCCATCCGGTCAACAGCCCGCCGATC
GACAAGGACCCCGAGGTGAAGCCGCCGGTGCCGACGCTCGCTATCTGGTC
GCGGCGCGACGGCATCGTCTCTCCGGCGGGCGCGCGCGGGCGGGAGGGAG
AGCGCGACGCCGAGCTCGAGCTCGACTGCAGCCACATGGGCTTTGCGGTC
AGCGCCAGGGCTTATCCCAAGATCGTGGAGGCGGTGCGGGCGTTTCCGGA
AAACATCCGTTCGCGCTGA SEQ ID NO: 8 (encoded by SEQ ID NO: 7):
MRLREGGALVSRAYRAFGRLGERGPADGPPLMVIPGFLATDRTTLGLQRA
LAKGGYKVTGWGMGLNSGVTEDIVDRIAARVERFGAGRKVILVGWSLGGL
YARVVAQERPDLVDKVVTLGSPFSGDRRRNNNVWRLYEFVAGHPVNSPPI
DKDPEVKPPVPTLAIWSRRDGIVSPAGARGREGERDAELELDCSHMGFAV
SARAYPKIVEAVRAFPENIRSR SEQ ID NO: 9:
ATGAAGCCGCCGCCCGGATGGATGAAGATCCGGGAGGCGGGCTCGCTCCT
CGCGCGCTTCTACCGCGCGTTCGGCAAGCTCGAGCCGCGCGGGCCGGCGG
ACGGGCCGAAGCTGATGGTGATCCCGGGTTTCCTCGCGGGCGACAGGACG
ACGCTCGGGCTGCAGCGAGCGCTGGCCGGCGGCGGCTACCGGGTCGCCGG
CTGGGGGCTGGGGGTGAACCGCGGCGTTTCGGAGGACGTGGTCGACCGGA
TCGCCCAGCAAGTCGCGCGGTTCGGGGCGGGCGAGAAGGTGATCCTGGTC
GGCTGGAGCCTTGGCGGGCTTTATGCGCGCGTGGTGGCGCAGGAGCGGCC
CGACCTCGTCGAGAAGGTGGTGACCTTGGGCTCGCCGTTTTCGGGCGACC
GGCGGCGCAACAACAATGTGTGGCGGCTCTATGAGTGGGTGGCTGGGCAT

```
CCGGTGAACGATCCGCCGATCGACAAGGACCCGGCGAAGAAGCCCCGGT
GCCGACGCTCGCGATCTGGTCGCGGCGTGATGGGATCGTGGCGGTCGAAG
GCGCGCGGGGCGGCCGGAGGAGCGGGATGCCGAGCTGGAGATCGATTGC
AGCCACATGGGGTTTGGGGTCAGCGGCAAGGCGTTTCCCCGAATCGTAGA
GGCGGTGAAGGGGTTCTAA
```

SEQ ID NO: 10 (encoded by SEQ ID NO: 9):
```
MKPPPGWMKIREAGSLLARFYRAFGKLEPRGPADGPKLMVIPGFLAGDRT
TLGLQRALAGGGYRVAGWGLGVNRGVSEDVVDRIGQQVARFGAGEKVILV
GWSLGGLYARVVAQERPDLVEKVVTLGSPFSGDRRRNNNVWRLYEWVAGH
PVNDPPIDKDPAKKPPVPTLAIWSRRDGIVAVEGARGRPEERDAELEIDC
SHMGFGVSGKAFPRIVEAVKGF
```

SEQ ID NO: 11:
```
GTGTTGGTGCTGCCGGCGTTCCTCGCCAACGACCTTCCCACTTCGCTTCT
CCGCAGGACGCTGAAGGCGAACGGGTTTCGCCCGTTCGGCTGGGCGAACG
GTTTCAACTTAGGTGCACGGCCGGACACGCTCCAGCGCCTGAGCGCACGG
CTCGATGCGGTGGTTCAGGAAGCGGGCAGGCCGGTTGCATTGATCGGCTG
GAGCCTTGGCGGGCTTTATGCCCGAGAGCTGGCGAAACGCAGGTCGGCTG
AGGTGTCGGCAGTGATCACGCTCGGCACGCCCTTCTCGGTTGACCTCAGA
CGCAACAACGCCTGGAAGCTGTACGAGCTCATCAACGATCATCCTGTCGA
TGCCCCTCCCTTGGATGTTCAGGTCGACGCGAAGCCACCCGTCCGAACCT
TCGCTTTGTGGTCGCGTCGCGACGGGATCGTAGCGCCCGCGAGCGCGCAC
GGCATGGAGGGCGAGTTCGACCAGGCGATCGAGCTGCAGTGCACGCACAA
CGAGATGGTCAGTGATCCGGAGGCCCTCTCCACGATCGTTACCTTGCTGC
GGGAAAATGTTGGCTCCTGA
```

SEQ ID NO: 12 (encoded by SEQ ID NO: 11):
```
MLVLPAFLANDLPTSLLRRTLKANGFRPFGWANGFNLGARPDTLQRLSAR
LDAVVQEAGRPVALIGWSLGGLYARELAKRRSAEVSAVITLGTPFSVDLR
RNNAWKLYELINDHPVDAPPLDVQVDAKPPVRTFALWSRRDGIVAPASAH
GMEGEFDQAIELQCTHNEMVSDPEALSTIVTLLRENVGS
```

SEQ ID NO: 13:
```
GTGAATACAGCCGACCTATTGAAGCCACCACCCGCAAGCATGACAGTTCT
CGAGGCGAGAGCGCTGCTGGACATATGCAAGATGAGCGCCCCATTGGCGC
GCTTGCTATTCAAAAAGAACTCGCCCTGGCGCAAACAACGGGTTCTCGTA
ATACCTGGCTTTGGCGCTGATGATCGCTACACCTGGCCGTTGCGCAATTT
CGTCCAGGCACAGGGCTATGCCACGACTGGCTGGGGCCTGGGCACCAACA
AGGCAGGTCTCAATATGCCGCATCAACTATCCGACGTCCACCCCAGATGG
AAGCTAAAACCCAAGACGCCGTACCGTGGTGAGGCGGGCGTACCTTACGT
GATTGACCGCTTGATCGAACGGTTTGACGAATTGGCATCGACGGATCCGC
AACCCATCGCACTTATAGGTTGGAGTCTGGGTGGTTTCATGGCCCGTGAA
GTTGCCCGAGAGCGCCCAAACCAGGTGAGTCAGGTTATTACCCTCGGTTC
TCCTGTCATCGGAGGCCCAAAATACACCCTCGCTGCATCGGCTTTCATCC
GGCGCAAATACGATTTGGACTGGGTGGAGCAAGTGATCGCGGAGCGGGAA
GATCGCCCCATTACTGTTCCTATTACAGCAATAGTCAGCCAGTCTGATGG
CATCGTCGGATATTCAGCGGCAATCGATCACCACAGTCCCGCTGTGCAGC
ATTTACATATGGATGTTGCCCATTTGGGCTTTCCTTACAACACGAGGGTT
TGGTCAGAAATCGCCAATGCGCTCAACTCTTTAGAGGTGGAGAAGGAGCG
TGTTTAG
```

SEQ ID NO: 14 (encoded by SEQ ID NO: 13):
```
MNTADLLKPPPASMTVLEARALLDICKMSAPLARLLFKKNSPWRKQRVLV
IPGFGADDRYTWPLRNFVQAQGYATTGWGLGTNKAGLNMPHQLSDVHPRW
KLKPKTPYRGEAGVPYVIDRLIERFDELASTDPQPIALIGWSLGGFMARE
VARERPNQVSQVITLGSPVIGGPKYTLAASAFIRRKYDLDWVEQVIAERE
DRPITVPITAIVSQSDGIVGYSAAIDHHSPAVQHLHMDVAHLGFPYNTRV
WSEIANALNSLEVEKERV
```

SEQ ID NO: 15:
```
ATGGAGCTCGCCAAGGTCACCGCCCTGATGAAGGCCACCGCCCTCGAGAT
CGCGATCCTCACCGGCCACCTCGTCCTCTACCCCTCCGGGATCGTGGCCG
AGCGCCTCGCGGCCGCCCCCTCTTCACCGTCCTCCCCGTCCGCGGGCCCG
ACGGGCCGACGTCCGGTCGTCCTGCTGCACGGTTTCGTGGACAACCGCTC
GGTCTTCGTCCTGCTGCGCCGTGCCCTCACCCGGAGCGGCCGTGACTGCG
TCGAGTCGCTCAACTACTCGCCGCTCACCTGCGACCTGCGGGCCGCCGCC
GAACTGCTGGGCGCCGGGTGGACGAGATCCGCGCCCGGACCGGACACGC
CGAGGTCGACATCGTCGGCCACAGCCTGGGCGGGCTCATCGCCCGTTATT
ACGTACAGCGTCTCGGCGGTGACAGCCGGGTGCGCACCCTGGTCATGCTC
GGCACCCCGCACTCCGGCACCACCGTGGCCCGGCTCGCCGACGCGCATCC
GCTGGTGCGGCAGATGCGGCCGGGTTCGGAGGTGCTGCGGGAGCTCGCCG
CGCCCTCGCCCGGCTGCCGTACCCGGTTCGTGAGCTTCTGGAGCGACCTC
GACCAGGTGATGGTGCCGGTGGACACGGCCTGCCTGGACCACCCCGACCT
GCTGGTGCACAACGTCCGGGTCAGCGGGATCGGTCATCTCGCGCTGCCGG
TCCATCCCACGGTGGCGGCCGGGGTCCGGGAGGCCCTCGACGCGAGCGGC
GCGGGGGTCCCGGGGGTGCGGGAGGAGGGGCCCGGCGCCGGCGCCGTGGC
GTGA
```

SEQ ID NO: 16 (encoded by SEQ ID NO: 15):
```
MELAKVTALMKATALEIAILTGHLVLYPSGIVAERLAAAPSSPSSPSAGP
TGRRPVVLLHGFVDNRSVFVLLRRALTRSGRDCVESLNYSPLTCDLRAAA
ELLGRRVDEIRARTGHAEVDIVGHSLGGLIARYYVQRLGGDSRVRTLVML
GTPHSGTTVARLADAHPLVRQMRPGSEVLRELAAPSPGCRTRFVSFWSDL
DQVMVPVDTACLDHPDLLVHNVRVSGIGHLALPVHPTVAAGVREALDASG
AGVPGVREEGPGAGAVA
```

SEQ ID NO: 17:
```
GTGGCCGCCGCGGACAGCGGGACGGCGGAAGGGCAAAGGCTTCGGCCGCC
GAGCCTGTTCCTGATGCTGGCCGAGGCGAGGGGCTTGCTCGAACTGAACT
CGAGCCTGTTGTTGTCGCCGCTGTTGTTGCGGGCGCCGAAGGGCGACGGA
CATCCGGTGCTGGCGCTGCCGGGCTTTCTCGCCAGCGATCTGTCGATGGC
GCCGATGCGGCGCTATCTGAAAGAACTCGGCTACGATGCCCATGCGTGGA
```

```
ACATGGCCGCAATCTCGGCGGCGTCGCGTCCAAGCGCGAAGCCTTGCGC

GACCTGTTGCGGCGCATTTACAGCCAGACGGGCCGCAAGGTCAGCCTGGT

CGGCTGGAGTCTCGGCGGCGTCTATGCGCGCGATCTCGCTTTGCAGGCGC

CCGACATGGTGCGTTCCGTGATCACGCTCGGCAGTCCGTTTGCCAGCGAC

ATCAGGGCGACCAACGCCACGCGGCTCTACGAGGCGCTGTCGGGAGAAAG

GGTCGACGACAATCCGGAGTTAACAGCGGCGATCGCCGGCGACCTGCCGG

TGCCGGCGACCTCGATCTATTCCCGTACCGACGGTATCGTGAACTGGCAC

ACCAGCCTGCTGCGTCCTTCCGCAACGGCTGAAAACATCGAGGTTTACTT

CGCCAGCCATATCGGGCTCGGCGTCAACCCGGCAGCGCTGTGGGCGGTGG

CCGACCGCCTGGCGCAGCCCGAGGGGGAATTTAAGCATTTTGACCGGTCG

GGTCCCTTTGCCATTGCCTATGGCCCCCCTGAAAATGCACAATCCTGA

SEQ ID NO: 18 (encoded by SEQ ID NO: 17):
MAAADSGTAEGQRLRPPSLFLMLAEARGLLELNSSLLLSPLLLRAPKGDG

HPVLALPGFLASDLSMAPMRRYLKELGYDAHAWNMGRNLGGVASKREALR

DLLRRIYSQTGRKVSLVGWSLGGVYARDLALQAPDMVRSVITLGSPFASD

IRATNATRLYEALSGERVDDNPELTAAIAGDLPVPATSIYSRTDGIVNWH

TSLLRPSATAENIEVYFASHIGLGVNPAALWAVADRLAQPEGEFKHFDRS

GPFAIAYGPPENAQS

SEQ ID NO: 19:
ATGCCGGAGCGAAACGAAGCGCAGGCCCCGCCGCGTCTTCGTCCGCCGGG

GCTCGGGCTGTTCCTCGCCGAAGCGCGGGGCATTTTCGAGCTCAACGCGA

GCCTGTTGCTGTCGCCGCTTCTGTTGCGCGCGCCGCGCGGCGACGGCCAT

CCGGTGCTGGCGTTGCCGGGCTTTCTTGCCAGTGATCTATCGATGGCGCC

GTTGCGCCGCTACCTCACCGAGCTCGGCTACGACACCCACGCCTGGCGCA

TGGGCCGCAATGTCGGCGGCATCGCGAAGATGCGGATCGCGCTGCTCGAG

CGGCTCACGCAGATCCATGCCGAGTGCGGCCGCAAGGTCTCGATTGTCGG

CTGGAGTCTCGGCGGCGTCTATGCGCGCGACCTCGCGTTGCAGGCGCCCG

AGATGGTGCGCTACGTCGTCACCCTCGGCAGCCCCTTCGCCAGCGACGTC

CGCGCCACCAATGCGACGCGGCTCTATGAGGCGATGTCGGGCGAAACGGT

CGGCGACAATGTCGACCTCGTGCAGGCGATTGCCGGCGACCTGCCGGTTC

CCGTGACCTCGATCTATTCGAAGAGCGACGGCATCGTGAACTGGCGGACC

TGCCTGCTGCGCCCGTCCGCGACCGCCGAGAATATCGAGGTCTATTTCGC

GAGCCATGTCGGCATCGGCGTCAATCCGGCCGCGTGTGGGCGATCGCGG

ACCGGCTGGCCCAGCGGGAAGGCGAATTCCGCCCCTTCGACCGGTCCGGT

CCTTTTGCCATTGCCTACGCGCCCCCGGAACAGGCACAATCGATCTGA

SEQ ID NO: 20 (encoded by SEQ ID NO: 19):
MPERNEAQAPPRLRPPGLGLFLAEARGIFELNASLLLSPLLLRAPRGDGH

PVLALPGFLASDLSMAPLRRYLTELGYDTHAWRMGRNVGGIAKMRIALLE

RLTQIHAECGRKVSIVGWSLGGVYARDLALQAPEMVRYVVTLGSPFASDV

RATNATRLYEAMSGETVGDNVDLVQAIAGDLPVPVTSIYSKSDGIVNWRT

CLLRPSATAENIEVYFASHVGIGVNPAALWAIADRLAQREGEFRPFDRSG

PFAIAYAPPEQAQSI
```

Provided herein are methods for discovering new hydrolase sequences using the nucleic acids as provided herein. Also provided are methods for modifying the nucleic acids as provided herein by, e.g., GSSM[SM] and GeneReassembly[SM] technologies. The nucleic acids as provided herein can be made, isolated and/or manipulated by, e.g., cloning and expression of cDNA libraries, amplification of message or genomic DNA by PCR, and the like.

The initial source of selected exemplary polypeptides and nucleic acids are:

| SEQ ID NO: | Source |
|---|---|
| 1, 2 | Obtained from environmental sample |
| 3, 4 | Obtained from environmental sample |
| 5, 6 | Obtained from environmental sample |
| 7, 8 | Obtained from environmental sample |
| 9, 10 | Obtained from environmental sample |
| 11, 12 | Obtained from environmental sample |
| 13, 14 | Obtained from environmental sample |
| 15, 16 | Bacteria |
| 17, 18 | Obtained from environmental sample |
| 19, 20 | Obtained from environmental sample |

In practicing the methods as provided herein, homologous genes can be modified by manipulating a template nucleic acid, as described herein. The claimed subject matter can be practiced in conjunction with any method or protocol or device known in the art, which are well described in the scientific and patent literature.

General Techniques

In certain embodiments, provided herein are nucleic acids including RNA, RNAi (e.g., siRNA, miRNA), antisense nucleic acid, cDNA, genomic DNA, vectors, viruses or hybrids thereof, nucleic acids isolated from a variety of sources, genetically engineered, amplified, and/or expressed/generated recombinantly. Recombinant polypeptides generated from these nucleic acids can be individually isolated or cloned and tested for a desired activity (e.g., hydrolase, such as e.g., a lipase, saturase, palmitase and/or stearatase activity). Any recombinant expression system can be used, including bacterial, mammalian, yeast, fungal, insect or plant cell expression systems.

Alternatively, these nucleic acids can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Another useful means of obtaining and manipulating nucleic acids used to practice the methods as provided herein is to clone from genomic samples, and, if desired, screen and re-clone inserts isolated or amplified from, e.g., genomic clones or cDNA clones. Sources of nucleic acid used in the methods as provided herein include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kern (1997) Biotechniques 23:120-124; cosmids, recombinant viruses, phages or plasmids.

The phrases "nucleic acid" or "nucleic acid sequence" can include an oligonucleotide, nucleotide, polynucleotide, or a fragment of any of these, DNA or RNA (e.g., mRNA, rRNA, tRNA, RNAi) of genomic or synthetic origin which may be single-stranded or double-stranded and may represent a sense or antisense strand, a peptide nucleic acid (PNA), or any DNA-like or RNA-like material, natural or synthetic in origin, including, e.g., RNAi (double-stranded "interfering" RNA), ribonucleoproteins (e.g., iRNPs). The term encompasses nucleic acids, i.e., oligonucleotides, containing known analogues of natural nucleotides. The term also encompasses nucleic-acid-like structures with synthetic backbones, see e.g., Mata (1997) Toxicol. Appl. Pharmacol. 144:189-197; Strauss-Soukup (1997) Biochemistry 36:8692-8698; Samstag (1996) Antisense Nucleic Acid Drug Dev 6:153-156.

As used herein, the term "promoter" includes all sequences capable of driving transcription of a coding sequence in a cell, e.g., a plant cell. Thus, promoters used in the constructs as provided herein include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) transcription. "Constitutive" promoters are those that drive expression continuously under most environmental conditions and states of development or cell differentiation. "Inducible" or "regulatable" promoters direct expression of the nucleic acid as provided herein under the influence of environmental conditions or developmental conditions. Examples of environmental conditions that may affect transcription by inducible promoters include anaerobic conditions, elevated temperature, drought, or the presence of light.

"Tissue-specific" promoters are transcriptional control elements that are only active in particular cells or tissues or organs, e.g., in plants or animals. Tissue-specific regulation may be achieved by certain intrinsic factors which ensure that genes encoding proteins specific to a given tissue are expressed. Such factors are known to exist in mammals and plants so as to allow for specific tissues to develop.

The term "plant" includes whole plants, plant parts (e.g., leaves, stems, flowers, roots, etc.), plant protoplasts, seeds and plant cells and progeny of same. The class of plants which can be used in the method as provided herein is generally as broad as the class of higher plants amenable to transformation techniques, including angiosperms (monocotyledonous and dicotyledonous plants), as well as gymnosperms. It includes plants of a variety of ploidy levels, including polyploid, diploid, haploid and hemizygous states. As used herein, the term "transgenic plant" includes plants or plant cells into which a heterologous nucleic acid sequence has been inserted, e.g., the nucleic acids and various recombinant constructs (e.g., expression cassettes) as provided herein.

In one aspect, a nucleic acid encoding a polypeptide as provided herein is assembled in appropriate phase with a leader sequence capable of directing secretion of the translated polypeptide or fragment thereof.

In one embodiment, provided herein are fusion proteins and nucleic acids encoding them. A polypeptide as provided herein can be fused to a heterologous peptide or polypeptide, such as N-terminal identification peptides which impart desired characteristics, such as increased stability or simplified purification. Peptides and polypeptides as provided herein can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequence, such as Factor Xa or enterokinase cleavage sequences (Invitrogen, San Diego Calif.) between a purification domain and the motif-comprising peptide or polypeptide, can facilitate purification. For example, an expression vector can include an epitope-encoding nucleic acid sequence linked to six histidine residues followed by a thioredoxin and an enterokinase cleavage site (see e.g., Williams (1995) Biochemistry 34:1787-1797; Dobeli (1998) Protein Expr. Purif. 12:404-414). The histidine residues facilitate detection and purification while the enterokinase cleavage site provides a means for purifying the epitope from the remainder of the fusion protein. Technology pertaining to vectors encoding fusion proteins and application of fusion proteins are well described in the scientific and patent literature, see e.g., Kroll (1993) DNA Cell. Biol., 12:441-53.

Transcriptional and Translational Control Sequences

In another embodiment, provided herein are nucleic acid (e.g., DNA, iRNA) sequences operatively linked to expression (e.g., transcriptional or translational) control sequence(s), e.g., promoters or enhancers, to direct or modulate RNA synthesis/expression. The expression control sequence can be in an expression vector. Exemplary bacterial promoters include lacI, lacZ, T3, T7, gpt, lambda PR, PL and trp. Exemplary eukaryotic promoters include CMV immediate early, HSV thymidine kinase, early and late SV40, LTRs from retrovirus, and mouse metallothionein.

Promoters suitable for expressing a polypeptide in bacteria include the E. coli lac or trp promoters, the lacI promoter, the lacZ promoter, the T3 promoter, the T7 promoter, the gpt promoter, the lambda PR promoter, the lambda PL promoter, promoters from operons encoding glycolytic enzymes such as 3-phosphoglycerate kinase (PGK), and the acid phosphatase promoter. Eukaryotic promoters include the CMV immediate early promoter, the HSV thymidine kinase promoter, heat shock promoters, the early and late SV40 promoter, LTRs from retroviruses, and the mouse metallothionein-I promoter. Other promoters known to control expression of genes in prokaryotic or eukaryotic cells or their viruses may also be used.

Tissue-Specific Plant Promoters

In one embodiment, provided herein are expression cassettes that can be expressed in a tissue-specific manner, e.g., that can express a hydrolase as provided herein in a tissue-specific manner. In another embodiment, provided herein are plants or seeds that express a hydrolase as provided herein in a tissue-specific manner. The tissue-specificity can be seed specific, stem specific, leaf specific, root specific, fruit specific and the like.

In one aspect, a constitutive promoter such as the CaMV 35S promoter can be used for expression in specific parts of the plant or seed or throughout the plant. For example, for overexpression of a hydrolase as provided herein, a plant promoter fragment can be employed which will direct expression of a nucleic acid in some or all tissues of a plant, e.g., a regenerated plant. Such "constitutive" promoters are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefaciens*, and other transcription initiation regions from various plant genes known to those of skill. Such genes include, e.g., ACT11 from *Arabidopsis* (Huang (1996) Plant Mol. Biol. 33:125-139); Cat3 from *Arabidopsis* (GenBank No. U43147, Zhong (1996) Mol. Gen. Genet. 251:196-203); the gene encoding stearoyl-acyl carrier protein desaturase from *Brassica napus* (Genbank No. X74782, Solocombe (1994) Plant Physiol. 104: 1167-1176); GPc1 from maize (GenBank No. X15596; Martinez (1989) J. Mol. Biol 208:551-565); the Gpc2 from maize (GenBank No. U45855, Manjunath (1997) Plant Mol. Biol. 33:97-112); plant promoters described in U.S. Pat. Nos. 4,962,028; 5,633,440.

In one embodiment, provided herein are tissue-specific or constitutive promoters derived from viruses which can include, e.g., the tobamovirus subgenomic promoter (Kumagai (1995) Proc. Natl. Acad. Sci. USA 92:1679-1683; the rice tungro bacilliform virus (RTBV), which replicates only in phloem cells in infected rice plants, with its promoter which drives strong phloem-specific reporter gene expression; the cassava vein mosaic virus (CVMV) promoter, with highest activity in vascular elements, in leaf mesophyll cells, and in root tips (Verdaguer (1996) Plant Mol. Biol. 31:1129-1139).

Alternatively, the plant promoter may direct expression of a hydrolase-expressing nucleic acid in a specific tissue, organ or cell type (i.e. tissue-specific promoters) or may be otherwise under more precise environmental or developmental control or under the control of an inducible promoter. Examples of environmental conditions that may affect transcription include anaerobic conditions, elevated temperature, the presence of light, or sprayed with chemicals/hormones. In one embodiment, provided herein are drought-inducible promoters of maize (Busk (1997) supra); the cold, drought, and high salt inducible promoter from potato (Kirch (1997) Plant Mol. Biol. 33:897 909).

Tissue-specific promoters can promote transcription only within a certain time frame of developmental stage within that tissue. See, e.g., Blazquez (1998) Plant Cell 10:791-800, characterizing the *Arabidopsis* LEAFY gene promoter. See also Cardon (1997) Plant J 12:367-77, describing the transcription factor SPL3, which recognizes a conserved sequence motif in the promoter region of the *A. thaliana* floral meristem identity gene AP1; and Mandel (1995) Plant Molecular Biology, Vol. 29, pp 995-1004, describing the meristem promoter eIF4. Tissue specific promoters which are active throughout the life cycle of a particular tissue can be used. In one aspect, the nucleic acids as provided herein are operably linked to a promoter active primarily only in cotton fiber cells. In one aspect, the nucleic acids as provided herein are operably linked to a promoter active primarily during the stages of cotton fiber cell elongation, e.g., as described by Rinehart (1996) supra. The nucleic acids can be operably linked to the Fb12A gene promoter to be preferentially expressed in cotton fiber cells (Ibid). See also, John (1997) Proc. Natl. Acad. Sci. USA 89:5769-5773; John, et al., U.S. Pat. Nos. 5,608,148 and 5,602,321, describing cotton fiber-specific promoters and methods for the construction of transgenic cotton plants. Root-specific promoters may also be used to express the nucleic acids as provided herein. Examples of root-specific promoters include the promoter from the alcohol dehydrogenase gene (DeLisle (1990) Int. Rev. Cytol. 123:39-60). Other promoters that can be used to express the nucleic acids as provided herein include, e.g., ovule-specific, embryo-specific, endosperm-specific, integument-specific, seed coat-specific promoters, or some combination thereof; a leaf-specific promoter (see, e.g., Busk (1997) Plant J. 11:1285 1295, describing a leaf-specific promoter in maize); the ORF13 promoter from *Agrobacterium rhizogenes* (which exhibits high activity in roots, see, e.g., Hansen (1997) supra); a maize pollen specific promoter (see, e.g., Guerrero (1990) Mol. Gen. Genet. 224:161 168); a tomato promoter active during fruit ripening, senescence and abscission of leaves and, to a lesser extent, of flowers can be used (see, e.g., Blume (1997) Plant J. 12:731 746); a pistil-specific promoter from the potato SK2 gene (see, e.g., Ficker (1997) Plant Mol. Biol. 35:425 431); the Blec4 gene from pea, which is active in epidermal tissue of vegetative and floral shoot apices of transgenic alfalfa making it a useful tool to target the expression of foreign genes to the epidermal layer of actively growing shoots or fibers; the ovule-specific BEL1 gene (see, e.g., Reiser (1995) Cell 83:735-742, GenBank No. U39944); and/or, the promoter in Klee, U.S. Pat. No. 5,589,583, describing a plant promoter region is capable of conferring high levels of transcription in meristematic tissue and/or rapidly dividing cells.

Alternatively, plant promoters which are inducible upon exposure to plant hormones, such as auxins, are used to express the nucleic acids as provided herein. In one embodiment, provided herein are promoters comprising auxin-response elements E1 promoter fragment (AuxREs) in the soybean (*Glycine max* L.) (Liu (1997) Plant Physiol. 115:397-407); the auxin-responsive *Arabidopsis*-GST6 promoter (also responsive to salicylic acid and hydrogen peroxide) (Chen (1996) Plant J. 10: 955-966); the auxin-inducible parC promoter from tobacco (Sakai (1996) 37:906-913); a plant biotin response element (Streit (1997) Mol. Plant Microbe Interact. 10:933-937); and, the promoter responsive to the stress hormone abscisic acid (Sheen (1996) Science 274: 1900-1902).

The nucleic acids as provided herein can also be operably linked to plant promoters which are inducible upon exposure to chemicals reagents which can be applied to the plant, such as herbicides or antibiotics. For example, the maize In2-2 promoter, activated by benzenesulfonamide herbicide safeners, can be used (De Veylder (1997) Plant Cell Physiol. 38:568-577); application of different herbicide safeners induces distinct gene expression patterns, including expression in the root, hydathodes, and the shoot apical meristem. Coding sequences can be under the control of, e.g., a tetracycline-inducible promoter, e.g., as described with transgenic tobacco plants containing the *Avena sativa* L. (oat) arginine decarboxylase gene (Masgrau (1997) Plant J. 11:465-473); or, a salicylic acid-responsive element (Stange (1997) Plant J. 11:1315-1324). Using chemically- (e.g., hormone- or pesticide-) induced promoters, i.e., promoter responsive to a chemical which can be applied to the transgenic plant in the field, expression of a polypeptide as provided herein can be induced at a particular stage of development of the plant. In certain embodiments, provided herein are transgenic plants containing an inducible gene encoding for polypeptides as provided herein whose host range is limited to target plant species, such as corn, rice, barley, wheat, potato or other crops, inducible at any stage of development of the crop.

Tissue-specific plant promoters may drive expression of operably linked sequences in tissues other than the target tissue. Thus, a tissue-specific promoter is one that drives expression preferentially in the target tissue or cell type, but may also lead to some expression in other tissues as well.

The nucleic acids as provided herein can also be operably linked to plant promoters which are inducible upon exposure to chemicals reagents. These reagents include, e.g., herbicides, synthetic auxins, or antibiotics which can be applied, e.g., sprayed, onto transgenic plants. Inducible expression of the hydrolase-producing nucleic acids as provided herein will allow the grower to select plants with the optimal starch:sugar ratio. The development of plant parts can thus be controlled.

In one embodiment, provided herein are means to facilitate the harvesting of plants and plant parts. For example, in various embodiments, the maize In2-2 promoter, activated by benzenesulfonamide herbicide safeners, is used (De Veylder (1997) Plant Cell Physiol. 38:568-577); application of different herbicide safeners induces distinct gene expression patterns, including expression in the root, hydathodes, and the shoot apical meristem. Coding sequences as provided herein are also under the control of a tetracycline-inducible promoter, e.g., as described with transgenic tobacco plants containing the *Avena sativa* L. (oat) arginine decarboxylase gene (Masgrau (1997) Plant J. 11:465-473); or, a salicylic acid-responsive element (Stange (1997) Plant J. 11: 1315-1324).

If proper polypeptide expression is desired, a polyadenylation region at the 3'-end of the coding region should be included. The polyadenylation region can be derived from the natural gene, from a variety of other plant genes, or from genes in the *Agrobacterial* T-DNA.

Expression Vectors and Cloning Vehicles

In one embodiment, provided herein are expression vectors, expression cassettes and cloning vehicles comprising nucleic acids, e.g., sequences encoding the hydrolases and antibodies. Expression vectors and cloning vehicles as provided herein can comprise viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as *bacillus, Aspergillus* and yeast). Vectors as provided herein can include chromosomal, non-chromosomal and synthetic DNA sequences. Large numbers of suitable vectors are known to those of skill in the art, and are commercially available. Exemplary vectors include: bacterial: pQE vectors (Qiagen), pBLUESCRIPT™ plasmids, pNH vectors, (lambda-ZAP vectors (Stratagene); ptrc99a, pKK223-3, pDR540, pRIT2T (Pharmacia); Eukaryotic: pXT1, pSG5 (Stratagene), pSVK3, pBPV, pMSG, pSV-LSV40 (Pharmacia). However, any other plasmid or other vector may be used so long as they are replicable and viable in the host. Low copy number or high copy number vectors may be employed.

In one embodiment, an "expression cassette" as provided herein comprises a nucleotide sequence which is capable of effecting expression of a structural gene (i.e., a protein coding sequence, such as a hydrolase as provided herein) in a host compatible with such sequences. Expression cassettes include at least a promoter operably linked with the polypeptide coding sequence; and, optionally, with other sequences, e.g., transcription termination signals. Additional factors necessary or helpful in effecting expression may also be used, e.g., enhancers. "Operably linked" as used herein refers to linkage of a promoter upstream from a DNA sequence such that the promoter mediates transcription of the DNA sequence. Thus, expression cassettes also include plasmids, expression vectors, recombinant viruses, any form of recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and includes both the expression and non-expression plasmids. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

The expression vector may comprise a promoter, a ribosome binding site for translation initiation and a transcription terminator. The vector may also include appropriate sequences for amplifying expression. Mammalian expression vectors can comprise an origin of replication, any necessary ribosome binding sites, a polyadenylation site, splice donor and acceptor sites, transcriptional termination sequences, and 5' flanking non-transcribed sequences. In some aspects, DNA sequences derived from the SV40 splice and polyadenylation sites may be used to provide the required non-transcribed genetic elements.

In one aspect, the expression vectors contain one or more selectable marker genes to permit selection of host cells containing the vector. Such selectable markers include genes encoding dihydrofolate reductase or genes conferring neomycin resistance for eukaryotic cell culture, genes conferring tetracycline or ampicillin resistance in *E. coli*, and the *S. cerevisiae* TRP1 gene. Promoter regions can be selected from any desired gene using chloramphenicol transferase (CAT) vectors or other vectors with selectable markers.

Vectors for expressing the polypeptide or fragment thereof in eukaryotic cells may also contain enhancers to increase expression levels. Enhancers are cis-acting elements of DNA, usually from about 10 to about 300 bp in length that act on a promoter to increase its transcription. Examples include the SV40 enhancer on the late side of the replication origin bp 100 to 270, the cytomegalovirus early promoter enhancer, the polyoma enhancer on the late side of the replication origin, and the adenovirus enhancers.

A DNA sequence may be inserted into a vector by a variety of procedures. In general, the DNA sequence is ligated to the desired position in the vector following digestion of the insert and the vector with appropriate restriction endonucleases. Alternatively, blunt ends in both the insert and the vector may be ligated. A variety of cloning techniques are known in the art, e.g., as described in Ausubel and Sambrook. Such procedures and others are deemed to be within the scope of those skilled in the art.

The vector may be in the form of a plasmid, a viral particle, or a phage. Other vectors include chromosomal, non-chromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by, e.g., Sambrook.

Particular bacterial vectors which may be used include the commercially available plasmids comprising genetic elements of the well known cloning vector pBR322 (ATCC 37017), pKK223-3 (Pharmacia Fine Chemicals, Uppsala, Sweden), GEM1™ (Promega Biotec, Madison, Wis., USA) pQE70, pQE60, pQE-9 (Qiagen), pD10, psiX174 Pbluescript II KS™, pNH8A, pNH16a, pNH18A, pNH46A (Stratagene), ptrc99a, pKK223-3, pKK233-3, DR540, pRIT5 (Pharmacia), pKK232-8 and pCM7. Particular eukaryotic vectors include pSV2CAT, pOG44, pXT1, pSG (Stratagene) pSVK3, pBPV, pMSG, and pSVL (Pharmacia). However, any other vector may be used as long as it is replicable and viable in the host cell.

The nucleic acids as provided herein can be expressed in expression cassettes, vectors or viruses and transiently or stably expressed in plant cells and seeds. One exemplary transient expression system uses episomal expression systems, e.g., cauliflower mosaic virus (CaMV) viral RNA generated in the nucleus by transcription of an episomal minichromosome containing supercoiled DNA, see, e.g., Covey (1990) Proc. Natl. Acad. Sci. USA 87:1633-1637. Alternatively, coding sequences, i.e., all or sub-fragments of sequences as provided herein can be inserted into a plant host cell genome becoming an integral part of the host chromosomal DNA. Sense or antisense transcripts can be expressed in this manner. A vector comprising the sequences (e.g., promoters or coding regions) from nucleic acids as provided herein can comprise a marker gene that confers a selectable phenotype on a plant cell or a seed. For example, the marker may encode biocide resistance, particularly antibiotic resistance, such as resistance to kanamycin, G418, bleomycin, hygromycin, or herbicide resistance, such as resistance to chlorosulfuron or Basta.

Expression vectors capable of expressing nucleic acids and proteins in plants are well known in the art, and can include, e.g., vectors from *Agrobacterium* spp., potato virus X (see, e.g., Angell (1997) EMBO J. 16:3675-3684), tobacco mosaic virus (see, e.g., Casper (1996) Gene 173:69-73), tomato bushy stunt virus (see, e.g., Hillman (1989) Virology 169:42-50), tobacco etch virus (see, e.g., Dolja (1997) Virology 234:243-252), bean golden mosaic virus (see, e.g., Morinaga (1993) Microbiol Immunol. 37:471-476), cauliflower mosaic virus (see, e.g., Cecchini (1997) Mol. Plant Microbe Interact. 10: 1094-1101), maize Ac/Ds transposable element (see, e.g., Rubin (1997) Mol. Cell. Biol. 17:6294-6302; Kunze (1996) Curr. Top. Microbiol. Immunol. 204:161-194), and the maize suppressor-mutator (Spm) transposable element (see, e.g., Schlappi (1996) Plant Mol. Biol. 32:717-725); and derivatives thereof.

In one aspect, the expression vector can have two replication systems to allow it to be maintained in two organisms, for example in mammalian, yeast, fungal or insect cells for expression and in a prokaryotic host for cloning and amplification. Furthermore, for integrating expression vectors, the expression vector can contain at least one sequence homologous to the host cell genome. It can contain two homologous sequences which flank the expression construct. The integrating vector can be directed to a specific locus in the host cell by selecting the appropriate homologous sequence for inclusion in the vector. Constructs for integrating vectors are well known in the art.

Expression vectors as provided herein may also include a selectable marker gene to allow for the selection of bacterial strains that have been transformed, e.g., genes which render the bacteria resistant to drugs such as ampicillin, chloramphenicol, erythromycin, kanamycin, neomycin and tetracycline. Selectable markers can also include biosynthetic genes, such as those in the histidine, tryptophan and leucine biosynthetic pathways.

Host Cells and Transformed Cells

In one embodiment, provided herein are transformed cells comprising a nucleic acid sequence, e.g., a sequence encoding a hydrolase or an antibody, or a vector as provided herein. The host cell may be any of the host cells familiar to those skilled in the art, including prokaryotic cells, eukaryotic cells, such as bacterial cells, fungal cells, yeast cells, mammalian cells, insect cells, or plant cells.

Enzymes as provided herein can be expressed in any host cell, e.g., any bacterial cell, any yeast cell, any *Saccharomyces* or *Schizosaccharomyces* spp., any *Pichia* spp., e.g., *Pichia pastoris, Saccharomyces cerevisiae* or *Schizosaccharomyces pombe*. Exemplary bacterial cells include any *Streptomyces* or *Bacillus* spp., e.g., *E. coli, Lactococcus lactis, Bacillus subtilis, Bacillus cereus, Salmonella typhimurium* or any species within the genera *Bacillus, Streptomyces* and *Staphylococcus*. Exemplary insect cells include *Drosophila* S2 and *Spodoptera* Sf9. Exemplary animal cells include CHO, COS or Bowes melanoma or any mouse or human cell line. The selection of an appropriate host is within the abilities of those skilled in the art. Techniques for transforming a wide variety of higher plant species are well known and described in the technical and scientific literature. See, e.g., Weising (1988) Ann. Rev. Genet. 22:421-477, U.S. Pat. No. 5,750, 870.

The vector may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (Davis, L., Dibner, M., Battey, I., Basic Methods in Molecular Biology, (1986)).

Where appropriate, the engineered host cells can be cultured in conventional nutrient media modified as appropriate for activating promoters, selecting transformants or amplifying the genes as provided herein. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

In one aspect, the nucleic acids or vectors as provided herein are introduced into the cells for screening, thus, the nucleic acids enter the cells in a manner suitable for subsequent expression of the nucleic acid. The method of introduction is largely dictated by the targeted cell type. Exemplary methods include $CaPO_4$ precipitation, liposome fusion, lipofection (e.g., LIPOFECTIN™), electroporation, viral infection, etc. The candidate nucleic acids may stably integrate into the genome of the host cell (for example, with retroviral introduction) or may exist either transiently or stably in the cytoplasm (i.e. through the use of traditional plasmids, utilizing standard regulatory sequences, selection markers, etc.). Alternative embodiments comprise retroviral vectors capable of transfecting such targets (e.g., mammalian, human cells) because, e.g., many pharmaceutically important screens require human or model mammalian cell targets.

Cells can be harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides as provided herein may or may not also include an initial methionine amino acid residue.

Cell-free translation systems can also be employed to produce a polypeptide as provided herein. Cell-free translation systems can use mRNAs transcribed from a DNA construct comprising a promoter operably linked to a nucleic acid encoding the polypeptide or fragment thereof. In some aspects, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The expression vectors can contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

Amplification of Nucleic Acids

In another embodiment, provided herein are nucleic acids encoding the polypeptides, or modified nucleic acids, can be reproduced by, e.g., amplification. In one embodiment, provided herein are amplification primer pairs for amplifying nucleic acids encoding a hydrolase, e.g., a lipase, saturase, palmitase and/or stearatase, where the primer pairs are capable of amplifying nucleic acid sequences as provided herein. One of skill in the art can design amplification primer sequence pairs for any part of or the full length of these sequences.

Amplification reactions can also be used to quantify the amount of nucleic acid in a sample (such as the amount of message in a cell sample), label the nucleic acid (e.g., to apply it to an array or a blot), detect the nucleic acid, or quantify the amount of a specific nucleic acid in a sample. In one aspect as provided herein, message isolated from a cell or a cDNA library is amplified. The skilled artisan can select and design suitable oligonucleotide amplification primers. Amplification methods are also well known in the art, and include, e.g., polymerase chain reaction, PCR (see, e.g., PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y., ligase chain reaction (LCR) (see, e.g., Wu (1989) Genomics 4:560; Landegren (1988) Science 241:1077; Barringer (1990) Gene 89:117); transcription amplification (see, e.g., Kwoh (1989) Proc. Natl. Acad. Sci. USA 86:1173); and, self-sustained sequence replication (see, e.g., Guatelli (1990) Proc. Natl. Acad. Sci. USA 87:1874); Q Beta replicase amplification (see, e.g., Smith (1997) J. Clin. Microbiol. 35:1477-1491), automated Q-beta replicase amplification assay (see, e.g., Burg (1996) Mol. Cell. Probes 10:257-271) and other RNA polymerase mediated techniques (e.g., NASBA, Cangene, Mississauga, Ontario); see also Berger (1987) Methods Enzymol. 152:307-316; Sambrook; Ausubel; U.S. Pat. Nos. 4,683,195 and 4,683,202; Sooknanan (1995) Biotechnology 13:563-564.

In one embodiment, provided herein are amplification primer pairs comprising sequences as provided herein, for example, wherein the primer pair comprises a first member having a sequence as set forth by about the first (the 5') 12, 13, 14, 15, 16, 17, 18, 19, 20, 21, 22, 23, 24, 25, 26, 27, 28, 29, 30, 31, 32, 33, 34, 35, 36, 37, 38, 39 or 40 or more residues of a nucleic acid as provided herein, and a second member having a sequence as set forth by about the first (the 5') 12, 13, 14, 15, 16, 17, 18, 19, 20, 21, 22, 23, 24, 25, 26, 27, 28, 29, 30, 31, 32, 33, 34, 35, 36, 37, 38, 39 or 40 or more residues of the complementary strand of the first member.

Determining the Degree of Sequence Identity

In one embodiment, provided herein are nucleic acids having at least nucleic acid, or complete (100%) sequence identity to a nucleic acid as provided herein, e.g., an exemplary nucleic acid as provided herein (e.g., having a sequence as set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19 or SEQ ID NO:1 modified to encode one, two, three, four, five, six, seven, eight or more (several) or all the base variations described in Table 3 or Table 4, or the equivalent thereof); and polypeptides having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to a polypeptide as provided herein, e.g., an exemplary polypeptide having a sequence as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20 or SEQ ID NO:2 having one, two, three, four, five, six, seven, eight or more (several) or all the amino acid variations described in Table 3 or Table 4, or the equivalent thereof. In alternative aspects, the sequence identity can be over a region of at least about 5, 10, 20, 30, 40, 50, 100, 150, 200, 250, 300, 350, 400, 450, 500, 550, 600, 650, 700, 750, 800, 850, 900, 950, 1000, or more consecutive residues, or the full length of the nucleic acid or polypeptide. The extent of sequence identity (homology) may be determined using any computer program and associated parameters, including those described herein, such as BLAST 2.2.2. or FASTA version 3.0t78, with the default parameters. As used herein, the terms "computer," "computer program"

and "processor" are used in their broadest general contexts and incorporate all such devices, as described in detail, below.

The table below describes selected characteristics of exemplary nucleic acids and polypeptides as provided herein, including sequence identity comparison of the exemplary sequences to public databases to identify activity of enzymes as provided herein by homology (sequence identity) analysis. All sequences described in the table (all the exemplary sequences as provided herein) have been subject to a BLAST search (as described in detail, below) against two sets of databases. The first database set is available through NCBI (National Center for Biotechnology Information). All results from searches against these databases are found in the columns entitled "NR Description", "NR Accession Code", "NR Evalue" or "NR Organism". "NR" refers to the Non-Redundant nucleotide database maintained by NCBI. This database is a composite of GenBank, GenBank updates, and EMBL updates. The entries in the column "NR Description" refer to the definition line in any given NCBI record, which includes a description of the sequence, such as the source organism, gene name/protein name, or some description of the function of the sequence—thus identifying an activity of the listed exemplary enzymes as provided herein by homology (sequence identity) analysis. The entries in the column "NR Accession Code" refer to the unique identifier given to a sequence record. The entries in the column "NR Evalue" refer to the Expect value (Evalue), which represents the probability that an alignment score as good as the one found between the query sequence (the sequences as provided herein) and a database sequence would be found in the same number of comparisons between random sequences as was done in the present BLAST search. The entries in the column "NR Organism" refer to the source organism of the sequence identified as the closest BLAST (sequence homology) hit. The second set of databases is collectively known as the GENESEQ™ database, which is available through Thomson Derwent (Philadelphia, Pa.). All results from searches against this database are found in the columns entitled "GENESEQ™ Protein Description", "GENESEQ™ Protein Accession Code", "GENESEQ™ Protein Evalue", "GENESEQ™ DNA Description", "GENESEQ™ DNA Accession Code" or "GENESEQ™ DNA Evalue". The information found in these columns is comparable to the information found in the NR columns described above, except that it was derived from BLAST searches against the GENESEQ™ database instead of the NCBI databases. The columns "Query DNA Length" and "Query Protein Length" refer to the number of nucleotides or the number amino acids, respectively, in the sequence as provided herein that was searched or queried against either the NCBI or GENESEQ™ databases. The columns "GENESEQ™ or NR DNA Length" and "GENESEQ™ or NR Protein Length" refer to the number of nucleotides or the number amino acids, respectively, in the sequence of the top match from the BLAST search. The results provided in these columns are from the search that returned the lower Evalue, either from the NCBI databases or the Geneseq database. The columns "GENESEQ™/NR % ID Protein" and "GENESEQ™/NR % ID DNA" refer to the percent sequence identity between the sequence as provided herein and the sequence of the top BLAST match. The results provided in these columns are from the search that returned the lower Evalue, either from the NCBI databases or the GENESEQ™ database.

| SEQ ID NO: | NR Description | NR Accession Code | NR Evalue | NR Organism | Geneseq Protein Description | Geneseq Protein Accession Code | Geneseq Protein Evalue | Geneseq DNA Description | Geneseq DNA Accession Code | Geneseq DNA Evalue | Geneseq/NR % ID DNA |
|---|---|---|---|---|---|---|---|---|---|---|---|
| 1, 2 | hypothetical protein Sala_0282 [Sphingopyxis alaskensis RB2256] gi\|98975854\|gb\|ABF52005.1\| conserved hypothetical protein [Sphingopyxis alaskensis RB2256] | 103485777 | 7.00E-40 | Sphingopyxis alaskensis RB2256 | Hydrolase activity expressing peptide SEQ ID NO: 2. | AQZ64879 | 1.00E-127 | Hydrolase activity expressing peptide SEQ ID NO: 2. | AQZ64878 | 0 | |
| 3, 4 | hypothetical protein Sala_0282 [Sphingopyxis alaskensis RB2256] gi\|98975854\|gb\|ABF52005.1\| conserved hypothetical protein [Sphingopyxis alaskensis RB2256] | 103485777 | 2.00E-40 | Sphingopyxis alaskensis RB2256 | Hydrolase activity expressing peptide SEQ ID NO: 2. | AQZ64879 | 3.00E-39 | Protein encoded by Prokaryotic essential gene #30232. | ACA26233 | 1.8 | |
| 5, 6 | hypothetical protein Sala_0282 [Sphingopyxis alaskensis RB2256] gi\|98975854\|gb\|ABF52005.1\| conserved hypothetical protein [Sphingopyxis alaskensis RB2256] | 103485777 | 8.00E-42 | Sphingopyxis alaskensis RB2256 | Hydrolase activity expressing peptide SEQ ID NO: 2. | AQZ64879 | 3.00E-39 | Hydrolase activity expressing peptide SEQ ID NO: 2. | AQZ64878 | 0.53 | |
| 7, 8 | hypothetical protein Sala_0282 [Sphingopyxis alaskensis RB2256] gi\|98975854\|gb\|ABF52005.1\| conserved hypothetical protein | 103485777 | 1.00E-46 | Sphingopyxis alaskensis RB2256 | Hydrolase activity expressing peptide SEQ ID NO: 2. | AQZ64879 | 7.00E-44 | Hydrolase activity expressing peptide SEQ ID NO: 2. | AQZ64878 | 1.00E-04 | |

| SEQ ID NO: | NR Description | NR Accession Code | NR Evalue | NR Organism | Geneseq Protein Description | Geneseq Protein Accession Code | Geneseq Protein Evalue | Geneseq DNA Description | Geneseq DNA Accession Code | Geneseq DNA Evalue | Geneseq/NR % ID DNA |
|---|---|---|---|---|---|---|---|---|---|---|---|
| | [Sphingopyxis alaskensis RB2256] | | | | | | | | | | |
| 9, 10 | hypothetical protein Sala_0282 [Sphingopyxis alaskensis RB2256] gi|98975854|gb|ABF52005.1| conserved hypothetical protein [Sphingopyxis alaskensis RB2256] | 103485777 | 3.00E−51 | Sphingopyxis alaskensis RB2256 | Hydrolase activity expressing peptide SEQ ID NO: 2. | AQZ64879 | 2.00E−42 | Hydrolase activity expressing peptide SEQ ID NO: 2. | AQZ64878 | 1.00E−07 | |
| 11, 12 | hypothetical protein SKA58_17128 [Sphingomonas sp. SKA58] gi|94422701|gb|EAT07736.1| hypothetical protein SKA58_17128 [Sphingomonas sp. SKA58] | 94497812 | 4.00E−46 | Sphingomonas sp. SKA58 | Hydrolase activity expressing peptide SEQ ID NO: 2. | AQZ64879 | 3.00E−42 | Human diagnostic and therapeutic pprotein SEQ ID NO: 2739. | ACN41328 | 1.6 | |
| 13, 14 | hypothetical protein PPSIR1_24779 [Plesiocystis pacifica SIR-1] gi|149817999|gb|EDM77458.1| hypothetical protein PPSIR1_24779 [Plesiocystis pacifica SIR-1] | 149921112 | 3.00E−32 | Plesiocystis pacifica SIR-1 | Hydrolase activity containing protein, SEQ ID 2. | AOG53993 | 1.00E−155 | Hydrolase activity containing protein, SEQ ID 2. | AOG53992 | 0 | |
| 15, 16 | lipase [Streptomyces avermitilis MA-4680] gi|29607114|dbj|BAC71173.1| putative lipase [Streptomyces avermitilis MA-4680] | 29830004 | 1.00E−100 | Streptomyces avermitilis MA-4680 | Hydrolase activity expressing peptide SEQ ID NO: 2. | AQZ64645 | 5.00E−21 | M. xanthus protein sequence, seq id 9726. | ACL64205 | 0.003 | |

-continued

| SEQ ID NO: | NR Description | NR Accession Code | NR Evalue | NR Organism | Geneseq Protein Description | Geneseq Protein Accession Code | Geneseq Protein Evalue | Geneseq DNA Description | Geneseq DNA Accession Code | Geneseq DNA Evalue | Geneseq/NR % ID DNA |
|---|---|---|---|---|---|---|---|---|---|---|---|
| 17, 18 | hypothetical protein blr2879 [*Bradyrhizobium japonicum* USDA 110] gi\|27351136\|dbj\|BAC48144.1\| blr2879 [*Bradyrhizobium japonicum* USDA 110] | 27377990 | 1.00E−115 | *Bradyrhizobium japonicum* USDA 110 | *Mycobacterium tuberculosis* mycobacterial antigen protein SEQ ID NO: 5. | ABM15916 | 8.00E−48 | Hydrolase activity expressing peptide SEQ ID NO: 2. | AQZ64878 | 1.00E−05 | |
| 19, 20 | hypothetical protein blr2879 [*Bradyrhizobium japonicum* USDA 110] gi\|27351136\|dbj\|BAC48144.1\| blr2879 [*Bradyrhizobium japonicum* USDA 110] | 27377990 | 1.00E−118 | *Bradyrhizobium japonicum* USDA 110 | *Mycobacterium tuberculosis* mycobacterial antigen protein SEQ ID NO: 5. | ABM15916 | 1.00E−44 | Hydrolase activity expressing peptide SEQ ID NO: 2. | AQZ64878 | 2.00E−04 | |

| SEQ ID NO: | NR Description | Query DNA Length | Query Protein Length | Geneseq/NR DNA Length | Geneseq/NR Protein Length | Geneseq/NR % ID Protein | Geneseq/NR % ID DNA |
|---|---|---|---|---|---|---|---|
| 1, 2 | hypothetical protein Sala_0282 [*Sphingopyxis alaskensis* RB2256] gi|98975854|gb|ABF52005.1| conserved hypothetical protein [*Sphingopyxis alaskensis* RB2256] | 684 | 227 | 684 | 227 | | |
| 3, 4 | hypothetical protein Sala_0282 [*Sphingopyxis alaskensis* RB2256] gi|98975854|gb|ABF52005.1| conserved hypothetical protein [*Sphingopyxis alaskensis* RB2256] | 633 | 210 | 0 | 249 | 47 | |
| 5, 6 | hypothetical protein Sala_0282 [*Sphingopyxis alaskensis* RB2256] gi|98975854|gb|ABF52005.1| conserved hypothetical protein [*Sphingopyxis alaskensis* RB2256] | 711 | 236 | 0 | 249 | 42 | |
| 7, 8 | hypothetical protein Sala_0282 [*Sphingopyxis alaskensis* RB2256] gi|98975854|gb|ABF52005.1| conserved hypothetical protein [*Sphingopyxis alaskensis* RB2256] | 669 | 222 | 0 | 249 | 46 | |
| 9, 10 | hypothetical protein Sala_0282 [*Sphingopyxis alaskensis* RB2256] gi|98975854|gb|ABF52005.1| conserved hypothetical protein [*Sphingopyxis alaskensis* RB2256] | 669 | 222 | 0 | 249 | 48 | |
| 11, 12 | hypothetical protein SKA58_17128 [*Sphingomonas* sp. SKA58] gi|94422701|gb|EAT07736.1| hypothetical protein SKA58_17128 [*Sphingomonas* sp. SKA58] | 570 | 189 | 0 | 298 | 46 | |
| 13, 14 | hypothetical protein PPSIR1_24779 [*Plesiocystis pacifica* SIR-1] gi|149817999|gb|EDM77458.1| hypothetical protein PPSIR1_24779 [*Plesiocystis pacifica* SIR-1] | 807 | 268 | 807 | 268 | | |
| 15, 16 | lipase [*Streptomyces avermitilis* MA-4680] gi|29607114|dbj|BAC71173.1|putative lipase [*Streptomyces avermitilis* MA-4680] | 804 | 267 | 0 | 286 | 69 | |
| 17, 18 | hypothetical protein blr2879 [*Bradyrhizobium japonicum* USDA 110] gi|27351136|dbj|BAC48144.1| blr2879 [*Bradyrhizobium japonicum* USDA 110] | 798 | 265 | 0 | 266 | 79 | |
| 19, 20 | hypothetical protein blr2879 [*Bradyrhizobium japonicum* USDA 110] gi|27351136|dbj|BAC48144.1| blr2879 [*Bradyrhizobium japonicum* USDA 110] | 798 | 265 | 0 | 266 | 79 | |

Homologous sequences also include RNA sequences in which uridines replace the thymines in the nucleic acid sequences. The homologous sequences may be obtained using any of the procedures described herein or may result from the correction of a sequencing error. It will be appreciated that the nucleic acid sequences as set forth herein can be represented in the traditional single character format (see, e.g., Stryer, Lubert. Biochemistry, 3rd Ed., W.H Freeman & Co., New York) or in any other format which records the identity of the nucleotides in a sequence.

Various sequence comparison programs identified herein and known to one of skill in the art can be used for comparison of sequences. Protein and/or nucleic acid sequence identities (homologies) may be evaluated using any of the variety of sequence comparison algorithms and programs known in the art. Such algorithms and programs include, but are not limited to, TBLASTN, BLASTP, FASTA, TFASTA, and CLUSTALW (Pearson and Lipman, Proc. Natl. Acad. Sci. USA 85(8):2444-2448, 1988; Altschul et al., J. Mol. Biol. 215(3): 403-410, 1990; Thompson et al., Nucleic Acids Res. 22(2): 4673-4680, 1994; Higgins et al., Methods Enzymol. 266:383-402, 1996; Altschul et al., J. Mol. Biol. 215(3):403-410, 1990; Altschul et al., Nature Genetics 3:266-272, 1993).

Homology or identity can be measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection. For sequence comparison, one sequence can act as a reference sequence (e.g., an exemplary nucleic acid or polypeptide sequence as provided herein) to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the numbers of contiguous residues. For example, in alternative aspects as provided herein, contiguous residues ranging anywhere from 20 to the full length of an exemplary polypeptide or nucleic acid sequence, are compared to a reference sequence of the same number of contiguous positions after the two sequences are optimally aligned. If the reference sequence has the requisite sequence identity to an exemplary polypeptide or nucleic acid sequence, e.g., in alternative aspects, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary polypeptide or nucleic acid sequence as provided herein, that sequence is within the scope as provided herein. In alternative embodiments, subsequences ranging from about 20 to 600, about 50 to 200, and about 100 to 150 are compared to a reference sequence of the same number of contiguous positions after the two sequences are optimally aligned. Methods of alignment of sequence for comparison are well known in the art. Optimal alignment of sequences for comparison can be conducted, e.g., by the local homology algorithm of Smith & Waterman, Adv. Appl. Math. 2:482, 1981, by the homology alignment algorithm of Needleman & Wunsch, J. Mol. Biol. 48:443, 1970, by the search for similarity method of person & Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection. Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences. A number of genome databases are available, for example, a substantial portion of the human genome is available as part of the Human Genome Sequencing Project (Gibbs, 1995). Several genomes have been sequenced, e.g., *M. genitalium* (Fraser et al., 1995), *M. jannaschii* (Bult et al., 1996), *H. influenzae* (Fleischmann et al., 1995), *E. coli* (Blattner et al., 1997), and yeast (*S. cerevisiae*) (Mewes et al., 1997), and *D. melanogaster* (Adams et al., 2000). Significant progress has also been made in sequencing the genomes of model organisms, such as mouse, *C. elegans*, and *Arabadopsis* sp. Databases containing genomic information annotated with some functional information are maintained by different organizations, and are accessible via the internet.

BLAST, BLAST 2.0 and BLAST 2.2.2 algorithms are also used. They are described, e.g., in Altschul (1977) Nuc. Acids Res. 25:3389-3402; Altschul (1990) J. Mol. Biol. 215:403-410. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul (1990) supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectations (E) of 10, and the BLOSUM62 scoring matrix (see Henikoff & Henikoff (1989) Proc. Natl. Acad. Sci. USA 89:10915) alignments (B) of 50, expectation (E) of 10, M=5, N=−4, and a comparison of both strands. The BLAST algorithm also performs a statistical analysis of the similarity between two sequences (see, e.g., Karlin & Altschul (1993) Proc. Natl. Acad. Sci. USA 90:5873). One measure of similarity provided by BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, or alternatively, less than about 0.01, or alternatively, less than about 0.001.

In one aspect, protein and nucleic acid sequence homologies are evaluated using the Basic Local Alignment Search Tool ("BLAST"). For example, five specific BLAST programs can be used to perform the following task: (1) BLASTP and BLAST3 compare an amino acid query sequence against a protein sequence database; (2) BLASTN compares a nucleotide query sequence against a nucleotide sequence database; (3) BLASTX compares the six-frame conceptual translation products of a query nucleotide sequence (both strands) against a protein sequence database; (4) TBLASTN compares a query protein sequence against a nucleotide sequence database translated in all six reading frames (both strands); and, (5) TBLASTX compares the six-frame translations of a nucleotide query sequence against the six-frame translations of a nucleotide sequence database.

In one aspect, the BLAST programs identify homologous sequences by identifying similar segments, which are referred to herein as "high-scoring segment pairs," between a query amino or nucleic acid sequence and a test sequence which is alternatively obtained from a protein or nucleic acid sequence database. High-scoring segment pairs can be alternatively identified (i.e., aligned) by means of a scoring matrix, many of which are known in the art. In one aspect, the scoring matrix used is the BLOSUM62 matrix (Gonnet et al., Science 256:1443-1445, 1992; Henikoff and Henikoff, Proteins 17:49-61, 1993). In one aspect, the PAM or PAM250 matrices may also be used (see, e.g., Schwartz and Dayhoff, eds., 1978, Matrices for Detecting Distance Relationships:

Atlas of Protein Sequence and Structure, Washington: National Biomedical Research Foundation).

In one aspect, to determine if a nucleic acid has the requisite sequence identity to be within the scope as provided herein, the NCBI BLAST 2.2.2 programs is used, default options to blastp. There are about 38 setting options in the BLAST 2.2.2 program. In this exemplary aspect as provided herein, all default values are used except for the default filtering setting (i.e., all parameters set to default except filtering which is set to OFF); in its place a "-F F" setting is used, which disables filtering. Use of default filtering often results in Karlin-Altschul violations due to short length of sequence.

The default values used in this exemplary aspect as provided herein, include:
"Filter for low complexity: ON
Word Size: 3
Matrix: Blosum62
Gap Costs: Existence: 11
Extension: 1"

Other default settings are: filter for low complexity OFF, word size of 3 for protein, BLOSUM62 matrix, gap existence penalty of −11 and a gap extension penalty of −1. In one aspect, the "−W" option defaults to 0. This means that, if not set, the word size defaults to 3 for proteins and 11 for nucleotides.

Computer Systems and Computer Program Products

To determine and identify sequence identities, structural homologies, motifs and the like in silico, the sequence as provided herein can be stored, recorded, and manipulated on any medium which can be read and accessed by a computer. In certain embodiments, provided herein are computers, computer systems, computer readable media, computer program products and the like, containing therein (comprising) nucleic acid and polypeptide sequences as provided herein recorded or stored thereon. As used herein, the words "recorded" and "stored" refer to a process for storing information on a computer medium. A skilled artisan can readily adopt any known methods for recording information on a computer readable medium to generate manufactures comprising one or more of the nucleic acid and/or polypeptide sequences as provided herein.

Another aspect as provided herein is a computer readable medium having recorded thereon at least one nucleic acid and/or polypeptide sequence as provided herein. Computer readable media include magnetically readable media, optically readable media, electronically readable media and magnetic/optical media. For example, the computer readable media may be a hard disk, a floppy disk, a magnetic tape, CD-ROM, Digital Versatile Disk (DVD), Random Access Memory (RAM), or Read Only Memory (ROM) as well as other types of other media known to those skilled in the art.

Aspects as provided herein include systems (e.g., internet based systems), particularly computer systems, which store and manipulate the sequences and sequence information described herein. One example of a computer system 100 is illustrated in block diagram form in FIG. 1. As used herein, "a computer system" refers to the hardware components, software components, and data storage components used to analyze a nucleotide or polypeptide sequence as provided herein. The computer system 100 can include a processor for processing, accessing and manipulating the sequence data. The processor 105 can be any well-known type of central processing unit, such as, for example, the Pentium III from Intel Corporation, or similar processor from Sun, Motorola, Compaq, AMD or International Business Machines. The computer system 100 is a general purpose system that comprises the processor 105 and one or more internal data storage components 110 for storing data, and one or more data retrieving devices for retrieving the data stored on the data storage components. A skilled artisan can readily appreciate that any one of the currently available computer systems are suitable.

In one aspect, the computer system 100 includes a processor 105 connected to a bus which is connected to a main memory 115 (alternatively implemented as RAM) and one or more internal data storage devices 110, such as a hard drive and/or other computer readable media having data recorded thereon. The computer system 100 can further include one or more data retrieving device 118 for reading the data stored on the internal data storage devices 110. The data retrieving device 118 may represent, for example, a floppy disk drive, a compact disk drive, a magnetic tape drive, or a modem capable of connection to a remote data storage system (e.g., via the internet) etc. In some embodiments, the internal data storage device 110 is a removable computer readable medium such as a floppy disk, a compact disk, a magnetic tape, etc. containing control logic and/or data recorded thereon. The computer system 100 may advantageously include or be programmed by appropriate software for reading the control logic and/or the data from the data storage component once inserted in the data retrieving device. The computer system 100 includes a display 120 which is used to display output to a computer user. It should also be noted that the computer system 100 can be linked to other computer systems 125a-c in a network or wide area network to provide centralized access to the computer system 100. Software for accessing and processing the nucleotide or amino acid sequences as provided herein can reside in main memory 115 during execution. In some aspects, the computer system 100 may further comprise a sequence comparison algorithm for comparing a nucleic acid sequence as provided herein. The algorithm and sequence(s) can be stored on a computer readable medium. A "sequence comparison algorithm" refers to one or more programs which are implemented (locally or remotely) on the computer system 100 to compare a nucleotide sequence with other nucleotide sequences and/or compounds stored within a data storage means. For example, the sequence comparison algorithm may compare the nucleotide sequences as provided herein stored on a computer readable medium to reference sequences stored on a computer readable medium to identify homologies or structural motifs.

Figure 2:
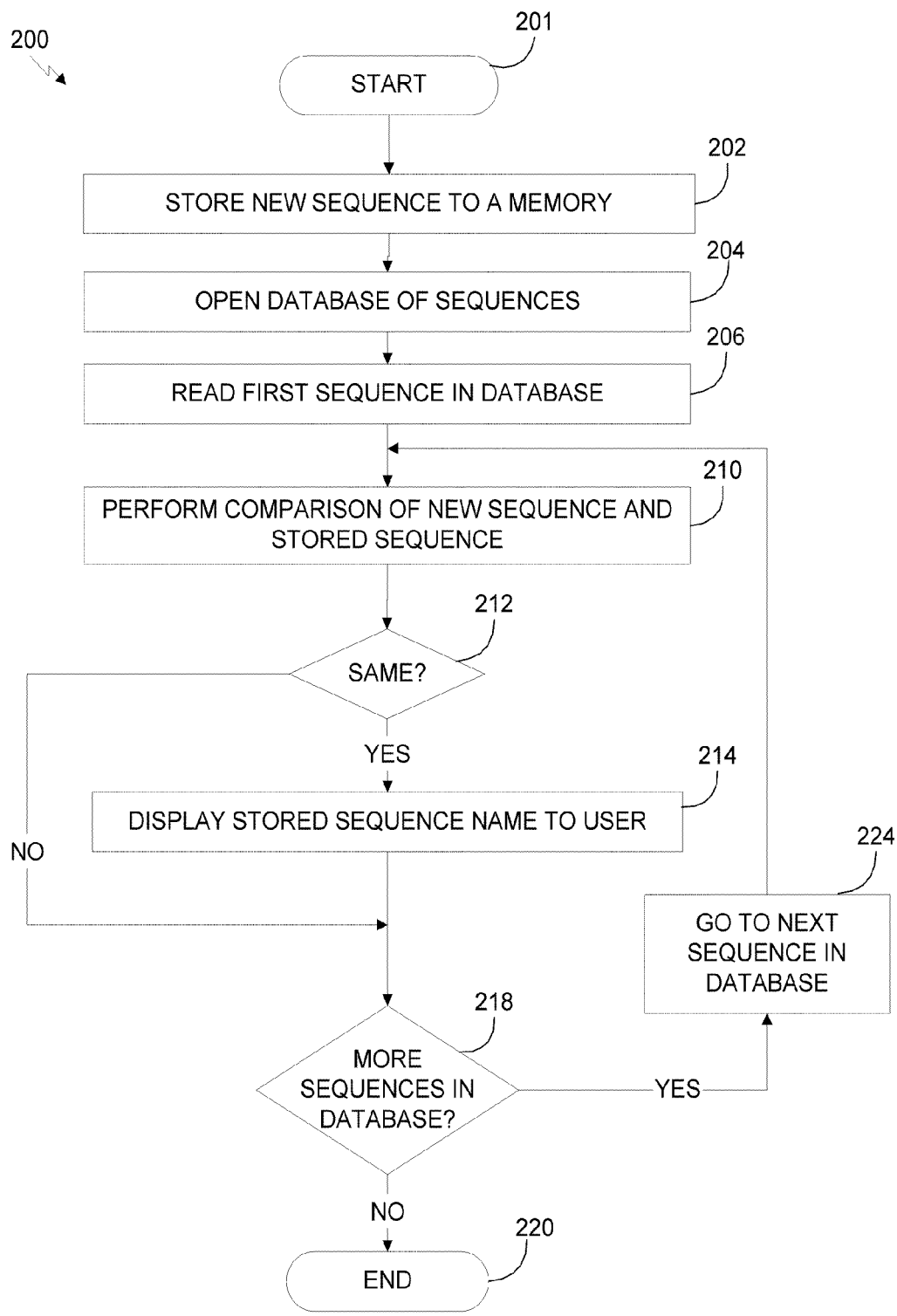
FIG. 2 is a flow diagram illustrating one aspect of a process for comparing a new nucleotide or protein sequence with a database of sequences in order to determine the homology levels between the new sequence and the sequences in the database.
Figure 3:
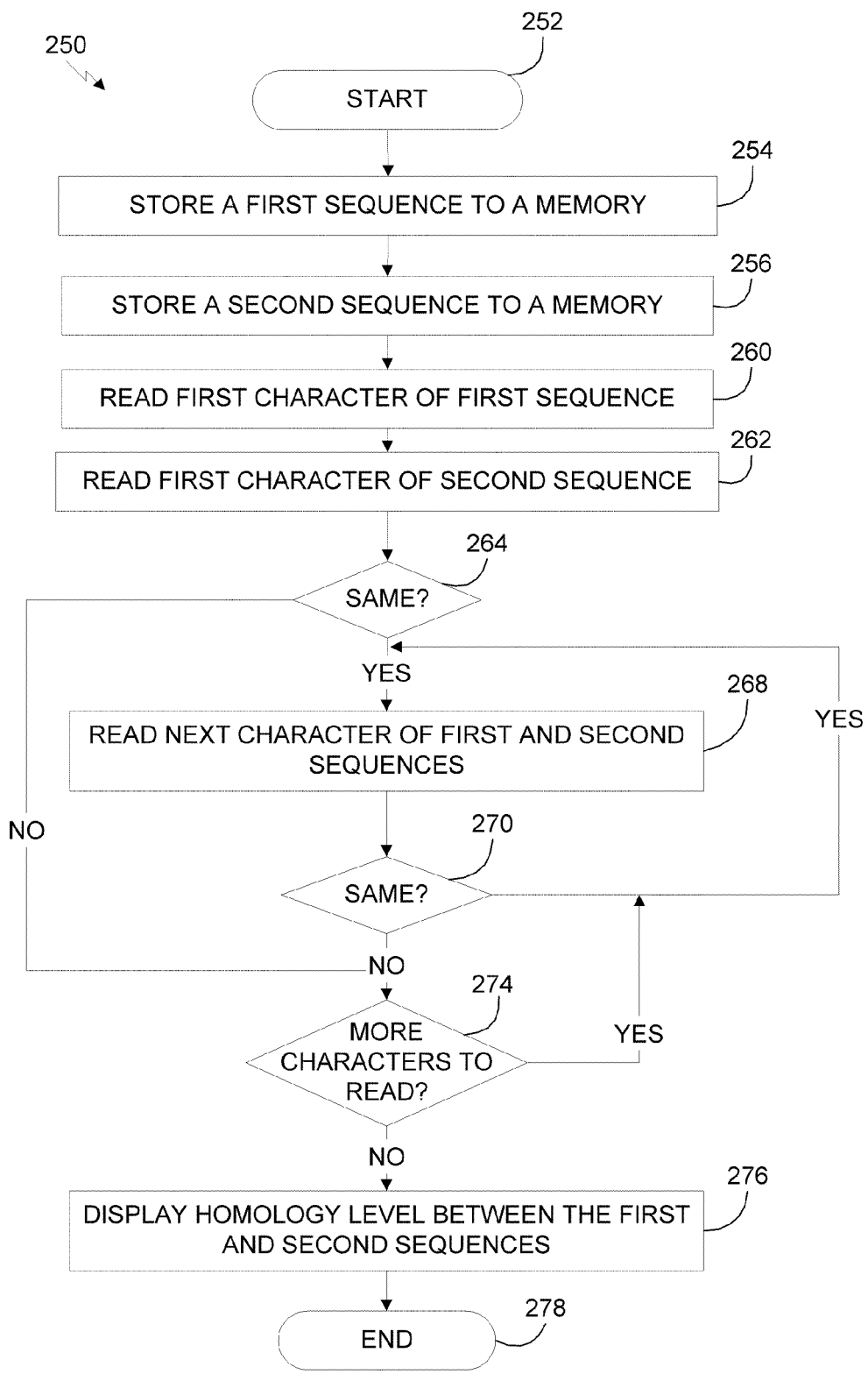
FIG. 3 is a flow diagram illustrating one aspect of a process in a computer for determining whether two sequences are homologous.

The parameters used with the above algorithms may be adapted depending on the sequence length and degree of homology studied. In some aspects, the parameters may be the default parameters used by the algorithms in the absence of instructions from the user. FIG. 2 is a flow diagram illustrating one aspect of a process 200 for comparing a new nucleotide or protein sequence with a database of sequences in order to determine the homology levels between the new sequence and the sequences in the database. The database of sequences can be a private database stored within the computer system 100, or a public database such as GENBANK that is available through the Internet. The process 200 begins at a start state 201 and then moves to a state 202 wherein the new sequence to be compared is stored to a memory in a computer system 100. As discussed above, the memory could be any type of memory, including RAM or an internal storage device. The process 200 then moves to a state 204 wherein a database of sequences is opened for analysis and comparison. The process 200 then moves to a state 206 wherein the first sequence stored in the database is read into a memory on the computer. A comparison is then performed at a state 210 to determine if the first sequence is the same as the second sequence. It is important to note that this step is not limited to performing an exact comparison between the new sequence and the first sequence in the database. Well-known methods are known to those of skill in the art for comparing two nucleotide or protein sequences, even if they are not identical. For example, gaps can be introduced into one sequence in order to raise the homology level between the two tested sequences. The parameters that control whether gaps or other features are introduced into a sequence during comparison are normally entered by the user of the computer system. Once a comparison of the two sequences has been performed at the state 210, a determination is made at a decision state 210 whether the two sequences are the same. Of course, the term "same" is not limited to sequences that are absolutely identical. Sequences that are within the homology parameters entered by the user will be marked as "same" in the process 200. If a determination is made that the two sequences are the same, the process 200 moves to a state 214 wherein the name of the sequence from the database is displayed to the user. This state notifies the user that the sequence with the displayed name fulfills the homology constraints that were entered. Once the name of the stored sequence is displayed to the user, the process 200 moves to a decision state 218 wherein a determination is made whether more sequences exist in the database. If no more sequences exist in the database, then the process 200 terminates at an end state 220. However, if more sequences do exist in the database, then the process 200 moves to a state 224 wherein a pointer is moved to the next sequence in the database so that it can be compared to the new sequence. In this manner, the new sequence is aligned and compared with every sequence in the database. It should be noted that if a determination had been made at the decision state 212 that the sequences were not homologous, then the process 200 would move immediately to the decision state 218 in order to determine if any other sequences were available in the database for comparison. Accordingly, one aspect as provided herein is a computer system comprising a processor, a data storage device having stored thereon a nucleic acid sequence as provided herein and a sequence comparer for conducting the comparison. The sequence comparer may indicate a homology level between the sequences compared or identify structural motifs, or it may identify structural motifs in sequences which are compared to these nucleic acid codes and polypeptide codes. FIG. 3 is a flow diagram illustrating one embodiment of a process 250 in a computer for determining whether two sequences are homologous. The process 250 begins at a start state 252 and then moves to a state 254 wherein a first sequence to be compared is stored to a memory. The second sequence to be compared is then stored to a memory at a state 256. The process 250 then moves to a state 260 wherein the first character in the first sequence is read and then to a state 262 wherein the first character of the second sequence is read. It should be understood that if the sequence is a nucleotide sequence, then the character would normally be either A, T, C, G or U. If the sequence is a protein sequence, then it can be a single letter amino acid code so that the first and sequence sequences can be easily compared. A determination is then made at a decision state 264 whether the two characters are the same. If they are the same, then the process 250 moves to a state 268 wherein the next characters in the first and second sequences are read. A determination is then made whether the next characters are the same. If they are, then the process 250 continues this loop until two characters are not the same. If a determination is made that the next two characters are not the same, the process 250 moves to a decision state 274 to determine whether there are any more characters either sequence to read. If there are not any more characters to read, then the process 250 moves to a state 276 wherein the level of homology between the first and second sequences is displayed to the user. The level of homology is determined by calculating the proportion of characters between the sequences that were the same out of the total number of sequences in the first sequence. Thus, if every character in a first 100 nucleotide sequence aligned with an every character in a second sequence, the homology level would be 100%.

Alternatively, the computer program can compare a reference sequence to a sequence as provided herein to determine whether the sequences differ at one or more positions. The program can record the length and identity of inserted, deleted or substituted nucleotides or amino acid residues with respect to the sequence of either the reference or a sequence as provided herein. The computer program may be a program which determines whether a reference sequence contains a single nucleotide polymorphism (SNP) with respect to a sequence as provided herein, or, whether a sequence as provided herein comprises a SNP of a known sequence. Thus, in some aspects, the computer program is a program which identifies SNPs. The method may be implemented by the computer systems described above and the method illustrated in FIG. 3. The method can be performed by reading a sequence as provided herein and the reference sequences through the use of the computer program and identifying differences with the computer program.

Figure 4:
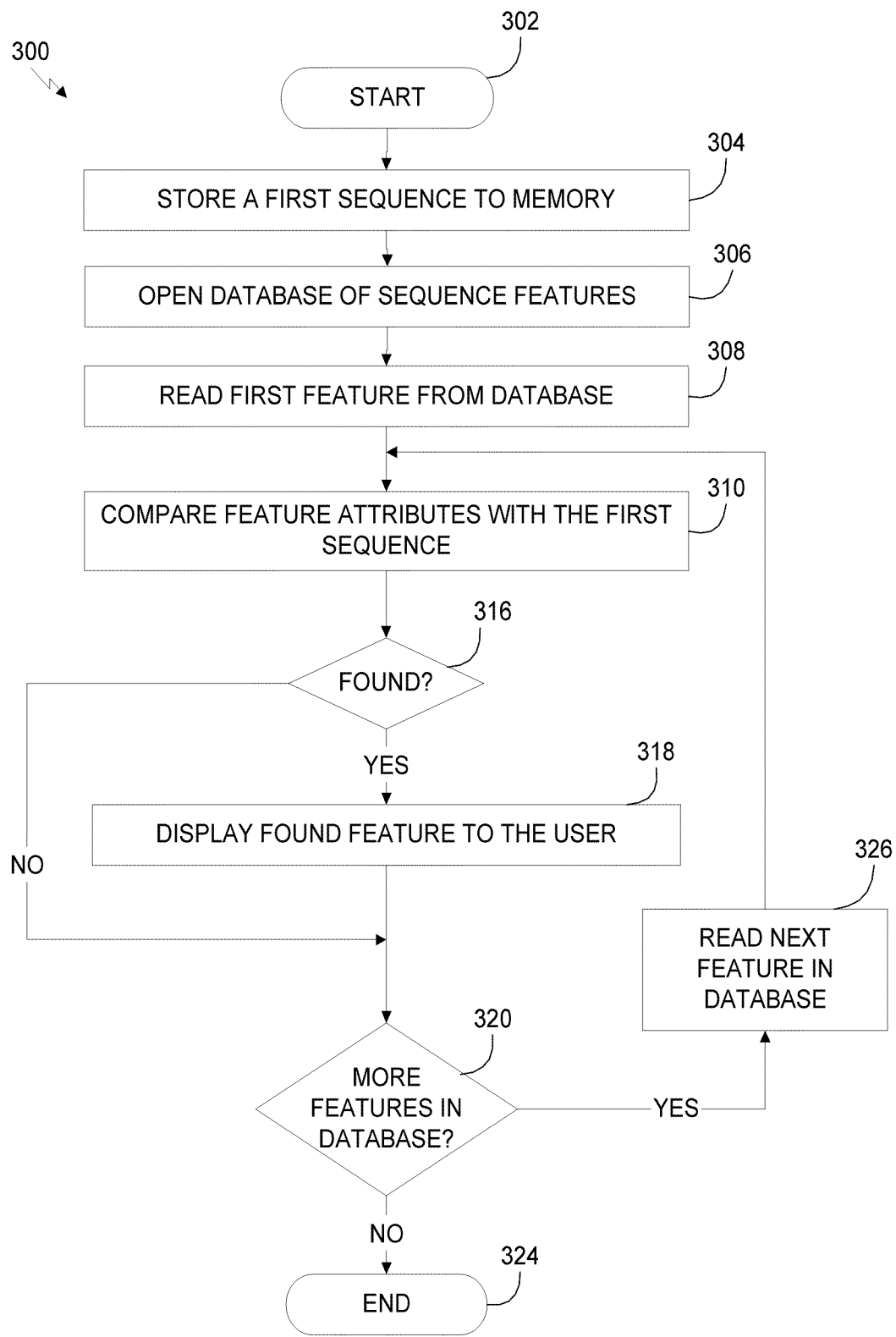
FIG. 4 is a flow diagram illustrating one aspect of an identifier process 300 for detecting the presence of a feature in a sequence.

In other aspects the computer based system comprises an identifier for identifying features within a nucleic acid or polypeptide as provided herein. An "identifier" refers to one or more programs which identifies certain features within a nucleic acid sequence. For example, an identifier may comprise a program which identifies an open reading frame (ORF) in a nucleic acid sequence. FIG. 4 is a flow diagram illustrating one aspect of an identifier process 300 for detecting the presence of a feature in a sequence. The process 300 begins at a start state 302 and then moves to a state 304 wherein a first sequence that is to be checked for features is stored to a memory 115 in the computer system 100. The process 300 then moves to a state 306 wherein a database of sequence features is opened. Such a database would include a list of each feature's attributes along with the name of the feature. For example, a feature name could be "Initiation Codon" and the attribute would be "ATG". Another example would be the feature name "TAATAA Box" and the feature attribute would be "TAATAA". An example of such a database is produced by the University of Wisconsin Genetics Computer Group. Alternatively, the features may be structural polypeptide motifs such as alpha helices, beta sheets, or functional polypeptide motifs such as enzymatic active sites, helix-turn-helix motifs or other motifs known to those skilled in the art. Once the database of features is opened at the state 306, the process 300 moves to a state 308 wherein the first feature is read from the database. A comparison of the attribute of the first feature with the first sequence is then made at a state 310. A determination is then made at a decision state 316 whether the attribute of the feature was found in the first sequence. If the attribute was found, then the process 300 moves to a state 318 wherein the name of the found feature is displayed to the user. The process 300 then moves to a decision state 320 wherein a determination is made whether move features exist in the database. If no more features do exist, then the process 300 terminates at an end state 324. However, if more features do exist in the database, then the process 300 reads the next sequence feature at a state 326 and loops back to the state 310 wherein the attribute of the next feature is compared against the first sequence. If the feature attribute is not found in the first sequence at the decision state 316, the process 300 moves directly to the decision state 320 in order to determine if any more features exist in the database. Thus, in one aspect, a computer program that identifies open reading frames (ORFs).

A polypeptide or nucleic acid sequence as provided herein may be stored and manipulated in a variety of data processor programs in a variety of formats. For example, a sequence can be stored as text in a word processing file, such as MICROSOFT WORD™ or WORDPERFECT™ or as an ASCII file in a variety of database programs familiar to those of skill in the art, such as DB2, SYBASE, or ORACLE™. In addition, many computer programs and databases may be used as sequence comparison algorithms, identifiers, or sources of reference nucleotide sequences or polypeptide sequences to be compared to a nucleic acid sequence as provided herein. The programs and databases can comprise: MACPATTERN™ (EMBL), DISCOVERYBASE™ (Molecular Applications Group), GENEMINE™ (Molecular Applications Group), LOOK™ (Molecular Applications Group), MACLOOK™ (Molecular Applications Group), BLAST and BLAST2 (NCBI), BLASTN and BLASTX (Altschul et al, J. Mol. Biol. 215: 403, 1990), FASTA (Pearson and Lipman, Proc. Natl. Acad. Sci. USA, 85: 2444, 1988), FASTDB™ (Brutlag et al. Comp. App. Biosci. 6:237-245, 1990), CATALYST™ (Molecular Simulations Inc.), CATALYST™/SHAPE™ (Molecular Simulations Inc.), CERIUS2.DBACCESS™ (Molecular Simulations Inc.), HYPOGEN™ (Molecular Simulations Inc.), Insight II, (Molecular Simulations Inc.), DISCOVER™ (Molecular Simulations Inc.), CHARMm™ (Molecular Simulations Inc.), FELIX™ (Molecular Simulations Inc.), DELPHI™s (Molecular Simulations Inc.), QUANTEMM™, (Molecular Simulations Inc.), HOMOLOGY™ (Molecular Simulations Inc.), MODELER™ (Molecular Simulations Inc.), ISIS™ (Molecular Simulations Inc.), Quanta/Protein Design (Molecular Simulations Inc.), WEBLAB™ (Molecular Simulations Inc.), WEBLAB™ Diversity Explorer (Molecular Simulations Inc.), GENE EXPLORER™ (Molecular Simulations Inc.), SEQFOLD™ (Molecular Simulations Inc.), the MDL Available Chemicals Directory database, the MDL Drug Data Report data base, the Comprehensive Medicinal Chemistry database, Derwent's World Drug Index database, the BioByteMasterFile database, the Genbank database, and the Genseqn database. Many other programs and data bases would be apparent to one of skill in the art given the present disclosure.

Motifs which may be detected using the above programs include sequences encoding leucine zippers, helix-turn-helix motifs, glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites.

Hybridization of Nucleic Acids

In certain embodiments, provided herein are isolated, synthetic or recombinant nucleic acids that hybridize under stringent conditions to nucleic acid provided herein, e.g., an exemplary sequence provided herein, e.g., a sequence as set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19 or SEQ ID NO:1 modified to encode one, two, three, four, five, six, seven, eight or more (several) or all the base variations described in Table 3 or Table 4, or the equivalent thereof, and subsequences and complementary sequences thereof, or a nucleic acid that encodes a polypeptide as provided herein. The stringent conditions can be highly stringent conditions, medium stringency conditions, low stringency conditions, including the high and reduced stringency conditions described herein.

"Hybridization" refers to the process by which a nucleic acid strand joins with a complementary strand through base pairing. Hybridization reactions can be sensitive and selective so that a particular sequence of interest can be identified even in samples in which it is present at low concentrations. Stringent conditions can be defined by, for example, the concentrations of salt or formamide in the prehybridization and hybridization solutions, or by the hybridization temperature, and are well known in the art. For example, stringency can be increased by reducing the concentration of salt, increasing the concentration of formamide, or raising the hybridization temperature, altering the time of hybridization, as described in detail, below. In alternative aspects, nucleic acids as provided herein are defined by their ability to hybridize under various stringency conditions (e.g., high, medium, and low), as set forth herein.

In alternative embodiments, nucleic acids as provided herein as defined by their ability to hybridize under stringent conditions can be between about five residues and the full length of nucleic acid as provided herein; e.g., they can be at least 5, 10, 15, 20, 25, 30, 35, 40, 50, 55, 60, 65, 70, 75, 80, 90, 100, 150, 200, 250, 300, 350, 400, 450, 500, 550, 600, 650, 700, 750, 800, 850, 900, 950, 1000, or more, residues in length. Nucleic acids shorter than full length are also included. These nucleic acids can be useful as, e.g., hybridization probes, labeling probes, PCR oligonucleotide probes, iRNA, antisense or sequences encoding antibody binding peptides (epitopes), motifs, active sites and the like.

In one aspect, nucleic acids as provided herein are defined by their ability to hybridize under high stringency comprises conditions of about 50% formamide at about 37° C. to 42° C. In one aspect, nucleic acids as provided herein are defined by their ability to hybridize under reduced stringency comprising conditions in about 35% to 25% formamide at about 30° C. to 35° C.

Alternatively, nucleic acids as provided herein are defined by their ability to hybridize under high stringency comprising conditions at 42° C. in 50% formamide, 5×SSPE, 0.3% SDS, and a repetitive sequence blocking nucleic acid, such as cot-1 or salmon sperm DNA (e.g., 200 ug/ml sheared and denatured salmon sperm DNA). In one aspect, nucleic acids as provided herein are defined by their ability to hybridize under reduced stringency conditions comprising 35% formamide at a reduced temperature of 35° C.

Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

The temperature range corresponding to a particular level of stringency can be further narrowed by calculating the purine to pyrimidine ratio of the nucleic acid of interest and adjusting the temperature accordingly. Nucleic acids as provided herein are also defined by their ability to hybridize under high, medium, and low stringency conditions as set forth in Ausubel and Sambrook. Variations on the above ranges and conditions are well known in the art. Hybridization conditions are discussed further, below.

The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5° C. from 68° C. to 42° C. in a hybridization buffer having a Na+ concentration of approximately 1M. Following hybridization, the filter may be washed with 2×SSC, 0.5% SDS at the temperature of hybridization. These conditions are considered to be "moderate" conditions above 50° C. and "low" conditions below 50° C. A specific example of "moderate" hybridization conditions is when the above hybridization is conducted at 55° C. A specific example of "low stringency" hybridization conditions is when the above hybridization is conducted at 45° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

However, the selection of a hybridization format is not critical—it is the stringency of the wash conditions that set forth the conditions which determine whether a nucleic acid is within the scope as provided herein. Wash conditions used to identify nucleic acids within the scope as provided herein include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. See Sambrook, Tijssen and Ausubel for a description of SSC buffer and equivalent conditions.

These methods may be used to isolate nucleic acids as provided herein.

Oligonucleotides Probes and Methods for Using Them

In certain embodiments, provided herein are nucleic acid probes for identifying nucleic acids encoding a polypeptide with a hydrolase activity, e.g., lipase, saturase, palmitase and/or stearatase activity. In one aspect, the probe comprises at least 10 consecutive bases of a nucleic acid as provided herein. Alternatively, a probe as provided herein can be at least about 5, 6, 7, 8, 9, 10, 15, 20, 25, 30, 35, 40, 45, 50, 60, 70, 80, 90, 100, 110, 120, 130, 150, 160, 170, 180, 190, 200 or more, or about 10 to 50, about 20 to 60 about 30 to 70, consecutive bases of a sequence as set forth in a nucleic acid as provided herein. The probes identify a nucleic acid by binding and/or hybridization. The probes can be used in arrays as provided herein, see discussion below, including, e.g., capillary arrays. The probes as provided herein can also be used to isolate other nucleic acids or polypeptides.

The probes as provided herein can be used to determine whether a biological sample, such as a soil sample, contains an organism having a nucleic acid sequence as provided herein (e.g., a hydrolase-encoding nucleic acid) or an organism from which the nucleic acid was obtained. In such procedures, a biological sample potentially harboring the organism from which the nucleic acid was isolated is obtained and nucleic acids are obtained from the sample. The nucleic acids are contacted with the probe under conditions which permit the probe to specifically hybridize to any complementary sequences present in the sample. Where necessary, conditions which permit the probe to specifically hybridize to complementary sequences may be determined by placing the probe in contact with complementary sequences from samples known to contain the complementary sequence, as well as control sequences which do not contain the complementary sequence. Hybridization conditions, such as the salt concentration of the hybridization buffer, the formamide concentration of the hybridization buffer, or the hybridization temperature, may be varied to identify conditions which allow the probe to hybridize specifically to complementary nucleic acids (see discussion on specific hybridization conditions).

If the sample contains the organism from which the nucleic acid was isolated, specific hybridization of the probe is then detected. Hybridization may be detected by labeling the probe with a detectable agent such as a radioactive isotope, a fluorescent dye or an enzyme capable of catalyzing the formation of a detectable product. Many methods for using the labeled probes to detect the presence of complementary nucleic acids in a sample are familiar to those skilled in the art. These include Southern Blots, Northern Blots, colony hybridization procedures, and dot blots. Protocols for each of these procedures are provided in Ausubel and Sambrook.

Alternatively, more than one probe (at least one of which is capable of specifically hybridizing to any complementary sequences which are present in the nucleic acid sample), may be used in an amplification reaction to determine whether the sample contains an organism containing a nucleic acid sequence as provided herein (e.g., an organism from which the nucleic acid was isolated). In one aspect, the probes comprise oligonucleotides. In one aspect, the amplification reaction may comprise a PCR reaction. PCR protocols are described in Ausubel and Sambrook (see discussion on amplification reactions). In such procedures, the nucleic acids in the sample are contacted with the probes, the amplification reaction is performed, and any resulting amplification product is detected. The amplification product may be detected by performing gel electrophoresis on the reaction products and staining the gel with an intercalator such as ethidium bromide. Alternatively, one or more of the probes may be labeled with a radioactive isotope and the presence of a radioactive amplification product may be detected by autoradiography after gel electrophoresis.

Probes derived from sequences near the 3' or 5' ends of a nucleic acid sequence as provided herein can also be used in chromosome walking procedures to identify clones containing additional, e.g., genomic sequences. Such methods allow the isolation of genes which encode additional proteins of interest from the host organism.

In one aspect, nucleic acid sequences as provided herein are used as probes to identify and isolate related nucleic acids. In some aspects, the so-identified related nucleic acids may be cDNAs or genomic DNAs from organisms other than the one from which the nucleic acid as provided herein was first isolated. In such procedures, a nucleic acid sample is contacted with the probe under conditions which permit the probe to specifically hybridize to related sequences. Hybridization of the probe to nucleic acids from the related organism is then detected using any of the methods described above.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter. Hybridization may be carried out under conditions of low stringency, moderate stringency or high stringency. As an example of nucleic acid hybridization, a polymer membrane containing immobilized denatured nucleic acids is first prehybridized for 30 minutes at 45° C. in a solution consisting of 0.9 M NaCl, 50 mM $NaH_2PO_4$, pH 7.0, 5.0 mM $Na_2EDTA$, 0.5% SDS, 10×Denhardt's, and 0.5 mg/ml polyriboadenylic acid. Approximately $2 \times 10^7$ cpm (specific activity $4-9 \times 10^8$ cpm/ug) of $^{32}P$ end-labeled oligonucleotide probe are then added to the solution. After 12-16 hours of incubation, the membrane is washed for 30 minutes at room temperature (RT) in 1×SET (150 mM NaCl, 20 mM Tris hydrochloride, pH 7.8, 1 mM $Na_2EDTA$) containing 0.5% SDS, followed by a 30 minute wash in fresh 1×SET at Tm-10° C. for the oligonucleotide probe. The membrane is then exposed to auto-radiographic film for detection of hybridization signals.

By varying the stringency of the hybridization conditions used to identify nucleic acids, such as cDNAs or genomic DNAs, which hybridize to the detectable probe, nucleic acids having different levels of homology to the probe can be identified and isolated. Stringency may be varied by conducting the hybridization at varying temperatures below the melting temperatures of the probes. The melting temperature, Tm, is the temperature (under defined ionic strength and pH) at which 50% of the target sequence hybridizes to a perfectly complementary probe. Very stringent conditions are selected to be equal to or about 5° C. lower than the Tm for a particular probe. The melting temperature of the probe may be calculated using the following exemplary formulas. For probes between 14 and 70 nucleotides in length the melting temperature (Tm) is calculated using the formula: Tm=81.5+16.6(log [Na+])+0.41(fraction G+C)−(600/N) where N is the length of the probe. If the hybridization is carried out in a solution containing formamide, the melting temperature may be calculated using the equation: Tm=81.5+16.6(log [Na+])+0.41 (fraction G+C)−(0.63% formamide)−(600/N) where N is the length of the probe. Prehybridization may be carried out in 6×SSC, 5×Denhardt's reagent, 0.5% SDS, 100 µg denatured fragmented salmon sperm DNA or 6×SSC, 5×Denhardt's reagent, 0.5% SDS, 100 µg denatured fragmented salmon sperm DNA, 50% formamide. Formulas for SSC and Denhardt's and other solutions are listed, e.g., in Sambrook.

In one aspect, hybridization is conducted by adding the detectable probe to the prehybridization solutions listed above. Where the probe comprises double stranded DNA, it is denatured before addition to the hybridization solution. The filter is contacted with the hybridization solution for a sufficient period of time to allow the probe to hybridize to cDNAs or genomic DNAs containing sequences complementary thereto or homologous thereto. For probes over 200 nucleotides in length, the hybridization may be carried out at 15-25° C. below the Tm. For shorter probes, such as oligonucleotide probes, the hybridization may be conducted at 5-10° C. below the Tm. In one aspect, hybridizations in 6×SSC are conducted at approximately 68° C. In one aspect, hybridizations in 50% formamide containing solutions are conducted at approximately 42° C. All of the foregoing hybridizations would be considered to be under conditions of high stringency.

In one aspect, following hybridization, the filter is washed to remove any non-specifically bound detectable probe. The stringency used to wash the filters can also be varied depending on the nature of the nucleic acids being hybridized, the length of the nucleic acids being hybridized, the degree of complementarity, the nucleotide sequence composition (e.g., GC v. AT content), and the nucleic acid type (e.g., RNA v. DNA). Examples of progressively higher stringency condition washes are as follows: 2×SSC, 0.1% SDS at room temperature for 15 minutes (low stringency); 0.1×SSC, 0.5% SDS at room temperature for 30 minutes to 1 hour (moderate stringency); 0.1×SSC, 0.5% SDS for 15 to 30 minutes at between the hybridization temperature and 68° C. (high stringency); and 0.15M NaCl for 15 minutes at 72° C. (very high stringency). A final low stringency wash can be conducted in 0.1×SSC at room temperature. The examples above are merely illustrative of one set of conditions that can be used to wash filters. One of skill in the art would know that there are numerous recipes for different stringency washes.

Nucleic acids which have hybridized to the probe can be identified by autoradiography or other conventional techniques. The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5° C. from 68° C. to 42° C. in a hybridization buffer having a Na+ concentration of approximately 1M. Following hybridization, the filter may be washed with 2×SSC, 0.5% SDS at the temperature of hybridization. These conditions are considered to be "moderate" conditions above 50° C. and "low" conditions below 50° C. An example of "moderate" hybridization conditions is when the above hybridization is conducted at 55° C. An example of "low stringency" hybridization conditions is when the above hybridization is conducted at 45° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

These probes and methods as provided herein can be used to isolate, or identify (e.g., using an array), nucleic acids having a sequence with at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, sequence identity to a nucleic acid sequence as provided herein comprising at least about 10, 15, 20, 25, 30, 35, 40, 50, 75, 100, 150, 200, 250, 300, 350, 400, 500, 550, 600, 650, 700, 750, 800, 850, 900, 950, 1000, or more consecutive bases thereof, and the sequences complementary thereto. Homology may be measured using an alignment algorithm, as discussed herein. For example, the homologous polynucleotides may have a coding sequence which is a naturally occurring allelic variant of one of the coding sequences described herein. Such allelic variants may have a substitution, deletion or addition of one or more nucleotides when compared to a nucleic acid as provided herein.

Additionally, the probes and methods as provided herein may be used to isolate, or identify (e.g., using an array), nucleic acids which encode polypeptides having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity (homology) to a polypeptide as provided herein comprising at least 5, 10, 15, 20, 25, 30, 35, 40, 50, 75, 100, or 150 or more consecutive amino acids thereof as determined using a sequence alignment algorithm, e.g., such as the FASTA version 3.0t78 algorithm with the default parameters, or a BLAST 2.2.2 program with exemplary settings as set forth herein.

Inhibiting Expression of Hydrolases

In certain embodiments, provided herein are nucleic acids complementary to (e.g., antisense sequences to) the nucleic acid sequences as provided herein, e.g., hydrolase-encoding sequences. Antisense sequences are capable of inhibiting the transport, splicing or transcription of hydrolase-encoding genes. The inhibition can be effected through the targeting of genomic DNA or messenger RNA. The inhibition can be effected using DNA, e.g., an inhibitory ribozyme, or an RNA, e.g., a double-stranded iRNA, comprising a sequence as provided herein. The transcription or function of targeted nucleic acid can be inhibited, for example, by hybridization and/or cleavage. Provided herein are sets of inhibitors comprising oligonucleotides capable of binding hydrolase gene and/or message, in either case preventing or inhibiting the production or function of hydrolase. The association can be through sequence specific hybridization. Another useful class of inhibitors includes oligonucleotides which cause inactivation or cleavage of hydrolase message. The oligonucleotide can have enzyme activity which causes such cleavage, such as ribozymes. The oligonucleotide can be chemically modified or conjugated to an enzyme or composition capable of cleaving the complementary nucleic acid. One may screen a pool of many different such oligonucleotides for those with the desired activity.

Antisense Oligonucleotides

In certain embodiments, provided herein are antisense oligonucleotides capable of binding hydrolase message which can inhibit hydrolase activity by targeting mRNA or genomic DNA. Strategies for designing antisense oligonucleotides are well described in the scientific and patent literature, and the skilled artisan can design such hydrolase oligonucleotides using the novel reagents as provided herein. For example, gene walking/RNA mapping protocols to screen for effective antisense oligonucleotides are well known in the art, see, e.g., Ho (2000) Methods Enzymol. 314:168-183, describing an RNA mapping assay, which is based on standard molecular techniques to provide an easy and reliable method for potent antisense sequence selection. See also Smith (2000) Eur. J. Pharm. Sci. 11:191-198.

In one aspect, recombinantly generated, or, isolated naturally occurring nucleic acids are used as antisense oligonucleotides. The antisense oligonucleotides can be of any length; for example, in alternative aspects, the antisense oligonucleotides are between about 5 to 100, about 10 to 80, about 15 to 60, about 18 to 40. The antisense oligonucleotides can be single stranded or double-stranded RNA or DNA. The optimal length can be determined by routine screening. The antisense oligonucleotides can be present at any concentration. The optimal concentration can be determined by routine screening. A wide variety of synthetic, non-naturally occurring nucleotide and nucleic acid analogues are known which can address this potential problem. For example, peptide nucleic acids (PNAS) containing non-ionic backbones, such as N-(2-aminoethyl) glycine units can be used. Antisense oligonucleotides having phosphorothioate linkages can also be used, as described in WO 97/03211; WO 96/39154; Mata (1997) Toxicol Appl Pharmacol 144:189-197; Antisense Therapeutics, ed. Agrawal (Humana Press, Totowa, N.J., 1996). Provided herein are antisense oligonucleotides having synthetic DNA backbone analogues, which also can include phosphoro-dithioate, methylphosphonate, phosphoramidate, alkyl phosphotriester, sulfamate, 3'-thioacetal, methylene(methylimino), 3'-N-carbamate, and morpholino carbamate nucleic acids, as described above.

Combinatorial chemistry methodology can be used to create vast numbers of oligonucleotides that can be rapidly screened for specific oligonucleotides that have appropriate binding affinities and specificities toward any target, such as the sense and antisense hydrolase sequences as provided herein (see, e.g., Gold (1995) J. of Biol. Chem. 270:13581-13584).

Inhibitory Ribozymes

In certain embodiments, provided herein are ribozymes capable of binding hydrolase message that can inhibit hydrolase activity by targeting mRNA. Strategies for designing ribozymes and selecting the hydrolase-specific antisense sequence for targeting are well described in the scientific and patent literature, and the skilled artisan can design such ribozymes using the novel reagents as provided herein. Ribozymes act by binding to a target RNA through the target RNA binding portion of a ribozyme which is held in close proximity to an enzymatic portion of the RNA that cleaves the target RNA. Thus, the ribozyme recognizes and binds a target RNA through complementary basepairing, and once bound to the correct site, acts enzymatically to cleave and inactivate the target RNA. Cleavage of a target RNA in such a manner will destroy its ability to direct synthesis of an encoded protein if the cleavage occurs in the coding sequence. After a ribozyme has bound and cleaved its RNA target, it is typically released from that RNA and so can bind and cleave new targets repeatedly.

In some circumstances, the enzymatic nature of a ribozyme can be advantageous over other technologies, such as antisense technology (where a nucleic acid molecule simply binds to a nucleic acid target to block its transcription, translation or association with another molecule) as the effective concentration of ribozyme necessary to effect a therapeutic treatment can be lower than that of an antisense oligonucleotide. This potential advantage reflects the ability of the ribozyme to act enzymatically. Thus, a single ribozyme molecule is able to cleave many molecules of target RNA. In addition, a ribozyme is typically a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, the specificity of action of a ribozyme can be greater than that of antisense oligonucleotide binding the same RNA site.

The enzymatic ribozyme RNA molecule can be formed in a hammerhead motif, but may also be formed in the motif of a hairpin, hepatitis delta virus, group I intron or RNase P-like RNA (in association with an RNA guide sequence). Examples of such hammerhead motifs are described by Rossi (1992) Aids Research and Human Retroviruses 8:183; hairpin motifs by Hampel (1989) Biochemistry 28:4929, and Hampel (1990) Nuc. Acids Res. 18:299; the hepatitis delta virus motif by Perrotta (1992) Biochemistry 31:16; the RNaseP motif by Guerrier-Takada (1983) Cell 35:849; and the group I intron by Cech (U.S. Pat. No. 4,987,071). The recitation of these specific motifs is not intended to be limiting; those skilled in the art will recognize that an enzymatic RNA molecule as provided herein can have a specific substrate binding site complementary to one or more of the target gene RNA regions, and has nucleotide sequence within or surrounding that substrate binding site which imparts an RNA cleaving activity to the molecule.

RNA Interference (RNAi)

In certain embodiments, provided herein are RNA inhibitory molecules, so-called "RNAi" molecules, comprising a hydrolase sequence as provided herein. The RNAi molecule can comprise a double-stranded RNA (dsRNA) molecule, e.g., siRNA and/or miRNA. The RNAi can inhibit expression of a hydrolase (e.g., lipase, saturase, palmitase and/or stearatase) gene or transcript. In one aspect, the RNAi molecule, e.g., siRNA and/or miRNA, is about 10, 11, 12, 13, 14, 15, 16, 17, 18, 19, 20, 21, 22, 23, 24, 25, 26, 27, 28, 29 or 30 or more duplex nucleotides in length. While the invention is not limited by any particular mechanism of action, the RNAi can enter a cell and cause the degradation of a single-stranded RNA (ssRNA) of similar or identical sequences, including endogenous mRNAs. When a cell is exposed to double-stranded RNA (dsRNA), mRNA from the homologous gene is selectively degraded by a process called RNA interference (RNAi). A possible basic mechanism behind RNAi is the breaking of a double-stranded RNA (dsRNA) matching a specific gene sequence into short pieces called short interfering RNA, which trigger the degradation of mRNA that matches its sequence.

In one aspect, the RNAi's as provided herein are used in gene-silencing therapeutics, see, e.g., Shuey (2002) Drug Discov. Today 7:1040-1046. In certain embodiments, provided herein are methods to selectively degrade RNA using the RNAi's. The process may be practiced in vitro, ex vivo or in vivo. In one aspect, the RNAi molecules as provided herein can be used to generate a loss-of-function mutation in a cell, an organ or an animal. Methods for making and using RNAi molecules for selectively degrade RNA are well known in the art, see, e.g., U.S. Pat. Nos. 6,506,559; 6,511,824; 6,515,109; 6,489,127.

Modification of Nucleic Acids

In certain embodiments, provided herein are methods of generating variants of the nucleic acids, e.g., those encoding a hydrolase or an antibody as provided herein. These methods can be repeated or used in various combinations to generate hydrolases or antibodies having an altered or different activity or an altered or different stability from that of a hydrolase or antibody encoded by the template nucleic acid. These methods also can be repeated or used in various combinations, e.g., to generate variations in gene/message expression, message translation or message stability. In another aspect, the genetic composition of a cell is altered by, e.g., modification of a homologous gene ex vivo, followed by its reinsertion into the cell.

The term "variant" can include polynucleotides or polypeptides as provided herein modified at one or more base pairs, codons, introns, exons, or amino acid residues (respectively) yet still retain the biological activity of a hydrolase as provided herein. Variants can be produced by any number of means included methods such as, for example, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, GeneReassembly, GSSM$^{SM}$ and any combination thereof. Techniques for producing variant hydrolases having activity at a pH or temperature, for example, that is different from a wild-type hydrolase, are included herein.

A nucleic acid as provided herein can be altered by any means. For example, random or stochastic methods, or, non-stochastic, or "directed evolution," methods, see, e.g., U.S. Pat. No. 6,361,974. Methods for random mutation of genes are well known in the art, see, e.g., U.S. Pat. No. 5,830,696. For example, mutagens can be used to randomly mutate a gene. Mutagens include, e.g., ultraviolet light or gamma irradiation, or a chemical mutagen, e.g., mitomycin, nitrous acid, photoactivated psoralens, alone or in combination, to induce DNA breaks amenable to repair by recombination. Other chemical mutagens include, for example, sodium bisulfite, nitrous acid, hydroxylamine, hydrazine or formic acid. Other mutagens are analogues of nucleotide precursors, e.g., nitrosoguanidine, 5-bromouracil, 2-aminopurine, or acridine. These agents can be added to a PCR reaction in place of the nucleotide precursor thereby mutating the sequence. Intercalating agents such as proflavine, acriflavine, quinacrine and the like can also be used.

Any technique in molecular biology can be used, e.g., random PCR mutagenesis, see, e.g., Rice (1992) Proc. Natl. Acad. Sci. USA 89:5467-5471; or, combinatorial multiple cassette mutagenesis, see, e.g., Crameri (1995) Biotechniques 18:194-196. Alternatively, nucleic acids, e.g., genes, can be reassembled after random, or "stochastic," fragmentation, see, e.g., U.S. Pat. Nos. 6,291,242; 6,287,862; 6,287,861; 5,955,358; 5,830,721; 5,824,514; 5,811,238; 5,605,793. In alternative aspects, modifications, additions or deletions are introduced by error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, Gene Site Saturation Mutagenesis$^{SM}$ (GSSM$^{SM}$), synthetic ligation reassembly (SLR or GeneReassembly), recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation, and/or a combination of these and other methods.

The following publications describe a variety of recursive recombination procedures and/or methods which can be incorporated into the methods as provided herein: Stemmer (1999) "Molecular breeding of viruses for targeting and other clinical properties" Tumor Targeting 4:1-4; Ness (1999) Nature Biotechnology 17:893-896; Chang (1999) "Evolution of a cytokine using DNA family shuffling" Nature Biotechnology 17:793-797; Minshull (1999) "Protein evolution by molecular breeding" Current Opinion in Chemical Biology 3:284-290; Christians (1999) "Directed evolution of thymidine kinase for AZT phosphorylation using DNA family shuffling" Nature Biotechnology 17:259-264; Crameri (1998) "DNA shuffling of a family of genes from diverse species accelerates directed evolution" Nature 391:288-291; Crameri (1997) "Molecular evolution of an arsenate detoxification pathway by DNA shuffling," Nature Biotechnology 15:436-438; Zhang (1997) "Directed evolution of an effective fucosidase from a galactosidase by DNA shuffling and screening" Proc. Natl. Acad. Sci. USA 94:4504-4509; Patten et al. (1997) "Applications of DNA Shuffling to Pharmaceuticals and Vaccines" Current Opinion in Biotechnology 8:724-733; Crameri et al. (1996) "Construction and evolution of antibody-phage libraries by DNA shuffling" Nature Medicine 2:100-103; Gates et al. (1996) "Affinity selective isolation of ligands from peptide libraries through display on a lac repressor 'headpiece dimer'" Journal of Molecular Biology 255: 373-386; Stemmer (1996) "Sexual PCR and Assembly PCR" In: The Encyclopedia of Molecular Biology. VCH Publishers, New York. pp. 447-457; Crameri and Stemmer (1995) "Combinatorial multiple cassette mutagenesis creates all the permutations of mutant and wildtype cassettes" BioTechniques 18:194-195; Stemmer et al. (1995) "Single-step assembly of a gene and entire plasmid form large numbers of oligodeoxyribonucleotides" Gene, 164:49-53; Stemmer (1995) "The Evolution of Molecular Computation" Science 270: 1510; Stemmer (1995) "Searching Sequence Space" Bio/Technology 13:549-553; Stemmer (1994) "Rapid evolution of a protein in vitro by DNA shuffling" Nature 370:389-391; and Stemmer (1994) "DNA shuffling by random fragmentation and reassembly: In vitro recombination for molecular evolution." Proc. Natl. Acad. Sci. USA 91:10747-10751.

Mutational methods of generating diversity include, for example, site-directed mutagenesis (Ling et al. (1997) "Approaches to DNA mutagenesis: an overview" Anal Biochem. 254(2): 157-178; Dale et al. (1996) "Oligonucleotide-directed random mutagenesis using the phosphorothioate method" Methods Mol. Biol. 57:369-374; Smith (1985) "In vitro mutagenesis" Ann. Rev. Genet. 19:423-462; Botstein & Shortle (1985) "Strategies and applications of in vitro mutagenesis" Science 229:1193-1201; Carter (1986) "Site-directed mutagenesis" Biochem. J. 237:1-7; and Kunkel (1987) "The efficiency of oligonucleotide directed mutagenesis" in Nucleic Acids & Molecular Biology (Eckstein, F. and Lilley, D. M. J. eds., Springer Verlag, Berlin)); mutagenesis using uracil containing templates (Kunkel (1985) "Rapid and efficient site-specific mutagenesis without phenotypic selection" Proc. Natl. Acad. Sci. USA 82:488-492; Kunkel et al. (1987) "Rapid and efficient site-specific mutagenesis without phenotypic selection" Methods in Enzymol. 154, 367-382; and Bass et al. (1988) "Mutant Trp repressors with new DNA-binding specificities" Science 242:240-245); oligonucleotide-directed mutagenesis (Methods in Enzymol. 100: 468-500 (1983); Methods in Enzymol. 154: 329-350 (1987); Zoller & Smith (1982) "Oligonucleotide-directed mutagenesis using M13-derived vectors: an efficient and general procedure for the production of point mutations in any DNA fragment" Nucleic Acids Res. 10:6487-6500; Zoller & Smith (1983) "Oligonucleotide-directed mutagenesis of DNA fragments cloned into M13 vectors" Methods in Enzymol. 100: 468-500; and Zoller & Smith (1987) Oligonucleotide-directed mutagenesis: a simple method using two oligonucleotide primers and a single-stranded DNA template" Methods in Enzymol. 154:329-350); phosphorothioate-modified DNA mutagenesis (Taylor et al. (1985) "The use of phosphorothioate-modified DNA in restriction enzyme reactions to prepare nicked DNA" Nucl. Acids Res. 13: 8749-8764; Taylor et al. (1985) "The rapid generation of oligonucleotide-directed mutations at high frequency using phosphorothioate-modified DNA" Nucl. Acids Res. 13: 8765-8787 (1985); Nakamaye (1986) "Inhibition of restriction endonuclease Nci I cleavage by phosphorothioate groups and its application to oligonucleotide-directed mutagenesis" Nucl. Acids Res. 14: 9679-9698; Sayers et al. (1988) "Y-T Exonucleases in phosphorothioate-based oligonucleotide-directed mutagenesis" Nucl. Acids Res. 16:791-802; and Sayers et al. (1988) "Strand specific cleavage of phosphorothioate-containing DNA by reaction with restriction endonucleases in the presence of ethidium bromide" Nucl. Acids Res. 16: 803-814); mutagenesis using gapped duplex DNA (Kramer et al. (1984) "The gapped duplex DNA approach to oligonucleotide-directed mutation construction" Nucl. Acids Res. 12: 9441-9456; Kramer & Fritz (1987) Methods in Enzymol. "Oligonucleotide-directed construction of mutations via gapped duplex DNA" 154:350-367; Kramer et al. (1988) "Improved enzymatic in vitro reactions in the gapped duplex DNA approach to oligonucleotide-directed construction of mutations" Nucl. Acids Res. 16: 7207; and Fritz et al. (1988) "Oligonucleotide-directed construction of mutations: a gapped duplex DNA procedure without enzymatic reactions in vitro" Nucl. Acids Res. 16: 6987-6999).

Additional protocols used in the methods as provided herein include point mismatch repair (Kramer (1984) "Point Mismatch Repair" Cell 38:879-887), mutagenesis using repair-deficient host strains (Carter et al. (1985) "Improved oligonucleotide site-directed mutagenesis using M13 vectors" Nucl. Acids Res. 13: 4431-4443; and Carter (1987) "Improved oligonucleotide-directed mutagenesis using M13 vectors" Methods in Enzymol. 154: 382-403), deletion mutagenesis (Eghtedarzadeh (1986) "Use of oligonucleotides to generate large deletions" Nucl. Acids Res. 14: 5115), restriction-selection and restriction-selection and restriction-purification (Wells et al. (1986) "Importance of hydrogen-bond formation in stabilizing the transition state of subtilisin" Phil. Trans. R. Soc. Lond. A 317: 415-423), mutagenesis by total gene synthesis (Nambiar et al. (1984) "Total synthesis and cloning of a gene coding for the ribonuclease S protein" Science 223: 1299-1301; Sakamar and Khorana (1988) "Total synthesis and expression of a gene for the a-subunit of bovine rod outer segment guanine nucleotide-binding protein (transducin)" Nucl. Acids Res. 14: 6361-6372; Wells et al. (1985) "Cassette mutagenesis: an efficient method for generation of multiple mutations at defined sites" Gene 34:315-323; and Grundstrom et al. (1985) "Oligonucleotide-directed mutagenesis by microscale 'shotgun' gene synthesis" Nucl. Acids Res. 13: 3305-3316), double-strand break repair (Mandecki (1986); Arnold (1993) "Protein engineering for unusual environments" Current Opinion in Biotechnology 4:450-455. "Oligonucleotide-directed double-strand break repair in plasmids of *Escherichia coli*: a method for site-specific mutagenesis" Proc. Natl. Acad. Sci. USA, 83:7177-7181). Additional details on many of the above methods can be found in Methods in Enzymology Volume 154, which also describes useful controls for trouble-shooting problems with various mutagenesis methods.

Additional protocols used in the methods as provided herein include those discussed in U.S. Pat. No. 5,605,793 to Stemmer (Feb. 25, 1997), "Methods for In Vitro Recombination;" U.S. Pat. No. 5,811,238 to Stemmer et al. (Sep. 22, 1998) "Methods for Generating Polynucleotides having Desired Characteristics by Iterative Selection and Recombination;" U.S. Pat. No. 5,830,721 to Stemmer et al. (Nov. 3, 1998), "DNA Mutagenesis by Random Fragmentation and Reassembly;" U.S. Pat. No. 5,834,252 to Stemmer, et al. (Nov. 10, 1998) "End-Complementary Polymerase Reaction;" U.S. Pat. No. 5,837,458 to Minshull, et al. (Nov. 17, 1998), "Methods and Compositions for Cellular and Metabolic Engineering;" WO 95/22625, Stemmer and Crameri, "Mutagenesis by Random Fragmentation and Reassembly;" WO 96/33207 by Stemmer and Lipschutz "End Complementary Polymerase Chain Reaction;" WO 97/20078 by Stemmer and Crameri "Methods for Generating Polynucleotides having Desired Characteristics by Iterative Selection and Recombination;" WO 97/35966 by Minshull and Stemmer, "Methods and Compositions for Cellular and Metabolic Engineering;" WO 99/41402 by Punnonen et al. "Targeting of Genetic Vaccine Vectors;" WO 99/41383 by Punnonen et al. "Antigen Library Immunization;" WO 99/41369 by Punnonen et al. "Genetic Vaccine Vector Engineering;" WO 99/41368 by Punnonen et al. "Optimization of Immunomodulatory Properties of Genetic Vaccines;" EP 752008 by Stemmer and Crameri, "DNA Mutagenesis by Random Fragmentation and Reassembly;" EP 0932670 by Stemmer "Evolving Cellular DNA Uptake by Recursive Sequence Recombination;" WO 99/23107 by Stemmer et al., "Modification of Virus Tropism and Host Range by Viral Genome Shuffling;" WO 99/21979 by Apt et al., "Human Papillomavirus Vectors;" WO 98/31837 by del Cardayre et al. "Evolution of Whole Cells and Organisms by Recursive Sequence Recombination;" WO 98/27230 by Patten and Stemmer, "Methods and Compositions for Polypeptide Engineering;" WO 98/27230 by Stemmer et al., "Methods for Optimization of Gene Therapy by Recursive Sequence Shuffling and Selection," WO 00/00632, "Methods for Generating Highly Diverse Libraries," WO 00/09679, "Methods for Obtaining in Vitro Recombined Polynucleotide Sequence Banks and Resulting Sequences," WO 98/42832 by Arnold et al., "Recombination of Polynucleotide Sequences Using Random or Defined Primers," WO 99/29902 by Arnold et al., "Method for Creating Polynucleotide and Polypeptide Sequences," WO 98/41653 by Vind, "An in Vitro Method for Construction of a DNA Library," WO 98/41622 by Borchert et al., "Method for Constructing a Library Using DNA Shuffling," and WO 98/42727 by Pati and Zarling, "Sequence Alterations using Homologous Recombination."

Protocols that can be used (providing details regarding various diversity generating methods) are described, e.g., in U.S. patent application Ser. No. 09/407,800, "SHUFFLING OF CODON ALTERED GENES" by Patten et al. filed Sep. 28, 1999; "EVOLUTION OF WHOLE CELLS AND ORGANISMS BY RECURSIVE SEQUENCE RECOMBINATION" by del Cardayre et al., U.S. Pat. No. 6,379,964; "OLIGONUCLEOTIDE MEDIATED NUCLEIC ACID RECOMBINATION" by Crameri et al., U.S. Pat. Nos. 6,319,714; 6,368,861; 6,376,246; 6,423,542; 6,426,224 and PCT/US00/01203; "USE OF CODON-VARIED OLIGONUCLEOTIDE SYNTHESIS FOR SYNTHETIC SHUFFLING" by Welch et al., U.S. Pat. No. 6,436,675; "METHODS FOR MAKING CHARACTER STRINGS, POLYNUCLEOTIDES & POLYPEPTIDES HAVING DESIRED CHARACTERISTICS" by Selifonov et al., filed Jan. 18, 2000, (PCT/US00/01202) and, e.g. "METHODS FOR MAKING CHARACTER STRINGS, POLYNUCLEOTIDES & POLYPEPTIDES HAVING DESIRED CHARACTERISTICS" by Selifonov et al., filed Jul. 18, 2000 (U.S. Ser. No. 09/618,579); "METHODS OF POPULATING DATA STRUCTURES FOR USE IN EVOLUTIONARY SIMULATIONS" by Selifonov and Stemmer, filed Jan. 18, 2000 (PCT/US00/01138); and "SINGLE-STRANDED NUCLEIC ACID TEMPLATE-MEDIATED RECOMBINATION AND NUCLEIC ACID FRAGMENT ISOLATION" by Affholter, filed Sep. 6, 2000 (U.S. Ser. No. 09/656,549); and U.S. Pat. Nos. 6,177,263; 6,153,410.

Non-stochastic, or "directed evolution," methods include, e.g., gene site saturation mutagenesis$^{SM}$ (GSSM$^{SM}$), synthetic ligation reassembly (SLR or GeneReassembly), or a combination thereof are used to modify the nucleic acids as provided herein to generate hydrolases with new or altered properties (e.g., activity under highly acidic or alkaline conditions, high temperatures, and the like). Polypeptides encoded by the modified nucleic acids can be screened for an activity before testing for proteolytic or other activity. Any testing modality or protocol can be used, e.g., using a capillary array platform. See, e.g., U.S. Pat. Nos. 6,361,974; 6,280,926; 5,939,250.

Saturation Mutagenesis, or, GSSM$^{SM}$ Technology

In one aspect as provided herein, non-stochastic gene modification, a "directed evolution process," is used to generate hydrolases and antibodies with new or altered properties. Variations of this method have been termed "Gene Site Saturation Mutagenesis," "site-saturation mutagenesis," "saturation mutagenesis" or simply "GSSM$^{SM}$." It can be used in combination with other mutagenization processes. In one aspect, provided herein are methods for making enzymes and antibodies using GSSM$^{SM}$ technology, e.g., as described herein and also in U.S. Pat. Nos. 6,171,820; 6,579,258; 6,238,884.

In one aspect, GSSM$^{SM}$ technology comprises providing a template polynucleotide and a plurality of oligonucleotides, wherein each oligonucleotide comprises a sequence homologous to the template polynucleotide, thereby targeting a specific sequence of the template polynucleotide, and a sequence that is a variant of the homologous gene; generating progeny polynucleotides comprising non-stochastic sequence variations by replicating the template polynucleotide with the oligonucleotides, thereby generating polynucleotides comprising homologous gene sequence variations.

In one aspect, codon primers containing a degenerate N,N,G/T sequence are used to introduce point mutations into a polynucleotide, so as to generate a set of progeny polypeptides in which a full range of single amino acid substitutions is represented at each amino acid position, e.g., an amino acid residue in an enzyme active site or ligand binding site targeted to be modified. These oligonucleotides can comprise a contiguous first homologous sequence, a degenerate N,N,G/T sequence, and, optionally, a second homologous sequence. The downstream progeny translational products from the use of such oligonucleotides include all possible amino acid changes at each amino acid site along the polypeptide, because the degeneracy of the N,N,G/T sequence includes codons for all 20 amino acids. In one aspect, one such degenerate oligonucleotide (comprised of, e.g., one degenerate N,N,G/T cassette) is used for subjecting each original codon in a parental polynucleotide template to a full range of codon substitutions. In another aspect, at least two degenerate cassettes are used—either in the same oligonucleotide or not, for subjecting at least two original codons in a parental polynucleotide template to a full range of codon substitutions. For example, more than one N,N,G/T sequence can be contained in one oligonucleotide to introduce amino acid mutations at more than one site. This plurality of N,N,G/T sequences can be directly contiguous, or separated by one or more additional nucleotide sequence(s). In another aspect, oligonucleotides serviceable for introducing additions and deletions can be used either alone or in combination with the codons containing an N,N,G/T sequence, to introduce any combination or permutation of amino acid additions, deletions, and/or substitutions.

In one aspect, simultaneous mutagenesis of two or more contiguous amino acid positions is done using an oligonucleotide that contains contiguous N,N,G/T triplets, i.e. a degenerate (N,N,G/T)n sequence. In another aspect, degenerate cassettes having less degeneracy than the N,N,G/T sequence are used. For example, it may be desirable in some instances to use (e.g. in an oligonucleotide) a degenerate triplet sequence comprised of only one N, where said N can be in the first second or third position of the triplet. Any other bases including any combinations and permutations thereof can be used in the remaining two positions of the triplet. Alternatively, it may be desirable in some instances to use (e.g. in an oligo) a degenerate N,N,N triplet sequence.

In one aspect, use of degenerate triplets (e.g., N,N,G/T triplets) allows for systematic and easy generation of a full range of possible natural amino acids (for a total of 20 amino acids) into each and every amino acid position in a polypeptide (in alternative aspects, the methods also include generation of less than all possible substitutions per amino acid residue, or codon, position). For example, for a 100 amino acid polypeptide, 2000 distinct species (i.e. 20 possible amino acids per position×100 amino acid positions) can be generated. Through the use of an oligonucleotide or set of oligonucleotides containing a degenerate N,N,G/T triplet, 32 individual sequences can code for all 20 possible natural amino acids. Thus, in a reaction vessel in which a parental polynucleotide sequence is subjected to saturation mutagenesis using at least one such oligonucleotide, there are generated 32 distinct progeny polynucleotides encoding 20 distinct polypeptides. In contrast, the use of a nondegenerate oligonucleotide in site-directed mutagenesis leads to only one progeny polypeptide product per reaction vessel. Nondegenerate oligonucleotides can optionally be used in combination with degenerate primers disclosed; for example, nondegenerate oligonucleotides can be used to generate specific point mutations in a working polynucleotide. This provides one means to generate specific silent point mutations, point mutations leading to corresponding amino acid changes, and point mutations that cause the generation of stop codons and the corresponding expression of polypeptide fragments.

In one aspect, each saturation mutagenesis reaction vessel contains polynucleotides encoding at least 20 progeny polypeptide (e.g., hydrolase, e.g., lipase, saturase, palmitase and/or stearatase) molecules such that all 20 natural amino acids are represented at the one specific amino acid position corresponding to the codon position mutagenized in the parental polynucleotide (other aspects use less than all 20 natural combinations). The 32-fold degenerate progeny polypeptides generated from each saturation mutagenesis reaction vessel can be subjected to clonal amplification (e.g. cloned into a suitable host, e.g., *E. coli* host, using, e.g., an expression vector) and subjected to expression screening. When an individual progeny polypeptide is identified by screening to display a favorable change in property (when compared to the parental polypeptide, such as increased selectivity for hydrolysis of palmitate esters versus hydrolysis of oleate esters), it can be sequenced to identify the correspondingly favorable amino acid substitution contained therein.

In one aspect, upon mutagenizing each and every amino acid position in a parental polypeptide using saturation mutagenesis as disclosed herein, favorable amino acid changes may be identified at more than one amino acid position. One or more new progeny molecules can be generated that contain a combination of all or part of these favorable amino acid substitutions. For example, if 2 specific favorable amino acid changes are identified in each of 3 amino acid positions in a polypeptide, the permutations include 3 possibilities at each position (no change from the original amino acid, and each of two favorable changes) and 3 positions. Thus, there are 3×3×3 or 27 total possibilities, including 7 that were previously examined—6 single point mutations (i.e. 2 at each of three positions) and no change at any position.

In another aspect, site-saturation mutagenesis can be used together with another stochastic or non-stochastic means to vary sequence, e.g., synthetic ligation reassembly (see below), shuffling, chimerization, recombination and other mutagenizing processes and mutagenizing agents. Provided herein are mutagenizing process(es), including saturation mutagenesis, used in an iterative manner.

Synthetic Ligation Reassembly (SLR)

In one aspect provided herein are non-stochastic gene modification systems termed "synthetic ligation reassembly," or simply "SLR,", also known as "GeneReassembly" technology, a "directed evolution process," to generate polypeptides, e.g., enzymes (such as hydrolases, e.g., lipases, saturases, palmitases and/or stearatases) or antibodies as provided herein, with new or altered properties. SLR is a method of ligating oligonucleotide fragments together non-stochastically. This method differs from stochastic oligonucleotide shuffling in that the nucleic acid building blocks are not shuffled, concatenated or chimerized randomly, but rather are assembled non-stochastically. See, e.g., U.S. Pat. Nos. 6,773, 900; 6,740,506; 6,713,282; 6,635,449; 6,605,449; 6,537,776.

In one aspect, SLR comprises the following steps: (a) providing a template polynucleotide, wherein the template polynucleotide comprises sequence encoding a homologous gene; (b) providing a plurality of building block polynucleotides, wherein the building block polynucleotides are designed to cross-over reassemble with the template polynucleotide at a predetermined sequence, and a building block polynucleotide comprises a sequence that is a variant of the homologous gene and a sequence homologous to the template polynucleotide flanking the variant sequence; (c) combining a building block polynucleotide with a template polynucleotide such that the building block polynucleotide cross-over reassembles with the template polynucleotide to generate polynucleotides comprising homologous gene sequence variations.

SLR does not depend on the presence of high levels of homology between polynucleotides to be rearranged. Thus, this method can be used to non-stochastically generate libraries (or sets) of progeny molecules comprised of over $10^{100}$ different chimeras. SLR can be used to generate libraries comprised of over $10^{1000}$ different progeny chimeras. In one aspect provided herein are non-stochastic methods of producing a set of finalized chimeric nucleic acid molecules having an overall assembly order that is chosen by design. This method includes the steps of generating by design a plurality of specific nucleic acid building blocks having serviceable mutually compatible ligatable ends, and assembling these nucleic acid building blocks, such that a designed overall assembly order is achieved.

The mutually compatible ligatable ends of the nucleic acid building blocks to be assembled are considered to be "serviceable" for this type of ordered assembly if they enable the building blocks to be coupled in predetermined orders. Thus, the overall assembly order in which the nucleic acid building blocks can be coupled is specified by the design of the ligatable ends. If more than one assembly step is to be used, then the overall assembly order in which the nucleic acid building blocks can be coupled is also specified by the sequential order of the assembly step(s). In one aspect, the annealed building pieces are treated with an enzyme, such as a ligase (e.g. T4 DNA ligase), to achieve covalent bonding of the building pieces.

In one aspect, the design of the oligonucleotide building blocks is obtained by analyzing a set of progenitor nucleic acid sequence templates that serve as a basis for producing a progeny set of finalized chimeric polynucleotides. These parental oligonucleotide templates thus serve as a source of sequence information that aids in the design of the nucleic acid building blocks that are to be mutagenized, e.g., chimerized or shuffled. In one aspect of this method, the sequences of a plurality of parental nucleic acid templates are aligned in order to select one or more demarcation points. The demarcation points can be located at an area of homology, and are comprised of one or more nucleotides. These demarcation points are alternatively shared by at least two of the progenitor templates. The demarcation points can thereby be used to delineate the boundaries of oligonucleotide building blocks to be generated in order to rearrange the parental polynucleotides. The demarcation points identified and selected in the progenitor molecules serve as potential chimerization points in the assembly of the final chimeric progeny molecules. A demarcation point can be an area of homology (comprised of at least one homologous nucleotide base) shared by at least two parental polynucleotide sequences. Alternatively, a demarcation point can be an area of homology that is shared by at least half of the parental polynucleotide sequences, or, it can be an area of homology that is shared by at least two thirds of the parental polynucleotide sequences. In alternative embodiments, a serviceable demarcation point is an area of homology that is shared by at least three fourths of the parental polynucleotide sequences, or, it can be shared by at almost all of the parental polynucleotide sequences. In one aspect, a demarcation point is an area of homology that is shared by all of the parental polynucleotide sequences.

In one aspect, a ligation reassembly process is performed exhaustively in order to generate an exhaustive library of progeny chimeric polynucleotides. In other words, all possible ordered combinations of the nucleic acid building blocks are represented in the set of finalized chimeric nucleic acid molecules. At the same time, in another aspect, the assembly order (i.e. the order of assembly of each building block in the 5' to 3 sequence of each finalized chimeric nucleic acid) in each combination is by design (or non-stochastic) as described above. Provided herein are non-stochastic methods that reduce the possibility of unwanted side products.

In another aspect, the ligation reassembly method is performed systematically. For example, the method is performed in order to generate a systematically compartmentalized library of progeny molecules, with compartments that can be screened systematically, e.g. one by one. Provided herein are methods comprising selective and judicious use of specific nucleic acid building blocks, coupled with the selective and judicious use of sequentially stepped assembly reactions, a design can be achieved where specific sets of progeny products are made in each of several reaction vessels. This allows a systematic examination and screening procedure to be performed. Thus, these methods allow a potentially very large number of progeny molecules to be examined systematically in smaller groups. Because of its ability to perform chimerizations in a manner that is highly flexible yet exhaustive and systematic as well, particularly when there is a low level of homology among the progenitor molecules, these methods provide for the generation of a library (or set) comprised of a large number of progeny molecules. Because of the non-stochastic nature of the instant ligation reassembly methods, the progeny molecules generated can comprise a library of finalized chimeric nucleic acid molecules having an overall assembly order that is chosen by design. The saturation mutagenesis and optimized directed evolution methods also can be used to generate different progeny molecular species.

In one aspect, the methods herein provide freedom of choice and control regarding the selection of demarcation points, the size and number of the nucleic acid building blocks, and the size and design of the couplings. The requirement for intermolecular homology can be highly relaxed. In fact, demarcation points can even be chosen in areas of little or no intermolecular homology. For example, because of codon wobble, i.e. the degeneracy of codons, nucleotide substitutions can be introduced into nucleic acid building blocks without altering the amino acid originally encoded in the corresponding progenitor template. Alternatively, a codon can be altered such that the coding for an original amino acid is altered. In one aspect, substitutions can be introduced into the nucleic acid building block in order to increase the incidence of intermolecular homologous demarcation points and thus to allow an increased number of couplings to be achieved among the building blocks, which in turn allows a greater number of progeny chimeric molecules to be generated.

In another aspect, the synthetic nature of the step in which the building blocks are generated allows the design and introduction of nucleotides (e.g., one or more nucleotides, which may be, for example, codons or introns or regulatory sequences) that can later be optionally removed in an in vitro process (e.g. by mutagenesis) or in an in vivo process (e.g. by utilizing the gene splicing ability of a host organism). It is appreciated that in many instances the introduction of these nucleotides may also be desirable for many other reasons in addition to the potential benefit of creating a serviceable demarcation point.

In one aspect, a nucleic acid building block is used to introduce an intron. Thus, functional introns are introduced into a man-made gene manufactured according to the methods described herein. The artificially introduced intron(s) can be functional in a host cells for gene splicing much in the way that naturally-occurring introns serve functionally in gene splicing.

Optimized Directed Evolution System

In certain embodiments, provided herein are non-stochastic gene modification systems termed "optimized directed evolution system" to generate hydrolases and antibodies with new or altered properties. Optimized directed evolution is directed to the use of repeated cycles of reductive reassortment, recombination and selection that allow for the directed molecular evolution of nucleic acids through recombination. Optimized directed evolution allows generation of a large population of evolved chimeric sequences, wherein the generated population is significantly enriched for sequences that have a predetermined number of crossover events.

A crossover event is a point in a chimeric sequence where a shift in sequence occurs from one parental variant to another parental variant. Such a point is normally at the juncture of where oligonucleotides from two parents are ligated together to form a single sequence. This method allows calculation of the correct concentrations of oligonucleotide sequences so that the final chimeric population of sequences is enriched for the chosen number of crossover events. This provides more control over choosing chimeric variants having a predetermined number of crossover events.

In addition, this method provides a convenient means for exploring a tremendous amount of the possible protein variant space in comparison to other systems. Previously, if one generated, for example, $10^{13}$ chimeric molecules during a reaction, it would be extremely difficult to test such a high number of chimeric variants for a particular activity. Moreover, a significant portion of the progeny population would have a very high number of crossover events which resulted in proteins that were less likely to have increased levels of a particular activity. By using these methods, the population of chimerics molecules can be enriched for those variants that have a particular number of crossover events. Thus, although one can still generate $10^{13}$ chimeric molecules during a reaction, each of the molecules chosen for further analysis most likely has, for example, only three crossover events. Because the resulting progeny population can be skewed to have a predetermined number of crossover events, the boundaries on the functional variety between the chimeric molecules is reduced. This provides a more manageable number of variables when calculating which oligonucleotide from the original parental polynucleotides might be responsible for affecting a particular trait.

One method for creating a chimeric progeny polynucleotide sequence is to create oligonucleotides corresponding to fragments or portions of each parental sequence. In alternative embodiments, each oligonucleotide includes a unique region of overlap so that mixing the oligonucleotides together results in a new variant that has each oligonucleotide fragment assembled in the correct order. Alternatively protocols for practicing these methods as provided herein can be found in U.S. Pat. Nos. 6,773,900; 6,740,506; 6,713,282; 6,635,449; 6,605,449; 6,537,776; 6,361,974.

The number of oligonucleotides generated for each parental variant bears a relationship to the total number of resulting crossovers in the chimeric molecule that is ultimately created. For example, three parental nucleotide sequence variants might be provided to undergo a ligation reaction in order to find a chimeric variant having, for example, greater activity at high temperature. As one example, a set of 50 oligonucleotide sequences can be generated corresponding to each portions of each parental variant. Accordingly, during the ligation reassembly process there could be up to 50 crossover events within each of the chimeric sequences. The probability that each of the generated chimeric polynucleotides will contain oligonucleotides from each parental variant in alternating order is very low. If each oligonucleotide fragment is present in the ligation reaction in the same molar quantity it is likely that in some positions oligonucleotides from the same parental polynucleotide will ligate next to one another and thus not result in a crossover event. If the concentration of each oligonucleotide from each parent is kept constant during any ligation step in this example, there is a ⅓ chance (assuming 3 parents) that an oligonucleotide from the same parental variant will ligate within the chimeric sequence and produce no crossover.

Accordingly, a probability density function (PDF) can be determined to predict the population of crossover events that are likely to occur during each step in a ligation reaction given a set number of parental variants, a number of oligonucleotides corresponding to each variant, and the concentrations of each variant during each step in the ligation reaction. The statistics and mathematics behind determining the PDF is described below. By utilizing these methods, one can calculate such a probability density function, and thus enrich the chimeric progeny population for a predetermined number of crossover events resulting from a particular ligation reaction. Moreover, a target number of crossover events can be predetermined, and the system then programmed to calculate the starting quantities of each parental oligonucleotide during each step in the ligation reaction to result in a probability density function that centers on the predetermined number of crossover events. These methods are directed to the use of repeated cycles of reductive reassortment, recombination and selection that allow for the directed molecular evolution of a nucleic acid encoding a polypeptide through recombination. This system allows generation of a large population of evolved chimeric sequences, wherein the generated population is significantly enriched for sequences that have a predetermined number of crossover events. A crossover event is a point in a chimeric sequence where a shift in sequence occurs from one parental variant to another parental variant. Such a point is normally at the juncture of where oligonucleotides from two parents are ligated together to form a single sequence. The method allows calculation of the correct concentrations of oligonucleotide sequences so that the final chimeric population of sequences is enriched for the chosen number of crossover events. This provides more control over choosing chimeric variants having a predetermined number of crossover events.

Determining Crossover Events

Aspects as provided herein include a system and software that receive a desired crossover probability density function (PDF), the number of parent genes to be reassembled, and the number of fragments in the reassembly as inputs. The output of this program is a "fragment PDF" that can be used to determine a recipe for producing reassembled genes, and the estimated crossover PDF of those genes. The processing described herein is alternatively performed in MATLAB™ (The Mathworks, Natick, Mass.) a programming language and development environment for technical computing.

Iterative Processes

In certain embodiments, provided herein are processes that can be iteratively repeated. For example a nucleic acid (or, the nucleic acid) responsible for an altered hydrolase or antibody phenotype is identified, re-isolated, again modified, re-tested for activity. This process can be iteratively repeated until a desired phenotype is engineered. For example, an entire biochemical anabolic or catabolic pathway can be engineered into a cell, including proteolytic activity.

Similarly, if it is determined that a particular oligonucleotide has no affect at all on the desired trait (e.g., a new hydrolase phenotype), it can be removed as a variable by synthesizing larger parental oligonucleotides that include the sequence to be removed. Since incorporating the sequence within a larger sequence prevents any crossover events, there will no longer be any variation of this sequence in the progeny polynucleotides. This iterative practice of determining which oligonucleotides are most related to the desired trait, and which are unrelated, allows more efficient exploration all of the possible protein variants that might be provide a particular trait or activity.

In Vivo Shuffling

In vivo shuffling of molecules is used in methods as provided herein that provide variants of polypeptides as provided herein, e.g., antibodies, hydrolases, and the like. In vivo shuffling can be performed utilizing the natural property of cells to recombine multimers. While recombination in vivo has provided the major natural route to molecular diversity, genetic recombination remains a relatively complex process that involves 1) the recognition of homologies; 2) strand cleavage, strand invasion, and metabolic steps leading to the production of recombinant chiasma; and finally 3) the resolution of chiasma into discrete recombined molecules. The formation of the chiasma requires the recognition of homologous sequences.

In certain embodiments, provided herein are methods for producing a hybrid polynucleotide from at least a first polynucleotide and a second polynucleotide. In other embodiments, provided herein are methods used to produce a hybrid polynucleotide by introducing at least a first polynucleotide and a second polynucleotide which share at least one region of partial sequence homology into a suitable host cell. The regions of partial sequence homology promote processes which result in sequence reorganization producing a hybrid polynucleotide. In one aspect, the term "hybrid polynucleotide" encompasses any nucleotide sequence which results from a method as provided herein, and in one embodiment contains sequence from at least two original polynucleotide sequences. Such hybrid polynucleotides can result from intermolecular recombination events which promote sequence integration between DNA molecules. In addition, such hybrid polynucleotides can result from intramolecular reductive reassortment processes which utilize repeated sequences to alter a nucleotide sequence within a DNA molecule.

Producing Sequence Variants

In certain embodiments, provided herein are methods of making sequence variants of the nucleic acid and hydrolase and antibody sequences as provided herein or isolating hydrolases using the nucleic acids and polypeptides as provided herein. In certain embodiments, provided herein are variants of a hydrolase gene as provided herein, which can be altered by any means, including, e.g., random or stochastic methods, or, non-stochastic, or "directed evolution," methods, as described above.

Provided herein are methods of generating a variant of a nucleic acid encoding a polypeptide having hydrolase activity, e.g. lipase, saturase, palmitase and/or stearatase activity, comprising the steps of: (a) providing a template nucleic acid comprising a nucleic acid as provided herein; and (b) modifying, deleting or adding one or more nucleotides in the template sequence, or a combination thereof, to generate a variant of the template nucleic acid. In one aspect, the method can further comprise expressing the variant nucleic acid to generate a variant hydrolase, e.g. a lipase, saturase, palmitase and/or stearatase polypeptide. The modifications, additions or deletions can be introduced by a method comprising error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, Gene Site Saturation Mutagenesi$^{SM}$ (GSSM$^{SM}$), synthetic ligation reassembly (SLR or GeneReassembly) or a combination thereof. In another aspect, the modifications, additions or deletions are introduced by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and a combination thereof.

In one aspect, the method can be iteratively repeated until a hydrolase, e.g. a lipase, a saturase, a palmitase and/or a stearatase having an altered or different activity or an altered or different stability from that of a polypeptide encoded by the template nucleic acid is produced. In one aspect, the variant hydrolase, e.g. lipase, saturase, palmitase and/or stearatase polypeptide is thermotolerant, and retains some activity after being exposed to an elevated temperature. In another aspect, the variant hydrolase, e.g. lipase, saturase, palmitase and/or stearatase polypeptide has increased glycosylation as compared to the hydrolase, e.g. lipase, saturase, palmitase and/or stearatase encoded by a template nucleic acid. Alternatively, the variant hydrolase, e.g. lipase, saturase, palmitase and/or stearatase polypeptide has hydrolase, e.g. lipase, saturase, palmitase and/or stearatase activity under a high temperature, wherein the hydrolase, e.g. lipase, saturase, palmitase and/or stearatase encoded by the template nucleic acid is not active under the high temperature. In one aspect, the method can be iteratively repeated until a hydrolase, e.g. a lipase, a saturase, a palmitase and/or a stearatase coding sequence having an altered codon usage from that of the template nucleic acid is produced. In another aspect, the method can be iteratively repeated until a hydrolase gene, e.g. a lipase, a saturase, a palmitase and/or a stearatase gene, having higher or lower levels of message expression or stability from that of the template nucleic acid is produced. In another aspect, formulation of the final hydrolase product, e.g. lipase, saturase, palmitase and/or stearatase product, enables an increase or modulation of the performance of the hydrolase, e.g. lipase, saturase, palmitase and/or stearatase in the product.

The isolated variants may be naturally occurring. Variants can also be created in vitro. Variants may be created using genetic engineering techniques such as site directed mutagenesis, random chemical mutagenesis, Exonuclease III deletion procedures, and standard cloning techniques. Alternatively, such variants, fragments, analogs, or derivatives may be created using chemical synthesis or modification procedures. Other methods of making variants are also familiar to those skilled in the art. These include procedures in which nucleic acid sequences obtained from natural isolates are modified to generate nucleic acids which encode polypeptides having characteristics which enhance their value in industrial or laboratory applications. In such procedures, a large number of variant sequences having one or more nucleotide differences with respect to the sequence obtained from the natural isolate are generated and characterized. These nucleotide differences can result in amino acid changes with respect to the polypeptides encoded by the nucleic acids from the natural isolates.

For example, variants may be created using error prone PCR. In error prone PCR, PCR is performed under conditions where the copying fidelity of the DNA polymerase is low, such that a high rate of point mutations is obtained along the entire length of the PCR product. Error prone PCR is described, e.g., in Leung, D. W., et al., Technique, 1:11-15, 1989) and Caldwell, R. C. & Joyce G. F., PCR Methods Applic., 2:28-33, 1992. Briefly, in such procedures, nucleic acids to be mutagenized are mixed with PCR primers, reaction buffer, MgCl$_2$, MnCl$_2$, Taq polymerase and an appropriate concentration of dNTPs for achieving a high rate of point mutation along the entire length of the PCR product. For example, the reaction may be performed using 20 fmoles of nucleic acid to be mutagenized, 30 pmole of each PCR primer, a reaction buffer comprising 50 mM KCl, 10 mM Tris HCl (pH 8.3) and 0.01% gelatin, 7 mM MgCl$_2$, 0.5 mM MnCl$_2$, 5 units of Taq polymerase, 0.2 mM dGTP, 0.2 mM dATP, 1 mM dCTP, and 1 mM dTTP. PCR may be performed for 30 cycles of 94° C. for 1 min, 45° C. for 1 min, and 72° C. for 1 min. However, it will be appreciated that these parameters may be varied as appropriate. The mutagenized nucleic acids are cloned into an appropriate vector and the activities of the polypeptides encoded by the mutagenized nucleic acids are evaluated.

Variants may also be created using oligonucleotide directed mutagenesis to generate site-specific mutations in any cloned DNA of interest. Oligonucleotide mutagenesis is described, e.g., in Reidhaar-Olson (1988) Science 241:53-57. Briefly, in such procedures a plurality of double stranded oligonucleotides bearing one or more mutations to be introduced into the cloned DNA are synthesized and inserted into the cloned DNA to be mutagenized. Clones containing the mutagenized DNA are recovered and the activities of the polypeptides they encode are assessed.

Another method for generating variants is assembly PCR. Assembly PCR involves the assembly of a PCR product from a mixture of small DNA fragments. A large number of different PCR reactions occur in parallel in the same vial, with the products of one reaction priming the products of another reaction. Assembly PCR is described in, e.g., U.S. Pat. No. 5,965,408.

Still another method of generating variants is sexual PCR mutagenesis. In sexual PCR mutagenesis, forced homologous recombination occurs between DNA molecules of different but highly related DNA sequence in vitro, as a result of random fragmentation of the DNA molecule based on sequence homology, followed by fixation of the crossover by primer extension in a PCR reaction. Sexual PCR mutagenesis is described, e.g., in Stemmer (1994) Proc. Natl. Acad. Sci. USA 91:10747-10751. Briefly, in such procedures a plurality of nucleic acids to be recombined are digested with DNase to generate fragments having an average size of 50-200 nucleotides. Fragments of the desired average size are purified and resuspended in a PCR mixture. PCR is conducted under conditions which facilitate recombination between the nucleic acid fragments. For example, PCR may be performed by resuspending the purified fragments at a concentration of 10-30 ng/l in a solution of 0.2 mM of each dNTP, 2.2 mM $MgCl_2$, 50 mM KCL, 10 mM Tris HCl, pH 9.0, and 0.1% Triton X-100. 2.5 units of Taq polymerase per 100:1 of reaction mixture is added and PCR is performed using the following regime: 94° C. for 60 seconds, 94° C. for 30 seconds, 50-55° C. for 30 seconds, 72° C. for 30 seconds (30-45 times) and 72° C. for 5 minutes. However, it will be appreciated that these parameters may be varied as appropriate. In some aspects, oligonucleotides may be included in the PCR reactions. In other aspects, the Klenow fragment of DNA polymerase I may be used in a first set of PCR reactions and Taq polymerase may be used in a subsequent set of PCR reactions. Recombinant sequences are isolated and the activities of the polypeptides they encode are assessed.

Variants may also be created by in vivo mutagenesis. In some aspects, random mutations in a sequence of interest are generated by propagating the sequence of interest in a bacterial strain, such as an *E. coli* strain, which carries mutations in one or more of the DNA repair pathways. Such "mutator" strains have a higher random mutation rate than that of a wild-type parent. Propagating the DNA in one of these strains will eventually generate random mutations within the DNA. Mutator strains suitable for use for in vivo mutagenesis are described, e.g., in PCT Publication No. WO 91/16427.

Variants may also be generated using cassette mutagenesis. In cassette mutagenesis a small region of a double stranded DNA molecule is replaced with a synthetic oligonucleotide "cassette" that differs from the native sequence. The oligonucleotide often contains completely and/or partially randomized native sequence.

Recursive ensemble mutagenesis may also be used to generate variants. Recursive ensemble mutagenesis is an algorithm for protein engineering (protein mutagenesis) developed to produce diverse populations of phenotypically related mutants whose members differ in amino acid sequence. This method uses a feedback mechanism to control successive rounds of combinatorial cassette mutagenesis. Recursive ensemble mutagenesis is described, e.g., in Arkin (1992) Proc. Natl. Acad. Sci. USA 89:7811-7815.

In some aspects, variants are created using exponential ensemble mutagenesis. Exponential ensemble mutagenesis is a process for generating combinatorial libraries with a high percentage of unique and functional mutants, wherein small groups of residues are randomized in parallel to identify, at each altered position, amino acids which lead to functional proteins. Exponential ensemble mutagenesis is described, e.g., in Delegrave (1993) Biotechnology Res. 11:1548-1552. Random and site-directed mutagenesis are described, e.g., in Arnold (1993) Current Opinion in Biotechnology 4:450-455.

In some aspects, the variants are created using shuffling procedures wherein portions of a plurality of nucleic acids which encode distinct polypeptides are fused together to create chimeric nucleic acid sequences which encode chimeric polypeptides as described in, e.g., U.S. Pat. Nos. 5,965,408; 5,939,250.

Provided herein are variants of polypeptides comprising sequences in which one or more of the amino acid residues (e.g., of an exemplary polypeptide, e.g., SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20 or SEQ ID NO:2 having one, two, three, four, five, six, seven, eight or more (several) or all the amino acid variations described in Table 3 or Table 4, or the equivalent thereof) are substituted with a conserved or non-conserved amino acid residue (e.g., a conserved amino acid residue) and such substituted amino acid residue may or may not be one encoded by the genetic code. Conservative substitutions are those that substitute a given amino acid in a polypeptide by another amino acid of like characteristics. Thus, polypeptides herein include those with conservative substitutions of sequences, e.g., the exemplary sequences as provided herein (e.g., SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20 or SEQ ID NO:2 having one, two, three, four, five, six, seven, eight or more (several) or all the amino acid variations described in Table 3 or Table 4, or the equivalent thereof), including but not limited to the following replacements: replacements of an aliphatic amino acid such as alanine, valine, leucine and isoleucine with another aliphatic amino acid; replacement of a serine with a threonine or vice versa; replacement of an acidic residue such as aspartic acid and glutamic acid with another acidic residue; replacement of a residue bearing an amide group, such as asparagine and glutamine, with another residue bearing an amide group; exchange of a basic residue such as lysine and arginine with another basic residue; and replacement of an aromatic residue such as phenylalanine, tyrosine, or tryptophan with another aromatic residue. Other variants are those in which one or more of the amino acid residues of the polypeptides as provided herein includes a substituent group.

Other variants within the scope as provided herein are those in which the polypeptide is associated with another compound, such as a compound to increase the half-life of the polypeptide, for example, polyethylene glycol. Additional variants within the scope as provided herein are those in which additional amino acids are fused to the polypeptide, such as a leader sequence, a secretory sequence, a proprotein sequence or a sequence which facilitates purification, enrichment, or stabilization of the polypeptide. In some aspects, the variants, fragments, derivatives and analogs of the polypeptides as provided herein retain the same biological function or activity as the exemplary polypeptides, e.g., a proteolytic activity, as described herein. In other aspects, the variant, fragment, derivative, or analog includes a proprotein, such that the variant, fragment, derivative, or analog can be activated by cleavage of the proprotein portion to produce an active polypeptide.

Optimizing Codons to Achieve High Levels of Protein Expression in Host Cells

In certain embodiments, provided herein are methods for modifying hydrolase-encoding nucleic acids to modify codon usage. In one embodiment, provided herein are methods for modifying codons in a nucleic acid encoding a hydrolase to increase or decrease its expression in a host cell, e.g., a bacterial, insect, mammalian, yeast or plant cell. Further provided herein are nucleic acids encoding a hydrolase modified to increase its expression in a host cell, hydrolase so modified, and methods of making the modified hydrolases. The method comprises identifying a "non-preferred" or a "less preferred" codon in hydrolase-encoding nucleic acid and replacing one or more of these non-preferred or less preferred codons with a "preferred codon" encoding the same amino acid as the replaced codon and at least one non-preferred or less preferred codon in the nucleic acid has been replaced by a preferred codon encoding the same amino acid. A preferred codon is a codon over-represented in coding sequences in genes in the host cell and a non-preferred or less preferred codon is a codon under-represented in coding sequences in genes in the host cell.

Host cells for expressing the nucleic acids, expression cassettes and vectors as provided herein include bacteria, yeast, fungi, plant cells, insect cells and mammalian cells. In certain embodiments, provided herein are methods for optimizing codon usage in all of these cells, codon-altered nucleic acids and polypeptides made by the codon-altered nucleic acids. Exemplary host cells include gram negative bacteria, such as *Escherichia coli* and *Pseudomonas fluorescens*; gram positive bacteria, such as *Lactobacillus gasseri, Lactococcus lactis, Lactococcus cremoris, Bacillus subtilis*. Exemplary host cells also include eukaryotic organisms, e.g., various yeast, such as *Saccharomyces* sp., including *Saccharomyces cerevisiae, Schizosaccharomyces pombe, Pichia pastoris*, and *Kluyveromyces lactis, Hansenula polymorpha, Aspergillus niger*, and mammalian cells and cell lines and insect cells and cell lines. Other exemplary host cells include bacterial cells, such as *E. coli, Streptomyces, Bacillus subtilis, Bacillus cereus, Salmonella typhimurium* and various species within the genera *Pseudomonas, Streptomyces* and *Staphylococcus*, fungal cells, such as *Aspergillus*, yeast such as any species of *Pichia, Saccharomyces, Schizosaccharomyces, Schwanniomyces*, including *Pichia pastoris, Saccharomyces cerevisiae*, or *Schizosaccharomyces pombe*, insect cells such as *Drosophila* S2 and *Spodoptera* Sf9, animal cells such as CHO, COS or Bowes melanoma and adenoviruses. The selection of an appropriate host is within the abilities of those skilled in the art. In certain embodiments, provided herein are nucleic acids and polypeptides optimized for expression in these organisms and species.

For example, the codons of a nucleic acid encoding a hydrolase isolated from a bacterial cell are modified such that the nucleic acid is optimally expressed in a bacterial cell different from the bacteria from which the hydrolase was derived, a yeast, a fungi, a plant cell, an insect cell or a mammalian cell. Methods for optimizing codons are well known in the art, see, e.g., U.S. Pat. No. 5,795,737; Baca (2000) Int. J. Parasitol. 30:113-118; Hale (1998) Protein Expr. Purif. 12:185-188; Narum (2001) Infect. Immun. 69:7250-7253. See also Narum (2001) Infect. Immun. 69:7250-7253, describing optimizing codons in mouse systems; Outchkourov (2002) Protein Expr. Purif. 24:18-24, describing optimizing codons in yeast; Feng (2000) Biochemistry 39:15399-15409, describing optimizing codons in *E. coli*; Humphreys (2000) Protein Expr. Purif. 20:252-264, describing optimizing codon usage that affects secretion in *E. coli*.

Transgenic Non-Human Animals

In certain embodiments, provided herein are transgenic non-human animals comprising a nucleic acid, a polypeptide (e.g., a hydrolase or an antibody as provided herein), an expression cassette, a vector, a transfected or a transformed cell as provided herein. The transgenic non-human animals can be, e.g., goats, rabbits, sheep, pigs, cows, rats and mice, comprising the nucleic acids as provided herein. These animals can be used, e.g., as in vivo models to study hydrolase activity, or, as models to screen for agents that change the hydrolase activity in vivo. The coding sequences for the polypeptides to be expressed in the transgenic non-human animals can be designed to be constitutive, or, under the control of tissue-specific, developmental-specific or inducible transcriptional regulatory factors. Transgenic non-human animals can be designed and generated using any method known in the art; see, e.g., U.S. Pat. Nos. 6,211,428; 6,187,992; 6,156,952; 6,118,044; 6,111,166; 6,107,541; 5,959,171; 5,922,854; 5,892,070; 5,880,327; 5,891,698; 5,639,940; 5,573,933; 5,387,742; 5,087,571, describing making and using transformed cells and eggs and transgenic mice, rats, rabbits, sheep, pigs and cows. See also, e.g., Pollock (1999) J. Immunol. Methods 231:147-157, describing the production of recombinant proteins in the milk of transgenic dairy animals; Baguisi (1999) Nat. Biotechnol. 17:456-461, demonstrating the production of transgenic goats. U.S. Pat. No. 6,211,428, describes making and using transgenic non-human mammals which express in their brains a nucleic acid construct comprising a DNA sequence. U.S. Pat. No. 5,387,742, describes injecting cloned recombinant or synthetic DNA sequences into fertilized mouse eggs, implanting the injected eggs in pseudo-pregnant females, and growing to term transgenic mice whose cells express proteins related to the pathology of Alzheimer's disease. U.S. Pat. No. 6,187,992, describes making and using a transgenic mouse whose genome comprises a disruption of the gene encoding amyloid precursor protein (APP).

"Knockout animals" can also be used to practice the methods as provided herein. For example, in one aspect, the transgenic or modified animals as provided herein comprise a "knockout animal," e.g., a "knockout mouse," engineered not to express an endogenous gene, which is replaced with a gene expressing a hydrolase, or, a fusion protein comprising a hydrolase as provided herein. As noted above, functional knockouts can also be generated using antisense sequences as provided herein, e.g., double-stranded RNAi molecules.

Transgenic Plants and Seeds

In certain embodiments, provided herein are transgenic plants and seeds comprising a nucleic acid, a polypeptide (e.g., a hydrolase or an antibody as provided herein), an expression cassette or vector or a transfected or transformed cell as provided herein. The transgenic plant can be dicotyledonous (a dicot) or monocotyledonous (a monocot). In one embodiment, provided herein are methods of making and using these transgenic plants and seeds. The transgenic plant or plant cell expressing a polypeptide as provided herein may be constructed in accordance with any method known in the art. See, for example, U.S. Pat. No. 6,309,872.

Nucleic acids and expression constructs as provided herein can be introduced into a plant cell by any means. For example, nucleic acids or expression constructs can be introduced into the genome of a desired plant host, or, the nucleic acids or expression constructs can be episomes. Introduction into the genome of a desired plant can be such that the host's hydrolase production is regulated by endogenous transcriptional or translational control elements. In one aspect, provided herein are "knockout plants" where insertion of gene sequence by, e.g., homologous recombination, has disrupted the expression of the endogenous gene. Means to generate "knockout" plants are well-known in the art, see, e.g., Strepp (1998) Proc Natl. Acad. Sci. USA 95:4368-4373; Miao (1995) Plant J 7:359-365. See discussion on transgenic plants, below.

The nucleic acids as provided herein can be used to confer desired traits on essentially any plant, e.g., on oilseed producing plants, including rice bran, rapeseed (canola), sunflower, olive, palm or soy, and the like, or on glucose or starch-producing plants, such as corn, potato, wheat, rice, barley, and the like. Nucleic acids as provided herein can be used to manipulate metabolic pathways of a plant in order to optimize or alter host's expression of a hydrolase or a substrate or product of a hydrolase, e.g., an oil, a lipid, such as a mono-, di- or tri-acylglyceride and the like. The can change the ratios of lipids, lipid conversion and turnover in a plant. This can facilitate industrial processing of a plant. Alternatively, hydrolases as provided herein can be used in production of a transgenic plant to produce a compound not naturally produced by that plant. This can lower production costs or create a novel product.

In one aspect, the first step in production of a transgenic plant involves making an expression construct for expression in a plant cell. These techniques are well known in the art. They can include selecting and cloning a promoter, a coding sequence for facilitating efficient binding of ribosomes to mRNA and selecting the appropriate gene terminator sequences. One exemplary constitutive promoter is CaMV35S, from the cauliflower mosaic virus, which generally results in a high degree of expression in plants. Other promoters are more specific and respond to cues in the plant's internal or external environment. An exemplary light-inducible promoter is the promoter from the cab gene, encoding the major chlorophyll a/b binding protein.

In one aspect, the nucleic acid is modified to achieve greater expression in a plant cell. For example, a sequence as provided herein is likely to have a higher percentage of A-T nucleotide pairs compared to that seen in a plant, some of which prefer G-C nucleotide pairs. Therefore, A-T nucleotides in the coding sequence can be substituted with G-C nucleotides without significantly changing the amino acid sequence to enhance production of the gene product in plant cells.

Selectable marker gene can be added to the gene construct in order to identify plant cells or tissues that have successfully integrated the transgene. This may be necessary because achieving incorporation and expression of genes in plant cells is a rare event, occurring in just a few percent of the targeted tissues or cells. Selectable marker genes encode proteins that provide resistance to agents that are normally toxic to plants, such as antibiotics or herbicides. Only plant cells that have integrated the selectable marker gene will survive when grown on a medium containing the appropriate antibiotic or herbicide. As for other inserted genes, marker genes also require promoter and termination sequences for proper function.

In one aspect, making transgenic plants or seeds comprises incorporating sequences as provided herein and, optionally, marker genes into a target expression construct (e.g., a plasmid, a phage), along with positioning of the promoter and the terminator sequences. This can involve transferring the modified gene into the plant through a suitable method. For example, a construct may be introduced directly into the genomic DNA of the plant cell using techniques such as electroporation and microinjection of plant cell protoplasts, or the constructs can be introduced directly to plant tissue using ballistic methods, such as DNA particle bombardment. For example, see, e.g., Christou (1997) Plant Mol. Biol. 35:197-203; Pawlowski (1996) Mol. Biotechnol. 6:17-30; Klein (1987) Nature 327:70-73; Takumi (1997) Genes Genet. Syst. 72:63-69, discussing use of particle bombardment to introduce transgenes into wheat; and Adam (1997) supra, for use of particle bombardment to introduce YACs into plant cells. For example, Rinehart (1997) supra, used particle bombardment to generate transgenic cotton plants. Apparatus for accelerating particles is described U.S. Pat. No. 5,015,580; and, the commercially available BioRad (Biolistics) PDS-2000 particle acceleration instrument; see also, John, U.S. Pat. No. 5,608,148; and Ellis, U.S. Pat. No. 5,681,730, describing particle-mediated transformation of gymnosperms.

In one aspect, protoplasts can be immobilized and injected with a nucleic acids, e.g., an expression construct. Although plant regeneration from protoplasts is not easy with cereals, plant regeneration is possible in legumes using somatic embryogenesis from protoplast derived callus. Organized tissues can be transformed with naked DNA using gene gun technique, where DNA is coated on tungsten microprojectiles, shot 1/100th the size of cells, which carry the DNA deep into cells and organelles. Transformed tissue is then induced to regenerate, usually by somatic embryogenesis. This technique has been successful in several cereal species including maize and rice.

Nucleic acids, e.g., expression constructs, can also be introduced in to plant cells using recombinant viruses. Plant cells can be transformed using viral vectors, such as, e.g., tobacco mosaic virus derived vectors (Rouwendal (1997) Plant Mol. Biol. 33:989-999), see Porta (1996) "Use of viral replicons for the expression of genes in plants," Mol. Biotechnol. 5:209-221.

Alternatively, nucleic acids, e.g., an expression construct, can be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, e.g., Horsch (1984) Science 233:496-498; Fraley (1983) *Proc. Natl. Acad. Sci. USA* 80:4803 (1983); *Gene Transfer to Plants*, Potrykus, ed. (Springer-Verlag, Berlin 1995). The DNA in an *A. tumefaciens* cell is contained in the bacterial chromosome as well as in another structure known as a Ti (tumor-inducing) plasmid. The Ti plasmid contains a stretch of DNA termed T-DNA (~20 kb long) that is transferred to the plant cell in the infection process and a series of vir (virulence) genes that direct the infection process. *A. tumefaciens* can only infect a plant through wounds: when a plant root or stem is wounded it gives off certain chemical signals, in response to which, the vir genes of *A. tumefaciens* become activated and direct a series of events necessary for the transfer of the T-DNA from the Ti plasmid to the plant's chromosome. The T-DNA then enters the plant cell through the wound. One speculation is that the T-DNA waits until the plant DNA is being replicated or transcribed, then inserts itself into the exposed plant DNA. In order to use *A. tumefaciens* as a transgene vector, the tumor-inducing section of T-DNA have to be removed, while retaining the T-DNA border regions and the vir genes. The transgene is then inserted between the T-DNA border regions, where it is transferred to the plant cell and becomes integrated into the plant's chromosomes.

In certain embodiments, provided herein are methods for the transformation of monocotyledonous plants using the nucleic acids as provided herein, including important cereals, see Hiei (1997) Plant Mol. Biol. 35:205-218. See also, e.g., Horsch, Science (1984) 233:496; Fraley (1983) Proc. Natl. Acad. Sci USA 80:4803; Thykjaer (1997) supra; Park (1996)

Plant Mol. Biol. 32:1135-1148, discussing T-DNA integration into genomic DNA. See also D'Halluin, U.S. Pat. No. 5,712,135, describing a process for the stable integration of a DNA comprising a gene that is functional in a cell of a cereal, or other monocotyledonous plant.

In one aspect, the third step can involve selection and regeneration of whole plants capable of transmitting the incorporated target gene to the next generation. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., *Protoplasts Isolation and Culture, Handbook of Plant Cell Culture*, pp. 124-176, MacMillilan Publishing Company, New York, 1983; and Binding, *Regeneration of Plants, Plant Protoplasts*, pp. 21-73, CRC Press, Boca Raton, 1985. Regeneration can also be obtained from plant callus, explants, organs, or parts thereof. Such regeneration techniques are described generally in Klee (1987) Ann. Rev. of Plant Phys. 38:467-486. To obtain whole plants from transgenic tissues such as immature embryos, they can be grown under controlled environmental conditions in a series of media containing nutrients and hormones, a process known as tissue culture. Once whole plants are generated and produce seed, evaluation of the progeny begins.

After the expression cassette is stably incorporated in transgenic plants, it can be introduced into other plants by sexual crossing. Any of a number of standard breeding techniques can be used, depending upon the species to be crossed. Since transgenic expression of the nucleic acids as provided herein leads to phenotypic changes, plants comprising the recombinant nucleic acids as provided herein can be sexually crossed with a second plant to obtain a final product. Thus, the seed as provided herein can be derived from a cross between two transgenic plants as provided herein, or a cross between a plant as provided herein and another plant. The desired effects (e.g., expression of the polypeptides as provided herein to produce a plant with altered, increased and/or decreased lipid or oil content) can be enhanced when both parental plants express the polypeptides as provided herein. The desired effects can be passed to future plant generations by standard propagation means.

The nucleic acids and polypeptides as provided herein are expressed in or inserted in any plant or seed. Transgenic plants as provided herein can be dicotyledonous or monocotyledonous. Examples of monocot transgenic plants as provided herein are grasses, such as meadow grass (blue grass, *Poa*), forage grass such as festuca, lolium, temperate grass, such as *Agrostis*, and cereals, e.g., wheat, oats, rye, barley, rice, sorghum, and maize (corn). Examples of dicot transgenic plants as provided herein are tobacco, legumes, such as lupins, potato, sugar beet, pea, bean and soybean, and cruciferous plants (family Brassicaceae), such as cauliflower, rape seed, and the closely related model organism *Arabidopsis thaliana*. Thus, the transgenic plants and seeds as provided herein include a broad range of plants, including, but not limited to, species from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannisetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna*, and *Zea*.

In alternative embodiments, the nucleic acids as provided herein are expressed in plants which contain fiber cells, including, e.g., cotton, silk cotton tree (Kapok, Ceiba pentandra), desert willow, creosote bush, winterfat, balsa, ramie, kenaf, hemp, roselle, jute, sisal abaca and flax. In alternative embodiments, the transgenic plants as provided herein can be members of the genus *Gossypium*, including members of any *Gossypium* species, such as *G. arboreum; G. herbaceum, G. barbadense*, and *G. hirsutum*.

In certain embodiments, the transgenic plants herein can be used for producing large amounts of the polypeptides (e.g., antibodies, hydrolases) as provided herein. For example, see Palmgren (1997) Trends Genet. 13:348; Chong (1997) Transgenic Res. 6:289-296 (producing human milk protein beta-casein in transgenic potato plants using an auxin-inducible, bidirectional mannopine synthase (mas1',2') promoter with *Agrobacterium tumefaciens*-mediated leaf disc transformation methods).

Using known procedures, one of skill can screen for plants as provided herein by detecting the increase or decrease of transgene mRNA or protein in transgenic plants. Means for detecting and quantitation of mRNAs or proteins are well known in the art.

Provided herein are fatty acids or fatty acid derivatives from transgenic plants as provided herein, e.g., transgenic oleaginous plants. In one aspect, transgenic oleaginous plants comprising at least one hydrolase as provided herein are produced. In one aspect, the transgenic plant comprises a hydrolase gene operably linked to a promoter, permitting an expression of the gene either in cellular, extracellular or tissue compartments other than those in which the plant lipids accumulate, or permitting exogenous induction of the hydrolase. In one aspect, seeds and/or fruits containing the lipids of the plants are collected, the seeds and/or fruits are crushed (if necessary after hydrolase (e.g., lipase, saturase, palmitase and/or stearatase) gene-induction treatment) so as to bring into contact the lipids and hydrolase as provided herein contained in the seeds and/or fruits. The mixture can be allowed to incubate to allow enzymatic hydrolysis of the lipids of the ground material by catalytic action of the lipase as provided herein contained in the crushed material. In one aspect, the fatty acids formed by the hydrolysis are extracted and/or are converted in order to obtain the desired fatty acid derivatives.

This enzymatic hydrolysis process as provided herein uses mild operating conditions and can be small-scale and use inexpensive installations. In this aspect the plant as provided herein is induced to produce the hydrolase for transformation of plant lipids. Using this strategy, the enzyme is prevented from coming into contact with stored plant lipids so as to avoid any risk of premature hydrolysis ("self-degradation of the plant") before harvesting. The crushing and incubating units can be light and small-scale; many are known in the agricultural industry and can be carried out at the sites where the plants are harvested.

In one aspect, transgenic plants as provided herein are produced by transformation of natural oleaginous plants. The genetically transformed plants as provided herein are then reproduced sexually so as to produce transgenic seeds as provided herein. These seeds can be used to obtain transgenic plant progeny.

In one aspect, the hydrolase gene is operably linked to an inducible promoter to prevent any premature contact of hydrolase and plant lipid. This promoter can direct the expression of the gene in compartments other than those where the lipids accumulate or the promoter can initiate the expression of the hydrolase at a desired time by an exogenous induction.

Polypeptides and Peptides

In certain embodiments, provided herein are isolated, synthetic or recombinant polypeptides having a sequence identity (e.g., at least 50% sequence identity) to SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20 or SEQ ID NO:2 having one, two, three, four, five, six, seven, eight or more (several) or all the amino acid variations described in Table 3 or Table 4, or the equivalent thereof. In certain embodiments, provided herein are nucleic acids encoding polypeptides having a sequence as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20 or SEQ ID NO:2 having one, two, three, four, five, six, seven, eight or more (several) or all the amino acid variations described in Table 3 or Table 4, or the equivalent thereof.

The sequence identity can be over the full length of the polypeptide, or, the identity can be over a region of at least about 50, 60, 70, 80, 90, 100, 150, 200, 250, 300, 350, 400, 450, 500, 550, 600, 650, 700 or more residues. Polypeptides as provided herein can also be shorter than the full length of exemplary polypeptides. In one aspect provided herein are polypeptides comprising only a subsequence of a sequence as provided herein, exemplary subsequences can be about 5, 10, 15, 20, 25, 30, 35, 40, 45, 50, 55, 60, 65, 70, 75, 80, 85, 90, 100, 125, 150, 175, 200, 250, 300, 350, 400, 450, 500, 550, 600, 650, 700, or more residues. In alternative aspects, polypeptides (peptides, fragments) can range in size between about 5 and the full length of a polypeptide, e.g., an enzyme as provided herein; exemplary sizes being of about 5, 10, 15, 20, 25, 30, 35, 40, 45, 50, 55, 60, 65, 70, 75, 80, 85, 90, 100, 125, 150, 175, 200, 250, 300, 350, 400, 450, 500, 550, 600, 650, 700, or more residues, e.g., contiguous residues of an exemplary hydrolase as provided herein. Peptides as provided herein can be useful as, e.g., labeling probes, antigens, toleragens, motifs, hydrolase active sites.

Polypeptides as provided herein also include antibodies capable of binding to a hydrolase as provided herein.

Polypeptides as provided herein also include amino acid sequences that are "substantially identical" to sequences as provided herein, including sequences that differ from a reference sequence by one or more conservative or non-conservative amino acid substitutions, deletions, or insertions, particularly when such a substitution occurs at a site that is not the active site of the molecule, and provided that the polypeptide essentially retains its functional properties. A conservative amino acid substitution, for example, substitutes one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid or glutamine for asparagine). One or more amino acids can be deleted, for example, from a hydrolase, resulting in modification of the structure of the polypeptide, without significantly altering its biological activity. For example, amino- or carboxyl-terminal amino acids that are not required for hydrolase activity can be removed.

"Amino acid" or "amino acid sequence" can include an oligopeptide, peptide, polypeptide, or protein sequence, or to a fragment, portion, or subunit of any of these, and to naturally occurring or synthetic molecules.

The terms "polypeptide" and "protein" can include amino acids joined to each other by peptide bonds or modified peptide bonds, i.e., peptide isosteres, and may contain modified amino acids other than the 20 gene-encoded amino acids. The term "polypeptide" also includes peptides and polypeptide fragments, motifs and the like. The term also includes glycosylated polypeptides. The peptides and polypeptides as provided herein also include all "mimetic" and "peptidomimetic" forms, as described in further detail, below.

The polypeptides as provided herein include hydrolases in an active or inactive form. For example, the polypeptides as provided herein include proproteins before "maturation" or processing of prepro sequences, e.g., by a proprotein-processing enzyme, such as a proprotein convertase to generate an "active" mature protein. The polypeptides as provided herein include hydrolases inactive for other reasons, e.g., before "activation" by a post-translational processing event, e.g., an endo- or exo-peptidase or proteinase action, a phosphorylation event, an amidation, a glycosylation or a sulfation, a dimerization event, and the like. Methods for identifying "prepro" domain sequences and signal sequences are well known in the art, see, e.g., Van de Ven (1993) Crit. Rev. Oncog. 4(2):115-136. For example, to identify a prepro sequence, the protein is purified from the extracellular space and the N-terminal protein sequence is determined and compared to the unprocessed form.

The polypeptides as provided herein include all active forms, including active subsequences, e.g., catalytic domains or active sites, of an enzyme as provided herein. In certain embodiments, provided herein are catalytic domains or active sites as set forth below. In other embodiments, provided herein are peptides or polypeptides comprising or consisting of an active site domain as predicted through use of a database such as Pfam (which is a large collection of multiple sequence alignments and hidden Markov models covering many common protein families, The Pfam protein families database, A. Bateman, E. Birney, L. Cerruti, R. Durbin, L. Etwiller, S. R. Eddy, S. Griffiths-Jones, K. L. Howe, M. Marshall, and E. L. L. Sonnhammer, Nucleic Acids Research, 30(1):276-280, 2002) or equivalent.

In certain embodiments, provided herein are polypeptides with or without a signal sequence and/or a prepro sequence. In one embodiment, provided herein are polypeptides with heterologous signal sequences and/or prepro sequences. The prepro sequence (including a sequence as provided herein used as a heterologous prepro domain) can be located on the amino terminal or the carboxy terminal end of the protein. In another embodiment, provided herein are isolated, synthetic or recombinant signal sequences, prepro sequences and catalytic domains (e.g., "active sites") comprising or consisting of sequences as provided herein. The signal sequence, prepro domains and/or catalytic domain as provided herein can be part of a fusion protein, e.g., as a heterologous domain in a chimeric protein. In certain embodiments, provided herein are nucleic acids encoding these catalytic domains (CDs), prepro domains and signal sequences (SPs, e.g., a peptide having a sequence comprising/consisting of amino terminal residues of a polypeptide as provided herein). In certain embodiments, provided herein are signal sequences comprising a peptide comprising/consisting of a sequence as set forth in residues 1 to 12, 1 to 13, 1 to 14, 1 to 15, 1 to 16, 1 to 17, 1 to 18, 1 to 19, 1 to 20, 1 to 21, 1 to 22, 1 to 23, 1 to 24, 1 to 25, 1 to 26, 1 to 27, 1 to 28, 1 to 28, 1 to 30, 1 to 31, 1 to 32, 1 to 33, 1 to 34, 1 to 35, 1 to 36, 1 to 37, 1 to 38, 1 to 39, 1 to 40, 1 to 41, 1 to 42, 1 to 43, 1 to 44, 1 to 45, 1 to 46, 1 to 47, 1 to 48, 1 to 49 or 1 to 50, of a polypeptide as provided herein.

Polypeptides and peptides as provided herein can be isolated from natural sources, be synthetic, or be recombinantly generated polypeptides. Peptides and proteins can be recombinantly expressed in vitro or in vivo. The peptides and polypeptides as provided herein can be made and isolated using any method known in the art. Polypeptide and peptides as provided herein can also be synthesized, whole or in part, using chemical methods well known in the art. See e.g., Caruthers (1980) Nucleic Acids Res. Symp. Ser. 215-223; Horn (1980) Nucleic Acids Res. Symp. Ser. 225-232; Banga, A. K., Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge (1995) Science 269:202; Merrifield (1997) Methods Enzymol. 289:3-13) and automated synthesis may be achieved, e.g., using the ABI 431A Peptide Synthesizer (Perkin Elmer) in accordance with the instructions provided by the manufacturer.

The peptides and polypeptides as provided herein can also be glycosylated. The glycosylation can be added post-translationally either chemically or by cellular biosynthetic mechanisms, wherein the later incorporates the use of known glycosylation motifs, which can be native to the sequence or can be added as a peptide or added in the nucleic acid coding sequence. The glycosylation can be O-linked or N-linked.

"Recombinant" polypeptides or proteins refer to polypeptides or proteins produced by recombinant DNA techniques; i.e., produced from cells transformed by an exogenous DNA construct encoding the desired polypeptide or protein. "Synthetic" nucleic acids (including oligonucleotides), polypeptides or proteins as provided herein include those prepared by any chemical synthesis, e.g., as described, below.

"Fragments" as used herein are a portion of a naturally occurring protein which can exist in at least two different conformations. Fragments can have the same or substantially the same amino acid sequence as the naturally occurring protein. "Enzymatically active fragments" as used herein are a portion of an amino acid sequence (encoding a protein) which retains at least one functional activity of the protein to which it is related. "Substantially the same" means that an amino acid sequence is largely, but not entirely, the same, but retains at least one functional activity of the sequence to which it is related. In general two amino acid sequences are "substantially the same" or "substantially homologous" if they are at least about 85% identical. Fragments which have different three dimensional structures as the naturally occurring protein are also included. An example of this, is a "proform" molecule, such as a low activity proprotein that can be modified by cleavage to produce a mature enzyme with significantly higher activity.

The peptides and polypeptides as provided herein, as defined above, include all "mimetic" and "peptidomimetic" forms. The terms "mimetic" and "peptidomimetic" refer to a synthetic chemical compound which has substantially the same structural and/or functional characteristics of the polypeptides as provided herein. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions, as long as such substitutions also do not substantially alter the mimetic's structure and/or activity. As with polypeptides as provided herein which are conservative variants, routine experimentation will determine whether a mimetic is within the scope as provided herein, i.e., that its structure and/or function is not substantially altered. Thus, in one aspect, a mimetic composition is within the scope as provided herein if it has a hydrolase activity.

Polypeptide mimetic compositions as provided herein can contain any combination of non-natural structural components. In alternative aspect, mimetic compositions as provided herein include one or all of the following three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. For example, a polypeptide as provided herein can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in Chemistry and Biochemistry of Amino Acids, Peptides and Proteins, Vol. 7, pp 267-357, "Peptide Backbone Modifications," Marcell Dekker, NY).

A polypeptide as provided herein can also be characterized as a mimetic by containing all or some non-natural residues in place of naturally occurring amino acid residues. Non-natural residues are well described in the scientific and patent literature; a few exemplary non-natural compositions useful as mimetics of natural amino acid residues and guidelines are described below. Mimetics of aromatic amino acids can be generated by replacing by, e.g., D- or L-naphylalanine; D- or L-phenylglycine; D- or L-2 thieneylalanine; D- or L-1, -2,3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluoro-phenylalanine; D- or L-p-biphenylphenylalanine; D- or L-p-methoxy-biphenylphenylalanine; D- or L-2-indole(alkyl)alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

Mimetics of acidic amino acids can be generated by substitution by, e.g., non-carboxylate amino acids while maintaining a negative charge; (phosphono)alanine; sulfated threonine. Carboxyl side groups (e.g., aspartyl or glutamyl) can also be selectively modified by reaction with carbodiimides (R'—N=C=N—R') such as, e.g., 1-cyclohexyl-3(2-morpholinyl-(4-ethyl) carbodiimide or 1-ethyl-3(4-azonia-4,4-dimetholpentyl)carbodiimide. Aspartyl or glutamyl can also be converted to asparaginyl and glutaminyl residues by reaction with ammonium ions. Mimetics of basic amino acids can be generated by substitution with, e.g., (in addition to lysine and arginine) the amino acids ornithine, citrulline, or (guanidino)-acetic acid, or (guanidino)alkyl-acetic acid, where alkyl is defined above. Nitrile derivative (e.g., containing the CN-moiety in place of COOH) can be substituted for asparagine or glutamine. Asparaginyl and glutaminyl residues can be deaminated to the corresponding aspartyl or glutamyl residues. Arginine residue mimetics can be generated by reacting arginyl with, e.g., one or more conventional reagents, including, e.g., phenylglyoxal, 2,3-butanedione, 1,2-cyclo-hexanedione, or ninhydrin, alternatively under alkaline conditions. Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively. Cysteine residue mimetics can be generated by reacting cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl) propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole. Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitro-benzenesulfonic acid, O-methylisourea, 2,4, pentanedione, and transamidase-catalyzed reactions with glyoxylate. Mimetics of methionine can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3,-dimethylproline. Histidine residue mimetics can be generated by reacting histidyl with, e.g., diethylprocarbonate or para-bromophenacyl bromide. Other mimetics include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

A residue, e.g., an amino acid, of a polypeptide as provided herein can also be replaced by an amino acid (or peptidomimetic residue) of the opposite chirality. Thus, any amino acid naturally occurring in the L-configuration (which can also be referred to as the R or S, depending upon the structure of the chemical entity) can be replaced with the amino acid of the same chemical structural type or a peptidomimetic, but of the opposite chirality, referred to as the D-amino acid, but also can be referred to as the R- or S-form.

In certain embodiments, provided herein are methods for modifying the polypeptides as provided herein by either natural processes, such as post-translational processing (e.g., phosphorylation, acylation, etc), or by chemical modification techniques, and the resulting modified polypeptides. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pegylation, proteolytic processing, phosphorylation, prenylation, racemization, selenoylation, sulfation, and transfer-RNA mediated addition of amino acids to protein such as arginylation. See, e.g., Creighton, T. E., Proteins—Structure and Molecular Properties 2nd Ed., W.H. Freeman and Company, New York (1993); Posttranslational Covalent Modification of Proteins, B. C. Johnson, Ed., Academic Press, New York, pp. 1-12 (1983).

Solid-phase chemical peptide synthesis methods can also be used to synthesize the polypeptides, or fragments thereof, as provided herein. Such method have been known in the art since the early 1960's (Merrifield, R. B., J. Am. Chem. Soc., 85:2149-2154, 1963) (See also Stewart, J. M. and Young, J. D. Solid Phase Peptide Synthesis, 2nd Ed., Pierce Chemical Co., Rockford, Ill., pp. 11-12)) and have recently been employed in commercially available laboratory peptide design and synthesis kits (Cambridge Research Biochemicals). Such commercially available laboratory kits have generally utilized the teachings of H. M. Geysen et al, Proc. Natl. Acad. Sci., USA, 81:3998 (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431A™ automated peptide synthesizer. Such equipment provides ready access to the peptides as provided herein, either by direct synthesis or by synthesis of a series of fragments that can be coupled using other known techniques.

Enzymes

In certain embodiments, provided herein are hydrolases, e.g. lipases, saturases, palmitases and/or stearatases, e.g., proteins comprising at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity, to an exemplary polypeptide as provided herein (e.g., SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, or SEQ ID NO:20 or SEQ ID NO:2 having one, two, three, four, five, six, seven, eight or more (several) or all the amino acid variations described in Table 3 or Table 4, or the equivalent thereof, antibodies that bind them, and methods for making and using them. The polypeptides as provided herein can have any hydrolase activity, e.g., lipase, saturase, palmitase and/or stearatase activity. In alternative aspects, an activity of an enzyme as provided herein comprises hydrolysis or synthesis of lipids or oils. The hydrolases as provided herein can modify oils by hydrolysis, acidolysis, alcoholysis, glycerolysis, esterification, transesterification and/or interesterification, including "forced migration" reactions.

In alternative aspects, the hydrolases as provided herein can have modified or new activities as compared to the exemplary hydrolases or the activities described herein. Provided herein are hydrolases with and without signal sequences and the signal sequences themselves. Provided herein are immobilized hydrolases, anti-hydrolase antibodies and fragments thereof. Provided herein are proteins for inhibiting hydrolase activity, e.g., antibodies that bind to the hydrolase active site. Provided herein are homodimers and heterocomplexes, e.g., fusion proteins, heterodimers, etc., comprising the hydrolases as provided herein. Provided herein are hydrolases having activity over a broad range of high and low temperatures and pH's (e.g., acidic and basic aqueous conditions).

In one aspect, one or more hydrolases (e.g., lipases, saturases, palmitases and/or stearatases) as provided herein is used for the biocatalytic synthesis of structured lipids, i.e., lipids that contain a defined set of fatty acids distributed in a defined manner on the glycerol backbone, including cocoa butter alternatives, poly-unsaturated fatty acids (PUFAs), 1,3-diacyl glycerides (DAGs), 2-monoacylglycerides (MAGs) and triacylglycerides (TAGs).

Provided herein are methods of generating enzymes having altered (higher or lower) $K_{cat}/K_m$. In one aspect, site-directed mutagenesis is used to create additional hydrolase enzymes with alternative substrate specificities. This can be done, for example, by redesigning the substrate binding region or the active site of the enzyme. In one aspect, hydrolases as provided herein are more stable at high temperatures, such as 80° C. to 85° C. to 90° C. to 95° C., as compared to hydrolases from conventional or moderate organisms.

Various proteins as provided herein have a hydrolase activity, e.g., lipase, saturase, palmitase and/or stearatase activity, under various conditions. Provided herein are methods of making hydrolases with different catalytic efficiency and stabilities towards temperature, oxidizing agents and pH conditions. These methods can use, e.g., the techniques of site-directed mutagenesis and/or random mutagenesis. In one aspect, directed evolution can be used to produce hydrolases with alternative specificities and stability.

The proteins as provided herein are used in methods that can identify hydrolase modulators, e.g., activators or inhibitors. Briefly, test samples (e.g., compounds, such as members of peptide or combinatorial libraries, broths, extracts, and the like) are added to hydrolase assays to determine their ability to modulate, e.g., inhibit or activate, substrate cleavage. These inhibitors can be used in industry and research to reduce or prevent undesired isomerization. Modulators found using the methods as provided herein can be used to alter (e.g., decrease or increase) the spectrum of activity of a hydrolase.

In one aspect, provided herein are methods of discovering hydrolases using the nucleic acids, polypeptides and antibodies as provided herein. In one aspect, lambda phage libraries are screened for expression-based discovery of hydrolases. Provided herein are lambda phage libraries for use in screening to allow detection of toxic clones; improved access to substrate; reduced need for engineering a host, by-passing the potential for any bias resulting from mass excision of the library; and, faster growth at low clone densities. Screening of lambda phage libraries can be in liquid phase or in solid phase. Provided herein are methods for screening in liquid phase. This can give a greater flexibility in assay conditions; additional substrate flexibility; higher sensitivity for weak clones; and ease of automation over solid phase screening.

In other embodiments, provided herein are screening methods using the proteins and nucleic acids as provided herein involving robotic automation. This enables the execution of many thousands of biocatalytic reactions and screening assays in a short period of time, e.g., per day, as well as ensuring a high level of accuracy and reproducibility (see discussion of arrays, below). As a result, a library of derivative compounds can be produced in a matter of weeks.

In certain embodiments, provided herein are hydrolase enzymes which are non-naturally occurring hydrolases having a different hydrolase activity, stability, substrate specificity, pH profile and/or performance characteristic as compared to the non-naturally occurring hydrolase. These hydrolases have an amino acid sequence not found in nature. They can be derived by substitution of a plurality of amino acid residues of a precursor hydrolase with different amino acids. The precursor hydrolase may be a naturally-occurring hydrolase or a recombinant hydrolase. In one aspect, the hydrolase variants encompass the substitution of any of the naturally occurring L-amino acids at the designated amino acid residue positions.

Hydrolase Signal Sequences, Prepro and Catalytic Domains

In certain embodiments, provided herein are signal sequences (e.g., signal peptides (SPs)), prepro domains and catalytic domains (CDs). The SPs, prepro domains and/or CDs as provided herein can be isolated, synthetic or recombinant peptides or can be part of a fusion protein, e.g., as a heterologous domain in a chimeric protein. In certain embodiments, provided herein are nucleic acids encoding these catalytic domains (CDs), prepro domains and signal sequences (SPs, e.g., a peptide having a sequence comprising/consisting of amino terminal residues of a polypeptide as provided herein). In certain embodiments, provided herein are signal sequences comprising a peptide comprising/consisting of a sequence as set forth in residues 1 to 12, 1 to 13, 1 to 14, 1 to 15, 1 to 16, 1 to 17, 1 to 18, 1 to 19, 1 to 20, 1 to 21, 1 to 22, 1 to 23, 1 to 24, 1 to 25, 1 to 26, 1 to 27, 1 to 28, 1 to 28, 1 to 30, 1 to 31, 1 to 32, 1 to 33, 1 to 34, 1 to 35, 1 to 36, 1 to 37, 1 to 38, 1 to 39, 1 to 40, 1 to 41, 1 to 42, 1 to 43, 1 to 44 (or a longer peptide) of a polypeptide as provided herein. In one embodiment, provided herein are isolated, synthetic or recombinant signal sequences comprising/consisting of a signal sequence as provided herein derived from another enzyme as provided herein, or another type of enzyme or polypeptide.

The hydrolase signal sequences (SPs), CDs, and/or prepro sequences as provided herein can be isolated peptides, or, sequences joined to another hydrolase or a non-hydrolase polypeptide, e.g., as a fusion (chimeric) protein. In certain embodiments, provided herein are polypeptides comprising hydrolase signal sequences as provided herein. In one aspect, polypeptides comprising hydrolase signal sequences SPs, CDs, and/or prepro as provided herein comprise sequences heterologous to hydrolases as provided herein (e.g., a fusion protein comprising an SP, CD, and/or prepro as provided herein and sequences from another hydrolase or a non-hydrolase protein). Provided herein are hydrolases as provided herein with heterologous SPs, CDs, and/or prepro sequences, e.g., sequences with a yeast signal sequence. A hydrolase as provided herein can comprise a heterologous SP and/or prepro in a vector, e.g., a pPIC series vector (Invitrogen, Carlsbad, Calif.).

In one aspect, SPs, CDs, and/or prepro sequences as provided herein are identified following identification of novel hydrolase polypeptides. The pathways by which proteins are sorted and transported to their proper cellular location are often referred to as protein targeting pathways. One of the most important elements in all of these targeting systems is a short amino acid sequence at the amino terminus of a newly synthesized polypeptide called the signal sequence. This signal sequence directs a protein to its appropriate location in the cell and is removed during transport or when the protein reaches its final destination. Most lysosomal, membrane, or secreted proteins have an amino-terminal signal sequence that marks them for translocation into the lumen of the endoplasmic reticulum. The signal sequences can vary in length from 13 to 45 or more amino acid residues. Various methods of recognition of signal sequences are known to those of skill in the art. For example, in one aspect, novel hydrolase signal peptides are identified by a method referred to as SignalP. SignalP uses a combined neural network which recognizes both signal peptides and their cleavage sites. (Nielsen, et al., "Identification of prokaryotic and eukaryotic signal peptides and prediction of their cleavage sites." Protein Engineering, vol. 10, no. 1, p. 1-6 (1997).

It should be understood that in some aspects hydrolases as provided herein may not have SPs and/or prepro sequences, and/or catalytic domains (CDs). In one aspect, provided herein are polypeptides (e.g., hydrolases) lacking all or part of an SP, a CD and/or a prepro domain. In another aspect, provided herein are nucleic acids encoding a signal sequence (SP), a CD, and/or prepro from one hydrolase operably linked to a nucleic acid sequence of a different hydrolase or, optionally, a signal sequence (SPs) and/or prepro domain from a non-hydrolase protein may be desired.

In certain embodiments, provided herein are isolated, synthetic or recombinant polypeptides comprising signal sequences (SPs), prepro domain and/or catalytic domains (CDs) as provided herein and heterologous sequences. The heterologous sequences are sequences not naturally associated (e.g., to a hydrolase) with an SP, prepro domain and/or CD. The sequence to which the SP, prepro domain and/or CD are not naturally associated can be on the SP's, prepro domain and/or CD's amino terminal end, carboxy terminal end, and/or on both ends of the SP and/or CD. In certain embodiments, provided herein are isolated, synthetic or recombinant polypeptides comprising (or consisting of) a polypeptide comprising a signal sequence (SP), prepro domain and/or catalytic domain (CD) as provided herein with the proviso that it is not associated with any sequence to which it is naturally associated (e.g., hydrolase sequence). Provided herein are isolated or recombinant nucleic acids encoding these polypeptides. Thus, in one aspect, the isolated, synthetic or recombinant nucleic acid as provided herein comprises coding sequence for a signal sequence (SP), prepro domain and/or catalytic domain (CD) as provided herein and a heterologous sequence (i.e., a sequence not naturally associated with the a signal sequence (SP), prepro domain and/or catalytic domain (CD) as provided herein). The heterologous sequence can be on the 3' terminal end, 5' terminal end, and/or on both ends of the SP, prepro domain and/or CD coding sequence.

In certain embodiments, provided herein are fusion of N-terminal or C-terminal subsequences of enzymes as provided herein (e.g., signal sequences, prepro sequences) with other polypeptides, active proteins or protein fragments. The production of an enzyme as provided herein (e.g., a hydrolase, e.g., a lipase, saturase, palmitase and/or stearatase) may also be accomplished by expressing the enzyme as an inactive fusion protein that is later activated by a proteolytic cleavage event (using either an endogenous or exogenous protease activity, e.g. trypsin) that results in the separation of the fusion protein partner and the mature enzyme, e.g., hydrolase as provided herein. In one aspect, the fusion protein as provided herein is expressed from a hybrid nucleotide construct that encodes a single open reading frame containing the following elements: the nucleotide sequence for the fusion protein, a linker sequence (defined as a nucleotide sequence that encodes a flexible amino acid sequence that joins two less flexible protein domains), protease cleavage recognition site, and the mature enzyme (e.g., any enzyme as provided herein, e.g., a hydrolase) sequence. In alternative aspects, the fusion protein can comprise a pectate lyase sequence, a xylanase sequence, a phosphatidic acid phosphatase sequence, or another sequence, e.g., a sequence that has previously been shown to be over-expressed in a host system of interest. Any host system can be used (see discussion, above), for example, *E. coli* or *Pichia pastoris*. The arrangement of the nucleotide sequences in the chimeric nucleotide construction can be determined based on the protein expression levels achieved with each fusion construct. Proceeding from the 5' end of the nucleotide construct to the 3' prime end of the construct, in one aspect, the nucleotide sequences is assembled as follows: Signal sequence/fusion protein/linker sequence/protease cleavage recognition site/mature enzyme (e.g., any enzyme as provided herein, e.g., a hydrolase) or Signal sequence/pro sequence/mature enzyme/linker sequence/fusion protein. The expression of enzyme (e.g., any enzyme as provided herein, e.g., a hydrolase) as an inactive fusion protein may improve the overall expression of the enzyme's sequence, may reduce any potential toxicity associated with the overproduction of active enzyme and/or may increase the shelf life of enzyme prior to use because enzyme would be inactive until the fusion protein e.g. pectate lyase is separated from the enzyme, e.g., hydrolase as provided herein.

In one embodiment, provided herein are specific formulations for the activation of a hydrolase as provided herein expressed as a fusion protein. In one aspect, the activation of the hydrolase activity initially expressed as an inactive fusion protein is accomplished using a proteolytic activity or potentially a proteolytic activity in combination with an amino-terminal or carboxyl-terminal peptidase (the peptidase can be an enzyme as provided herein, or, another enzyme). This activation event may be accomplished in a variety of ways and at a variety of points in the manufacturing/storage process prior to application in oil degumming. Exemplary processes as provided herein include: cleavage by an endogenous activity expressed by the manufacturing host upon secretion of the fusion construct into the fermentation media; cleavage by an endogenous protease activity that is activated or comes in contact with intracellularly expressed fusion construct upon rupture of the host cells; passage of the crude or purified fusion construct over a column of immobilized protease activity to accomplish cleavage and enzyme (e.g., hydrolase as provided herein, e.g., e.g., a lipase, saturase, palmitase and/or stearatase) activation prior to enzyme formulation; treatment of the crude or purified fusion construct with a soluble source of proteolytic activity; activation of a hydrolase (e.g., a hydrolase as provided herein) at the oil refinery using either a soluble or insoluble source of proteolytic activity immediately prior to use in the process; and/or, activation of the hydrolase (e.g., a lipase, saturase, palmitase and/or stearatase as provided herein) activity by continuously circulating the fusion construct formulation through a column of immobilized protease activity at reduced temperature (for example, any between about 4° C. and 20° C.). This activation event may be accomplished prior to delivery to the site of use or it may occur on-site at the oil refinery.

Glycosylation

The peptides and polypeptides as provided herein (e.g., hydrolases, antibodies) can also be glycosylated, for example, in one aspect, comprising at least one glycosylation site, e.g., an N-linked or O-linked glycosylation. In one aspect, the polypeptide can be glycosylated after being expressed in a *P. pastoris* or a *S. pombe*. The glycosylation can be added post-translationally either chemically or by cellular biosynthetic mechanisms, wherein the later incorporates the use of known glycosylation motifs, which can be native to the sequence or can be added as a peptide or added in the nucleic acid coding sequence.

Hybrid Hydrolases and Peptide Libraries

In certain embodiments, provided herein are hybrid hydrolases (e.g., synthetic proteins) and fusion proteins, including peptide libraries, comprising sequences as provided herein. The peptide libraries as provided herein can be used to isolate peptide modulators (e.g., activators or inhibitors) of targets. The peptide libraries as provided herein can be used to identify formal binding partners of targets, such as ligands, e.g., cytokines, hormones and the like.

In one aspect, the fusion proteins as provided herein (e.g., the peptide moiety) are conformationally stabilized (relative to linear peptides) to allow a higher binding affinity for targets. In another aspect, provided herein are fusions of hydrolases as provided herein and other peptides, including known and random peptides. They can be fused in such a manner that the structure of the enzyme or antibody (e.g., hydrolase) is not significantly perturbed and the peptide is metabolically or structurally conformationally stabilized. This allows the creation of a peptide library that is easily monitored both for its presence within cells and its quantity.

Amino acid sequence variants as provided herein can be characterized by a predetermined nature of the variation, a feature that sets them apart from a naturally occurring form, e.g., an allelic or interspecies variation of a hydrolase sequence. In one aspect, the variants as provided herein exhibit the same qualitative biological activity as the naturally occurring analogue. Alternatively, the variants can be selected for having modified characteristics. In one aspect, while the site or region for introducing an amino acid sequence variation is predetermined, the mutation per se need not be predetermined. For example, in order to optimize the performance of a mutation at a given site, random mutagenesis may be conducted at the target codon or region and the expressed hydrolase variants screened for the optimal combination of desired activity. Techniques for making substitution mutations at predetermined sites in DNA having a known sequence are well known, as discussed herein for example, M13 primer mutagenesis and PCR mutagenesis. Screening of the mutants can be done using assays of proteolytic activities. In alternative aspects, amino acid substitutions can be single residues; insertions can be on the order of from about 1 to 20 amino acids, although considerably larger insertions can be done. Deletions can range from about 1 to about 20, 30, 40, 50, 60, 70 residues or more. To obtain a final derivative with the optimal properties, substitutions, deletions, insertions or any combination thereof may be used. Generally, these changes are done on a few amino acids to minimize the alteration of the molecule. However, larger changes may be tolerated in certain circumstances.

In certain embodiments, provided herein are hydrolases where the structure of the polypeptide backbone, the secondary or the tertiary structure, e.g., an alpha-helical or beta-sheet structure, has been modified. In one aspect, the charge or hydrophobicity has been modified. In one aspect, the bulk of a side chain has been modified. Substantial changes in function or immunological identity are made by selecting substitutions that are less conservative. For example, substitutions can be made which more significantly affect: the structure of the polypeptide backbone in the area of the alteration, for example an alpha-helical or a beta-sheet structure; a charge or a hydrophobic site of the molecule, which can be at an active site; or a side chain. In other embodiments, provided herein are proteins comprising sequence substitutions as provided herein, e.g., where (a) a hydrophilic residues, e.g. seryl or threonyl, are substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine. The variants can exhibit the same qualitative biological activity (i.e. hydrolase activity) although variants can be selected to modify the characteristics of the hydrolases as needed.

In one aspect, hydrolases as provided herein comprise epitopes or purification tags, signal sequences or other fusion sequences, etc. In one aspect, the hydrolases as provided herein can be fused to a random peptide to form a fusion polypeptide. By "fused" or "operably linked" herein it is meant that the random peptide and the hydrolase are linked together, in such a manner as to minimize the disruption to the stability of the hydrolase structure, e.g., it retains hydrolase activity. The fusion polypeptide (or fusion polynucleotide encoding the fusion polypeptide) can comprise further components as well, including multiple peptides at multiple loops.

In one aspect, the peptides (e.g., hydrolase subsequences) and nucleic acids encoding them are randomized, either fully randomized or they are biased in their randomization, e.g. in nucleotide/residue frequency generally or per position. "Randomized" means that each nucleic acid and peptide consists of essentially random nucleotides and amino acids, respectively. In one aspect, the nucleic acids which give rise to the peptides can be chemically synthesized, and thus may incorporate any nucleotide at any position. Thus, when the nucleic acids are expressed to form peptides, any amino acid residue may be incorporated at any position. The synthetic process can be designed to generate randomized nucleic acids, to allow the formation of all or most of the possible combinations over the length of the nucleic acid, thus forming a library of randomized nucleic acids. The library can provide a sufficiently structurally diverse population of randomized expression products to affect a probabilistically sufficient range of cellular responses to provide one or more cells exhibiting a desired response. Provided herein are interaction libraries large enough so that at least one of its members will have a structure that gives it affinity for some molecule, protein, or other factor.

Screening Methodologies and "On-Line" Monitoring Devices

In practicing the methods as provided herein, a variety of apparatus and methodologies can be used to in conjunction with the polypeptides and nucleic acids as provided herein, e.g., to screen polypeptides for hydrolase activity, to screen compounds as potential activators or inhibitors of a hydrolase activity (e.g., for potential drug screening), for antibodies that bind to a polypeptide as provided herein, for nucleic acids that hybridize to a nucleic acid as provided herein, to screen for cells expressing a polypeptide as provided herein and the like. See, e.g., U.S. Pat. No. 6,337,187.

Capillary Arrays

Capillary arrays, such as the GIGAMATRIX™, Diversa Corporation, San Diego, Calif., can be used to in the methods as provided herein. Nucleic acids or polypeptides as provided herein can be immobilized to or applied to an array, including capillary arrays. Arrays can be used to screen for or monitor libraries of compositions (e.g., small molecules, antibodies, nucleic acids, etc.) for their ability to bind to or modulate the activity of a nucleic acid or a polypeptide as provided herein. Capillary arrays provide another system for holding and screening samples. For example, a sample screening apparatus can include a plurality of capillaries formed into an array of adjacent capillaries, wherein each capillary comprises at least one wall defining a lumen for retaining a sample. The apparatus can further include interstitial material disposed between adjacent capillaries in the array, and one or more reference indicia formed within of the interstitial material. A capillary for screening a sample, wherein the capillary is adapted for being bound in an array of capillaries, can include a first wall defining a lumen for retaining the sample, and a second wall formed of a filtering material, for filtering excitation energy provided to the lumen to excite the sample.

A polypeptide or nucleic acid, e.g., a ligand or a substrate, can be introduced into a first, component into at least a portion of a capillary of a capillary array. Each capillary of the capillary array can comprise at least one wall defining a lumen for retaining the first component. An air bubble can be introduced into the capillary behind the first component. A second component can be introduced into the capillary, wherein the second component is separated from the first component by the air bubble. A sample of interest can be introduced as a first liquid labeled with a detectable particle into a capillary of a capillary array, wherein each capillary of the capillary array comprises at least one wall defining a lumen for retaining the first liquid and the detectable particle, and wherein the at least one wall is coated with a binding material for binding the detectable particle to the at least one wall. The method can further include removing the first liquid from the capillary tube, wherein the bound detectable particle is maintained within the capillary, and introducing a second liquid into the capillary tube.

The capillary array can include a plurality of individual capillaries comprising at least one outer wall defining a lumen. The outer wall of the capillary can be one or more walls fused together. Similarly, the wall can define a lumen that is cylindrical, square, hexagonal or any other geometric shape so long as the walls form a lumen for retention of a liquid or sample. The capillaries of the capillary array can be held together in close proximity to form a planar structure. The capillaries can be bound together, by being fused (e.g., where the capillaries are made of glass), glued, bonded, or clamped side-by-side. The capillary array can be formed of any number of individual capillaries, for example, a range from 100 to 4,000,000 capillaries. A capillary array can form a micro titer plate having about 100,000 or more individual capillaries bound together.

Arrays, or "Biochips"

Nucleic acids or polypeptides as provided herein can be immobilized to or applied to an array. Arrays can be used to screen for or monitor libraries of compositions (e.g., small molecules, antibodies, nucleic acids, etc.) for their ability to bind to or modulate the activity of a nucleic acid or a polypeptide as provided herein. For example, in one aspect as provided herein, a monitored parameter is transcript expression of a hydrolase gene. One or more, or, all the transcripts of a cell can be measured by hybridization of a sample comprising transcripts of the cell, or, nucleic acids representative of or complementary to transcripts of a cell, by hybridization to immobilized nucleic acids on an array, or "biochip." By using an "array" of nucleic acids on a microchip, some or all of the transcripts of a cell can be simultaneously quantified. Alternatively, arrays comprising genomic nucleic acid can also be used to determine the genotype of a newly engineered strain made by the methods as provided herein. Polypeptide arrays" can also be used to simultaneously quantify a plurality of proteins. The present invention can be practiced with any known "array," also referred to as a "microarray" or "nucleic acid array" or "polypeptide array" or "antibody array" or "biochip," or variation thereof. Arrays are generically a plurality of "spots" or "target elements," each target element comprising a defined amount of one or more biological molecules, e.g., oligonucleotides, immobilized onto a defined area of a substrate surface for specific binding to a sample molecule, e.g., mRNA transcripts.

The "arrays" or "microarrays" or "biochips" or "chips" as provided herein can comprise a plurality of target elements, each target element comprising a defined amount of one or more polypeptides (including antibodies) or nucleic acids immobilized onto a defined area of a substrate surface.

In one aspect, the hydrolases are used as immobilized forms. Any immobilization method can be used, e.g., immobilization upon an inert support such as diethylaminoethyl-cellulose, porous glass, chitin or cells. Cells that express hydrolases as provided herein can be immobilized by cross-linking, e.g. with glutaraldehyde to a substrate surface.

In practicing the methods as provided herein, any known array and/or method of making and using arrays can be incorporated in whole or in part, or variations thereof, as described, for example, in U.S. Pat. Nos. 6,277,628; 6,277,489; 6,261,776; 6,258,606; 6,054,270; 6,048,695; 6,045,996; 6,022,963; 6,013,440; 5,965,452; 5,959,098; 5,856,174; 5,830,645; 5,770,456; 5,632,957; 5,556,752; 5,143,854; 5,807,522; 5,800,992; 5,744,305; 5,700,637; 5,556,752; 5,434,049; see also, e.g., WO 99/51773; WO 99/09217; WO 97/46313; WO 96/17958; see also, e.g., Johnston (1998) Curr. Biol. 8:R171-R174; Schummer (1997) Biotechniques 23:1087-1092; Kern (1997) Biotechniques 23:120-124; Solinas-Toldo (1997) Genes, Chromosomes & Cancer 20:399-407; Bowtell (1999) Nature Genetics Supp. 21:25-32. See also published U.S. patent applications Nos. 20010018642; 20010019827; 20010016322; 20010014449; 20010014448; 20010012537; 20010008765.

Antibodies and Antibody-Based Screening Methods

In certain embodiments, provided herein are isolated, synthetic or recombinant antibodies that specifically bind to a hydrolase as provided herein. These antibodies can be used to isolate, identify or quantify the hydrolase as provided herein or related polypeptides. These antibodies can be used to isolate other polypeptides as provided herein or other related hydrolases.

"Antibodies" as provided herein can comprise peptide(s) or polypeptide(s) derived from, modeled after or substantially encoded by an immunoglobulin gene or immunoglobulin genes, or fragments thereof, capable of specifically binding an antigen or epitope, see, e.g. Fundamental Immunology, Third Edition, W. E. Paul, ed., Raven Press, N.Y. (1993); Wilson (1994) J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody." Provided herein are antibodies, including antigen binding sites and single chain antibodies that specifically bind to a hydrolase as provided herein. In practicing the methods as provided herein, polypeptides having a hydrolase activity can also be used.

The antibodies can be used in immunoprecipitation, staining, immunoaffinity columns, and the like. If desired, nucleic acid sequences encoding for specific antigens can be generated by immunization followed by isolation of polypeptide or nucleic acid, amplification or cloning and immobilization of polypeptide onto an array as provided herein. Alternatively, the methods as provided herein can be used to modify the structure of an antibody produced by a cell to be modified, e.g., an antibody's affinity can be increased or decreased. Furthermore, the ability to make or modify antibodies can be a phenotype engineered into a cell by the methods as provided herein.

Methods of immunization, producing and isolating antibodies (polyclonal and monoclonal) ate known to those of skill in the art and described in the scientific and patent literature, see, e.g., Coligan, CURRENT PROTOCOLS IN IMMUNOLOGY, Wiley/Greene, NY (1991); Stites (eds.) BASIC AND CLINICAL IMMUNOLOGY (7th ed.) Lange Medical Publications, Los Altos, Calif. ("Stites"); Goding, MONOCLONAL ANTIBODIES: PRINCIPLES AND PRACTICE (2d ed.) Academic Press, New York, N.Y. (1986); Kohler (1975) Nature 256:495; Harlow (1988) ANTIBODIES, A LABORATORY MANUAL, Cold Spring Harbor Publications, New York. Antibodies also can be generated in vitro, e.g., using recombinant antibody binding site expressing phage display libraries, in addition to the traditional in vivo methods using animals. See, e.g., Hoogenboom (1997) Trends Biotechnol. 15:62-70; Katz (1997) Annu. Rev. Biophys. Biomol. Struct. 26:27-45.

Polypeptides or peptides can be used to generate antibodies, which bind specifically to the polypeptides as provided herein. The resulting antibodies may be used in immunoaffinity chromatography procedures to isolate or purify the polypeptide or to determine whether the polypeptide is present in a biological sample. In such procedures, a protein preparation, such as an extract, or a biological sample is contacted with an antibody capable of specifically binding to one of the polypeptides as provided herein.

In immunoaffinity procedures, the antibody is attached to a solid support, such as a bead or other column matrix. The protein preparation is placed in contact with the antibody under conditions in which the antibody specifically binds to one of the polypeptides as provided herein. After a wash to remove non-specifically bound proteins, the specifically bound polypeptides are eluted.

The ability of proteins in a biological sample to bind to the antibody may be determined using any of a variety of procedures familiar to those skilled in the art. For example, binding may be determined by labeling the antibody with a detectable label such as a fluorescent agent, an enzymatic label, or a radioisotope. Alternatively, binding of the antibody to the sample may be detected using a secondary antibody having such a detectable label thereon. Particular assays include ELISA assays, sandwich assays, radioimmunoassays, and Western Blots.

Polyclonal antibodies generated against the polypeptides as provided herein can be obtained by direct injection of the polypeptides into an animal or by administering the polypeptides to a non-human animal. The antibody so obtained will then bind the polypeptide itself. In this manner, even a sequence encoding only a fragment of the polypeptide can be used to generate antibodies which may bind to the whole native polypeptide. Such antibodies can then be used to isolate the polypeptide from cells expressing that polypeptide.

For preparation of monoclonal antibodies, any technique which provides antibodies produced by continuous cell line cultures can be used. Examples include the hybridoma technique, the trioma technique, the human B-cell hybridoma technique, and the EBV-hybridoma technique (see, e.g., Cole (1985) in Monoclonal Antibodies and Cancer Therapy, Alan R. Liss, Inc., pp. 77-96).

Techniques described for the production of single chain antibodies (see, e.g., U.S. Pat. No. 4,946,778) can be adapted to produce single chain antibodies to the polypeptides as provided herein. Alternatively, transgenic mice may be used to express humanized antibodies to these polypeptides or fragments thereof.

Antibodies generated against the polypeptides as provided herein (including anti-idiotype antibodies) may be used in screening for similar polypeptides from other organisms and samples. In such techniques, polypeptides from the organism are contacted with the antibody and those polypeptides which specifically bind the antibody are detected. Any of the procedures described above may be used to detect antibody binding.

Immobilized Hydrolases

In one aspect, the hydrolase as provided herein, e.g., lipases, saturases, palmitases and/or stearatases, are used as immobilized forms, e.g., to process lipids, in the structured synthesis of lipids, to digest proteins and the like. The immobilized lipases as provided herein can be used, e.g., for hydrolysis of triacylglycerides, diacylglycerides or esters or for the esterification or transesterification of fatty acids, diacylglycerides or triacylglycerides, or in the interesterification of fats. In one aspect, the lipase is specific for esterification of fatty acids with alcohol, 1,3-specific or specific for the hydrolysis of partial glycerides, esters or triacylglycerides. Immobilized lipases as provided herein can be used in a packed bed for continuous transesterification of solvent free fats. See, e.g., U.S. Pat. Nos. 4,818,695; 5,569,594.

Any immobilization method or form of support can be used, e.g., arrays, beads, capillary supports and the like, as described above. In one aspect, hydrolase immobilization can occur upon an inert support such as diethylaminoethyl-cellulose, porous glass, chitin or cells. Cells that express hydrolases as provided herein can be immobilized by cross-linking, e.g. with glutaraldehyde to a substrate surface. Immobilized hydrolases as provided herein can be prepared containing hydrolase bound to a dry, porous particulate hydrophobic support, with a surfactant, such as a polyoxyethylene sorbitan fatty acid ester or a polyglycerol fatty acid ester. The support can be an aliphatic olefinic polymer, such as a polyethylene or a polypropylene, a homo- or copolymer of styrene or a blend thereof or a pre-treated inorganic support. These supports can be selected from aliphatic olefinic polymers, oxidation polymers, blends of these polymers or pre-treated inorganic supports in order to make these supports hydrophobic. This pretreatment can comprise silanization with an organic silicon compound. The inorganic material can be a silica, an alumina, a glass or a ceramic. Supports can be made from polystyrene, copolymers of styrene, polyethylene, polypropylene or from co-polymers derived from (meth)acrylates. See, e.g., U.S. Pat. No. 5,773,266.

The hydrolase enzymes, fragments thereof and nucleic acids that encode the enzymes and fragments can be affixed to a solid support. This is often economical and efficient in the use of the hydrolases in industrial processes. For example, a consortium or cocktail of hydrolase enzymes (or active fragments thereof), which are used in a specific chemical reaction, can be attached to a solid support and dunked into a process vat. The enzymatic reaction can occur. Then, the solid support can be taken out of the vat, along with the enzymes affixed thereto, for repeated use. In one embodiment as provided herein, an isolated nucleic acid as provided herein is affixed to a solid support. In another embodiment as provided herein, the solid support is selected from the group of a gel, a resin, a polymer, a ceramic, a glass, a microelectrode and any combination thereof.

For example, solid supports provided herein include gels. Some examples of gels include SEPHAROSE™ (GE Healthcare, Piscataway, N.J.), gelatin, glutaraldehyde, chitosan-treated glutaraldehyde, albumin-glutaraldehyde, chitosan-xanthan, toyopearl gel (polymer gel), alginate, alginate-polylysine, carrageenan, agarose, glyoxyl agarose, magnetic agarose, dextran-agarose, poly(carbamoyl sulfonate) hydrogel, BSA-PEG hydrogel, phosphorylated polyvinyl alcohol (PVA), monoaminoethyl-N-aminoethyl (MANA), amino, or any combination thereof.

Other solid supports provided herein comprise resins or polymers. Some examples of resins or polymers include cellulose, acrylamide, nylon, rayon, polyester, anion-exchange resin, AMBERLITE™ XAD-7, AMBERLITE™ XAD-8, AMBERLITE™ IRA-94, AMBERLITE™ IRC-50 (Rohm and Haas, Philadelphia, Pa.), polyvinyl, polyacrylic, polymethacrylate, or any combination thereof.

Another type of solid support provided herein comprises ceramic. Some examples include non-porous ceramic, porous ceramic, $SiO_2$, $Al_2O_3$. Another type of solid support useful in the present invention is glass. Some examples include non-porous glass, porous glass, aminopropyl glass or any combination thereof. Another type of solid support that can be used is a microelectrode. An example is a polyethyleneimine-coated magnetite. Graphitic particles can be used as a solid support.

Another type of solid support provided herein comprises diatomaceous earth products and silicates. Some examples include CELITE®, KENITE®, DIACTIV®, PRIMISIL®, DIAFIL® diatomites and MICRO-CEL®, CALFLO®, SILASORB™, and CELKATE® (World Minerals Inc., Santa Barbara, Calif.) synthetic calcium and magnesium silicates.

Another example of a solid support is or comprises a cell, such as a red blood cell.

Kits

In certain embodiments, provided herein are kits comprising the compositions, e.g., nucleic acids, expression cassettes, vectors, cells, transgenic seeds or plants or plant parts, polypeptides (e.g., hydrolases) and/or antibodies as provided herein. The kits also can contain instructional material teaching the methodologies and industrial uses as provided herein, as described herein.

Industrial and Medical Applications

The hydrolases (e.g., lipases, saturases, palmitases and/or stearatases) provided herein have many industrial uses and medical applications, and a few exemplary uses and compositions are described below. The processes as provided herein comprise converting a non-hydratable phospholipid to a hydratable form, oil degumming, food processing, processing of oils (e.g., making a low saturate oil) from plants, fish, algae and the like, to name just a few applications.

Processing Foods and Feeds

In certain embodiments, provided herein are cheese-making processes using hydrolases (e.g., lipases, saturases, palmitases and/or stearatases) as provided herein. In other embodiments, provided herein are cheeses comprising hydrolases. In one aspect, the enzymes as provided herein (e.g., lipases, saturases, palmitases and/or stearatases or a combination thereof) are used to process cheeses for flavor enhancement, to increase yield and/or for "stabilizing" cheeses, e.g., by reducing the tendency for "oil-off," or, in one aspect, the enzymes as provided herein are used to produce cheese from cheese milk. These processes as provided herein can incorporate any method or protocol, e.g., as described, e.g., in U.S. Pat. Nos. 6,551,635, and 6,399,121, WO 03/070013, WO 00/054601. For example, in one aspect, hydrolases (e.g., lipases, saturases, palmitases and/or stearatases) as provided herein are used to stabilize fat emulsion in milk or milk-comprising compositions, e.g. cream, and are used to stabilize milk compositions, e.g. for the manufacturing of creams or cream liquors. In one embodiment, provided herein are processes for enhancing the flavor of a cheese using at least one enzyme as provided herein, the process comprising incubating a protein, a fat and a protease and a lipase (e.g., as provided herein) in an aqueous medium under conditions that produce an enhanced cheese flavor (e.g., reduced bitterness), e.g., as described in WO 99/66805. In one aspect, lipases as provided herein are used to enhance flavor in a cheese (e.g., a curd) by mixing with water, a protease, and a phospholipase at an elevated temperature, e.g., between about 75° C. to 95° C., as described, e.g., in U.S. Pat. No. 4,752,483. In one aspect, lipases as provided herein are used to accelerate cheese aging by adding an enzyme as provided herein to a cheese (e.g., a cheese milk) before adding a coagulant to the milk, or, adding an enzyme (e.g., a lipase) as provided herein to a curd with salt before pressing, e.g., as described, e.g., in U.S. Pat. No. 4,707,364. In one aspect, a lipase as provided herein is used to degrade a triacylglyceride in milk fat to liberate free fatty acids, resulting in flavor enhancement. An enzyme as provided herein also can be used in any of these processes as provided herein, see, e.g., Brindisi (2001) J. of Food Sci. 66:1100-1107.

Structured Synthesis and Processing of Oils

In certain embodiments, provided herein are methods for the structured synthesis of oils, lipids and the like using hydrolases (e.g., lipases, saturases, palmitases and/or stearatases) as provided herein. The methods as provided herein comprise a biocatalytic synthesis of structured lipids, i.e., lipids that contain a defined set of fatty acids distributed in a defined manner on a backbone, e.g., a glycerol backbone. Products generated using the hydrolases and practicing the methods as provided herein include low saturate oils, e.g., oils from vegetables (e.g., soy, canola), animals, plants, fish, algae, which oils have been processed or treated with a polypeptide as provided herein, and foods, feeds, supplements, pharmaceuticals and the like comprising low saturate oils made by practicing the methods and/or compositions (e.g., enzymes) as provided herein. Products generated using the hydrolases and practicing the methods as provided herein also include cocoa butter alternatives, lipids containing polyunsaturated fatty acids (PUFAs), lipids containing essential fatty acids, lipids containing monounsaturated fatty acids, lipids containing phospho-choline and phospho-serine, lipids containing phytosterols, 1,3-diacyl glycerides (DAGs), 2-monoacylglycerides (MAGs) and triacylglycerides (TAGs).

The methods as provided herein enable synthesis of lipids or fatty acids with defined regioselectivities and stereoselectivities. Provided herein are oils, lipids and the like, and oils that can be used in foods and feeds and cooking materials (e.g., cooking oils, frying oils, baking oils, sauces, marinades, condiments, spray oils, margarines, mayonnaise, spoonable and pourable dressings, cocoa butter alternatives, and the like) that have been processed or treated with polypeptides or peptides (e.g., hydrolases, such as lipases, saturases, palmitases and/or stearatases) as provided herein. In certain embodiments, provided herein are pharmaceuticals, nutraceuticals and cosmetics comprising polypeptides (e.g., hydrolases, such as lipases, saturases, palmitases and/or stearatases; or peptides or antibodies) as provided herein.

In certain embodiments, provided herein are methods for processing (modifying) oils, lipids and the like using hydrolases as provided herein. The methods can be used to process oils from plants, animals, microorganisms. The methods as provided herein can be used in the structured synthesis of oils similar to those found in plants, animals, and microorganisms. Lipids and oils can be processed to have a desired characteristic. Lipids and oils that can be processed by the methods as provided herein (using the hydrolases as provided herein) include cocoa butter alternatives, lipids containing poly-unsaturated fatty acids (PUFAs), lipids containing essential fatty acids, lipids containing monounsaturated fatty acids, lipids containing phospho-choline and phospho-serine, lipids containing phytosterols, 1,3-diacyl glycerides (DAGs), 2-monoacylglycerides (MAGs) and triacylglycerides (TAGs). In one aspect, the processed and synthetic oils and fats as provided herein (e.g., cocoa butters alternatives and vegetable oils) can be used in a variety of applications, e.g., in the production of foods (e.g., confectionaries, pastries) and in the formulation of pharmaceuticals, nutraceuticals and cosmetics. Provided herein are methods of processing fats and oils, e.g., oilseeds, from plants, including, e.g., canola, castor, coconut, coriander, corn, cottonseed, hazelnut, hempseed, linseed, meadowfoam, olive, palm oil, palm kernel, peanut, rapeseed, rice bran, safflower, sasanqua, soybean, sunflower, tall, tsubaki, varieties of "natural" oils having altered fatty acid compositions via Genetically Modified Organisms (GMO) or traditional breeding such as high oleic, low linolenic, or low saturate oils (high oleic canola, low linolenic soybean, or high stearic sunflower) or blends of any of the above using a hydrolase as provided herein.

In certain embodiments, provided herein are methods of processing oils from animals, e.g., fish (candlefish, codliver, orange roughy, sardine, herring, menhaden, and the like), mammals (pork, beef, and the like) and fowl (chicken, and the like), using the hydrolases as provided herein. In certain embodiments, provided herein are methods for the structured synthesis of oils similar to those found in animals, e.g., fish, fowl, and mammals and microorganisms, using the hydrolases as provided herein. In one aspect, these synthetic or processed oils are used as feed additives, foods, as ingredients in pharmaceutical formulations, nutraceuticals or in cosmetics. For example, in one aspect the hydrolases as provided herein are used to hydrolyze fatty acids away from fish oils so that the fatty acids can be recovered and used as a feed additive. In one aspect, the hydrolases as provided herein can be used to process oil from restaurant waste and rendered animal fats.

In other embodiments, provided herein are methods of processing fats and oils, e.g., from algal oils, including, e.g., *Neochloris oleoabundans* oil, *Scenedesmus dimorphus* oil, *Euglena gracilis* oil, *Phaeodactylum tricornutum* oil, *Pleurochrysis carterae* oil, *Prymnesium parvum* oil, *Tetraselmis chui* oil, *Tetraselmis suecica* oil, *Isochrysis galbana* oil, *Nannochloropsis salina* oil, *Botryococcus braunii* oil, *Dunaliella tertiolecta* oil, *Nannochloris* species oil, *Spirulina* species oil, *Chlorophycease* (green algae) oil, and *Bacilliarophy* oil or blends of any of said fats and oils.

In one aspect, the hydrolases as provided herein are versatile biocatalysts in organic synthesis, e.g., in the structured synthesis of oils, lipids and the like. Enzymes as provided herein (including hydrolases, e.g., lipases, saturases, palmitases and/or stearatases) can accept a broad range of substrates, including secondary and tertiary alcohols, e.g., from a natural product such as alpha-terpineol, linalool and the like. In some aspects, the hydrolases as provided herein have good to excellent enantiospecificity (e.g., stereospecificity).

In certain embodiments, provided herein is an oil (e.g., vegetable oils, cocoa butters, and the like) conversion process comprising at least one enzyme (e.g., a lipase, saturase, palmitase and/or stearatase) as provided herein. In one aspect, an oil conversion process comprises a controlled hydrolysis and acylation, e.g., a glycerol acylation, which can result in high purity for a broad range of products. In one aspect, hydrolases (e.g., a lipase, saturase, palmitase and/or stearatase) as provided herein are used to produce diacylglycerol oils and structured nutritional oils. In certain embodiments, provided herein are processes for the esterification of propylene glycol using an enzyme as provided herein, e.g., a regio- and/or chemo-selective lipase for mono-substituted esterification at the Sn-1 position. Provided herein are processes for the structured synthesis of oils with targeted saturated or unsaturated fatty acid profiles using an enzyme as provided herein, e.g., a regio- and/or chemo-selective lipase for the removal of a saturated fatty acid, or, for the targeted addition of a fatty acid to a glycerol backbone.

In one aspect, the methods as provided herein further comprise processes for the selective removal of fatty acids (e.g., undesirable fatty acids) from oils, e.g., separating saturated and/or unsaturated fatty acids from oils, using a hydrolase (e.g., a lipase, saturase, palmitase and/or stearatase) as provided herein. The process as provided herein can separate saturated and/or unsaturated fatty acids from any oil, e.g., a soy oil. The enzyme can be chemoselective and/or enantioselective. In one aspect, these processes generate high stability fats and oils, e.g., "healthy" frying oils. This exemplary process as provided herein can be used to generate oils with less sulfur, e.g., using a process comprising sulfur removal from crude oil. The enzymes as provided herein can also be used in interesterification processes for these and other purposes.

In one aspect, an enzyme as provided herein is used to generate a "no-trans" fat oil. In one aspect, a "no-trans" oil is generated from a partially hydrogenated oil to produce a cis-only oil. The enzyme can be chemoselective and/or enantioselective.

In another embodiments, provided herein are processes for modifying cocoa butters using an enzyme as provided herein. About 80% of cocoa butters comprise POP, SOS and POS triacylglycerides (P is palmitic fatty acid, O is oleic fatty acid, S is stearic fatty acid). The saturated-unsaturated-saturated fatty acid structure of cocoa butters imparts their characteristic melting profiles, e.g., in chocolates. In one aspect, the structured and direct synthetic processes as provided herein are used on cocoa butters to reduce cocoa butter variations or to produce synthetic cocoa butters ("cocoa butter alternatives"). In one aspect, a chemoselective and/or enantioselective (e.g., a regio-selective) hydrolase (e.g., lipase or esterase) as provided herein is used to make a cocoa butter alternative, e.g., a cocoa butter substitute, a cocoa butter replacer and/or a cocoa butter equivalent. Provided herein are cocoa butter alternatives, including cocoa butter substitutes, cocoa butter replacers and cocoa butter equivalents and their manufacturing intermediates comprising an enzyme as provided herein. A process as provided herein (using an enzyme as provided herein) for making cocoa butter alternatives can comprise blending a vegetable oil, e.g., a palm oil, with shea or equivalent, illipe or equivalent and Sal sterins or equivalent, and treating the blended oils with the polypeptides as provided herein. In one aspect, the process as provided herein comprises use of interesterification. The process as provided herein can generate compositional or crystalline forms that mimic "natural" cocoa butter.

In certain embodiments, provided herein are processes (using an enzyme as provided herein) for producing a diacylglycerol (DAG), e.g., 1,3 diacylglycerol, using a vegetable oil, e.g., a low cost oil. The enzyme can be chemoselective and/or enantioselective. The process as provided herein can result in a DAG-comprising composition having good stability, long shelf life and high temperature performance.

The enzymes (hydrolases, e.g., lipases, saturases palmitases and/or stearatases) as provided herein and methods as provided herein can also be used in the enzymatic treatment of edible oils, as described, e.g., in U.S. Pat. No. 6,025,171. In this exemplary method, enzymes as provided herein are immobilized by preparing an emulsion containing a continuous hydrophobic phase, such as a triacylglyceride oil, and a dispersed aqueous phase containing an amphiphilic enzyme, such as lipase as provided herein, and carrier material that is partly dissolved and partly undissolved in the aqueous phase, and removing water from the aqueous phase until the phase turns into solid enzyme coated carrier particles. The undissolved part of the carrier material may be a material that is insoluble in water and oil, or a water soluble material in undissolved form because the aqueous phase is already saturated with the water soluble material. The aqueous phase may be formed with a crude lipase fermentation liquid containing fermentation residues and biomass that can serve as carrier materials. Immobilized lipase is useful for ester re-arrangement and de-acidification in oils. After a reaction, the immobilized enzyme can be regenerated for a subsequent reaction by adding water to obtain partial dissolution of the carrier, and with the resultant enzyme and carrier-containing aqueous phase dispersed in a hydrophobic phase evaporating water to again form enzyme coated carrier particles.

The enzymes (e.g., lipases, saturases, palmitases and/or stearatases) as provided herein and methods as provided herein can also be used for preparing transesterified oils, as described, e.g., in U.S. Pat. No. 5,288,619. Provided herein are methods for enzymatic transesterification for preparing a margarine oil having both low trans-acid and low intermediate chain fatty acid content. The method includes the steps of providing a transesterification reaction mixture containing a stearic acid source material and an edible liquid vegetable oil, transesterifying the stearic acid source material and the vegetable oil using a 1-, 3-positionally specific lipase, and then finally hydrogenating the fatty acid mixture to provide a recycled stearic acid source material for a recyclic reaction with the vegetable oil. Provided herein are counter-current method for preparing a transesterified oil. The method includes the steps of providing a transesterification reaction zone containing a 1-, 3-positionally specific lipase, introducing a vegetable oil into the transesterification zone, introducing a stearic acid source material, conducting a supercritical gas or subcritical liquefied gas counter-current fluid, carrying out a transesterification reaction of the triacylglyceride stream with the stearic acid or stearic acid monoester stream in the reaction zone, withdrawing a transesterified triacylglyceride margarine oil stream, withdrawing a counter-current fluid phase, hydrogenating the transesterified stearic acid or stearic acid monoester to provide a hydrogenated recycle stearic acid source material, and introducing the hydrogenated recycle stearic acid source material into the reaction zone.

In one aspect, to allow the enzyme as provided herein to act, both phases, the oil phase and the aqueous phase that contain the enzyme, must be intimately mixed. It may not be sufficient to merely stir them. Good dispersion of the enzyme in the oil is aided if it is dissolved in a small amount of water, e.g., 0.5-5 weight-% (relative to the oil), and emulsified in the oil in this form, to form droplets of less than 10 micrometers in diameter (weight average). The droplets can be smaller than 1 micrometer. Turbulent stirring can be done with radial velocities above 100 cm/sec. The oil also can be circulated in the reactor using an external rotary pump. The aqueous phase containing the enzyme can also be finely dispersed by means of ultrasound action. A dispersion apparatus can be used.

In one aspect, an enzymatic reaction as provided herein takes place at the border surface between the oil phase and the aqueous phase. It is the goal of all these measures for mixing to create the greatest possible surface for the aqueous phase which contains the enzyme. The addition of surfactants increases the microdispersion of the aqueous phase. In some cases, therefore, surfactants with HLB values above 9, such as Na-dodecyl sulfate, are added to the enzyme solution, as described, e.g., in EP-A 0 513 709. A similar effective method for improving emulsification is the addition of lysolecithin. The amounts added can lie in the range of 0.001% to 1%, with reference to the oil. The temperature during enzyme treatment is not critical. Temperatures between 20° C. and 80° C. can be used, but the latter can only be applied for a short time. In this aspect, a lipase as provided herein having a good temperature and/or low pH tolerance is used. Application temperatures of between 30° C. and 50° C. are optimal. The treatment period depends on the temperature and can be kept shorter with an increasing temperature. Times of 0.1 to 10 hours, or, 1 to 5 hours are generally sufficient. The reaction takes place in a reactor, which can be divided into stages. Therefore continuous operation is possible, along with batch operation. The reaction can be carried out in different temperature stages. For example, incubation can take place for 3 hours at 40° C., then for 1 hour at 60° C. If the reaction proceeds in stages, this also opens up the possibility of adjusting different pH values in the individual stages. For example, in the first stage the pH of the solution can be adjusted to 7, for example, and in a second stage to 2.5, by adding citric acid or other suitable acids. In at least one stage, however, the pH of the enzyme solution must be below 4, or, below 3. If the pH was subsequently adjusted below this level, a deterioration of effect may be found. Therefore the citric acid can be added to the enzyme solution before the latter is mixed into the oil.

The enzymes (hydrolases, e.g., lipases, saturases, palmitases and/or stearatases) as provided herein and methods as provided herein can also be used for preparing oils, as described, e.g., in U.S. patent application Ser. No. 11/567,318, incorporated herein by reference in its entirety. Provided herein are continuous processes for enzymatic treatment of lipids. The method relates to a process and apparatus for the continuous enzymatic interesterification of lipid-containing compositions using a plurality of fixed bed reactors, wherein the flow of the lipid-containing composition through the apparatus can remain substantially constant even as the enzymatic activity of a fixed bed decreases over time, and even when a fixed bed is taken off-line such as for repair, replacement, or replenishment.

Nutraceuticals

In one aspect, the compositions and methods as provided herein can be used to make nutraceuticals by processing or synthesizing lipids and oils using the enzymes as provided herein, e.g., hydrolases, e.g., lipases, saturases, palmitases and/or stearatases as provided herein. In one aspect, the processed or synthesized lipids or oils include poly-unsaturated fatty acids (PUFAs), diacylglycerides, e.g., 1,3-diacyl glycerides (DAGs), monoacylglycerides, e.g., 2-monoacylglycerides (MAGs) and triacylglycerides (TAGs). In one aspect, the nutraceuticals are made by processing diacylglycerides, e.g., 1,3-diacyl glycerides (DAGs), monoacylglycerides, e.g., 2-monoacylglycerides (MAGS) and/or triacylglycerides (TAGs) from plant (e.g., oilseed) sources or from animal (e.g., fish oil) sources. In certain embodiments, provided herein are nutraceuticals (e.g., dietary compositions) comprising polypeptides (e.g., enzymes, peptides, antibodies) as provided herein.

In one aspect, the compositions and methods as provided herein can be used to fortify dietary compositions, especially cow's milk based products, e.g., cow's milk-based infant formulas, with bile salt-activated hydrolases. The compositions made by the methods and compositions as provided herein can be used to feed newborn and premature infants, including administration of a bile salt-activated hydrolase as provided herein to increase fat digestion and therefore growth rate. In certain embodiments, provided herein are compositions and methods for treating subjects for inadequate pancreatic enzyme production by administration of bile salt-activated hydrolase in conjunction with ingestion of fats; see also discussion, below.

In certain embodiments, provided herein are dietary compositions comprising a hydrolase, e.g., bile salt-activated hydrolase as provided herein. In certain embodiments, provided herein are dietary compositions comprising a nutritional base comprising a fat and an effective amount of bile salt-activated hydrolase as provided herein. In one embodiment, provided herein are cow's milk-based infant formulas comprising a hydrolase, e.g., bile salt-activated hydrolase as provided herein. In one aspect, the hydrolase as provided herein is active in the digestion of long chain fatty acids, e.g., $C_{12}$ to $C_{22}$, which make up a very high percentage of most milks, e.g., 99% of human breast milk. See, e.g., U.S. Pat. No. 5,000,975.

In certain embodiments, provided herein are dietary compositions comprising a vegetable oil fat and a hydrolase as provided herein. In other embodiments, provided herein are methods of processing milk based products and/or vegetable oil-comprising compositions to make dietary compositions. In one aspect, the processed compositions comprise a lauric acid oil, an oleic acid oil, a palmitic acid oil and/or a linoleic acid oil. In one aspect, a rice bran oil, sunflower oleic oil and/or canola oil may be used as oleic acids oils. In one aspect, fats and oils, e.g., oilseeds, from plants, including, e.g., canola, castor, coconut, coriander, corn, cottonseed, hazelnut, hempseed, linseed, meadowfoam, olive, palm oil, palm kernel, peanut, rapeseed, rice bran, safflower, sasanqua, soybean, sunflower, tall, tsubaki, varieties of "natural" oils having altered fatty acid compositions via Genetically Modified Organisms (GMO) or traditional "breeding such as high oleic, low linolenic, or low saturated oils (high oleic canola, low linolenic soybean, or high stearic sunflower), blends of any of the above for use in the nutraceuticals and dietary compositions are processed or made using a hydrolase as provided herein. See, e.g., U.S. Pat. No. 4,944,944.

In one aspect, the enzymes as provided herein are provided in a form that is stable to storage in the formula and/or the stomach, but active when the formulation reaches the portion of the gastrointestinal tract where the formula would normally be digested. Formulations (e.g., microcapsules) for release in the intestine are well known in the art, e.g., biodegradable polymers such as polylactide and polyglycolide, as described, e.g., in U.S. Pat. Nos. 4,767,628; 4,897,268; 4,925, 673; 5,902,617.

Confectionaries, Cacao (Cocoa) Butter and Foods

In one aspect, the compositions and methods as provided herein can be used to make and process hard butters, such as cocoa butter (cacao butter). In another aspect, provided herein are confectionaries, cacao butter and foods comprising polypeptides (e.g., enzymes, peptides, antibodies) as provided herein.

The compositions and methods as provided herein can be used to make cocoa butter alternatives by "structured" synthetic techniques using the enzymes, e.g., hydrolases, e.g., lipases, saturases, palmitases and/or stearatases as provided herein. For example, in one aspect, the methods as provided herein process or synthesize triacylglycerides, diacylglycerides and/or monoacylglycerides for use as, e.g., cocoa butter alternatives. In one aspect, the methods as provided herein generate a hard butter with a defined "plastic region" to maintain sufficient hardness below or at room temperature. In one aspect, the processed or synthesized lipid is designed to have a very narrow "plastic region," e.g., in one aspect, where it rapidly melts at about body temperature. Natural cocoa butter begins to soften at approximately 30° C. to 32° C., and completely melts at approximately 36° C. Natural cocoa butter can contain 70 wt % or more of three 1,3-disaturated-2-oleoyl glycerols, which are 1,3-dipalmitoyl-2-oleoyl glycerol (POP), 1-palmitoyl-2-oleoyl-3-stearoyl glycerol (POSt) and 1,3-distearoyl-2-oleoyl glycerol (StOSt). These three glycerols show a similar melting behavior to each other and are responsible for melting properties of the cocoa butter, exhibiting a very narrow plastic region. In certain embodiments, provided herein are synthetic cocoa butters or processed cocoa butters (synthesized or processed using a hydrolase as provided herein, all possible compositions are referred to as cocoa-butter alternatives) with varying percentages of 1,3-dipalmitoyl-2-oleoyl glycerol (POP), 1-palmitoyl-2-oleoyl glycerol (POSt) and 1,3-distearoyl-2-oleoyl glycerol (StOSt), depending on the desired properties of the synthetic cocoa butter, and, synthetic cocoa butters with more or less than 70 wt % of the three 1,3-disaturated-2-oleoyl glycerols. The synthetic cocoa butters as provided herein can partially or completely replace natural or unprocessed cocoa butters and can maintain or improve essential hard butter properties.

In certain embodiments, provided herein are synthetic cocoa butters or processed cocoa butters (synthesized or processed using a hydrolase as provided herein) with desired properties for use in confectionary, bakery and pharmaceutical products. In other embodiments, provided herein are confectioneries, bakery and pharmaceutical products, and the like, comprising a hydrolase as provided herein. In one aspect, the methods as provided herein make or process a lipid (a fat) from a confection (e.g., a chocolate) or to be used in a confection. In one aspect, a lipid is made or processed such that the chocolate shows less finger-imprinting than chocolate made from natural cocoa butter, while still having sharp melting characteristics in the mouth. In one aspect, a lipid is made or processed such that a confection (e.g., chocolate) can be made at a comparatively high ambient temperature, or, be made using a cooling water at a comparatively high temperature. In one aspect, the lipid is made or processed such that a confection (e.g., chocolate) can be stored under relatively warmer conditions, e.g., tropical or semi-tropical conditions or in centrally heated buildings. In one aspect, the lipids are made or processed such that a confection (e.g., chocolate) will have a lipid (fat) content of consistent composition and quality. The enzymes as provided herein can be used to provide a substitute composition for cocoa butter which can significantly improve its thermal stability and replace it in a wide range of applications.

Margarine and Shortening Production

In certain embodiments, provided herein are synthetic or processed fats, e.g., margarine and shortening, synthesized or processed using a hydrolase as provided herein. In other embodiments, provided herein are synthetic or processed fats, e.g., margarine and shortening, comprising polypeptides (e.g., enzymes, peptides, antibodies) as provided herein.

In one embodiment, provided herein are processed fats comprising a vegetable oil, such as canola, castor, coconut, coriander, corn, cottonseed, hazelnut, hempseed, linseed, meadowfoam, olive, palm oil, palm kernel, peanut, rapeseed, rice bran, safflower, sasanqua, sesame, soybean, sunflower, tall, tsubaki, varieties of "natural" oils having altered fatty acid compositions via Genetically Modified Organisms (GMO) or traditional "breeding" such as high oleic, low linolenic, or low saturated oils (high oleic canola, low linolenic soybean, or high stearic sunflower) type oils synthesized or processed using a hydrolase as provided herein. The synthetic or processed fats, e.g., margarine and shortening, are designed to have a desired "plasticity." Many of the plastic fat products, such as margarine and shortening, are produced from hard stocks and liquid oils as raw materials. For example, liquid oils such as canola, castor, coconut, coriander, corn, cottonseed, hazelnut, hempseed, linseed, meadowfoam, olive, palm oil, palm kernel, peanut, rapeseed, rice bran, safflower, sasanqua, sesame, soybean, sunflower, tall, tsubaki, varieties of "natural" oils having altered fatty acid compositions via Genetically Modified Organisms (GMO) or traditional "breeding" such as high oleic, low linolenic, or low saturated oils (high oleic canola, low linolenic soybean, or high stearic sunflower), are blended with their hardened oils (hard stocks), and the blend is adjusted to have an appropriate consistency (plasticity). The plastic fat products such as margarine and shortening so produced tend to cause the formation of relatively coarse crystallines because fats and oils used as the raw materials are composed of fatty acids having almost the same carbon chain length. In other words, they have a highly-unified composition of fatty acids. For this reason, the plasticity of these products can be maintained at an appropriate degree only within a narrow temperature range, so that the liquid oils contained therein have a tendency to exude. Provided herein are methods of making or processing fats designed such that they have a varied (and defined) composition of fatty acids. The resultant oil, e.g., margarine or shortening, can have a broader range of plasticity.

In one aspect, the methods and compositions as provided herein are used to make or process vegetable oils, such as canola, castor, coconut, coriander, corn, cottonseed, hazelnut, hempseed, linseed, meadowfoam, olive, palm oil, palm kernel, peanut, rapeseed, rice bran, safflower, sasanqua, sesame, soybean, sunflower, tall, tsubaki, varieties of "natural" oils having altered fatty acid compositions via Genetically Modified Organisms (GMO) or traditional "breeding" such as high oleic, low linolenic, or low saturated oils (high oleic canola, low linolenic soybean, or high stearic sunflower) type oils using the hydrolases as provided herein, including inter-esterification and enzymatic transesterification, see e.g., U.S. Pat. No. 5,288,619 and U.S. patent application Ser. No. 11/567,318. The methods and compositions as provided herein can be used in place of random inter-esterification as described in, e.g., U.S. Pat. No. 3,949,105. In one aspect, the methods and compositions as provided herein are used in enzymatic transesterification for preparing an oil, e.g., a margarine oil, having both low trans-acid and low intermediate chain fatty acid content.

In one aspect, the symmetric structure of an oil, e.g., a palm or lauric type oils is modified, e.g., into a random structure. Thus, the methods as provided herein can be used to modify the properties of plastic fat products. In one aspect, the modification of oils by the methods as provided herein can be designed to prevent or slow gradually hardening of the oil with time, particularly when the products are being stored.

In one aspect, the methods and compositions as provided herein in a trans-esterification reaction mixture comprising a stearic acid source material and an edible liquid vegetable oil, trans-esterifying the stearic acid source material and the vegetable oil using a 1,3-positionally specific lipase as provided herein, and then hydrogenating the fatty acid mixture to provide a recycle stearic acid source material for a recyclic reaction with the vegetable oil. See e.g., U.S. Pat. No. 5,288,619.

In one aspect, an inter-esterification reaction is conducted with a lipase as provided herein. In one aspect, the lipase as provided herein has selectivity for the 1- and 3-positions of triacylglyceride to slow or inhibit an increase in the amount of tri-saturated triacylglycerides in the oil. In this reaction as provided herein, deficiencies of conventional random inter-esterification and the difficulty of inter-esterification with a non-specific lipase can be overcome because the inter-esterification is conducted by an enzyme as provided herein having specificity for the 1- and 3-positions of triacylglycerides. In one aspect, the exudation of liquid oils contained in the products is slowed or prevented with a temperature increase in the reaction to inhibit a rise in the melting point caused by an increase in the amount of tri-saturated triacylglycerides. This addresses the problem of hardening of products during long-term storage.

Pharmaceutical Compositions and Treating Hydrolase Deficiencies

In certain embodiments, provided herein are methods and compositions (enzymes as provided herein, e.g., esterases, acylases, lipases, phospholipases or proteases as provided herein) that can be used in the treatment of a hydrolase deficiency in an animal, e.g., a mammal, such as a human. For example, in one aspect, the methods and compositions as provided herein are used to treat patients suffering from a deficiency of a pancreatic lipase. In one aspect, the lipase is administered orally. An enzyme as provided herein can be delivered in place of or with a preparation of pig pancreas enzyme.

In certain embodiments, provided herein are pharmaceutical compositions comprising polypeptides (e.g., enzymes, peptides, antibodies) as provided herein. These pharmaceutical compositions can be in the form of tablets, pills, gels, capsules, hydrogels, sprays, powders, aerosols, implants, liposomes, creams, ointments, liquids, a microsphere, a multiparticulate core particle, an emulsion, a suspension, nanostructures and the like. The pharmaceutical compositions comprising polypeptides (e.g., enzymes, peptides, antibodies) as provided herein can be administered in any form, e.g., orally, intradermally, intraperitoneally, by I.V., topically and the like. In one aspect, the pharmaceutical compositions as provided herein are formulated for topical, sublingual, oral, intravenous, subcutaneous, intramuscular, transdermal, intraarterial, intraarticular, or intradermal delivery.

In one aspect, the compositions as provided herein used for these treatments are active under acidic conditions. In one aspect, the compositions as provided herein are administered orally in formulations (e.g., tablets, pills, gels, capsules, hydrogels, sprays, powders, aerosols) that pass through the acid regions of the stomach and discharge the enzyme only in the relatively alkaline environment of the jejunum. In one aspect, a hydrolase as provided herein is formulated with a carrier such as lactose, saccharose, sorbitol, mannitol, starch, cellulose derivatives or gelatine or any other such excipient. A lubricant such as magnesium stearate, calcium stearate or polyethylene glycol wax also can be added. A concentrated sugar solution, which may contain additives such as talc, titanium dioxide, gelatine or gum Arabic, can be added as a coating. Soft or hard capsules can be used to encapsulate a hydrolase as a liquid or as a solid preparation. See, e.g., U.S. Pat. Nos. 5,691,181; 5,858,755.

Detergents

In certain embodiments, provided herein are methods and compositions (enzymes, e.g., lipases, saturases, palmitases and/or stearatases as provided herein) that can be used in making and using detergents. A hydrolase as provided herein can be added to, e.g., be blended with, any known detergent composition, solid or liquid, with or without changing the composition of the detergent composition. For examples, a hydrolase as provided herein can be added to any soap, e.g., aliphatic sulfates such as straight or branched chain alkyl or alkenyl sulfates, amide sulfates, alkyl or alkenyl ether sulfates having a straight or branched chain alkyl or alkenyl group to which one or more of ethylene oxide, propylene oxide and butylene oxide is added, aliphatic sulfonates such as alkyl sulfonates, amide sulfonates, dialkyl sulfosuccinates, sulfonates of alpha-olefins, of vinylidene-type olefins and of internal olefins, aromatic sulfonates such as straight or branched chain alkylbenzenesulfonates, alkyl or alkenyl ether carbonates or amides having a straight or branched chain alkyl or alkenyl group to which one or more of ethylene oxide, propylene oxide and butylene oxide is added, or amides, alpha-sulfo-fatty acid salts or esters, amino acid type surfactants, phosphate surfactants such as alkyl or alkenyl acidic phosphates, and alkyl or alkenyl phosphates, sulfonic acid type amphoteric surfactants, betaine type amphoteric surfactants, alkyl or alkenyl ethers or alcohols having a straight or branched chain alkyl or alkenyl group to which one or more of ethylene oxide, propylene oxide and butylene oxide is added, polyoxy-ethylenealkyl phenyl ethers having a straight or branched chain alkyl group to which one or more of ethylene oxide, propylene oxide and butylene oxide is added, higher fatty acid alkanolamides or alkylene oxide adducts thereof, sucrose fatty acid esters, fatty acid glycerol monoesters, alkyl- or alkenyl-amine oxides, tetraalkyl-ammonium salt type cationic surfactants, or a combination thereof. See, e.g., U.S. Pat. No. 5,827,718.

In some embodiments, provided herein are detergent compositions comprising one or more polypeptides (hydrolases) as provided herein. Surface-active and/or non-surface-active forms can be used. In one aspect, the amount of total hydrolase, surface-active and/or non-surface-active, can be from about 0.0001% to about 1.0%, or from about 0.0002% to about 0.5%, by weight, of the detergent composition. In one aspect, of the detergent composition, the surface-active hydrolase is from about 5% to about 67% and the non-surface-active hydrolase is from about 33% to about 95% of the total hydrolase activity in the enzymatic mixture. In one aspect, the optimum pH of the total enzymatic mixture is between about 5 to about 10.5.

In one aspect, the detergent compositions as provided herein include alkaline hydrolases as provided herein which function at alkaline pH values, since the pH of a washing solution can be in an alkaline pH range under ordinary washing conditions. See, e.g., U.S. Pat. No. 5,454,971

The polypeptides as provided herein (enzymes as provided herein) can be used in any detergent composition, which are well known in the art, see, e.g., U.S. Pat. Nos. 5,069,810; 6,322,595; 6,313,081. For example, in one aspect, a laundry detergent composition is provided. It can comprise 0.8 ppm to 80 ppm of a lipase as provided herein.

Any method of making and using detergent compositions can be used with enzymes as provided herein, see, e.g., U.S. Pat. Nos. 6,413,928; 6,399,561; 6,365,561; 6,380,147. The detergent compositions can be a one and two part aqueous composition, a non-aqueous liquid composition, a cast solid, a granular form, a particulate form, a compressed tablet, a gel form, a powder, a gel, a hydrogel, a liposome, an aerosol, a paste and/or a slurry form. The hydrolases as provided herein can also be used as a detergent additive product in a solid or a liquid form. Such additive products are intended to supplement or boost the performance of conventional detergent compositions and can be added at any stage of the cleaning process.

In certain embodiments, provided herein are methods capable of removing gross food soils, films of food residue and other minor food compositions using these detergent compositions. Hydrolases as provided herein can facilitate the removal of stains by means of catalytic hydrolysis of lipids, fats or oils. Hydrolases as provided herein can be used in dishwashing detergents and in textile laundering detergents.

The actual active enzyme content depends upon the method of manufacture of a detergent composition and is not critical, assuming the detergent composition has the desired enzymatic activity. In one aspect, the amount of hydrolases present in the final composition ranges from about 0.001 mg to 0.5 mg per gram of the detergent composition. The particular enzyme chosen for use in the process and products provided herein depends upon the conditions of final utility, including the physical product form, use pH, use temperature, and soil types to be degraded or altered. The enzyme can be chosen to provide optimum activity and stability for any given set of utility conditions. In one aspect, the hydrolases provided herein are active in the pH ranges of from about 4 to about 12 and in the temperature range of from about 20° C. to about 95° C. The detergents as provided herein can comprise cationic, semi-polar nonionic or zwitterionic surfactants; or, mixtures thereof.

In one embodiment, enzymes as provided herein can be formulated into powdered and liquid detergents having pH between 4.0 and 12.0 at levels of about 0.01 to about 5% (alternatively 0.1% to 0.5%) by weight. These detergent compositions can also include other enzymes such as proteases, cellulases, lipases or endoglycosidases, endo-beta-1,4-glucanases, beta-glucanases, endo-beta-1,3(4)-glucanases, cutinases, peroxidases, laccases, amylases, glucoamylases, pectinases, reductases, oxidases, phenoloxidases, ligninases, pullulanases, arabinanases, hemicellulases, mannanases, xyloglucanases, xylanases, pectin acetyl esterases, rhamnogalacturonan acetyl esterases, polygalacturonases, rhamnogalacturonases, galactanases, pectin lyases, pectin methylesterases, cellobiohydrolases and/or transglutaminases. These detergent compositions can also include builders and stabilizers.

The addition of hydrolases as provided herein to conventional cleaning compositions does not create any special use limitation. In other words, any temperature and pH suitable for the detergent is also suitable for the compositions as provided herein as long as the enzyme is active at or tolerant of the pH and/or temperature of the intended use. In addition, the hydrolases as provided herein can be used in a cleaning composition without detergents, again either alone or in combination with builders and stabilizers.

In certain embodiments, provided herein are cleaning compositions including detergent compositions for cleaning hard surfaces, detergent compositions for cleaning fabrics, dishwashing compositions, oral cleaning compositions, denture cleaning compositions, and contact lens cleaning solutions.

In certain embodiments, provided herein are methods for washing an object comprising contacting the object with a polypeptide as provided herein under conditions sufficient for washing. A hydrolase as provided herein may be included as a detergent additive. The detergent composition as provided herein may, for example, be formulated as a hand or machine laundry detergent composition comprising a polypeptide as provided herein. A laundry additive suitable for pre-treatment of stained fabrics can comprise a polypeptide as provided herein. A fabric softener composition can comprise a hydrolase as provided herein. Alternatively, a hydrolase as provided herein can be formulated as a detergent composition for use in general household hard surface cleaning operations. In alternative aspects, detergent additives and detergent compositions as provided herein may comprise one or more other enzymes such as a protease, a lipase, a cutinase, another protease, a carbohydrase, a cellulase, a pectinase, a mannanase, an arabinase, a galactanase, a xylanase, an oxidase, e.g., a lactase, and/or a peroxidase (see also, above). The properties of the enzyme(s) as provided herein are chosen to be compatible with the selected detergent (i.e. pH-optimum, compatibility with other enzymatic and non-enzymatic ingredients, etc.) and the enzyme(s) is present in effective amounts. In one aspect, enzymes as provided herein are used to remove malodorous materials from fabrics. Various detergent compositions and methods for making them that can be used are described in, e.g., U.S. Pat. Nos. 6,333,301; 6,329,333; 6,326,341; 6,297,038; 6,309,871; 6,204,232; 6,197,070; 5,856,164.

When formulated as compositions suitable for use in a laundry machine washing method, the hydrolases as provided herein can comprise both a surfactant and a builder compound. They can additionally comprise one or more detergent components, e.g., organic polymeric compounds, bleaching agents, additional enzymes, suds suppressors, dispersants, lime-soap dispersants, soil suspension and anti-redeposition agents and corrosion inhibitors. Laundry compositions as provided herein can also contain softening agents, as additional detergent components. Compositions containing hydrolases as provided herein can provide fabric cleaning, stain removal, whiteness maintenance, softening, color appearance, dye transfer inhibition and sanitization when formulated as laundry detergent compositions.

The density of the laundry detergent compositions as provided herein can range from about 200 to 1500 g/liter, or, about 400 to 1200 g/liter, or, about 500 to 950 g/liter, or, 600 to 800 g/liter, of composition; this can be measured at about 20° C.

The "compact" form of laundry detergent compositions as provided herein is best reflected by density and, in terms of composition, by the amount of inorganic filler salt. Inorganic filler salts are conventional ingredients of detergent compositions in powder form. In conventional detergent compositions, the filler salts are present in substantial amounts, typically 17% to 35% by weight of the total composition. In one aspect of the compact compositions, the filler salt is present in amounts not exceeding 15% of the total composition, or, not exceeding 10%, or, not exceeding 5% by weight of the composition. The inorganic filler salts can be selected from the alkali and alkaline-earth-metal salts of sulphates and chlorides, e.g., sodium sulphate.

Liquid detergent compositions as provided herein can also be in a "concentrated form." In one aspect, the liquid detergent compositions can contain a lower amount of water, compared to conventional liquid detergents. In alternative aspects, the water content of the concentrated liquid detergent is less than 40%, or, less than 30%, or, less than 20% by weight of the detergent composition. Detergent compounds as provided herein can comprise formulations as described in WO 97/01629.

Hydrolases as provided herein can be useful in formulating various cleaning compositions. A number of known compounds are suitable surfactants including nonionic, anionic, cationic, or zwitterionic detergents, e.g., as disclosed in U.S. Pat. Nos. 4,404,128; 4,261,868; 5,204,015. In addition, enzymes as provided herein can be used, for example, in bar or liquid soap applications, dish care formulations, contact lens cleaning solutions or products, peptide hydrolysis, waste treatment, textile applications, as fusion-cleavage enzymes in protein production, and the like. Hydrolases as provided herein may provide enhanced performance in a detergent composition as compared to another detergent protease, that is, the enzyme group may increase cleaning of certain enzyme sensitive stains such as grass or blood, as determined by usual evaluation after a standard wash cycle. Hydrolases as provided herein can be formulated into known powdered and liquid detergents having pH between 6.5 and 12.0 at levels of about 0.01 to about 5% (for example, about 0.1% to 0.5%) by weight. These detergent cleaning compositions can also include other enzymes such as other known esterases, phospholipases, proteases, amylases, cellulases, lipases or endoglycosidases, as well as builders and stabilizers.

Treating Foods and Food Processing

The hydrolases as provided herein can be used for separation of components of plant cell materials. For example, hydrolases as provided herein can be used in the separation of protein-rich material (e.g., plant cells) into components, e.g., sucrose from sugar beet or starch or sugars from potato, pulp or hull fractions. In one aspect, hydrolases as provided herein can be used to separate protein-rich or oil-rich crops into valuable protein and oil and hull fractions. The separation process may be performed by use of methods known in the art.

The hydrolases as provided herein can be used in the preparation of fruit or vegetable juices, syrups, extracts and the like to increase yield. The hydrolases as provided herein can be used in the enzymatic treatment (e.g., hydrolysis of proteins) of various plant cell wall-derived materials or waste materials, e.g. from wine or juice production, or agricultural residues such as vegetable hulls, bean hulls, sugar beet pulp, olive pulp, potato pulp, and the like. The hydrolases as provided herein can be used to modify the consistency and appearance of processed fruit or vegetables. The hydrolases as provided herein can be used to treat plant material to facilitate processing of plant material, including foods, facilitate purification or extraction of plant components. The hydrolases as provided herein can be used to improve feed value, decrease the water binding capacity, improve the degradability in waste water plants and/or improve the conversion of plant material to ensilage, and the like.

Animal Feeds and Food or Feed Additives

In certain embodiments, provided herein are methods for treating animal feeds and foods and food or feed additives using hydrolases as provided herein, animals including mammals (e.g., humans), birds, fish and the like. In other embodiments, provided herein are animal feeds, foods, feed and food supplements, and additives comprising hydrolases as provided herein.

In certain embodiments, provided herein are hydrolases for use in the modification of animal feed or a food, e.g., to process the food or feed either in vitro (by modifying components of the feed or food) or in vivo. In another aspect, hydrolase as provided herein can be supplied by expressing the enzymes directly in transgenic feed crops (as, e.g., transgenic plants, seeds and the like), such as corn, soy bean, rape seed, lupin and the like. In one aspect, provided herein are transgenic plants, plant parts and plant cells comprising a nucleic acid sequence encoding a polypeptide as provided herein. In one aspect, the nucleic acid is expressed such that the hydrolase as provided herein is produced in recoverable quantities. The hydrolase can be recovered from any plant or plant part. Alternatively, the plant or plant part containing the recombinant polypeptide can be used as such for improving the quality of a food or feed, e.g., improving nutritional value, palatability, and rheological properties, or to destroy an antinutritive factor.

Interesterification

In one aspect, the methods and compositions provided herein can be used to modify the properties of triacylglyceride mixtures, and, in one aspect, their consistency. In one aspect, an enzyme as provided herein can be used in the presence of a catalyst such as sodium metal or sodium methoxide to promote acyl migration between glyceride molecules such that the products consist of glyceride mixtures in which the fatty acyl residues are randomly distributed among the glyceride molecules.

In one aspect, the enzymes as provided herein can be used to produce interesterification products under reaction conditions in which hydrolysis of fat is minimized so that lipase-catalyzed interesterification becomes the dominant reaction. These conditions may include, for example, restricting the amount of water in the system.

In one aspect, enzymes as provided herein can be used to catalyze interesterification reactions using mixtures of triacylglycerides and free fatty acids, as described, e.g., in EP 0 093 602 B2. In these cases, free fatty acid can be exchanged with the acyl groups of the triacylglycerides to produce new triacylglycerides enriched in the added fatty acid. In one aspect, 1,3-specific lipases as provided herein can be used to confine the reaction to the 1- and 3-positions of the glycerides, which allow to obtain a mixture of triacylglycerides unobtainable by chemical interesterification or reaction with a non-specific lipase. In one aspect, non-specific lipases are used to attain results similar to chemical interesterification.

The ability to produce novel triacylglyceride mixtures using positionally specific lipases as provided herein is useful to the oils and fats industry because some of these mixtures have valuable properties. One example is the 1,3-specific lipase-catalyzed interesterification of 1,3-dipalmitoyl-2-monoleine (POP), which is the major triacylglyceride of the mid-fraction of palm oil, with either stearic acid or tristearin to give products enriched in the valuable 1-palmitoyl-3-stearoyl-2-monoleine (POSt) and 1,3-distearoyl-2-monoleine (StOSt). POSt and StOSt are the important components of cocoa butter. Thus, one aspect as provided herein provides an interesterification reaction to produce cocoa butter equivalents from cheap starting materials.

In one aspect, provided herein are methods of production of a hard fat replacer using the 1,3-specific lipases as provided herein. In one aspect, a hard fat replacer comprises a mixture of palm mid-fraction and StOSt, POSt or StOSt/POSt of at least 85% purity.

The invention will be further described with reference to the following examples; however, it is to be understood that the invention is not limited to such examples.

EXAMPLES

Example 1

Exemplary Lipase-Saturase Assays

The following example describes exemplary assays to screen for a hydrolase e.g., a lipase, a saturase, a palmitase and/or a stearatase activity. In one aspect, these exemplary assays can be used as routine screens to determine if a polypeptide is within the scope as provided herein. Such assays include use of pH indicator compounds to detect cleavage of fatty acids from triacylglycerides, spectrophotometric methods, HPLC, GC, MS, TLC and others. Jaeger (1994) FEMS Microbiol. Rev. 15:29-63; Ader (1997) Methods Enzymol. 286:351-386; Vorderwülbecke (1992) Enzyme Microb. Technol. 14:631-639; Renard (1987) Lipids 22: 539-541.

Screening for Lipase/Esterase Activity

Colonies are picked with sterile toothpicks and used to singly inoculate each of the wells of 96-well microtiter plates. The wells contained 250 µL of LB media with 100 µg/mL ampicillin, 80 µg/mL methicillin, and 10% v/v glycerol (LB Amp/Meth, glycerol). The cells were grown overnight at 37° C. without shaking. Each well thus contained a stock culture of E. coli cells, each of which contained a pBLUESCRIPT™ with a unique DNA insert.

The 96-well plates were used to multiply inoculate a single plate (the "condensed plate") containing in each well 200 µL of LB Amp/Meth, glycerol. This step was performed using the High Density Replicating Tool (HDRT) of a BIOMEK™ (Beckman Coulter, Inc., Fullerton, Calif.) with a 1% bleach, water, isopropanol, air-dry sterilization cycle in between each inoculation. Each well of the condensed plate thus contained 10 to 12 different pBLUESCRIPT™ clones from each of the source library plates. The condensed plate was grown for 16 hours at 37° C. and then used to inoculate two white 96-well microtiter daughter plates (Polyfiltronics, Inc., Rockland Mass.) containing in each well 250 µL of LB Amp/Meth (no glycerol). The original condensed plate was put in storage –80° C. The two condensed daughter plates were incubated at 37° C. for 18 hours.

The short chain esterase '600 µM substrate stock solution' was prepared as follows: 25 mg of each of the following compounds was dissolved in the appropriate volume of DMSO to yield a 25.2 mM solution. The compounds used were 4-methylumbelliferyl proprionoate, 4-methylumbelliferyl butyrate, and 4-methylumbelliferyl heptanoate. Two hundred fifty microliters of each DMSO solution was added to ca 9 mL of 50 mM, pH 7.5 HEPES buffer which contained 0.6% of Triton X-100 and 0.6 mg per ML of dodecyl maltoside (Anatrace, Maumee, Ohio). The volume was taken to 10.5 mL with the above HEPES buffer to yield a slightly cloudy suspension.

The long chain '600 µM substrate stock solution' was prepared as follows: 25 mg of each of the following compounds was dissolved in DMSO to 25.2 mM as above. The compounds used were 4-methylumbelliferyl elaidate, 4-methylumbelliferyl palmitate, 4-methylumbelliferyl oleate, and 4-methylumbelliferyl stearate. All required brief warming in a 70° C. bath to achieve dissolution. Two hundred fifty microliters of each DMSO solution was added to the HEPES buffer and diluted to 10.5 mL as above. All seven umbelliferyl derivatives were obtained from Sigma Chemical Co. (St. Louis, Mo.).

Fifty µL of the long chain esterase or short chain esterase '600 µM substrate stock solution' was added to each of the wells of a white condensed plate using the BIOMEK™ to yield a final concentration of substrate of about 100 µM. The fluorescence values were recorded (excitation=326 nm, emission=450 nm) on a plate-reading fluorometer immediately after addition of the substrate. The plate was incubated at 70° C. for 60 minutes in the case of the long chain substrates, and 30 minutes at RT in the case of the short chain substrates. The fluorescence values were recorded again. The initial and final fluorescence values were compared to determine if an active clone was present.

To isolate the individual clone which carried the activity, the Source GenBank plates were thawed and the individual wells used to singly inoculate a new plate containing LB Amp/Meth. As above, the plate was incubated at 37° C. to grow the cells, 50 μL of 600 μM substrate stock solution was added using the BIOMEK™ and the fluorescence was determined. Once the active well from the source plate was identified, cells from this active well were streaked on agar with LB/Amp/Meth and grown overnight at 37° C. to obtain single colonies. Eight single colonies were picked with a sterile toothpick and used to singly inoculate the wells of a 96-well microtiter plate. The wells contained 250 μL of LB Amp/Meth. The cells were grown overnight at 37° C. without shaking. A 200 μL aliquot was removed from each well and assayed with the appropriate long or short chain substrates as above. The most active clone was identified and the remaining 50 μL of culture was used to streak an agar plate with LB/Amp/Meth. Eight single colonies were picked, grown and assayed as above. The most active clone was used to inoculate 3 mL cultures of LB/Amp/Meth, which were grown overnight. The plasmid DNA was isolated from the cultures and utilized for sequencing.

Example 2

Exemplary Protocols for Determination by LCMS of Released Fatty Acid Profile Resulting from Enzymatic Hydrolysis of Vegetable Oil The following example describes exemplary methods (protocols) for conducting enzymatic hydrolysis of vegetable oil, such as soy oil (used in this example), (including enzyme preparation) using, for example, enzymes as provided herein. This example also describes exemplary methods (protocols) for detecting and quantifying the fatty acids released from the oil. The method is described using the lipase SEQ ID NO:2, but is applicable to other enzymes, including the enzymes as provided herein, e.g., the exemplary enzymes having a sequences as set forth in SEQ ID NO:2 and having one, two, three, four, five, six, seven, eight, nine, ten, eleven or twelve or more or all the amino acid residue modifications described in Table 3 or Table 4.

Expression of Protein in 96 Deep Well Plate:
1. Grow E. coli lipase clones overnight at 30° C. in 1 mL TB medium containing carbenicillin (100 μg/mL) in deep 96-well plates with. Record location and identity of clones.
2. Inoculate fresh deep 96-well plates containing TB medium (1 mL; 100 μg/mL carbenicillin) with the liquid cultures (10 μL/well).
3. Incubate culture overnight at 30° C. while shaking at 200 rpm.
4. Induce protein expression by transfer of 500 μL of each overnight cultures into a fresh 96 well plate containing of TB medium (500 μL/well; 100 μg/mL carbenicillin) and anhydrous tetracycline (200 ng/mL).
5. Incubate at 30° C. for 2 hours with shaking at 200 rpm
6. Harvest cells by centrifuging each plate for 10 minutes at 3000×g. Remove supernatant. Cell pellets may be used immediately for oil assays or stored at −20° C. for later use.

Enzymatic Oil Hydrolysis Reaction:
1. Add 100 μL of B-PER™ (Pierce Chemical, Rockford, Ill.) to each cell pellet. If pellets are stored at −20° C., allow to thaw for 10 min at room temperature before addition of B-PER™.
2. Add 400 μL of soy oil to each well of deep 96-well plate.
3. Add several beads (glass 710-1180 μm) per well. Seal plates with CAPMATS™ (Whatman, Florham Park, N.J.).
4. Cells are lysed and an oil/enzyme/buffer emulsion is generated using a mixer mill (Retsch Inc., Newtown, Pa.). Put a pair of sealed plates into the Mixer Mill and shake for 30 seconds at a frequency of 30 cycles/second.
5. Replace the CAPMATS™ seals with a gas permeable seal.
6. Incubate the plates for 2 hours at 37° C. while shaking at 200 rpm.

Fatty Acid Extraction:
1. Add 1 mL of extraction solvent ($CHCl_3$:MeOH:4N HCl (2:1:0.075)) to each well of the deep 96 well plate.
2. Pipet mixture up and down several times until it appears homogeneous.
3. Cover the plates with an aluminum foil seal.
4. Centrifuge for 5 minutes at 3000×g. Cut open seal using razor blade.
5. Penetrate pipet tip through upper phase and transfer 5 μL of lower phase to a new deep 96-well plate containing 995 μL/well of MeOH (i.e. a 1/200 dilution of the lower phase). Be careful not to contaminate with upper phase. Store separated extraction mixtures at 4° C.
6. Transfer 150 μL the 1/200 dilution of all samples to a polystyrene 96 well plate.
7. To prevent evaporation, heat-seal the plates. Be sure the seal does not contact MeOH as this will prevent proper adhesion.
8. Analyze the samples by LC/MS.

LC/MS Analysis:
1. Samples submitted in 96-well plate format are injected via an HTCPAL™ auto sampler (LEAP Technologies, Carrboro, N.C.) into an isocratic mixture of $H_2O$/MeCN (10/90, v/v) and 0.1% formic acid, delivered by LC-10ADVP™ pumps (Shimadzu, Kyoto, Japan) at 1.2 mL/min.
2. Separation is achieved with a SYNERGI MAX-RP™ (Phenomenex, Sutter Creek Calif.) 150×2.00 mm column and detection. Quantification is completed with an API 4000™ triple-quad mass spectrometer (Applied Biosystems, Foster, Calif.) using electrospray ionization (ESI) and multiple ion monitoring for masses 277, 279, 281, 255, 283 in the negative ion mode.
3. Instrumentation control and data generation is accomplished with ANALYST 1.3™ software (Applied Biosystems, Foster, Calif.).
4. LC/MS calibrated for each fatty acid in the range of 0.5 to 50 μg using standard samples (Sigma). This range best fits a quadratic regression standard curve which is used to calculate the amount of each fatty acid released in enzyme samples.

Example 3

Exemplary Protocols for HTP Screen of Lipase Evolution Libraries for Increased Selectivity for Hydrolysis of Palmitate or Stearate Esters Versus Oleate Esters The following example describes exemplary methods (protocols) for high through-put (HTP) screening of lipase "evolution libraries" for increased selectivity for hydrolysis of palmitate or stearate esters versus oleate esters. This exemplary method (protocol/HTP screen) describes screening lipase evolution libraries derived from SEQ ID NO:2, but is applicable to other enzymes, including the enzymes as provided herein, e.g., the exemplary enzymes having a sequences as set forth in SEQ ID NO:2 and having one, two, three, four, five, six, seven, eight, nine, ten, eleven or twelve or more or all the amino acid residue modifications described in Table 3 or Table 4; and this exemplary method (protocol) is applicable to other library types.

These exemplary HTP screens are conducted utilizing two fluorogenic substrates: palmitate or stearate methylumbelliferyl esters versus oleate methylumbelliferyl ester.

HTP Screen Flow:
1. Library clones are arrayed in microtiter plates and assayed in a primary HTP screen.
2. Clones identified as having improved selectivity are designated as primary hits.
3. Primary hits are re-arrayed in microtiter plates, and assayed in a secondary HTP screen.
4. Clones confirmed as having improved selectivity are designated as secondary hits.
5. Secondary hits are sequenced to identify sequence mutations present and assayed on oil (see separate protocol).

HTP Assay Protocol
1. Barcode label black 384-well assay plates; barcode label 384-well growth plates and fill 30 μL/well LB medium (100 μg/mL carbenicillin).
2. Pintool or cherry-pick clones into growth plates and grow overnight at 30° C. in a humidified incubator.
3. Induce lipase expression by addition of 30 μL/well LB medium (100 μg/mL carbenicillin) containing 4 μg/ml anhydrous tetracycline and incubate 2 hour at 30° C.
4. Lyse cells by adding 20 μl/well B-PER™ (Pierce Chemical, Rockford, Ill.); maintain at room temperature until placed on the robot.
5. Run lipase activity assay on robot (see below).
6. Clones identified as having increased selectivity for palmitate or stearate MeUMB esters over oleate MeUMB ester are designated as hits.
7. Cherry-pick hit clones into deep 96-well plates containing LB medium (1 mL/well; 100 μg/mL carbenicillin) and grow overnight at 30° C.
8. For primary hits, re-array in 384-well plates and repeat steps 1-8 in the secondary screen; designate hit clones as secondary hits.
9. For secondary hits, after step 8 submit for sequencing.

Automated HTP Screen Example Protocol
1. Apricot: Mix and transfer an aliquot (10 μL) of lysed cells from "Growth Plate" (see Steps 1-4 above) to each of two separate assay plates (1 & 2).
2. MULTIDROP™ (Thermo Electron Corporation, Milford, Mass.): Add 70 μL of substrate 1 (UMB-16:0) to assay plate 1; add 70 μL of substrate 2 (UMB-18:1) to assay plate 2
3. Incubate assay plates for 20 minutes at 37° C.
4. Read on fluorimeter: Excitation 360 nm and Emission 465 nm Secondary hit clones determined to have unique sequences are arrayed and grown in 96-well plates and assayed on soy oil (see below).

Structures of Fluorogenic Substrates used in HTP Screen

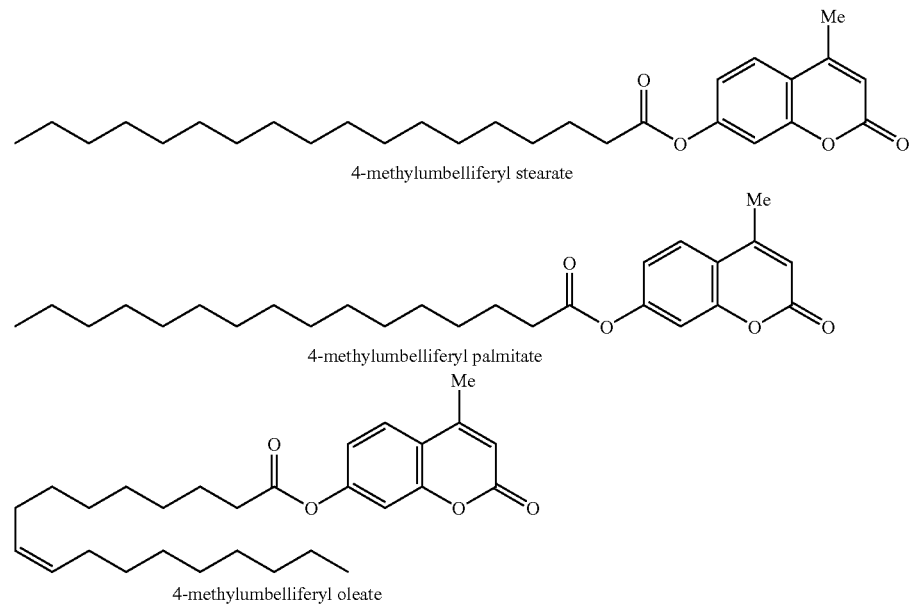

4-methylumbelliferyl stearate 4-methylumbelliferyl palmitate 4-methylumbelliferyl oleate Example 4

Exemplary Evolution for Improved Hydrolysis of Palmitate or Stearate Esters Using GSSM$^{SM}$ Technology The following example describes and summarizes the results of exemplary "enzyme evolution" and screening protocols that identified exemplary enzymes as provided herein, e.g., enzymes having a sequence as set forth in SEQ ID NO:2 but also having a residue modification as set forth in Table 3 or Table 4; or enzymes encoded by a nucleic acid having a sequence as set forth in SEQ ID NO:1 but also having a residue modification as set forth in Table 3 or Table 4. In one aspect, an exemplary screening assay to identify these exemplary enzymes as provided herein used soy oil as a substrate, and the fatty acids released (hydrolyzed) from the soy oil were characterized, e.g., as linolenic acid, linoleic acid, oleic acid, palmitic acid or stearic acid.

Soy oil has the following fatty acid distribution: Linolenic=8%; Linoleic=53%; Oleic=23%; Palmitic=12%;

Stearic=4%. Thus, if the percent of palmitic acid released (hydrolyzed) from soy oil by an exemplary enzyme as provided herein is greater than 12%, then that enzyme has a preference for hydrolyzing (releasing) palmitic acid.
Palmitase Screening: Making a "Palmitase Library"

A palmitase library of variants of SEQ ID NO:2 was made by GSSM$^{SM}$ technology (U.S. Pat. No. 6,171,820). Point mutations were introduced using degenerate oligonucleotides, one amino acid position at a time, so that each original codon is substituted with each of the 20 naturally-encoded amino acids. The mutated variants were transformed into the *Escherichia coli* host TOP 10 (Invitrogen, USA) for expression and screening. The library was constructed in an expression vector pASK-5, which was modified from the vector pASK-IBA (IBA GmbH, Germany). To make pASK-5, the original cloning linker was replaced with new cloning sites, specifically, the sequence from XbaI to HindIII of pASK-IBA was replaced with following sequence:

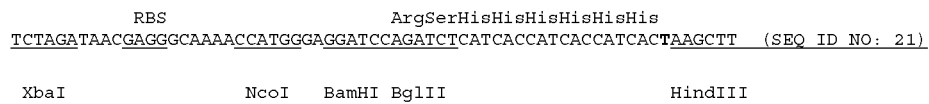

The expression of the GSSM$^{SM}$ variants was induced with anhydrotetracycline after the optimal host cell densities were achieved.

Enzymes having amino acid sequences generated by GSSM$^{SM}$ technology were screened by a high-through-put (HTP) screening protocol, e.g. the protocol described in Example 3, that determined what fatty acid was preferentially hydrolyzed from a fat—soy oil in this assay. The goal of the evolution project was to improve palmitate selectivity of the parental sequence, SEQ ID NO:2, on oil. The assay comprised contacting the new/sequence modified enzyme to soy oil, which comprises various fatty acids, including linolenic acid, linoleic acid, oleic acid, palmitic acid and stearic acid (see % distribution, listed above) and measuring the amount of each fatty acid hydrolyzed by each modified enzyme. A "library" of sequences were identified that enabled an enzyme to preferentially hydrolyze a palmitic acid (or a stearic acid, see below), from the soy oil (the so-called "Palmitate Library"):

Primary and secondary screens were conducted using an HTP screen e.g the method described in Example 3;

Sequencing of secondary hits identified amino acid mutations that resulted in the improved selectivity for palmitate hydrolysis versus oleate in the HTP screen compared with, for example the parental sequence, SEQ ID NO:2.

For each codon variant coding for an amino acid mutation, one clone was cherry-picked and arrayed in 96-well plates for assay on oil;

From the oil assays selectivity of the mutant enzymes for palmitate or stearate or other fatty acids was obtained (Table 3)

The top hit yielded palmitate as 59% of released fatty acids (FAs) versus (vs) 43% for SEQ ID NO:2 in the same assay; this corresponds to an increase in selectivity factor of 3.6 to 4.9;

Several clones also showed increases in stearate selectivity.

Table 1, below, summarizes GSSM$^{SM}$ mutations (see above) selected for inclusion in the "palmitate library" to be combined by GeneReassembly$^{SM}$ technology (see Example 5). In one exemplary assay, fourteen (14) single amino acid mutations were identified as yielding the greatest increases in palmitate hydrolysis in oil assays (see also Tables 1, 3 and 4, below). Residues are labeled according to the order that they occur in the parent SEQ ID NO:2 (see FIG. 7), amongst residues that yield significant increases in palmitate or stearate hydrolysis in oil assays. The "original AA" in SEQ ID NO:2 and beneficial mutations ("New Amino Acids"), i.e., exemplary sequences as provided herein, are given. In one aspect, the single mutations to arginine (R) at residue positions 163 and 164 can be included alternately such that this exemplary library will include clones with the sequences 163V-164D (SEQ ID NO:2), 163R-164D, and 163V-164R, but not the sequence 163R-164R.

TABLE 1

| Residue | Original Amino Acid | New Amino Acids |
|---------|---------------------|-----------------|
| 61      | D                   | A, E            |
| 72      | R                   | E, K            |
| 116     | E                   | A, Q, R, T, V   |
| 133     | S                   | A               |
| 151     | I                   | G, A            |
| 163     | V                   | R               |
| 164     | D                   | R               |

Figure 6A:
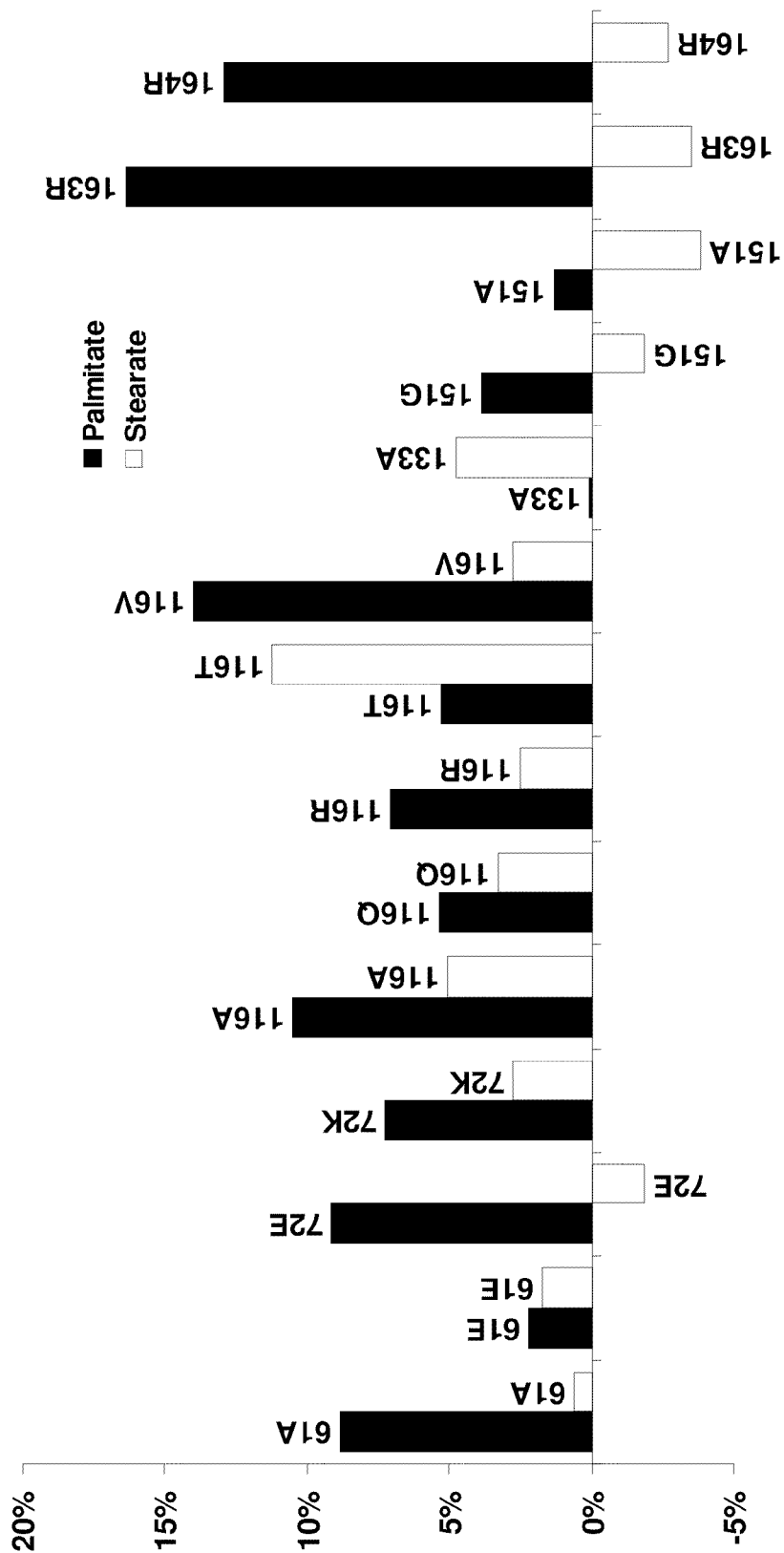
FIG. 6a illustrates the effects of exemplary palmitase GSSM$^{SM}$ mutations on palmitate and stearate hydrolysis relative to parental SEQ ID NO:2, as discussed in detail in Example 4, below.

FIG. 6a illustrates the effects of exemplary palmitase GSSM$^{SM}$ mutations on palmitate and stearate hydrolysis relative to parental SEQ ID NO:2. For each of the fourteen (14) single amino acid mutations selected for inclusion in the palmitase GeneReassembly$^{SM}$ library the percentage change in released palmitate and stearate, relative to parental SEQ ID NO:2, is graphed. Many of these mutations yielded significant increases in palmitate hydrolysis, accompanied by small to significant increases in stearate hydrolysis. However, several mutations cause slight decreases in stearate hydrolysis. Asterisks denote mutations identified as conveying increased saturase-type selectivity.
Stearate Screening: Making a "Stearate (Stearatase) Library"

A stearatase library of variants of SEQ ID NO:2 was made by GSSM$^{SM}$ technology (U.S. Pat. No. 6,171,820). Point mutations were introduced using degenerate oligonucleotides, one amino acid position at a time, so that each original codon could be substituted with each of the 20 naturally encoded amino acids. The mutated variants were transformed into the *Escherichia coli* host TOP10 (Invitrogen, USA) for expression and screening. The library was constructed in expression vector pASK-5 (as described above). The expression of the GSSM$^{SM}$ variants was induced with anhydrotetracycline after the optimal host cell densities were achieved.

Enzymes having amino acid sequences generated by GSSM$^{SM}$ technology were screened by a high-through-put (HTP) screening protocol, e.g. the protocol described in Example 3, that determined what fatty acid was preferentially hydrolyzed from a fat—soy oil in this assay. The assay comprised contacting the new/sequence modified enzyme to soy oil, which comprises various fatty acids, including linolenic acid, linoleic acid, oleic acid, palmitic acid and stearic acid (see % distribution, listed above) and measuring the amount of each fatty acid hydrolyzed by each modified enzyme. A "library" of sequences were identified that enabled an enzyme to preferentially hydrolyze a stearic acid (or a palmitic acid, see above), from the soy oil (the so-called "Stearate Library"):

Primary and secondary screens screens were conducted using an HTP screen e.g the method described in Example 3;

Sequencing of secondary hits identified amino acid mutations that resulted in the improved selectivity for stearate hydrolysis versus oleate in the HTP screen compared with, for example the parental sequence, SEQ ID NO:2.

For each codon variant coding for an amino acid mutation, one clone was cherry-picked and arrayed in 96-well plates for assay on oil.

Oil assays of sequenced secondary hits yielded the selectivity of the mutant enzymes for palmitate or stearate or other fatty acids (Table 3).

The top hit yielded stearate as 22% of released FAs vs 9% for the SEQ ID NO:2 in the same assay; this corresponds to an increase in selectivity factor of 2.3 to 5.5;

Several clones also showed increases in palmitate selectivity.

Table 2, below, summarizes GSSM$^{SM}$ mutations (see above) selected for inclusion in the "stearatase library" to be combined by GeneReassembly$^{SM}$ technology. In one exemplary assay, twenty two (22) single amino acid mutations were identified as yielding the greatest increases in stearate hydrolysis in oil assays (see also Tables 2, 3 and 4, below). Residues are labeled according to the order that they occur in the "parental" SEQ ID NO:2, amongst residues that yield significant increases in palmitate or stearate hydrolysis in oil assays. The "Original Amino Acid" in SEQ ID NO:2 and beneficial mutations ("New Amino Acids"), i.e., exemplary sequences as provided herein, are given. In one aspect, the single mutation to alanine (A) at residue position 223 is included as a fixed mutation so that every clone in this exemplary library contains this mutation.

TABLE 2

| Residue | Original Amino Acid | New Amino Acids |
|---------|--------------------|-----------------|
| 20      | I                  | L               |
| 62      | V                  | S               |
| 77      | G                  | P               |
| 83      | V                  | C               |
| 88      | D                  | H               |
| 113     | Y                  | G               |
| 116     | E                  | G, T            |
| 140     | H                  | K               |
| 146     | K                  | S               |
| 167     | I                  | S               |
| 180     | L                  | E               |
| 194     | E                  | M               |
| 211     | A                  | Q               |
| 212     | S                  | Y               |
| 215     | G                  | C, V, W         |
| 218     | A                  | H, S            |
| 223     | V                  | A               |
| 225     | A                  | Q, M            |

Figure 6B:
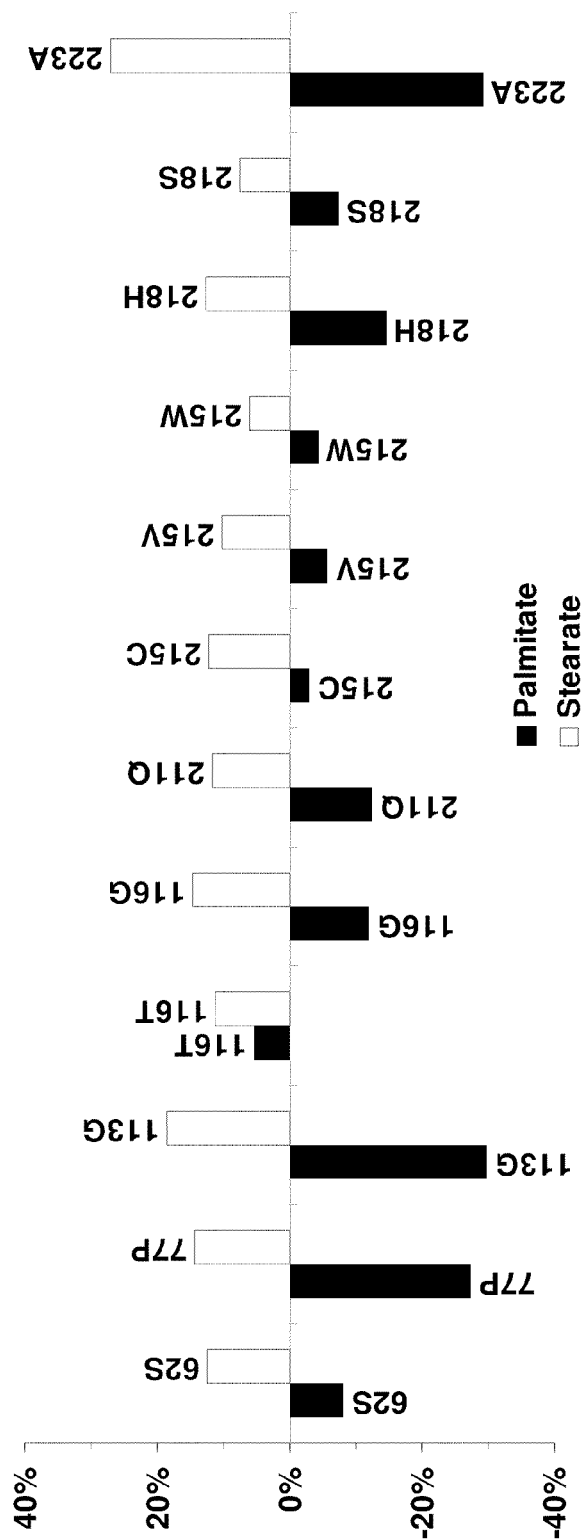
FIG. 6b illustrates the effects of exemplary stearatase GSSM$^{SM}$ mutations on palmitate and stearate hydrolysis relative to parental SEQ ID NO:2 as discussed in detail in Example 4, below.

FIG. 6b (see also above) illustrates the effects of twelve (12) of the twenty two (22) lead stearatase GSSM$^{SM}$ mutations on palmitate and stearate hydrolysis relative to parental SEQ ID NO:2. For each of the twelve (12) single amino acid mutations given in FIG. 6b and selected for inclusion in the stearatase GeneReassembly$^{SM}$ library the percentage change in released palmitate and stearate, relative to parental SEQ ID NO:2, is graphed. Most of these mutations yielded significant increases in stearate hydrolysis, but slight to significant decreases in palmitate hydrolysis. Asterisks denote mutations identified as conveying increased saturase-type selectivity i.e. increases in selectivity for hydrolysis of palmitate and stearate versus hydrolysis of unsaturated fatty acids in the oil e.g. oleate, linoleate and linolenate.

Summary

Screening of the "GSSM$^{SM}$ library" (see above where GSSM$^{SM}$ technology is described in detail) based on the parent SEQ ID NO:2 yielded single amino acid-mutant clones with significant improvements in palmitate and in stearate selectivity, and in saturate selectivity i.e. selectivity for hydrolysis of palmitate and stearate (e.g., selective hydrolysis of palmitate and/or stearate from soy oil);

Clones were found with significant improvements in stearate selectivity (selective hydrolysis of stearic acid over other fatty acids);

GSSM$^{SM}$ mutants with increased palmitate selectivity (selective hydrolysis of palmitic acid over other fatty acids) relative to the SEQ ID NO:2 enzyme were discovered.

Table 3 and Table 4, below, describe (further summarize) the sequences of the exemplary hydrolase enzymes as provided herein, e.g., the exemplary enzymes having a sequence as set forth in SEQ ID NO:2 and having at least one (one, several or all) of the amino acid residue changes described in the tables. Table 3 and Table 4 also summarize activity data for selected exemplary enzymes; the data including matching particular exemplary enzymes with their positive hydrolase activity comprising catalysis of hydrolysis of (release of) a palmitate or a stearate fatty acid from soy oil, as identified by a high throughput (HTP) screening protocol, as described above.

In Table 3 and Table 4, the term "Original Amino Acid" indicates the targeted amino acid residue (indicated under "Amino Acid residue") in the "parent" enzyme SEQ ID NO:2 ("targeted" for change); and term "New Amino Acids" indicates the newly designed amino acid residue (which replaced the corresponding "targeted" residue in the "old sequence") in the exemplary (new) enzyme as provided herein. Listing the "New Amino Acid" reside under the "stearate" versus the "palmitate" column indicates which of two high throughput (HTP) fatty acid screens (i.e., release of palmitic acid in one screen, and release of stearic acid in the other screen, see Example 3) was used to detect (identify) a particular enzyme with the indicated residue variation (new enzyme sequence, "New Amino Acid" reside).

For example, in the first row in Table 3, at amino acid residue 7, the tyrosine (or "Y") from the "parent" enzyme SEQ ID NO:2 is replaced by an arginine (or "R") amino acid residue, and this new enzyme (Y7R) has activity that differs from that of the parent enzyme (see Table 3); for example, the "Oil Data" summarizes the substrate (fatty acid) preference of the new enzyme (e.g., the Y7R enzyme) by listing the released (hydrolyzed) fatty acids generated when the enzyme was exposed to (contacted with) soy oil (assays described above), noting that the substrate soy oil has several possible hydrolyzable fatty acid constituent groups, including linolenic acid, linoleic acid, oleic acid, palmitic acid, stearic acid.

For example, in the first row, for the Y7R enzyme, 8.3% of the released fatty acids (from the reacted soy oil) were linolenic acid, 22.1% of the released fatty acids were linoleic acid; 19.7% of the released fatty acids were oleic acid; 41.5% of the released fatty acids were palmitic acid; 8.4% of the released fatty acids were stearic acid (these four numbers add up to 100%).

The P+S column adds up both the P and S data points to summarize how much of the total fatty acids released were palmitic acid and stearic acid (41.5% plus 8.4%=49.9% of the fatty acids hydrolyzed were palmitic acid and stearic acid, or "P+S").

TABLE 3

HTP Screen Hits

| Amino Acid Residue | Original Amino Acid | Palmitate New Amino Acid | Stearate New Amino Acid | P + S |
|---|---|---|---|---|
| 7 | Y | R | | 49.9% |
| 8 | G | E, A218R | | |
| 12 | R | | F | 47.8% |
| | | | K | 54.2% |
| | | | L | 45.4% |
| | | | M | 43.3% |
| 16 | D | M | | 43.2% |
| 18 | P | | G | 41.8% |
| 20 | I | | L | 50.3% |
| | | | V | 44.6% |
| 22 | T | | M, G215V | 52.1% |
| 27 | G | Q | | 57.2% |
| | | S | | 43.6% |
| 29 | A | | G | 51.5% |
| 32 | G | | E | scale |
| | | | D, L180E | 44.6% |
| 34 | L | | E | 45.8% |
| | | | V | scale |
| 36 | D | | A | 51.0% |
| | | | G | 50.9% |
| 40 | V | | P | 32.2% |
| 42 | V | | I | 47.2% |
| 43 | | | L | 47.8% |
| | L | V | | 51.5% |
| 45 | G | A | | 44.4% |
| | | L | | 52.7% |
| 48 | A | | G | 45.4% |
| | | | V | 70.1% |
| | | | V | 55.7% |
| | | | T | 33.60% |
| 54 | S | H | | 55.6% |
| 61 | D | A | | 60.5% |
| | | E | | 55.0% |
| | | S | | 49.8% |
| 62 | V | E | E | 53.0% |
| | | A | | 56.6% |
| | | G | | 56.5% |
| | | M | | 51.9% |
| | | N | | 49.7% |
| | | Q | | 52.4% |
| | | S | | 55.5% |
| | | T | | 50.7% |
| | | | D | 52.5% |
| | | | L | |
| | | | W | 50.2% |
| 66 | A | | N | 54.2% |
| | | | R | 52.1% |
| 72 | R | E | | 58.3% |
| | | K | | 61.0% |
| | | P | | 27.2% |
| | | S | | 55.3% |
| | | T | | 55.9% |
| | | Y | | 50.1% |
| 74 | F | I | | 53.8% |
| | | L | | 54.8% |
| | | P | | 52.3% |
| | | R | | 50.5% |
| 77 | G | P | | 38.1% |
| 78 | I | | D | 47.1% |
| | | | E | 37.1% |
| | | | P | 40.9% |
| 80 | G | P | | 51.9% |
| 82 | L | | P | 37.3% |
| 83 | V | C | | 47.7% |
| | | M | | 59.3% |
| 84 | D | V | | 40.2% |
| 87 | V | | A | 49.2% |
| | | | C | 46.1% |
| | | | D | 43.9% |
| | | | E | 46.6% |
| | | | G | |
| | | | P | 53.3% |
| | | | S | 45.2% |
| | | | T | 42.8% |
| | | | H | 52.9% |
| | | | N | 50.3% |
| 88 | D | | E | 44.6% |
| | | | F | 50.3% |
| | | | H | 45.9% |
| | | | L | 49.1% |
| | | | P | 59.6% |
| | | | P | 48.9% |
| | | | Q | 47.1% |
| 89 | R | S | | 54.5% |
| 92 | A | | D | 47.3% |
| | | | E | 59.3% |
| | | | R | 42.6% |
| | | | S | 48.7% |
| | | | T | 52.1% |
| | | | V | 57.5% |
| 93 | V | | M | 48.2% |
| 96 | A | C | C | 51.4% |
| | | I | I | scale |
| | | S | S | 46.8% |
| 98 | G | A | | 45.0% |
| | | L | | scale |
| 101 | K | | A | 49.8% |
| 103 | I | | L | 36.8% |
| 107 | W | | P | 46.20% |
| | | | A | 39.5% |
| | | | C | 39.4% |
| | | | G | 47.5% |
| | | | H | 42.0% |
| | | | R | 68.0% |
| | | | S | 36.8% |
| | | | L | 64.8% |
| | | | P, E217Q | 46.2% |
| | | | V | 37.8% |
| | | | V, E217Q | 44.80% |
| 108 | S | T, A218T | stop | 19.0% |
| | | | A | 43.0% |
| | | | C | 26.0% |
| | | | G | 47.5% |
| | | | K | 57.8% |
| | | | L | 44.0% |
| | | | P | 56.9% |
| | | | Q | 58.6% |
| | | | R | 54.7% |
| | | | V | 53.4% |
| | | | E, E217Q | 46.50% |
| 109 | L | | M | 49.0% |
| 110 | G | | L | 54.4% |
| 113 | Y | | E | 35.8% |
| | | | G | 39.8% |
| | | F | | 36.5% |
| 116 | E | A | | 66.6% |
| | | F | | 54.7% |
| | | G | | 53.8% |
| | | H | | 57.9% |
| | | L | | 58.5% |
| | | L | | 55.1% |
| | | P | | 58.0% |
| | | Q | | 59.6% |
| | | Q | | 60.5% |
| | | R, H140R | | 60.6% |
| | | R | | 61.8% |
| | | S | | 58.6% |
| | | S | | 59.7% |
| | | T | | 67.6% |
| | | V | | 67.8% |
| | | R, H140R | | |
| 117 | L | R, I161L | | 54.1% |
| | | | R | 51.6% |
| 120 | K | I | | 46.7% |
| | | L | L | 60.8% |
| | | F | | 52.6% |
| | | M | | 49.9% |
| | | S | S | 53.3% |

TABLE 3-continued

| | | | | |
|---|---|---|---|---|
| 132 | G | | D, S212A | 56.2% |
| 133 | S | | A | 53.2% |
| | | | A | 55.8% |
| | | | G | 45.6% |
| | | | P | 56.0% |
| | | | R | 51.7% |
| | | | T | 54.9% |
| | | | V, L139, H | 53.2% |
| 134 | P | | G | 7.2% |
| | | | R | |
| 135 | F | | K | 51.8% |
| 139 | L | | H, S133V | 53.2% |
| 140 | H | R, E116R | K | 45.5% |
| 141 | A | | R | 40.2% |
| | | | T | 43.3% |
| 142 | N | | M | 46.1% |
| | | | R | 53.8% |
| | | | S | 43.2% |
| | | | T | 64.3% |
| 144 | A | | T, N142K | 33.9% |
| 146 | K | | S | 50.2% |
| | | | G | 49.4% |
| | | | L | 51.6% |
| | | A | | 52.2% |
| 147 | I | | F | 56.5% |
| | | | F | 50.5% |
| | | | L | 52.2% |
| 150 | A | | L | 59.7% |
| | | | L | 53.3% |
| 151 | I | | A | 48.6% |
| | | | G | 53.0% |
| | | | H | 60.0% |
| | | | P | 33.7% |
| | | | S | 52.2% |
| | | | T | 49.2% |
| 152 | N | | E | 28.0% |
| | | | G | 53.0% |
| | | | H | 46.7% |
| | | | M | 35.7% |
| | | | R | 21.1% |
| 155 | T | C | | 51.1% |
| 157 | D | S | | 50.4% |
| | | G | | 48.7% |
| | | T | | 54.7% |
| 158 | N | A | | 51.2% |
| 159 | L | M | | 51.5% |
| 160 | P | T | | 52.8% |
| 161 | I | | L, L117R | 54.1% |
| | | | L | 51.6% |
| 162 | P | | K | scale |
| | | | R | scale |
| 163 | V | | E | 55.7% |
| | | | R | 63.9% |
| | | | T | 49.7% |
| 164 | D | | A | 42.1% |
| | | | E | scale |
| | | | H | 39.8% |
| | | | K | 49.4% |
| | | | L | scale |
| | | | R | 61.3% |
| | | | S | 47.9% |
| | | | T | 53.0% |
| | | | V | 42.3% |
| | | | W | scale |
| 166 | Q | | G | 49.9% |
| | | | N | 41.3% |
| | | | R | scale |
| 167 | I | R | R | 53.3% |
| | | S | S | 47.3% |
| 170 | P | | Q | 45.6% |
| | | | A | 52.5% |
| | | | A, S212H | 34.7% |
| 171 | V | | K | 34.1% |
| 172 | R | P | | 51.7% |
| | | Q | | 54.9% |
| | | S | | 40.2% |
| 178 | S | | K | 50.6% |
| 180 | L | | E | 54.0% |
| | | | H | 44.6% |
| | | | Q | scale |

TABLE 3-continued

| | | | | |
|---|---|---|---|---|
| | | | F, G32D | 44.6% |
| 183 | V | | I | scale |
| 193 | P | | | 49.4% |
| 194 | E | | A | scale |
| | | | M | 47.9% |
| | | | Q | scale |
| | | | D, P193S | 49.4% |
| 197 | D | K | | 39.4% |
| 198 | E | stop | | 56.1% |
| 200 | L | | V | 55.3% |
| 204 | V | | L | 45.9% |
| | | | R | 45.7% |
| 210 | A | V | | 50.2% |
| 211 | A | | E | 35.3% |
| | | | H | 48.1% |
| | | | K | 39.4% |
| | | | L | 45.0% |
| | | | Q | 50.3% |
| | | | F | 32.6% |
| | | | N | 46.1% |
| | | | P | 49.2% |
| | | | R | 55.2% |
| | | | W | 47.8% |
| | | | Y | 48.9% |
| | | | T | 50.8% |
| | | | S | 52.7% |
| | | | S | 52.7% |
| | | | I | 49.8% |
| | | | T, E217A | 46.2% |
| 212 | S | | C | 49.3% |
| | | | R | 50.3% |
| | | | A, G132D | 53.2% |
| | | | A | 36.8% |
| | | | E | 36.6% |
| | | | G | 44.3% |
| | | | H | 46.5% |
| | | | L | 53.2% |
| | | | P | 12.2% |
| | | | Q | 41.8% |
| | | | R | 50.2% |
| | | | T | 53.7% |
| | | | V | 38.7% |
| | | | W | 48.4% |
| | | | Y | 47.1% |
| | | | H, P170A | 34.7% |
| 213 | K | | I | 47.9% |
| | | | G | 57.7% |
| | | | T | 56.7% |
| | | | T | 55.5% |
| | | | stop | |
| 214 | T | | C | 51.6% |
| | | | G | 53.0% |
| | | V | V | 52.2% |
| | | | V | 54.5% |
| | | | P | 51.9% |
| | | | N | 56.9% |
| | | | R | 55.1% |
| | | | Y | 62.7% |
| | | | Y | 62.7% |
| 215 | G | | A | 56.6% |
| | | | I | 54.1% |
| | | | L | 29.9% |
| | | | H | 50.2% |
| | | | S | 52.1% |
| | | | M | 47.9% |
| | | | V | 55.6% |
| | | | P | 47.3% |
| | | | C | 60.4% |
| | | | W | 52.8% |
| | | | stop | 53.9% |
| | | | V, T22M | 52.1% |
| 216 | A | | T | 50.9% |
| | | | R | 41.9% |
| | | | Y | 34.8% |
| | | V | V | 56.9% |
| | | | C | 59.7% |
| | | S | S | 55.0% |
| | | | L | 55.6% |
| 217 | E | | Q | 36.6% |
| | | | R | 59.4% |

TABLE 3-continued

| Residue | | | | | | | | | | | | |
|---|---|---|---|---|---|---|---|---|---|---|---|---|
| | | S | | 53.5% | | | 6.1% | 23.2% | 18.2% | 47.1% | 5.4% | 52.5% |
| | | A | | 46.2% | | | 9.9% | 21.3% | 18.6% | 46.7% | 3.6% | 50.2% |
| | | G | | 44.8% | | 66 | 7.5% | 16.8% | 21.5% | 48.0% | 6.2% | 54.2% |
| | | P | | 46.2% | | | 11.4% | 18.0% | 18.5% | 47.2% | 4.8% | 52.1% |
| 218 | A | M | | 42.5% | | 72 | 7.9% | 16.5% | 17.3% | 54.2% | 4.1% | 58.3% |
| | | H | H | 49.1% | | | 4.4% | 20.7% | 13.9% | 52.2% | 8.7% | 61.0% |
| | | Q | Q | 47.7% | | | 6.8% | 44.6% | 21.4% | 20.2% | 7.0% | 27.2% |
| | | R | | 53.4% | | | 8.6% | 17.3% | 18.8% | 45.7% | 9.6% | 55.3% |
| | | W | | 51.9% | | | 7.5% | 17.4% | 19.3% | 45.1% | 10.7% | 55.9% |
| | | S | | 51.1% | | | 6.7% | 23.1% | 20.1% | 40.2% | 9.9% | 50.1% |
| | | T | | 50.0% | | 74 | 7.4% | 19.6% | 19.3% | 45.4% | 8.4% | 53.8% |
| | | K | | 52.4% | | | 8.0% | 19.3% | 18.0% | 44.8% | 10.0% | 54.8% |
| | | R, G8E | | | | | 8.7% | 20.5% | 18.6% | 42.2% | 10.1% | 52.3% |
| | | R, 228K | | | | | 7.1% | 21.7% | 20.7% | 41.1% | 9.4% | 50.5% |
| 223 | V | | A | 48.8% | | 77 | 10.3% | 41.0% | 10.6% | 17.8% | 20.4% | 38.1% |
| | | | M | 31.6% | | 78 | 9.8% | 22.5% | 20.6% | 43.8% | 3.4% | 47.1% |
| | | | R | 23.4% | | | 26.2% | 23.0% | 13.8% | 15.4% | 21.7% | 37.1% |
| | | | T | scale | | | 14.4% | 13.2% | 31.4% | 32.3% | 8.6% | 40.9% |
| 224 | A | | F | 49.5% | | 80 | 7.4% | 21.0% | 19.7% | 42.9% | 9.0% | 51.9% |
| | | | G | 58.2% | | 82 | 13.0% | 28.3% | 21.4% | 33.3% | 4.0% | 37.3% |
| | | | G | 48.4% | | 83 | 7.5% | 20.0% | 24.7% | 31.1% | 16.6% | 47.7% |
| | | | I | 41.7% | | | 6.8% | 18.6% | 15.3% | 51.5% | 7.8% | 59.3% |
| | | | Q | 46.4% | | 84 | 0.0% | 32.4% | 27.4% | 21.0% | 19.2% | 40.2% |
| | | | Y | 43.7% | | 87 | 12.7% | 11.9% | 26.2% | 39.7% | 9.5% | 49.2% |
| 225 | A | | G | 49.3% | | | 14.5% | 11.8% | 27.6% | 33.1% | 13.0% | 46.1% |
| | | | L | 54.3% | | | 9.3% | 12.3% | 34.5% | 32.7% | 11.2% | 43.9% |
| | | | M | 49.0% | | | 12.2% | 10.5% | 30.8% | 33.6% | 13.0% | 46.6% |
| | | | Q | 45.8% | | | 10.6% | 9.9% | 26.2% | 40.6% | 12.7% | 53.3% |
| | | | T | 43.2% | | | 14.4% | 12.4% | 27.9% | 36.0% | 9.2% | 45.2% |
| 226 | R | | H | 48.3% | | | 6.7% | 25.8% | 24.7% | 39.5% | 3.3% | 42.8% |
| | | | T | 41.2% | | | 4.4% | 23.2% | 19.4% | 48.5% | 4.5% | 52.9% |
| 227 | L | | R | 41.4% | | | 11.7% | 11.3% | 26.7% | 31.5% | 18.8% | 50.3% |
| | | | | | | 88 | 14.1% | 13.4% | 27.9% | 34.7% | 9.9% | 44.6% |

| Amino Acid Residue | Fatty Acids Released from Oil by Enzyme | | | | | |
|---|---|---|---|---|---|---|
| | Linolenic | Linoleic | Oleic | Palmitic | Stearic | P + S |
| 7 | 8.3% | 22.1% | 19.7% | 41.5% | 8.4% | 49.9% |
| 8 | | | | | | |
| 12 | 11.5% | 13.0% | 27.7% | 38.5% | 9.3% | 47.8% |
| | 5.2% | 22.1% | 18.5% | 47.2% | 7.1% | 54.2% |
| | 14.7% | 13.9% | 26.0% | 34.4% | 11.0% | 45.4% |
| | 10.3% | 12.8% | 33.6% | 34.0% | 9.4% | 43.3% |
| 16 | 7.2% | 25.1% | 24.6% | 36.1% | 7.1% | 43.2% |
| 18 | 12.5% | 20.0% | 25.7% | 36.2% | 5.6% | 41.8% |
| 20 | 8.2% | 21.2% | 20.3% | 38.5% | 11.7% | 50.3% |
| | 12.2% | 23.2% | 20.0% | 40.1% | 4.5% | 44.6% |
| 22 | 8.0% | 19.5% | 20.4% | 47.1% | 5.0% | 52.1% |
| 27 | 7.5% | 17.6% | 17.6% | 47.4% | 9.8% | 57.2% |
| | 9.1% | 23.2% | 24.0% | 35.8% | 7.8% | 43.6% |
| 29 | 9.0% | 19.9% | 19.6% | 40.9% | 10.7% | 51.5% |
| 32 | 19.8% | 29.1% | 34.0% | scale | 17.1% | scale |
| | 14.6% | 12.1% | 28.7% | 36.6% | 7.9% | 44.6% |
| 34 | 5.6% | 31.0% | 17.5% | 40.9% | 4.9% | 45.8% |
| | 21.1% | 35.3% | 37.1% | scale | 6.5% | scale |
| 36 | 7.1% | 22.1% | 19.9% | 43.8% | 7.1% | 51.0% |
| | 8.7% | 22.9% | 17.6% | 48.2% | 2.7% | 50.9% |
| 40 | 0.0% | 51.4% | 16.4% | 22.4% | 9.7% | 32.2% |
| 42 | 14.8% | 12.1% | 25.8% | 34.6% | 12.6% | 47.2% |
| 43 | 7.7% | 13.9% | 30.7% | 34.8% | 13.0% | 47.8% |
| | 8.9% | 19.9% | 19.7% | 44.4% | 7.1% | 51.5% |
| 45 | 10.3% | 23.8% | 21.5% | 38.5% | 5.9% | 44.4% |
| | 5.9% | 22.3% | 19.1% | 49.7% | 3.0% | 52.7% |
| 48 | 15.0% | 18.0% | 21.7% | 38.1% | 7.2% | 45.4% |
| | 4.3% | 11.5% | 14.2% | 61.0% | 9.1% | 70.1% |
| | 7.6% | 17.3% | 19.4% | 43.8% | 12.0% | 55.7% |
| | 23.6% | 13.4% | 29.3% | 22.5% | 11.1% | 33.60% |
| 54 | 8.1% | 19.3% | 17.0% | 48.4% | 7.3% | 55.6% |
| 61 | 5.6% | 19.8% | 14.1% | 53.9% | 6.6% | 60.5% |
| | 6.4% | 20.1% | 18.5% | 47.3% | 7.7% | 55.0% |
| | 7.7% | 19.9% | 22.6% | 41.5% | 8.3% | 49.8% |
| 62 | 7.6% | 18.8% | 20.7% | 44.6% | 8.3% | 53.0% |
| | 9.2% | 17.6% | 16.6% | 45.6% | 11.0% | 56.6% |
| | 6.7% | 20.3% | 16.5% | 47.6% | 8.8% | 56.5% |
| | 7.7% | 20.9% | 19.5% | 44.9% | 6.9% | 51.9% |
| | 7.9% | 21.7% | 20.7% | 40.7% | 9.0% | 49.7% |
| | 8.5% | 20.8% | 18.4% | 42.6% | 9.8% | 52.4% |
| | 5.4% | 26.0% | 13.1% | 37.0% | 18.5% | 55.5% |
| | 10.0% | 21.9% | 17.5% | 40.2% | 10.5% | 50.7% |
| | 13.4% | 15.2% | 21.0% | 36.7% | 13.6% | 50.3% |
| | 13.3% | 12.5% | 28.3% | 32.5% | 13.4% | 45.9% |
| | 13.0% | 9.2% | 28.7% | 40.3% | 8.8% | 49.1% |
| | 2.9% | 22.5% | 15.0% | 59.0% | 0.7% | 59.6% |
| | 4.2% | 35.5% | 11.4% | 35.6% | 13.3% | 48.9% |
| | 14.7% | 9.7% | 28.5% | 34.9% | 12.2% | 47.1% |
| 89 | 0.0% | 35.4% | 10.1% | 39.0% | 15.5% | 54.5% |
| 92 | 13.1% | 16.1% | 23.5% | 36.4% | 10.9% | 47.3% |
| | 12.0% | 10.4% | 18.2% | 48.0% | 11.4% | 59.3% |
| | 13.5% | 11.3% | 32.6% | 34.8% | 7.7% | 42.6% |
| | 8.3% | 25.1% | 17.9% | 46.1% | 2.6% | 48.7% |
| | 13.7% | 9.8% | 24.4% | 39.6% | 12.5% | 52.1% |
| | 4.9% | 20.0% | 17.5% | 51.7% | 5.8% | 57.5% |
| 93 | 11.7% | 9.3% | 30.8% | 40.8% | 7.4% | 48.2% |
| 96 | 10.3% | 12.4% | 25.9% | 37.8% | 13.6% | 51.4% |
| | 17.5% | 35.4% | 35.5% | scale | 11.6% | scale |
| | 12.5% | 12.0% | 28.7% | 33.3% | 13.6% | 46.8% |
| 98 | 13.4% | 19.9% | 21.7% | 39.7% | 5.3% | 45.0% |
| | 18.5% | 30.8% | 36.8% | scale | 13.9% | scale |
| 101 | 9.8% | 12.5% | 27.9% | 39.7% | 10.1% | 49.8% |
| 103 | 9.1% | 36.6% | 17.5% | 26.0% | 10.8% | 36.8% |
| 107 | 11.9% | 10.1% | 31.8% | 30.5% | 15.7% | 46.20% |
| | 0.0% | 20.4% | 40.1% | 12.1% | 27.4% | 39.5% |
| | 0.0% | 29.6% | 30.9% | 6.8% | 32.6% | 39.4% |
| | 0.0% | 29.6% | 22.9% | 9.5% | 38.0% | 47.5% |
| | 2.2% | 12.0% | 43.9% | 22.0% | 19.9% | 42.0% |
| | 30.4% | 12.5% | 46.2% | 10.9% | 57.1% | 68.0% |
| | 12.0% | 20.5% | 30.7% | 5.2% | 31.6% | 36.8% |
| | 5.0% | 16.0% | 14.2% | 62.2% | 2.6% | 64.8% |
| | 11.9% | 10.1% | 31.8% | 30.5% | 15.7% | 46.2% |
| | 0.0% | 15.6% | 46.5% | 10.2% | 27.6% | 37.8% |
| | 13.2% | 21.6% | 20.4% | 31.3% | 13.5% | 44.80% |
| 108 | 9.0% | 49.0% | 23.0% | 12.3% | 6.7% | 19.0% |
| | 0.0% | 51.0% | 6.1% | 33.1% | 9.9% | 43.0% |
| | 11.0% | 18.4% | 44.6% | 4.1% | 21.9% | 26.0% |
| | 0.0% | 29.6% | 22.9% | 9.5% | 38.0% | 47.5% |
| | 0.0% | 32.0% | 10.2% | 53.5% | 4.3% | 57.8% |
| | 0.0% | 45.6% | 10.4% | 38.2% | 5.8% | 44.0% |
| | 0.0% | 28.4% | 14.7% | 51.2% | 5.7% | 56.9% |
| | 5.4% | 18.9% | 17.2% | 52.8% | 5.8% | 58.6% |
| | 0.0% | 10.6% | 34.7% | 5.9% | 48.8% | 54.7% |
| | 0.0% | 21.9% | 24.7% | 32.7% | 20.8% | 53.4% |
| | 12.1% | 13.9% | 27.6% | 33.8% | 12.7% | 46.50% |
| 109 | 10.9% | 8.8% | 31.3% | 37.7% | 11.3% | 49.0% |
| 110 | 0.4% | 21.4% | 23.9% | 54.4% | 0.0% | 54.4% |

TABLE 3-continued

| | | | | | | |
|---|---|---|---|---|---|---|
| 113 | 5.0% | 44.1% | 15.1% | 21.0% | 14.8% | 35.8% |
| | 13.6% | 14.6% | 32.0% | 15.2% | 24.6% | 39.8% |
| | 13.9% | 25.9% | 23.7% | 36.5% | 0.0% | 36.5% |
| 116 | 4.8% | 17.4% | 11.2% | 55.5% | 11.1% | 66.6% |
| | 7.8% | 17.7% | 19.8% | 47.0% | 7.7% | 54.7% |
| | 3.3% | 26.7% | 16.1% | 33.1% | 20.7% | 53.8% |
| | 7.3% | 18.3% | 16.5% | 47.8% | 10.1% | 57.9% |
| | 4.3% | 22.9% | 14.2% | 54.3% | 4.2% | 58.5% |
| | 4.6% | 26.8% | 13.5% | 41.6% | 13.5% | 55.1% |
| | 0.0% | 32.4% | 9.6% | 38.3% | 19.8% | 58.0% |
| | 8.1% | 16.1% | 16.2% | 50.4% | 9.3% | 59.6% |
| | 7.3% | 20.5% | 11.7% | 49.2% | 11.2% | 60.5% |
| | 6.9% | 19.6% | 12.9% | 52.1% | 8.5% | 60.6% |
| | 5.4% | 17.4% | 15.4% | 50.8% | 11.0% | 61.8% |
| | 8.7% | 18.7% | 13.9% | 49.1% | 9.5% | 58.6% |
| | 6.7% | 22.8% | 10.8% | 46.3% | 13.4% | 59.7% |
| | 6.4% | 17.2% | 8.8% | 50.3% | 17.2% | 67.6% |
| | 5.6% | 17.6% | 9.0% | 59.0% | 8.8% | 67.8% |
| 117 | 6.2% | 21.4% | 18.3% | 46.0% | 8.0% | 54.1% |
| | 8.9% | 21.8% | 17.7% | 40.6% | 11.0% | 51.6% |
| 120 | 15.3% | 17.9% | 20.1% | 44.4% | 2.3% | 46.7% |
| | 7.5% | 15.4% | 16.3% | 51.3% | 9.5% | 60.8% |
| | 17.3% | 4.4% | 25.7% | 44.0% | 8.6% | 52.6% |
| | 4.1% | 25.5% | 20.5% | 36.9% | 13.0% | 49.9% |
| | 15.7% | 10.1% | 20.9% | 36.8% | 16.5% | 53.3% |
| 132 | 0.0% | 32.8% | 10.9% | 56.2% | 0.0% | 56.2% |
| 133 | 6.6% | 20.7% | 19.5% | 49.9% | 3.3% | 53.2% |
| | 9.3% | 18.3% | 16.5% | 45.1% | 10.8% | 55.8% |
| | 3.3% | 30.4% | 20.7% | 45.6% | 0.0% | 45.6% |
| | 0.0% | 34.3% | 9.6% | 56.0% | 0.0% | 56.0% |
| | 13.2% | 12.9% | 22.2% | 42.7% | 9.0% | 51.7% |
| | 10.1% | 11.6% | 23.3% | 46.5% | 8.4% | 54.9% |
| | 0.0% | 35.9% | 10.9% | 46.9% | 6.3% | 53.2% |
| 134 | 0.0% | 56.2% | 36.6% | 7.2% | 0.0% | 7.2% |
| 135 | 0.0% | 41.1% | 7.2% | 51.8% | 0.0% | 51.8% |
| 139 | 0.0% | 35.9% | 10.9% | 46.9% | 6.3% | 53.2% |
| 140 | 9.7% | 23.4% | 21.4% | 32.7% | 12.8% | 45.5% |
| 141 | 11.2% | 12.1% | 36.5% | 28.2% | 12.1% | 40.2% |
| | 14.7% | 13.9% | 28.1% | 38.3% | 5.0% | 43.3% |
| 142 | 16.3% | 18.8% | 18.8% | 10.3% | 35.7% | 46.1% |
| | 0.0% | 34.5% | 11.7% | 43.4% | 10.5% | 53.8% |
| | 8.6% | 15.8% | 32.5% | 22.8% | 20.4% | 43.2% |
| | 2.4% | 9.6% | 23.7% | 47.7% | 16.7% | 64.3% |
| 144 | 0.0% | 14.9% | 51.2% | 13.4% | 20.4% | 33.9% |
| 146 | 13.6% | 10.3% | 26.0% | 31.4% | 18.7% | 50.2% |
| | 12.6% | 12.4% | 25.5% | 36.5% | 12.9% | 49.4% |
| | 6.6% | 22.4% | 19.5% | 48.2% | 3.4% | 51.6% |
| | 9.0% | 19.7% | 19.0% | 41.7% | 10.5% | 52.2% |
| 147 | 8.0% | 17.9% | 17.6% | 48.8% | 7.7% | 56.5% |
| | 7.2% | 24.5% | 17.9% | 33.0% | 17.4% | 50.5% |
| | 9.5% | 20.6% | 17.7% | 42.2% | 9.9% | 52.2% |
| 150 | 7.7% | 15.1% | 17.5% | 50.4% | 9.2% | 59.7% |
| | 7.5% | 20.6% | 18.6% | 41.3% | 12.0% | 53.3% |
| 151 | 7.8% | 26.1% | 17.5% | 46.4% | 2.2% | 48.6% |
| | 5.0% | 29.6% | 12.4% | 48.9% | 4.1% | 53.0% |
| | 0.0% | 25.5% | 14.5% | 55.5% | 4.5% | 60.0% |
| | 0.0% | 14.2% | 52.1% | 20.0% | 13.7% | 33.7% |
| | 0.0% | 17.3% | 30.5% | 43.3% | 8.9% | 52.2% |
| | 8.0% | 22.7% | 20.2% | 44.0% | 5.1% | 49.2% |
| 152 | 0.0% | 56.3% | 15.7% | 23.6% | 4.4% | 28.0% |
| | 8.0% | 12.7% | 26.3% | 22.5% | 30.5% | 53.0% |
| | 0.0% | 27.1% | 26.2% | 26.2% | 20.5% | 46.7% |
| | 0.0% | 20.1% | 44.2% | 24.8% | 10.8% | 35.7% |
| | 9.5% | 31.2% | 38.3% | 2.2% | 18.9% | 21.1% |
| 155 | 18.4% | 4.9% | 25.6% | 41.5% | 9.6% | 51.1% |
| 157 | 7.9% | 19.5% | 22.2% | 41.2% | 9.2% | 50.4% |
| | 9.6% | 21.7% | 20.1% | 39.1% | 9.6% | 48.7% |
| | 7.2% | 25.2% | 13.0% | 34.9% | 19.8% | 54.7% |
| 158 | 14.0% | 1.2% | 33.5% | 42.8% | 8.5% | 51.2% |
| 159 | 6.3% | 28.4% | 13.8% | 36.7% | 14.8% | 51.5% |
| 160 | 5.6% | 20.8% | 20.8% | 46.6% | 6.2% | 52.8% |
| 161 | 6.2% | 21.4% | 18.3% | 46.0% | 8.0% | 54.1% |
| | 8.9% | 21.8% | 17.7% | 40.6% | 11.0% | 51.6% |
| 162 | 10.2% | 45.6% | 38.4% | scale | 5.7% | scale |
| | 22.1% | 39.2% | 32.7% | | 6.0% | scale |
| 163 | 5.9% | 22.9% | 15.5% | 47.4% | 8.3% | 55.7% |
| | 8.6% | 17.1% | 10.4% | 61.4% | 2.5% | 63.9% |
| | 6.4% | 23.5% | 20.4% | 45.7% | 4.0% | 49.7% |
| 164 | 8.4% | 26.9% | 22.6% | 39.2% | 2.9% | 42.1% |
| | 13.0% | 38.4% | 37.5% | scale | 11.2% | scale |
| | 9.6% | 29.5% | 21.1% | 35.1% | 4.7% | 39.8% |
| | 17.8% | 12.3% | 20.5% | 38.7% | 10.7% | 49.4% |
| | 23.3% | 23.1% | 39.1% | scale | 14.5% | scale |
| | 6.5% | 15.2% | 17.1% | 58.0% | 3.3% | 61.3% |
| | 9.1% | 23.1% | 19.8% | 40.1% | 7.8% | 47.9% |
| | 9.2% | 20.1% | 17.7% | 41.2% | 11.8% | 53.0% |
| | 15.6% | 17.7% | 24.4% | 29.9% | 12.4% | 42.3% |
| | 15.9% | 37.0% | 35.5% | scale | 11.7% | scale |
| 166 | 5.5% | 21.8% | 22.8% | 44.5% | 5.4% | 49.9% |
| | 14.6% | 22.3% | 21.8% | 33.2% | 8.1% | 41.3% |
| | 22.3% | 33.3% | 36.8% | scale | 7.6% | scale |
| 167 | 7.2% | 19.4% | 20.1% | 44.8% | 8.4% | 53.3% |
| | 10.0% | 21.9% | 20.7% | 36.3% | 11.0% | 47.3% |
| 170 | 12.5% | 12.4% | 29.4% | 37.8% | 7.8% | 45.6% |
| | 8.5% | 18.2% | 20.8% | 43.0% | 9.5% | 52.5% |
| | 3.5% | 22.0% | 39.8% | 8.9% | 25.9% | 34.7% |
| 171 | 8.0% | 22.4% | 35.5% | 33.4% | 0.7% | 34.1% |
| 172 | 8.0% | 18.8% | 21.4% | 43.6% | 8.1% | 51.7% |
| | 7.4% | 19.1% | 18.6% | 45.1% | 9.8% | 54.9% |
| | 22.5% | 0.0% | 37.3% | 40.2% | 0.0% | 40.2% |
| 178 | 14.5% | 12.9% | 22.0% | 32.3% | 18.3% | 50.6% |
| 180 | 8.6% | 19.0% | 18.5% | 42.1% | 11.8% | 54.0% |
| | 11.8% | 14.2% | 29.3% | 32.1% | 12.5% | 44.6% |
| | 11.5% | 40.0% | 36.3% | scale | 12.2% | scale |
| | 14.6% | 12.1% | 28.7% | 36.6% | 7.9% | 44.6% |
| 183 | 10.6% | 35.4% | 40.7% | scale | 13.3% | scale |
| 193 | 3.0% | 32.4% | 15.2% | 49.4% | 0.0% | 49.4% |
| 194 | 10.9% | 38.7% | 42.0% | scale | 8.4% | scale |
| | 9.6% | 21.8% | 20.7% | 34.6% | 13.2% | 47.9% |
| | 12.6% | 31.0% | 37.8% | scale | 18.6% | scale |
| | 3.0% | 32.4% | 15.2% | 49.4% | 0.0% | 49.4% |
| | 9.8% | 0.0% | 50.9% | 39.4% | 0.0% | 39.4% |
| 197 | 7.7% | 19.7% | 16.6% | 46.8% | 9.3% | 56.1% |
| 198 | 8.5% | 16.8% | 19.3% | 48.7% | 6.7% | 55.3% |
| 200 | 13.7% | 12.8% | 27.6% | 32.2% | 13.7% | 45.9% |
| 204 | 9.9% | 14.0% | 30.5% | 23.2% | 22.5% | 45.7% |
| 210 | 7.2% | 22.0% | 20.7% | 39.0% | 11.2% | 50.2% |
| 211 | 9.0% | 16.2% | 39.4% | 24.0% | 11.2% | 35.3% |
| | 10.2% | 17.0% | 24.7% | 35.7% | 12.4% | 48.1% |
| | 13.8% | 10.4% | 36.5% | 24.1% | 15.3% | 39.4% |
| | 6.5% | 12.2% | 36.3% | 30.5% | 14.5% | 45.0% |
| | 6.9% | 26.6% | 16.1% | 32.7% | 17.7% | 50.3% |
| | 3.4% | 36.2% | 27.7% | 32.6% | 0.0% | 32.6% |
| | 6.9% | 26.5% | 20.5% | 28.9% | 17.3% | 46.1% |
| | 0.0% | 35.1% | 15.6% | 39.6% | 9.7% | 49.2% |
| | 0.0% | 25.3% | 19.5% | 46.8% | 8.4% | 55.2% |
| | 6.6% | 19.7% | 25.9% | 37.2% | 10.6% | 47.8% |
| | 7.7% | 22.8% | 20.7% | 36.6% | 12.3% | 48.9% |
| | 16.3% | 4.6% | 28.2% | 49.1% | 1.7% | 50.8% |
| | 8.0% | 22.1% | 17.2% | 41.2% | 11.5% | 52.7% |
| | 8.0% | 22.1% | 17.2% | 41.2% | 11.5% | 52.7% |
| | 18.2% | 3.2% | 28.7% | 42.4% | 7.5% | 49.8% |
| | 11.9% | 10.1% | 31.8% | 30.5% | 15.7% | 46.2% |
| 212 | 7.5% | 25.6% | 17.6% | 36.5% | 12.8% | 49.3% |
| | 19.1% | 0.9% | 29.7% | 46.8% | 3.5% | 50.3% |
| | 8.8% | 28.4% | 9.6% | 33.7% | 19.5% | 53.2% |
| | 19.4% | 24.8% | 18.9% | 33.5% | 3.3% | 36.8% |
| | 19.1% | 26.9% | 17.5% | 31.6% | 4.9% | 36.6% |
| | 5.5% | 42.3% | 7.9% | 30.8% | 13.5% | 44.3% |
| | 4.6% | 23.9% | 25.1% | 35.5% | 11.0% | 46.5% |
| | 8.8% | 28.4% | 9.6% | 33.7% | 19.5% | 53.2% |
| | 0.0% | 65.4% | 22.4% | 10.5% | 1.7% | 12.2% |
| | 3.3% | 14.2% | 40.6% | 30.7% | 11.1% | 41.8% |
| | 11.2% | 13.6% | 25.0% | 40.3% | 9.9% | 50.2% |
| | 10.6% | 16.6% | 19.1% | 42.7% | 11.0% | 53.7% |
| | 21.1% | 22.7% | 17.4% | 17.5% | 21.2% | 38.7% |
| | 7.6% | 24.0% | 20.0% | 38.9% | 9.5% | 48.4% |
| | 10.3% | 20.4% | 22.2% | 33.7% | 13.4% | 47.1% |
| | 3.5% | 22.0% | 39.8% | 8.9% | 25.9% | 34.7% |
| 213 | 7.6% | 28.2% | 16.3% | 30.4% | 17.5% | 47.9% |
| | 5.3% | 18.8% | 18.1% | 41.3% | 16.4% | 57.7% |
| | 7.5% | 21.0% | 14.8% | 48.5% | 8.2% | 56.7% |
| | 8.3% | 17.8% | 18.5% | 44.6% | 10.9% | 55.5% |
| 214 | 9.1% | 20.2% | 19.1% | 47.0% | 4.5% | 51.6% |
| | 8.3% | 19.8% | 18.9% | 44.6% | 8.4% | 53.0% |
| | 7.7% | 20.5% | 19.6% | 45.3% | 7.0% | 52.2% |
| | 7.1% | 21.5% | 16.9% | 42.4% | 12.1% | 54.5% |
| | 7.0% | 25.9% | 15.1% | 39.9% | 12.0% | 51.9% |
| | 6.9% | 18.0% | 18.3% | 48.5% | 8.4% | 56.9% |
| | 7.4% | 19.2% | 18.2% | 45.6% | 9.5% | 55.1% |

TABLE 3-continued

| Position | | | | | | |
|---|---|---|---|---|---|---|
| | 5.3% | 21.1% | 10.9% | 47.3% | 15.4% | 62.7% |
| | 5.3% | 21.1% | 10.9% | 47.3% | 15.4% | 62.7% |
| 215 | 7.8% | 19.8% | 15.8% | 46.4% | 10.2% | 56.6% |
| | 7.9% | 20.2% | 17.7% | 40.6% | 13.6% | 54.1% |
| | 20.0% | 24.8% | 25.4% | 25.7% | 4.1% | 29.9% |
| | 4.4% | 26.2% | 19.2% | 45.1% | 5.1% | 50.2% |
| | 8.1% | 19.6% | 20.1% | 42.7% | 9.4% | 52.1% |
| | 2.3% | 30.1% | 19.7% | 31.8% | 16.1% | 47.9% |
| | 5.9% | 23.7% | 14.8% | 39.3% | 16.3% | 55.6% |
| | 9.6% | 26.0% | 17.0% | 36.5% | 10.9% | 47.3% |
| | 4.7% | 20.8% | 14.1% | 42.2% | 18.2% | 60.4% |
| | 4.2% | 31.0% | 12.0% | 40.7% | 12.1% | 52.8% |
| | 6.7% | 21.3% | 18.1% | 41.7% | 12.3% | 53.9% |
| | 8.0% | 19.5% | 20.4% | 47.1% | 5.0% | 52.1% |
| 216 | 8.3% | 21.9% | 18.9% | 40.9% | 10.0% | 50.9% |
| | 0.0% | 28.0% | 30.1% | 22.8% | 19.1% | 41.9% |
| | 34.6% | 0.0% | 30.6% | 33.7% | 1.1% | 34.8% |
| | 7.3% | 17.8% | 17.9% | 47.0% | 10.0% | 56.9% |
| | 6.6% | 16.6% | 17.2% | 50.0% | 9.7% | 59.7% |
| | 7.7% | 18.1% | 19.2% | 44.5% | 10.5% | 55.0% |
| | 7.5% | 20.3% | 16.5% | 45.0% | 10.6% | 55.6% |
| 217 | 0.0% | 42.3% | 21.0% | 24.3% | 12.3% | 36.6% |
| | 6.8% | 16.7% | 17.1% | 50.1% | 9.3% | 59.4% |
| | 7.4% | 20.5% | 18.7% | 44.1% | 9.4% | 53.5% |
| | 11.9% | 10.1% | 31.8% | 30.5% | 15.7% | 46.2% |
| | 13.2% | 21.6% | 20.4% | 31.3% | 13.5% | 44.8% |
| | 12.1% | 13.9% | 27.6% | 33.8% | 12.7% | 46.2% |
| 218 | 0.7% | 39.0% | 17.8% | 30.3% | 12.1% | 42.5% |
| | 4.7% | 26.8% | 19.4% | 30.5% | 18.7% | 49.1% |
| | 7.1% | 22.8% | 22.4% | 38.3% | 9.4% | 47.7% |
| | 7.2% | 19.9% | 19.6% | 44.1% | 9.2% | 53.4% |
| | 8.5% | 19.7% | 19.9% | 42.2% | 9.7% | 51.9% |
| | 7.2% | 25.9% | 15.8% | 37.6% | 13.5% | 51.1% |
| | 8.0% | 21.1% | 20.9% | 41.9% | 8.2% | 50.0% |
| | 8.7% | 19.9% | 19.0% | 42.9% | 9.4% | 52.4% |
| 223 | 4.5% | 29.5% | 17.2% | 15.8% | 33.0% | 48.8% |
| | 0.0% | 38.4% | 30.1% | 31.6% | 0.0% | 31.6% |
| | 20.2% | 22.8% | 33.6% | 17.3% | 6.0% | 23.4% |
| | 19.0% | 37.0% | 34.9% | scale | 9.1% | scale |
| 224 | 8.0% | 20.5% | 22.1% | 41.0% | 8.4% | 49.5% |
| | 6.6% | 18.2% | 17.1% | 51.4% | 6.8% | 58.2% |
| | 7.9% | 22.1% | 21.6% | 37.0% | 11.4% | 48.4% |
| | 14.4% | 19.0% | 24.9% | 33.1% | 8.5% | 41.7% |
| | 3.1% | 26.3% | 24.2% | 40.8% | 5.6% | 46.4% |
| | 10.3% | 20.1% | 25.8% | 38.1% | 5.7% | 43.7% |
| 225 | 9.7% | 22.2% | 18.8% | 41.8% | 7.5% | 49.3% |
| | 4.3% | 23.5% | 17.8% | 47.9% | 6.4% | 54.3% |
| | 12.0% | 21.9% | 17.1% | 39.1% | 9.9% | 49.0% |
| | 12.9% | 23.8% | 17.5% | 34.1% | 11.7% | 45.8% |
| | 15.9% | 22.6% | 18.3% | 38.0% | 5.2% | 43.2% |
| 226 | 4.9% | 24.9% | 21.9% | 45.8% | 2.5% | 48.3% |
| | 6.5% | 29.5% | 22.8% | 32.4% | 8.8% | 41.2% |
| 227 | 13.6% | 23.1% | 21.9% | 38.3% | 3.2% | 41.4% |

Table 4 is a summary, or further compilation, of data shown in Table 3 (above). For example, the term "position" indicated the amino acid residue position in SEQ ID NO:2; the term "Original Amino Acid.", as in Table 3, indicated the unaltered "parental" residue, while the term "New Amino Acid." as in Table 3, indicated the altered (new) amino acid residue in that position. The terms "WT_P" and "WT_S" indicate the substrate (fatty acid release) preference of the "parental" enzyme, e.g SEQ ID NO:2 for a particular substrate (fatty acid) by indicating the amount of fatty acid released (hydrolyzed) from the soy oil (as in Table 3), where "P" is palmitic acid, and "S" is stearic acid.

The "palmitate" and "stearate" columns indicate the amount of palmitic acid and stearic acid released (by enzymatic hydrolysis) from the soy oil, which comprises linolenic acid, linoleic acid, oleic acid, palmitic acid, stearic acid, as discussed above. "P+S" shows the combined amounts of fatty acids hydrolyzed that were palmitic acid and stearic acid, or "P+S". The terms "delta_P" and "delta_S" indicate the change in preference of an exemplary enzyme as provided herein (e.g., D61A from the first row) for hydrolyzing palmitic acid and stearic acid, respectively, as compared to the corresponding activity of SEQ ID NO:2. The term "delta P+S" indicates the total or summed change in preference of an exemplary enzyme as provided herein (e.g. D61A from the first row) for hydrolyzing palmitic acid and stearic acid as compared to the corresponding activity of SEQ ID NO:2. The section "palmitate mutations" summarizes the exemplary enzymes as provided herein having an activity (fatty acid hydrolysis) preference for releasing palmitic acid versus other fatty acids. The section "stearate mutations" summarizes the exemplary enzyme as provided herein having an activity preference for releasing stearic acid versus other fatty acids (from soy oil, assay described above).

TABLE 4

| Position | Original Amino Acid | New Amino Acid | WT_P | WT_S | Palmitate | Stearate |
|---|---|---|---|---|---|---|
| Exemplary Palmitate Mutations | | | | | | |
| 61 | D | A | 45% | 6% | 54% | 7% |
| 61 | D | E | 45% | 6% | 47% | 8% |
| 72 | R | E | 45% | 6% | 54% | 4% |
| 72 | R | K | 45% | 6% | 52% | 9% |
| 116 | E | A | 45% | 6% | 56% | 11% |
| 116 | E | Q | 45% | 6% | 50% | 9% |
| 116 | E | R | 45% | 6% | 52% | 9% |
| 116 | E | T | 45% | 6% | 50% | 17% |
| 116 | E | V | 45% | 6% | 59% | 9% |
| 133 | S | A | 45% | 6% | 45% | 11% |
| 151 | I | G | 45% | 6% | 49% | 4% |
| 151 | I | A | 45% | 6% | 46% | 2% |
| 163 | V | R* | 45% | 6% | 61% | 2% |
| 164 | D | R* | 45% | 6% | 58% | 3% |
| Stearate Mutations | | | | | | |
| 20 | I | L | 45% | 6% | 39% | 12% |
| 62 | V | S | 45% | 6% | 37% | 18% |
| 77 | G | P | 45% | 6% | 18% | 20% |
| 83 | V | C | 45% | 6% | 31% | 17% |
| 88 | D | H | 45% | 6% | 33% | 13% |
| 113 | Y | G | 45% | 6% | 15% | 25% |
| 116 | E | T | 45% | 6% | 50% | 17% |
| 116 | E | G | 45% | 6% | 33% | 21% |
| 140 | H | K | 45% | 6% | 33% | 13% |
| 146 | K | S | 45% | 6% | 31% | 19% |
| 167 | I | S | 45% | 6% | 36% | 11% |
| 180 | L | E | 45% | 6% | 42% | 12% |
| 194 | E | M | 45% | 6% | 35% | 13% |
| 211 | A | Q | 45% | 6% | 33% | 18% |
| 212 | S | Y | 45% | 6% | 34% | 13% |
| 215 | G | C | 45% | 6% | 42% | 18% |
| 215 | G | V | 45% | 6% | 39% | 16% |
| 215 | G | W | 45% | 6% | 41% | 12% |
| 218 | A | H | 45% | 6% | 30% | 19% |
| 218 | A | S | 45% | 6% | 38% | 14% |
| 223 | V | A | 45% | 6% | 16% | 33% |
| 225 | A | M | 45% | 6% | 39% | 10% |
| | | Q | 45% | 6% | 34% | 12% |

| Position | Original Amino Acid | New Amino Acid | P + S | delta_P | delta_S | delta_P +S |
|---|---|---|---|---|---|---|
| Palmitate Mutations | | | | | | |
| 61 | D | A | 60% | 9% | 1% | 9% |
| 61 | D | E | 55% | 2% | 2% | 4% |
| 72 | R | E | 58% | 9% | -2% | 7% |
| 72 | R | K | 61% | 7% | 3% | 10% |
| 116 | E | A | 67% | 11% | 5% | 16% |
| 116 | E | Q | 60% | 5% | 3% | 9% |
| 116 | E | R | 61% | 7% | 3% | 10% |
| 116 | E | T | 68% | 5% | 11% | 17% |
| 116 | E | V | 68% | 14% | 3% | 17% |
| 133 | S | A | 56% | 0% | 5% | 5% |
| 151 | I | G | 53% | 4% | -2% | 2% |
| 151 | I | A | 49% | 1% | -4% | -2% |
| 163 | V | R* | 64% | 16% | -4% | 13% |

TABLE 4-continued

| | | | | | | |
|---|---|---|---|---|---|---|
| 164 | D | R* | 61% | 13% | −3% | 10% |

Stearate Mutations

| | | | | | | |
|---|---|---|---|---|---|---|
| 20 | I | L | 51% | −6% | 6% | 0% |
| 62 | V | S | 55% | −8% | 12% | 4% |
| 77 | G | P | 38% | −27% | 14% | −13% |
| 83 | V | C | 48% | −14% | 11% | −3% |
| 88 | D | H | 46% | −12% | 7% | −5% |
| 113 | Y | G | 40% | −30% | 19% | −11% |
| 116 | E | T | 68% | 5% | 11% | 17% |
| 116 | E | G | 54% | −12% | 15% | 3% |
| 140 | H | K | 46% | −12% | 7% | −5% |
| 146 | K | S | 50% | −14% | 13% | −1% |
| 167 | I | S | 47% | −9% | 5% | −4% |
| 180 | L | E | 54% | −3% | 6% | 3% |
| 194 | E | M | 48% | −10% | 7% | −3% |
| 211 | A | Q | 50% | −12% | 12% | −1% |
| 212 | S | Y | 47% | −11% | 7% | −4% |
| 215 | G | C | 60% | −3% | 12% | 9% |
| 215 | G | V | 56% | −6% | 10% | 5% |
| 215 | G | W | 53% | −4% | 6% | 2% |
| 218 | A | H | 49% | −15% | 13% | −2% |
| 218 | A | S | 51% | −7% | 8% | 0% |
| 223 | V | A | 49% | −29% | 27% | −2% |
| 225 | A | M | 49% | −6% | 4% | −2% |
| | | Q | 46% | −11% | 6% | −5% |

Example 5

Exemplary Evolution for Improved Hydrolysis of Palmitate Using GeneReassembly$^{SM}$ Technology Fourteen (14) single amino acid mutations identified from the GSSM$^{SM}$ screening which cover seven (7) amino acid positions were combined by the GeneReassembly$^{SM}$ technology (U.S. Pat. No. 6,605,449). The full length nucleic acid sequences generated from the GeneReassembly phase were cloned into an expression vector pASK-5 (see description above) for expression in Escherichia coli host HMS175 (Novagen, USA). The expression of the GeneReassembly variants was induced with anhydrotetracycline after the optimal host cell densities were achieved.

The 14 mutations that yielded the greatest increases in palmitate hydrolysis, identified in Table 2, were selected for inclusion in a Palmitase GeneReassembly library generated by methods described above. Initial clones were screened on umbelliferyl palmitate for activity yielding about 145 sequence-unique clones, which were assayed for activity on soy oil, as described above.

FIG. 8 shows primary and secondary screen data for soy oil assays on selected clones from the palmitase library. Clones that yielded palmitate at greater than 70% of hydrolysed FAs in the primary assay (under the standard initial rate conditions of the assay method) were selected to be re-assayed on soy oil. For each soy oil assay, the extracted FAs were diluted 50-fold and 100-fold for analysis by LCMS or GC. Where additional, non-targeted mutations were found, this is also indicated. The FA hydrolysis ratios detected and the amounts of each FA detected are presented. In the figure, "high" and "low" indicate values that were outside the range of the calibration curve. The rows are sorted in order of percentage palmitate released in the secondary assay, and then by total palmitate released. Numerous clones showed significantly increased palmitate selectivity (up to 100%), compared with the parent SEQ ID NO:2 (61.2%)

The top 25 palmitase hits selected based on the secondary assay described above were subcloned into Pseudomonas systems (Dow Global Technologies Inc., US Patent PUB. APP. NO. 20050130160 and Dow Global Technologies Inc., US Patent PUB. APP. NO. 20050186666). The nucleic acid sequence encoding the enzyme or polypeptide was inserted either in the pMYC vector (Dow Global Technologies Inc., US Patent PUB. APP. NO. 20050130160) or in the pDOW1169 vector (Dow Global Technologies Inc., US Patent PUB. APP. NO. 20080058262) and then introduced into the Pseudomonas fluorescens host by electroporation. The transformed cells were selected either by growth in minimal medium for the pDOW1169 constructs or in rich media plus tetracycline for the pMYC constructs. The expression of the enzyme or polypeptide was induced with IPTG after the optimal host cell densities were achieved.

Table 5 shows data from assays on soy oil, run in duplicate, of the top 25 hits expressed in the Pseudomonas systems. The 4 hits constructed in the pDOW1169 vector are listed in bold underline typeface, all other hits were constructed in the pMYC vector. Enzyme was added to 5 g of crude oil resulting in 20% final water content. The mixture was then homogenized with a 7 mm probe and incubated for 40 hours at 25° C. with stir bar agitation. Aliquots were removed and analyzed for FA by converting FA to FAME and quantifying FAME by GC as described in Example 8. The 25 enzymes were loaded into the 5 g soy oil based upon equal UMB-palmitate activity units. In these reactions palmitate in oil was reduced significantly from 11% in untreated oil to 5% or less in enzyme treated oils indicating an increased preference for hydrolysis of palmitate compared with the parent enzyme SEQ ID NO:2.

TABLE 5

| | | | | | | Amino acid position & amino acid present | | | | | | | | | |
|---|---|---|---|---|---|---|---|---|---|---|---|---|---|---|---|
| Enzyme | Palmitate | Stearate | Oleate | Linoleate | Linolenate | 53 | 61 | 72 | 116 | 126 | 133 | 151 | 160 | 163 | 164 |
| 1 | 6.0% | 4.3% | 24.9% | 59.7% | 5.1% | | A | E | A | | A | | | R | |
| 1 | 6.4% | 4.3% | 24.8% | 59.3% | 5.2% | | A | E | A | | A | | | R | |
| 2 | 6.6% | 4.3% | 24.8% | 59.2% | 5.1% | | A | E | V | | A | | | R | |
| 2 | 6.9% | 4.3% | 24.7% | 59.0% | 5.1% | | A | E | V | | A | | | R | |
| 3 | 9.0% | 4.3% | 24.1% | 57.3% | 5.2% | | E | E | V | | A | | | | R |
| 3 | 8.4% | 4.3% | 24.3% | 57.8% | 5.2% | | E | E | V | | A | | | | R |
| 4 | 3.9% | 4.3% | 25.1% | 61.6% | 5.1% | A | A | K | A | | | | | R | |
| 4 | 5.8% | 4.4% | 25.0% | 59.7% | 5.2% | A | A | K | A | | | | | R | |
| 5 | 5.6% | 4.3% | 25.0% | 60.0% | 5.1% | | | E | V | | | | | R | |
| 5 | 5.8% | 4.3% | 25.0% | 59.8% | 5.1% | | | E | V | | | | | R | |
| 6 | 4.9% | 4.3% | 24.9% | 60.8% | 5.1% | | | E | V | | | | | | |
| 6 | 5.7% | 4.3% | 24.8% | 60.1% | 5.1% | | | E | V | | | | | | |
| 7 | 5.0% | 4.3% | 24.9% | 60.7% | 5.1% | | E | E | V | | A | A | | | |
| 7 | 4.9% | 4.3% | 24.9% | 60.8% | 5.1% | | E | E | V | | A | A | | | |
| 8 | 5.2% | 4.0% | 24.7% | 61.3% | 4.8% | | E | | V | | A | | | R | |
| 8 | 5.2% | 4.0% | 24.7% | 61.3% | 4.8% | | E | | V | | A | | | R | |
| 9 | 5.3% | 4.1% | 24.8% | 60.9% | 4.9% | | | | V | | A | | | R | |
| 9 | 5.5% | 4.2% | 24.9% | 60.6% | 4.9% | | | | V | | A | | | R | |

TABLE 5-continued

| Enzyme | Palmitate | Stearate | Oleate | Linoleate | Linolenate | 53 | 61 | 72 | 116 | 126 | 133 | 151 | 160 | 163 | 164 |
|---|---|---|---|---|---|---|---|---|---|---|---|---|---|---|---|
| 10 | 5.7% | 4.0% | 23.3% | 56.2% | 10.8% | | E | E | V | | A | | | R | |
| 10 | 5.6% | 4.3% | 25.0% | 60.1% | 5.0% | | E | E | V | | A | | | R | |
| 11 | 8.3% | 5.7% | 23.3% | 57.7% | 5.0% | T | E | E | A | | A | | P | | R |
| 11 | 5.9% | 3.8% | 24.5% | 60.6% | 5.2% | | E | E | A | | A | | | | R |
| 12 | 7.8% | 5.1% | 24.8% | 57.3% | 5.0% | | E | E | V | | | | | | R |
| 12 | 5.7% | 4.4% | 25.0% | 59.7% | 5.1% | | E | E | V | | | | | | R |
| 13 | 4.8% | 3.3% | 24.7% | 62.2% | 4.9% | | E | K | V | | | | | R | |
| 13 | 5.9% | 4.0% | 24.5% | 60.8% | 4.9% | | E | K | V | | | | | R | |
| 14 | 5.5% | 3.8% | 25.2% | 60.6% | 5.0% | | E | K | V | | | | | | |
| 14 | 5.9% | 4.5% | 24.8% | 59.9% | 4.9% | | E | K | V | | | | | | |
| 15 | 5.8% | 3.6% | 25.0% | 60.7% | 5.0% | | E | E | T | | | | | R | |
| 15 | 5.6% | 4.3% | 24.9% | 60.4% | 4.9% | | E | E | T | | | | | R | |
| 16 | 6.1% | 4.0% | 24.1% | 60.9% | 4.9% | | E | E | V | | A | | | | |
| 16 | 6.2% | 4.0% | 24.1% | 60.9% | 4.8% | | E | E | V | | A | | | | |
| 17 | 5.7% | 4.4% | 24.9% | 59.9% | 5.1% | | E | K | | | | | | R | |
| 17 | 5.0% | 4.3% | 25.0% | 60.8% | 4.9% | | E | K | | | | | | R | |
| 18 | 8.3% | 4.2% | 23.5% | 55.7% | 8.2% | | E | E | V | | | | | R | |
| 18 | 7.9% | 4.2% | 23.7% | 56.0% | 8.2% | | E | E | V | | | | | R | |
| 19 | 6.8% | 4.2% | 24.0% | 56.9% | 8.1% | | | K | V | | A | | | R | |
| 19 | 6.8% | 4.2% | 24.0% | 56.9% | 8.1% | | | K | V | | A | | | R | |
| 20 | 6.1% | 4.2% | 24.0% | 57.5% | 8.2% | | E | R | | A | | | | R | |
| 20 | 5.4% | 4.1% | 23.9% | 58.5% | 8.0% | | E | R | | A | | | | R | |
| 21 | 6.7% | 4.0% | 23.3% | 58.0% | 8.0% | | A | E | A | | A | | | | |
| 21 | 6.5% | 3.9% | 23.2% | 58.5% | 7.9% | | A | E | A | | A | | | | |
| 22 | 5.4% | 4.0% | 23.9% | 58.6% | 8.0% | | E | E | A | | A | | | R | |
| 22 | 5.3% | 4.1% | 24.0% | 58.7% | 8.0% | | E | E | A | | A | | | R | |
| 23 | 6.6% | 3.9% | 23.2% | 58.4% | 7.9% | | E | | V | | A | | | | |
| 23 | 6.4% | 3.9% | 23.1% | 58.8% | 7.8% | | E | | V | | A | | | | |
| 24 | 6.0% | 4.3% | 24.3% | 57.3% | 8.1% | | A | E | V | | | | | | |
| 24 | 5.7% | 4.3% | 24.3% | 57.6% | 8.1% | | A | E | V | | | | | | |
| 25 | ND | ND | ND | ND | ND | | A | E | V | | | | | R | |
| 25 | 6.0% | 4.0% | 24.0% | 58.1% | 8.0% | | A | E | V | | | | | R | |
| 26 | 4.8% | 4.2% | 24.2% | 58.9% | 7.9% | | E | K | | | | | | R | |

ND (Not Determined)

Table 6 below shows data for the thermostability of the top 25 palmitase hits selected based on the secondary assay described above. These data were obtained using the hits expressed in the *E. coli* HMS174 host. Clones were arrayed in 96-well plates and incubated for 10 minutes at room temperature (RT), 45, 50 or 55° C. then assayed at RT on MeUMB-palmitate. The percentage of residual activity is determined by dividing the activity after incubation at each temperature by the activity after incubation at RT. Also shown for each palmitases are the mutations present, and examples of palmitate selectivity and activity on soy oil. SEQ ID NO:2 retained approx. 15% of activity after incubation for 10 min. at 50° C., but had no activity after incubation at 55° C.

TABLE 6

| | % Stability | | | Amino acid position & amino acid present | | | | | | | |
|---|---|---|---|---|---|---|---|---|---|---|---|
| Enzyme | 55 C. | 50 C. | 45 C. | 61 | 72 | 116 | 133 | 151 | 163 | 164 | Other |
| 27 | | 23.0% | 62.7% | E | K | V | | | | | P162S |
| 28 | | 22.8% | 62.1% | E | K | V | | | R | | V62F |
| 29 | | | 55.9% | E | K | | | A | R | | |
| 30 | 24.1% | 68.8% | 75.6% | E | E | V | A | | | | |
| 31 | 22.0% | 68.1% | 82.5% | E | E | V | A | | R | | |
| 32 | | 27.1% | 58.4% | E | E | V | | | R | | |
| 33 | | 26.1% | 56.6% | E | E | V | | A | R | | |
| 34 | | 24.7% | 54.0% | E | E | V | A | | | R | |
| 35 | 8.1% | 64.1% | 67.6% | E | E | T | | | R | | |
| 36 | 10.3% | 53.8% | 75.7% | E | E | A | A | | R | | |
| 37 | 9.2% | 54.8% | 61.5% | E | E | A | | | R | | |
| 38 | | 45.4% | 68.4% | E | E | A | A | A | | | |
| 39 | | 22.9% | 61.9% | E | E | A | A | | | R | |
| 40 | | 35.3% | 77.1% | E | | V | A | | R | | |
| 41 | | 30.6% | 70.2% | E | | V | A | | | | |
| 42 | 20.3% | 71.8% | 79.3% | E | | A | A | G | R | | |
| 43 | | | 64.2% | E | | A | A | | | | |
| 44 | | | 63.2% | A | K | V | | | | | |
| 45 | | | 56.0% | A | K | V | A | A | R | | |
| 46 | | | 80.7% | A | K | A | | | R | | |
| 47 | 22.2% | 71.8% | 88.1% | A | E | V | A | | R | | |
| 48 | | 60.6% | 83.2% | A | E | V | | A | R | | |
| 49 | | 50.7% | 68.0% | A | E | V | | | | | |
| 50 | | 50.2% | 77.2% | A | E | V | | | R | | |

TABLE 6-continued

| | % Stability | | | Amino acid position & amino acid present | | | | | | | |
|---|---|---|---|---|---|---|---|---|---|---|---|
| Enzyme | 55 C. | 50 C. | 45 C. | 61 | 72 | 116 | 133 | 151 | 163 | 164 | Other |
| 51 | | 21.1% | 53.6% | A | E | V | | A | | R | |
| 52 | | | 56.5% | A | E | Q | A | A | R | | |
| 53 | | 73.6% | 118.3% | A | E | A | A | | | | |
| 54 | | 69.2% | 110.7% | A | E | A | A | | R | | |
| 55 | | | 82.2% | A | | V | | | | | |
| 56 | | | 51.4% | A | | A | A | | | | |
| 57 | | | 82.8% | | K | V | A | G | | | |
| 58 | | | 60.1% | | K | V | | | R | | |
| 59 | | | 58.3% | | K | V | A | | | | |
| 60 | | | 57.9% | | K | V | A | | R | | |
| 61 | | | 56.3% | | K | V | A | | R | | |
| 62 | | | 51.9% | | K | Q | A | | R | | |
| 63 | | | 74.8% | | K | A | | | | | |
| 64 | | | 58.8% | | K | A | A | | | | |
| 65 | | 49.6% | 72.0% | | E | V | | | R | | |
| 66 | | 46.3% | 66.0% | | E | V | | | | | |
| 67 | | | 55.1% | | E | V | A | | R | | |
| 68 | | | 51.7% | | E | V | A | A | | | |
| 69 | | 23.6% | 54.6% | | E | A | | | | | |
| 70 | | | 76.2% | | E | A | | | | R | |
| 71 | | | 59.2% | | | V | A | | | | |
| 72 | | | 51.8% | | | V | A | | R | | |

Example 6

Laboratory Protocol for Evaluation of Candidate Palmitase, Stearatase or Saturase Enzymes Exemplary enzymes and polypeptides as provided herein were expressed in the *Pseudomonas* system (Dow Global Technologies Inc., US Patent PUB. APP. NO. 20050130160). The nucleic acid encoding the enzyme or polypeptide is inserted into the pMYC vector (Dow Global Technologies Inc., US Patent PUB. APP. NO. 20050130160) and was then introduced into the auxotrophic *Pseudomonas fluorescens* host by electroporation. The transformed cells were selected by growth in minimal medium. The expression of the enzyme or polypeptide was induced with IPTG after the optimal host cell densities achieved.

The following procedure is to be used to evaluate the ability of an enzyme or other polypeptide as provided herein to hydrolyze an oil sample. Palmitase enzyme is added to 1 kg of crude oil resulting in 20% final water content. The mixture is then homogenized with an overhead mixer and incubated at room temperature with constant mixing using a paddle mixer. Aliquots (0.5 mL) were removed at 0 h, 21 h, 43 h, 65 h, and 72 h and treated for FAME conversion & GC analysis as described in Example 8.

The above procedure was used with SEQ ID NO:2, the oil sample was a crude soybean oil. After 72 h samples of both the untreated oil and enzyme-treated oil yielded the results shown in Table 7.

TABLE 7

| Fatty Acid Composition | Untreated Oil (%) | Enzyme Treated Oil (%) |
|---|---|---|
| C16:0 | 11.1 | 3.7 |
| C18:0 | 4.1 | 4.2 |
| C18:1 | 22.1 | 24.3 |
| C18:2 | 54.5 | 59.5 |
| C18:3 | 8.2 | 8.3 |

The results show a significant decrease in the amount of palmitic acid (C16:0), such a decrease being considered desirable

Example 7

Evaluation of Lipases, Saturase or Palmitases with Sequence Homology to the Exemplary Polypeptide SEQ ID NO:2

Several homologous lipase sequences were subcloned into the pMAL-c2x vector (New England Biolabs, USA) by the xi-cloning method (Genlantis, USA). The constructs containing SEQ ID NO:2, SEQ ID NO:6, SEQ ID NO: 14, or SEQ ID NO: 16 were transformed into the *Escherichia coli* host ArcticExpress RP (Stratagene, USA) for expression. The expression of the lipases is under the control of a promoter which is induced with IPTG after the optimal host cell densities achieved. The recombinant enzymes were tested on soy oil for FA selectivity (Table 8). The lipases comprising SEQ ID NO:2, SEQ ID NO:6, SEQ ID NO: 14, or SEQ ID NO: 16 were expressed and cleaved from the MBP fusion tag using standard conditions. A single colony was inoculated into LB medium containing 20 µg/ml gentamycin and shaken at 200 rpm overnight at 30° C. This overnight culture was inoculated into fresh LB medium containing 20 µg/ml gentamycin to an OD600 reading of 0.05. This culture was shaken at 200 rpm and 30° C. until an OD600 reading of 0.5 was obtained. Cultures were transferred to 12° C. shaking at 200 rpm and allowed to equilibrate to the lower temperature before induction of lipase expression by addition of 0.5 mM IPTG, followed by further growth for 24 hours. Cells were collected by centrifugation, suspended in Tris buffer pH8, containing NaCl, $CaCl_2$, DNaseI, and lysozyme, and then lysed by sonication. Cell lysates were clarified by centrifugation. Enzymes were cleaved from the MBP by incubation of the lipase-MBP fusion with Factor Xa for 6 hours at room temperature, followed by an additional 18 hours at 12° C. The clarified lysates with intact, active recombinant enzymes all showed strong and similar preferences for hydrolysis of palmitate over other FA when assayed on soy oil (Table 8).

TABLE 8

| Enzyme | Similarity to SEQ ID NO: 2 | | Fatty Acids (%) Hydrolyzed | | | | |
|---|---|---|---|---|---|---|---|
| | Identity | Similarity | Palmitate | Stearate | Oleate | Linoleate | Linolenate |
| Soy Oil | NA | NA | 11.0% | 4.3% | 24.9% | 59.7% | 5.1% |
| SEQ ID NO: 2 | 100% | 100 | 50.9% | 5.1% | 16.9% | 18.1% | 9.0% |
| SEQ ID NO: 14 | 27% | 42% | 45.8% | 2.0 | 14.2% | 37.9% | 0.0% |
| SEQ ID NO: 12 | 47% | 62% | 50.4% | 4.1% | 16.1% | 23.4% | 6.0% |
| SEQ ID NO: 6 | 41% | 56% | 37.0% | 6.2% | 28.5% | 20.7% | 7.6% |

Example 8

Method for Conversion of Free Fatty Acids or Triglycerides to Fatty Acid Methyl Esters (FAME) and Quantitation of FAME by Gas Chromatography Fatty acids released from lipids, triglycerides, fats or oils by the action of lipases, e.g. saturaes, palmitases and/or stearatases can be quantified directly by LCMS using the method described in Example 2. Alternatively these hydrolyzed fatty acids can be converted to Fatty Acid Methyl Esters (FAME) using acid catalyzed methanolysis, and then quantified by Gas Chromatography (GC). In this example:

The oil after reaction with lipases, e.g. saturaes, palmitases and/or stearatases is treated by addition of 1 mL of extraction solvent (CHCl$_3$:MeOH:4N HCl (2:1:0.075)) per 0.5 mL reaction volume.

A 45 µL aliquot of extracted oil is transferred into a 4 mL screw top vial. To each vial a small stir bar is added, followed by 2 mL hexane and 400 µL 20% (v/v) MeOH in HCl.

The vials are then sealed and heated with stirring for 15 minutes. The vials are then removed from heat and allowed to cool before adding 800 µL H$_2$O.

The mixture is then vortexed and a sample (500 µL) of the top hexane layer containing FAMES is transferred into an auto sampler vial for the GC. To each sample 500 µL of 0.5 mg/mL C15:0 FAME is added as an internal standard.

The FAME synthesized using this method are then analyzed by Gas Chromatography using the following operational parameters:

The equipment is a Hewlett Packard 6890 Series GC with autosampler

The column used is a Supelco SP-2380 Fused Silica Capillary Column 30 m×0.25 mm and 0.2 µm film thickness The injector and detector are set at 260° C.; Helium carrier gas flow is set at 0.6 mL/min; the oven is set at an initial temperature of 150° C.

Samples (1 mL) are injected with a 10:1 injection split. The GC method used has:
Ramp 1: 4 C/min for 10 min=190° C.
Ramp 2: 15 C/min for 4 min=250° C.
Hold: 250° C. for 2 min Triglyceride FA can also be analyzed by conversion to FAME, even in the presence of hydrolyzed fatty acids. Using the above method and the method below in combination can this be used to determine the fatty acid selectivity of a lipase, e.g. saturase, palmitase, and/or stearatase, and the effect of the enzyme on the oil. The method for analysis of FA bound to glycerol (or other alcohols) utilizes base catalyzed methanolysis:

The oil after reaction with lipases, e.g. saturaes, palmitases and/or stearatases is treated by addition of 1 mL of extraction solvent (CHCl$_3$:MeOH:4N HCl (2:1:0.075)) per 0.5 mL reaction volume.

A 45 µL aliquot of extracted oil is transferred into a microfuge tube. The 500 µL of heptane is added followed by 50 µL of 2 N methanolic KOH.

The mixture is vortexed vigorously for 30 seconds then centrifuged.

An aliquot (50 µL) of the top heptane layer containing FAME is transferred to an auto sampler vial and combine it with 450 µL of hexane containing the C15:0 internal standard.

Analysis of FAME by GC is as outlined above.

A number of embodiments as provided herein have been described. Nevertheless, it will be understood that various modifications may be made without departing from the spirit and scope as provided herein. Accordingly, other embodiments are within the scope of the following claims.

What is claimed is:

1. A method of hydrolyzing an oil or fat comprising the steps of:
   (a) obtaining a composition comprising an oil or fat, wherein the oil or fat can be hydrolyzed by a polypeptide having a palmitase activity, wherein the palmitase activity comprises hydrolyzing at least 45% palmitic acid from the oil or fat, said polypeptide being selected from the group consisting of isolated, synthetic and recombinant polypeptides having a palmitase activity and said polypeptide either
   i. being encoded by
      a nucleic acid comprising a nucleic acid sequence having at least 85% sequence identity to full length SEQ ID NO:1, and wherein the nucleic acid encodes at least one polypeptide having a palmitase activity and the polypeptide having at least one base residue change described below in Table A, or
   ii. having at least 85% sequence identity to full length SEQ ID NO:2, and having at least one amino acid residue change described in Table A,

TABLE A

| Amino Acid Residue | Original Amino Acid | New Amino Acid |
| --- | --- | --- |
| 27 | G | Q |
| 45 | G | L |
| 54 | S | H |
| 61 | D | A |
|  |  | E |
| 62 | V | A |
|  |  | G |
| 72 | R | E |
|  |  | K |
|  |  | S |
|  |  | T |
| 74 | F | I |
| 83 | V | M |
| 96 | A | I |
| 98 | G | L |
| 116 | E | A |
|  |  | F |
|  |  | H |
|  |  | L |
|  |  | Q |
|  |  | Q |
|  |  | R, H140R |
|  |  | R |
|  |  | S |
|  |  | S |
|  |  | T |
|  |  | V |
| 117 | L | R, I161L |
| 120 | K | L |
| 133 | S | A |
| 147 | I | F |
| 151 | I | A |
|  |  | G |

TABLE A-continued

| Amino Acid Residue | Original Amino Acid | New Amino Acid |
| --- | --- | --- |
|  |  | H |
| 160 | P | T |
| 172 | R | Q |
| 212 | S | R |
| 213 | K | T |
| 214 | T | V |
|  |  | N |
|  |  | R |
|  |  | Y |
| 215 | G | A |
|  |  | H |
| 216 | A | V |
|  |  | C |
|  |  | L | or
   iii. having at least 85% sequence identity to full length SEQ ID NO:2 but also comprising at least one of amino acid residue modification D61A; D61E; R72E; R72K; E116A; E116Q; E116R; E116T; E116V; S133A; I151G; I151A; V163R; D164R,
   (b) adding the polypeptide of step (a) to the composition comprising said oil or fat in an amount sufficient and under conditions sufficient to cause hydrolysis of the oil or fat, thereby hydrolyzing the oil or fat.

2. The method of claim 1, wherein said hydrolyzed oil or fat has a lower saturated fat content than said oil or fat prior to hydrolysis.

3. The method of claim 1, wherein said oil or fat comprises an algal oil, an animal oil, a vegetable oil, an oil having an altered fatty acid composition, a low saturated oil, fish oil or a combination thereof.

4. The method of claim 3, wherein said oil comprises Neochloris oleoabundans oil, Scenedesmus dimorphus oil, Euglena gracilis oil, Phaeodactylum tricornutum oil, Pleurochrysis carterae oil, Prymnesium parvum oil, Tetraselmis chui oil, Tetraselmis suecica oil, Isochrysis galbana oil, Nannochloropsis salina oil, Botryococcus braunii oil, Dunaliella tertiolecta oil, Nannochloris species oil, Spirulina species oil, Chlorophycease oil, Bacilliarophy oil, canola oil, castor oil, coconut oil, coriander oil, corn oil, cottonseed oil, hazelnut oil, other nut oils, hempseed oil, linseed oil, meadowfoam oil, olive oil, palm oil, palm kernel oil, peanut oil, rapeseed oil, rice bran oil, safflower oil, sasanqua oil, sesame oil, soybean oil, sunflower seed oil, tall oil, tsubaki oil, tallow, lard, butter fat, chicken fat, or a blend of any of said fats or oils.

5. The method of claim 3, wherein the altered fatty acid comprises high oleic oil, low linolenic oil or a combination thereof.

6. The method of claim 3, wherein the low saturated oil comprises high oleic canola oil, low linolenic soybean oil, high stearic sunflower oil or a combination thereof.

7. The method of claim 3, wherein the fish oil comprises candlefish oil, cod-liver oil, orange roughy oil, sardine oil, herring oil, menhaden oil or a combination thereof.

8. The method of claim 1, wherein said fats or oils comprise molecules having a triacylglyceride backbone and wherein during said hydrolysis palmitic acid is removed from at least some of the triacylglyceride backbones.

9. The method of claim 8, wherein said palmitic acid is selectively removed from an Sn1 or Sn3 position on the triacylglyceride backbone.

10. The method of claim 1, wherein said oil or fat is present in a feed or a food and said hydrolysis is accomplished prior to the consumption of said feed or food by an animal or an individual.

11. The method of claim 1, wherein said oil or fat comprises one or more of a triacylglycerol, a diacylglycerol, or a monoacylglycerol, and wherein said polypeptide of step (a) is contacted with said oil or fat under conditions wherein said polypeptide hydrolyzes one or more of said triacylglycerol, diacylglycerol or monoacylglycerol.

12. The method of claim 11 wherein said hydrolysis causes the amount of triacylglycerol, diacylglycerol or monoacylglycerol in the composition to decrease.

13. The method of claim 1, wherein the oil or fat comprises a glycerol ester of a polyunsaturated fatty acid.

14. The method of claim 1, wherein said hydrolyzed oil or fat comprises any one or more of a low-saturate oil or fat, a no-trans oil or fat, a lipid containing essential fatty acids, a lipid containing monounsaturated fatty acids, a lipid containing phospho-choline, a lipid containing phospho-serine, a lipid containing a phytosterol, a 1,3-diacylglyceride, a 2-monoacylglyceride, and a triacylglyceride.

15. The method of claim 1, wherein said composition comprises a milk or vegetable-based dietary composition, wherein the polypeptide can hydrolyze the oil or fat in the composition, thereby reducing its fat content.

16. The method of claim 1, wherein polypeptide comprises at least one of amino acid residue modification D61A; D61E; R72E; R72K; E116A; E116Q; E116R; E116T; E116V; S133A; I151G; I151A; V163R; D164R.

* * * * *

UNITED STATES PATENT AND TRADEMARK OFFICE
CERTIFICATE OF CORRECTION

PATENT NO. : 8,153,391 B2
APPLICATION NO. : 12/202204
DATED : April 10, 2012
INVENTOR(S) : Christopher L. G. Dayton et al.

It is certified that error appears in the above-identified patent and that said Letters Patent is hereby corrected as shown below:

In Claim 1, Col. 172, line 36,

"1151G" should read --I151G--, and "1151A" should read --I151A--.

In Claim 16, Col. 174, line 19,

"1151G" should read --I151G--, and "1151A" should read --I151A--.

Signed and Sealed this
Tenth Day of July, 2012

David J. Kappos
*Director of the United States Patent and Trademark Office*